(12) United States Patent
Duncia et al.

(10) Patent No.: US 7,550,500 B2
(45) Date of Patent: Jun. 23, 2009

(54) BICYCLIC AND TRICYCLIC AMINES AS MODULATORS OF CHEMOKINE RECEPTOR ACTIVITY

(75) Inventors: John V Duncia, Hockessin, DE (US); Joseph B Santella, III, Springfield, PA (US); Daniel S Gardner, Wilmington, DE (US); Dean A Wacker, Chadds Ford, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 501 days.

(21) Appl. No.: 11/225,227

(22) Filed: Sep. 13, 2005

(65) Prior Publication Data

US 2006/0014964 A1    Jan. 19, 2006

Related U.S. Application Data

(62) Division of application No. 10/842,949, filed on May 11, 2004, now Pat. No. 6,960,666, which is a division of application No. 10/427,814, filed on May 1, 2003, now Pat. No. 6,784,200, which is a division of application No. 09/687,602, filed on Oct. 13, 2000, now Pat. No. 6,586,446.

(60) Provisional application No. 60/159,882, filed on Oct. 15, 1999.

(51) Int. Cl.
| C07D 209/56 | (2006.01) |
| A61K 31/40 | (2006.01) |
| A61D 29/00 | (2006.01) |

(52) U.S. Cl. ........................ 514/411; 548/427
(58) Field of Classification Search ................ 514/411; 548/427

See application file for complete search history.

(56) References Cited

U.S. PATENT DOCUMENTS 5,321,034 A    6/1994 Duggan et al.
5,668,151 A    9/1997 Poindexter et al.
5,703,091 A    12/1997 Steiner et al.
5,716,961 A    2/1998 Sands
5,731,317 A    3/1998 Lu et al.
6,080,752 A    6/2000 Stemp et al.

FOREIGN PATENT DOCUMENTS

| DE | 4341400 | 8/1995 |
| EP | 0478362 | 6/1999 |
| WO | WO 92/18502 | 10/1992 |
| WO | WO 93/06108 | 4/1993 |
| WO | WO 95/04040 | 2/1995 |
| WO | WO 95/13069 | 5/1995 |
| WO | WO 96/02250 | 2/1996 |
| WO | WO 96/06081 | 2/1996 |
| WO | WO 97/19059 | 5/1997 |
| WO | WO 98/25604 | 6/1998 |
| WO | WO 98/25605 | 6/1998 |
| WO | WO 99/07672 | 2/1999 |
| WO | WO 00/35449 | 6/2000 |
| WO | WO 00/35451 | 6/2000 |
| WO | WO 00/35452 | 6/2000 |
| WO | WO 00/35453 | 6/2000 |
| WO | WO 00/35454 | 6/2000 |
| WO | WO 00/35876 | 6/2000 |
| WO | WO 00/35877 | 6/2000 |

OTHER PUBLICATIONS

Horuk and Ng, "Chemokine Receptor Antagonists", *Med. Res. Rev.*, vol. 20, pp. 155-168, 1999.

*Primary Examiner*—James O. Wilson
*Assistant Examiner*—Paul V. Ward
(74) *Attorney, Agent, or Firm*—Mary K. VanAtten

(57) ABSTRACT

The present application describes modulators of CCR3 of formula (I):

A—E—NR$^1$—G    (I)

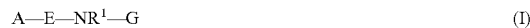

or pharmaceutically acceptable salt forms thereof, useful for the prevention of inflammatory diseases such as asthma and other allergic diseases.

27 Claims, No Drawings

BICYCLIC AND TRICYCLIC AMINES AS MODULATORS OF CHEMOKINE RECEPTOR ACTIVITY

CROSS-REFERENCE TO RELATED APPLICATIONS

This application is a Divisional of Ser. No. 10/842,949 filed on May 11, 2004 now U.S. Pat. No. 6,960,666 which is a Divisional of Ser. No. 10/427,814 filed May 1, 2003 now U.S. Pat. No. 6,784,200, which is a Divisional of Ser. No. 09/687,602 filed Oct. 13, 2000 now U.S. Pat. No. 6,586,446 and claims the priority benefits of U.S. Provisional Application No. 60/159,882 filed Oct. 15, 1999 which are expressly incorporated fully herein by reference.

FIELD OF THE INVENTION

This invention relates generally to modulators of chemokine receptor activity, pharmaceutical compositions containing the same, and methods of using the same as agents for treatment and prevention of inflammatory diseases such as asthma and allergic diseases, as well as autoimmune pathologies such as rheumatoid arthritis and atherosclerosis.

BACKGROUND OF THE INVENTION

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in Luster, New Eng. J. Med., 338, 436-445 (1998) and Rollins, Blood, 90, 909-928 (1997)). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1, -2, and -3) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seven-transmembrane-domain proteins (reviewed in Horuk, Trends Pharm. Sci., 15, 159-165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR-1 (or "CKR-1" or "CC-CKR-1") [MIP-1α, MCP-3, MCP-4, RANTES] (Ben-Barruch, et al., Cell, 72, 415-425 (1993), Luster, New Eng. J. Med., 338, 436-445 (1998)); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo et al., Proc. Natl. Acad. Sci. USA, 91, 2752-2756 (1994), Luster, New Eng. J. Med., 338, 436-445 (1998)); CCR-3 (or "CKR-3" or "CC-CKR-3") [eotaxin-1, eotaxin-2, RANTES, MCP-3, MCP-4] (Combadiere, et al., J. Biol. Chem., 270, 16491-16494 (1995), Luster, New Eng. J. Med., 338, 436-445 (1998)); CCR-4 (or "CKR-4" or "CC-CKR-4") [TARC, MIP-1α, RANTES, MCP-1] (Power et al., J. Biol. Chem., 270, 19495-19500 (1995), Luster, New Eng. J. Med., 338, 436-445 (1998)); CCR-5 (or "CKR-5" OR "CC-CKR-5") [MIP-1α, RANTES, MIP-1β] (Sanson, et al., Biochemistry, 35, 3362-3367 (1996)); CCR-6 (or "CKR-6" or "CC-CKR-6") [LARC] (Baba et al., J. Biol. Chem., 272, 14893-14898 (1997)); CCR-7 (or "CKR-7" or "CC-CKR-7") [ELC] (Yoshie et al., J. Leukoc. Biol. 62, 634-644 (1997)); CCR-8 (or "CKR-8" or "CC-CKR-8") [I-309, TARC, MIP-1β] (Napolitano et al., J. Immunol., 157, 2759-2763 (1996), Bernardini et al., Eur. J. Immunol., 28, 582-588 (1998)); and CCR-10 (or "CKR-10" or "CC-CKR-10") [MCP-1, MCP-3] (Bonini et al, DNA and Cell Biol., 16, 1249-1256 (1997)).

In addition to the mammalian chemokine receptors, mammalian cytomegaloviruses, herpesviruses and poxviruses have been shown to express, in infected cells, proteins with the binding properties of chemokine receptors (reviewed by Wells and Schwartz, Curr. Opin. Biotech., 8, 741-748 (1997)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis and atherosclerosis. For example, the chemokine receptor CCR-3 plays a pivotal role in attracting eosinophils to sites of allergic inflammation and in subsequently activating these cells. The chemokine ligands for CCR-3 induce a rapid increase in intracellular calcium concentration, increased expression of cellular adhesion molecules, cellular degranulation, and the promotion of eosinophil migration. Accordingly, agents which modulate chemokine receptors would be useful in such disorders and diseases. In addition, agents which modulate chemokine receptors would also be useful in infectious diseases such as by blocking infection of CCR3 expressing cells by HIV or in preventing the manipulation of immune cellular responses by viruses such as cytomegaloviruses.

A substantial body of art has accumulated over the past several decades with respect to substituted piperidines and pyrrolidines. These compounds have implicated in the treatment of a variety of disorders.

WO 98/25604 describes spiro-substituted azacycles which are useful as modulators of chemokine receptors:

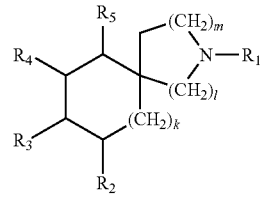

wherein $R_1$ is $C_{1-6}$ alkyl, optionally substituted with functional groups such as —$NR^6CONHR^7$, wherein $R^6$ and $R^7$ may be phenyl further substituted with hydroxy, alkyl, cyano, halo and haloalkyl. Such spiro compounds are not considered part of the present invention.

WO 95/13069 is directed to certain piperidine, pyrrolidine, and hexahydro-1H-azepine compounds of general formula:

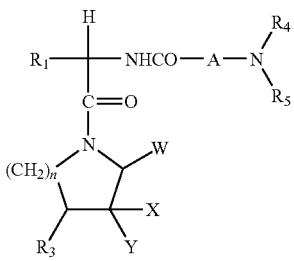

wherein A may be substituted alkyl or Z-substituted alkyl, with Z=$NR_{6a}$ or O. Compounds of this type are claimed to promote the release of growth hormone in humans and animals.

WO 93/06108 discloses pyrrolobenzoxazine derivatives as 5-hydroxytryptamine (5-HT) agonists and antagonists:

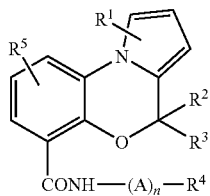

wherein A is lower alkylene and $R^4$ may be phenyl optionally substituted with halogen.

U.S. Pat. No. 5,668,151 discloses Neuropeptide Y (NPY) antagonists comprising 1,4-dihydropyridines with a piperidinyl or tetrahydropyridinyl-containing moiety attached to the 3-position of the 4-phenyl ring:

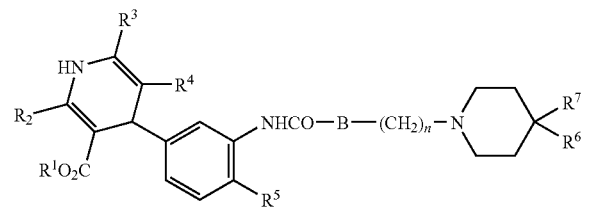

wherein B may be NH, $NR^1$, O, or a bond, and $R^7$ may be substituted phenyl, benzyl, phenethyl and the like.

These reference compounds are readily distinguished structurally by either the nature of the urea functionality, the attachment chain, or the possible substitution of the present invention. The prior art does not disclose nor suggest the unique combination of structural fragments which embody these novel piperidines and pyrrolidines as having activity toward the chemokine receptors.

SUMMARY OF THE INVENTION

Accordingly, one object of the present invention is to provide novel agonists or antagonists of CCR-3, or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating inflammatory and allergic disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of formula (I):

$$A—E—NR^1—G \qquad (I)$$

or stereoisomers or pharmaceutically acceptable salts thereof, wherein A, E, G and $R^1$ are defined below, are effective modulators of chemokine activity.

DETAILED DESCRIPTION OF THE EMBODIMENTS

[1] Thus, in a first embodiment, the present invention provides novel compounds of formula (I):

$$A—E—NR^1—G \qquad (I)$$

or stereoisomers or pharmaceutically acceptable salts thereof, wherein:

A is selected from

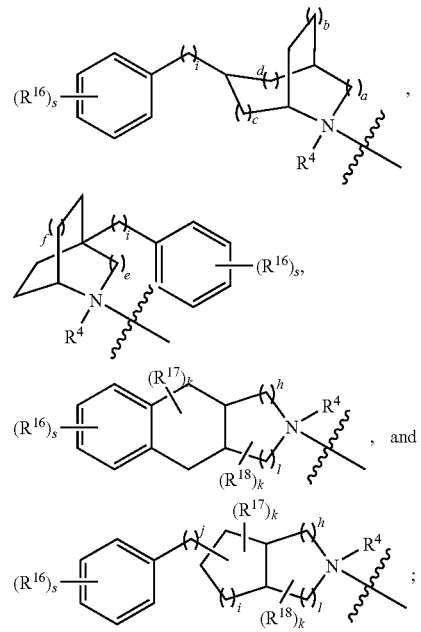

E is selected from —$(CR^7R^8)$—$(CR^9R^{10})_v$—$(CR^{11}R^{12})$,

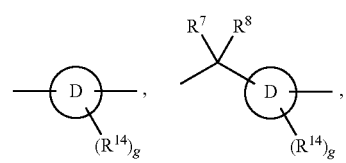

-continued

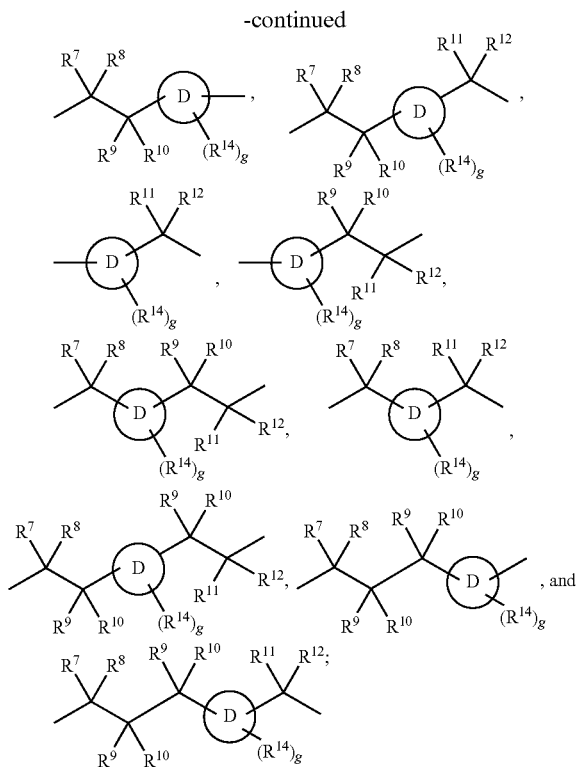

ring D is selected from a $C_{3-6}$ carbocyclic residue and a 5 or 6 membered heterocycle;

G is selected from —C(O)R³, —C(O)NR²R³, —C(O)OR³, —SO₂NR²R³, —SO₂R³, —C(=S)NR²R³, C(=NR^{1a})NR²R³, C(=CHCN)NR²R³, C(=CHNO₂)NR²R³, C(=C(CN)₂)NR²R³,

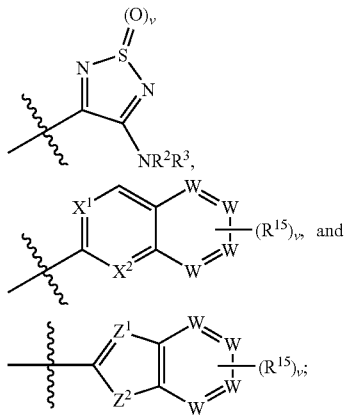

W, at each occurrence, is independently selected from C or N, provided at least two of W are C;

X¹ and X² are independently selected from C and N;

Z¹ is selected from C and N;

Z² is selected from NR^{1'}, O, S and C;

R¹, R^{1'} and R² are independently selected from H, $C_{1-8}$ alkyl, $C_{3-8}$ alkenyl, $C_{3-8}$ alkynyl, $(CH_2)_rC_{3-6}$ cycloalkyl, and a $(CH_2)_r$—$C_{3-10}$ carbocyclic residue substituted with 0-5 R^a;

R^{1a} is independently selected from H, $C_{1-6}$ alkyl, —OH, —CN, —NO₂, $(CH_2)_rC_{3-6}$ cycloalkyl, and a $(CH_2)_r$—$C_{3-10}$ carbocyclic residue substituted with 0-5 R^a;

R^a, at each occurrence, is selected from $C_{1-4}$ alkyl, $C_{2-8}$ alkenyl, $C_{2-8}$ alkynyl, (CHR')_r$C_{3-6}$ cycloalkyl, Cl, Br, I, F, $(CF_2)_rCF_3$, NO₂, CN, (CHR')_rNR^bR^b, (CHR')_rOH, (CHR')_r OR^c, (CHR')_rSH, (CHR')_rSR^c, (CHR')_rC(O)R^b, (CHR')_rC(O)NR^bR^b, (CHR')_rNR^bC(O)R^b, (CHR')_rC(O)OR^b, (CHR')_rOC(O)R^c, (CHR')_rCH(=NR^b)NR^bR^b, (CHR')_rNHC(=NR^b)NR^bR^b, (CHR')_rS(O)_pR^c, (CHR')_rS(O)_2NR^bR^b, (CHR')_rNR^bS(O)_2R^c, and (CHR')_rphenyl;

R^b, at each occurrence, is selected from H, $C_{1-6}$ alkyl, $C_{3-6}$ cycloalkyl, and phenyl;

R^c, at each occurrence, is selected from $C_{1-6}$ alkyl, $C_{3-6}$ cycloalkyl, and phenyl;

alternatively, R¹ and R² join to form a 5, 6, or 7-membered ring substituted with 0-3 R^a;

R³ is selected from a (CR³'R³'')_r—$C_{3-10}$ carbocyclic residue substituted with 0-5 R^{15} and a (CR³'R³'')_r-5-10 membered heterocyclic system containing 1-4 heteroatoms selected from N, O, and S, substituted with 0-3 R^{15};

R³' and R³'', at each occurrence, are selected from H, $C_{1-6}$ alkyl, $(CH_2)_rC_{3-6}$ cycloalkyl, and phenyl;

R⁴ is absent, taken with the nitrogen to which it is attached to form an N-oxide, or selected from $C_{1-8}$ alkyl, $C_{3-8}$ alkenyl, $C_{3-8}$ alkynyl, $(CH_2)_rC_{3-6}$ cycloalkyl, $(CH_2)_qC(O)R^{4b}$, $(CH_2)_qC(O)NR^{4a}R^{4a'}$, $(CH_2)_qC(O)OR^{4a}$, and a $(CH_2)_r$—$C_{3-10}$ carbocyclic residue substituted with 0-3 R^{4c};

R^{4a} and R^{4a'}, at each occurrence, are selected from H, $C_{1-6}$ alkyl, $(CH_2)_rC_{3-6}$ cycloalkyl, and phenyl;

R^{4b}, at each occurrence, is selected from $C_{1-6}$ alkyl, $C_{2-8}$ alkenyl, $(CH_2)_rC_{3-6}$ cycloalkyl, $C_{2-8}$ alkynyl, and phenyl;

R^{4c}, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, NO₂, $(CF_2)_rCF_3$, $(CH_2)_rOC_{1-5}$ alkyl, $(CH_2)_rOH$, $(CH_2)_rSC_{1-5}$ alkyl, $(CH_2)_rNR^{4a}R^{4a'}$, and $(CH_2)_r$phenyl;

R⁷, is selected from H, $C_{1-6}$ alkyl, $C_{2-8}$ alkenyl, $C_{2-8}$ alkynyl, (CHR')_qOH, (CHR')_qSH, (CHR')_qOR^{7d}, (CHR')_qSR^{7d}, $(CH_2CHR')_qNR^{7a}R^{7a'}$, (CHR')_rC(O)OH, (CHR')_rC(O)R^{7b}, (CHR')_rC(O)NR^{7a}R^{7a'}, (CHR')_qNR^{7a}C(O)R^{7b}, (CHR')_qNR^{7a}C(O)H, (CHR')_rC(O)OR^{7a}, (CHR')_qOC(O)R^{7b}, (CHR')_qS(O)_pR^{7b}, (CHR')_qS(O)_2NR^{7a}R^{7a'}, (CHR')_qNR^{7a}S(O)_2R^{7b}, (CHR')_qNHC(O)NR^{7a}R^{7a'}, (CHR')_qNHC(O)OR^{7a}, (CHR')_qOC(O)NR^{7a}R^{7a'}, $C_{1-6}$ haloalkyl, a (CHR')_r—$C_{3-10}$ carbocyclic residue substituted with 0-3 R^{7c}, and a (CHR')_r-5-10 membered heterocyclic system containing 1-4 heteroatoms selected from N, O, and S, substituted with 0-2 R^{7c};

R^{7a} and R^{7a'}, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 R^{7e}, and a $(CH_2)_r$-5-10 membered heterocyclic system containing 1-4 heteroatoms selected from N, O, and S, substituted with 0-3 R^{7e};

R^{7b}, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0-2 R^{7e}, and a $(CH_2)_r$-5-6 membered heterocyclic system containing 1-4 heteroatoms selected from N, O, and S, substituted with 0-3 R^{7e};

R^{7c}, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, NO₂, CN, $(CH_2)_rNR^{7f}R^{7f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{7b}$, $(CH_2)_rC(O)NR^{7f}R^{7f}$, $(CH_2)_rNR^{7f}C(O)R^{7b}$, $(CH_2)_r C(O)OC_{1-4}$ alkyl, $(CH_2)_rOC(O)R^{7b}$, $(CH_2)_rC(=NR^{7f})NR^{7f}R^{7f}$, $(CH_2)_rS(O)_pR^{7b}$, $(CH_2)_rNHC(=NR^{7f})NR^{7f}R^{7f}$, $(CH_2)_rS(O)_2NR^{7f}R^{7f}$, $(CH_2)_rNR^{7f}S(O)_2R^{7b}$, and $(CH_2)_r$phenyl substituted with 0-3 R^{7e};

R^{7d}, at each occurrence, is selected from methyl, CF₃, $C_{2-6}$ alkyl substituted with 0-3 R^{7e}, $C_{3-6}$ alkenyl, $C_{3-6}$ alkynyl, and a $C_{3-10}$ carbocyclic residue substituted with 0-3 R^{7e};

$R^{7e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{7f}$R$^{7f}$, and (CH$_2$)$_r$phenyl;

$R^{7f}$, at each occurrence, is selected from H, $C_{1-6}$ alkyl, and $C_{3-6}$ cycloalkyl;

$R^8$ is selected from H, $C_{1-6}$ alkyl, $C_{3-6}$ cycloalkyl, and (CH$_2$)$_r$phenyl substituted with 0-3 $R^{8a}$;

$R^{8a}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{7f}$R$^{7f}$, and (CH$_2$)$_r$phenyl;

alternatively, $R^7$ and $R^8$ join to form $C_{3-7}$ cycloalkyl, =NR$^{8b}$, or =O;

$R^{8b}$ is selected from H, $C_{1-6}$ alkyl, $C_{3-6}$ cycloalkyl, OH, CN, and (CH$_2$)$_r$-phenyl;

$R^9$, is selected from H, $C_{1-6}$ alkyl, $C_{2-8}$ alkenyl, $C_{2-8}$ alkynyl, F, Cl, Br, I, NO$_2$, CN, (CHR')$_r$OH, (CHR')$_r$SH, (CHR')$_r$OR$^{9d}$, (CHR')$_r$SR$^{9d}$, (CHR')$_r$NR$^{9a}$R$^{9a'}$, (CHR')$_r$C(O)OH, (CHR')$_r$C(O)R$^{9b}$, (CHR')$_r$C(O)NR$^{9a}$R$^{9a'}$, (CHR')$_r$NR$^{9a}$C(O)R$^{9b}$, (CHR')$_r$NR$^{9a}$C(O)H, (CHR')$_r$NR$^{9a}$C(O)NR$^{9a}$R$^{9a}$, (CHR')$_r$C(O)OR$^{9a}$, (CHR')$_r$OC(O)R$^{9b}$, (CHR')$_r$S(O)$_p$R$^{9b}$, (CHR')$_r$S(O)$_2$NR$^{9a}$R$^{9a'}$, (CHR')$_r$NR$^{9a}$S(O)$_2$R$^{9b}$, $C_{1-6}$ haloalkyl, a (CHR')$_r$—$C_{3-10}$ carbocyclic residue substituted with 0-5 $R^{9c}$, and a (CHR')$_r$-5-10 membered heterocyclic system containing 1-4 heteroatoms selected from N, O, and S, substituted with 0-3 $R^{9c}$;

$R^{9a}$ and $R^{9a'}$, at each occurrence, are selected from H, $C_{1-6}$ alkyl, $C_{3-8}$ alkenyl, $C_{3-8}$ alkynyl, a (CH$_2$)$_r$—$C_{3-10}$ carbocyclic residue substituted with 0-5 $R^{9e}$, and a (CH$_2$)$_r$-5-10 membered heterocyclic system containing 1-4 heteroatoms selected from N, O, and S, substituted with 0-3 $R^{9e}$;

$R^{9b}$, at each occurrence, is selected from $C_{1-6}$ alkyl, $C_{2-8}$ alkenyl, $C_{2-8}$ alkynyl, a (CH$_2$)$_r$—$C_{3-6}$ carbocyclic residue substituted with 0-2 $R^{9e}$, and a (CH$_2$)$_r$-5-6 membered heterocyclic system containing 1-4 heteroatoms selected from N, O, and S, substituted with 0-3 $R^{9e}$;

$R^{9c}$, at each occurrence, is selected from $C_{1-6}$ alkyl, $C_{2-8}$ alkenyl, $C_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{9f}$R$^{9f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{9b}$, (CH$_2$)$_r$C(O)NR$^{9f}$R$^{9f}$, (CH$_2$)$_r$NR$^{9f}$C(O)R$^{9b}$, (CH$_2$)$_r$C(O)OC$_{1-4}$ alkyl, (CH$_2$)$_r$OC(O)R$^{9b}$, (CH$_2$)$_r$C(=NR$^{9f}$)NR$^{9f}$R$^{9f}$, (CH$_2$)$_r$S(O)$_p$R$^{9b}$, (CH$_2$)$_r$NHC(=NR$^{9f}$)NR$^{9f}$R$^{9f}$, (CH$_2$)$_r$S(O)$_2$NR$^{9f}$R$^{9f}$, (CH$_2$)$_r$NR$^{9f}$S(O)$_2$R$^{9b}$, and (CH$_2$)$_r$phenyl substituted with 0-3 $R^{9e}$;

$R^{9d}$, at each occurrence, is selected from methyl, CF$_3$, $C_{2-6}$ alkyl substituted with 0-3 $R^{9e}$, $C_{3-6}$ alkenyl, $C_{3-6}$ alkynyl, a $C_{3-10}$ carbocyclic residue substituted with 0-3 $R^{9c}$, and a 5-6 membered heterocyclic system containing 1-4 heteroatoms selected from the group consisting of N, O, and S substituted with 0-3 $R^{9c}$;

$R^{9e}$, at each occurrence, is selected from $C_{1-6}$ alkyl, $C_{2-8}$ alkenyl, $C_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{9f}$R$^{9f}$, and (CH$_2$)$_r$phenyl;

$R^{9f}$ at each occurrence, is selected from H, $C_{1-6}$ alkyl, and $C_{3-6}$ cycloalkyl;

$R^{10}$, is selected from H, $C_{1-6}$ alkyl, $C_{2-8}$ alkenyl, $C_{2-8}$ alkynyl, F, Cl, Br, I, NO$_2$, CN, (CH$_2$)$_r$OH, (CH$_2$)$_r$OR$^{10d}$, (CH$_2$)$_r$SR$^{10d}$, (CH$_2$)$_r$NR$^{10a}$R$^{10a'}$, (CH$_2$)$_r$C(O)OH, (CH$_2$)$_r$C(O)R$^{10b}$, (CH$_2$)$_r$C(O)NR$^{10a}$R$^{10a'}$, (CH$_2$)$_r$NR$^{10a}$C(O)R$^{10a}$, (CH$_2$)$_r$NR$^{10a}$C(O)H, (CH$_2$)$_r$C(O)OR$^{10a}$, (CH$_2$)$_r$OC(O)R$^{10b}$, (CH$_2$)$_r$S(O)$_p$R$^{10b}$, (CH$_2$)$_r$S(O)$_2$NR$^{10a}$R$^{10a'}$, (CH$_2$)$_r$NR$^{10a}$S(O)$_2$R$^{10b}$, $C_{1-6}$ haloalkyl, a (CH$_2$)$_r$—$C_{3-10}$ carbocyclic residue substituted with 0-5 $R^{10c}$, and a (CH$_2$)$_r$-5-10 membered heterocyclic system containing 1-4 heteroatoms selected from N, O, and S, substituted with 0-3 $R^{10c}$;

$R^{10a}$ and $R^{10a'}$, at each occurrence, are selected from H, $C_{1-6}$ alkyl, $C_{3-8}$ alkenyl, $C_{3-8}$ alkynyl, a (CH$_2$)$_r$—$C_{3-10}$ carbocyclic residue substituted with 0-5 $R^{10e}$, and a (CH$_2$)$_r$-5-10 membered heterocyclic system containing 1-4 heteroatoms selected from N, O, and S, substituted with 0-3 $R^{10e}$;

$R^{10b}$, at each occurrence, is selected from $C_{1-6}$ alkyl, $C_{2-8}$ alkenyl, $C_{2-8}$ alkynyl, a (CH$_2$)$_r$—$C_{3-6}$ carbocyclic residue substituted with 0-2 $R^{10e}$, and a (CH$_2$)$_r$-5-6 membered heterocyclic system containing 1-4 heteroatoms selected from N, O, and S, substituted with 0-3 $R^{10e}$;

$R^{10c}$, at each occurrence, is selected from $C_{1-6}$ alkyl, $C_{2-8}$ alkenyl, $C_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{10f}$R$^{10f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{10b}$, (CH$_2$)$_r$C(O)NR$^{10f}$R$^{10f}$, (CH$_2$)$_r$NR$^{10f}$C(O)R$^{10a}$, (CH$_2$)$_r$C(O)OC$_{1-4}$ alkyl, (CH$_2$)$_r$OC(O)R$^{10b}$, (CH$_2$)$_r$C(=NR$^{10f}$)NR$^{10f}$R$^{10f}$, (CH$_2$)$_r$S(O)$_p$R$^{10b}$, (CH$_2$)$_r$NHC(=NR$^{10f}$)NR$^{10f}$R$^{10f}$, (CH$_2$)$_r$S(O)$_2$NR$^{10f}$R$^{10f}$, (CH$_2$)$_r$NR$^{10f}$S(O)$_2$R$^{10b}$, and (CH$_2$)$_r$phenyl substituted with 0-3 $R^{10e}$;

$R^{10d}$, at each occurrence, is selected from methyl, CF$_3$, $C_{2-6}$ alkyl substituted with 0-3 $R^{10e}$, $C_{3-6}$ alkenyl, $C_{3-6}$ alkynyl, a $C_{3-10}$ carbocyclic residue substituted with 0-3 $R^{10c}$, and a 5-6 membered heterocyclic system containing 1-4 heteroatoms selected from the group consisting of N, O, and S substituted with 0-3 $R^{10c}$;

$R^{10e}$, at each occurrence, is selected from $C_{1-6}$ alkyl, $C_{2-8}$ alkenyl, $C_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{10f}$R$^{10f}$, and (CH$_2$)$_r$phenyl;

$R^{10f}$, at each occurrence, is selected from H, $C_{1-6}$ alkyl, and $C_{3-6}$ cycloalkyl;

alternatively, $R^9$ and $R^{10}$ join to form $C_{3-7}$ cycloalkyl, 5-6-membered cyclic ketal, or =O;

with the proviso that when $R^{10}$ is —OH, $R^9$ is not halogen, cyano, or bonded to the carbon to which it is attached through a heteroatom;

$R^{11}$, is selected from H, $C_{1-6}$ alkyl, $C_{2-8}$ alkenyl, $C_{2-8}$ alkynyl, (CH$_2$)$_q$OH, (CH$_2$)$_q$SH, (CH$_2$)$_q$OR$^{11d}$, (CH$_2$)$_q$SR$^{11d}$, (CH$_2$)$_q$NR$^{11a}$R$^{11a'}$, (CH$_2$)$_r$C(O)OH, (CH$_2$)$_r$C(O)R$^{11b}$, (CH$_2$)$_r$C(O)NR$^{11a}$R$^{11a'}$, (CH$_2$)$_q$NR$^{11a}$C(O)R$^{11b}$, (CH$_2$)$_q$NR$^{11a}$C(O)NR$^{11a}$R$^{11a}$, (CH$_2$)$_r$C(O)OR$^{11a}$, (CH$_2$)$_q$OC(O)R$^{11b}$, (CH$_2$)$_q$S(O)$_p$R$^{11b}$, (CH$_2$)$_q$S(O)$_2$NR$^{11a}$R$^{11a'}$, (CH$_2$)$_q$NR$^{11a}$S(O)$_2$R$^{11b}$, $C_{1-6}$ haloalkyl, a (CH$_2$)$_r$—$C_{3-10}$ carbocyclic residue substituted with 0-5 $R^{11c}$, and a (CH$_2$)$_r$-5-10 membered heterocyclic system containing 1-4 heteroatoms selected from N, O, and S, substituted with 0-3 $R^{11c}$;

$R^{11a}$ and $R^{11a'}$, at each occurrence, are selected from H, $C_{1-6}$ alkyl, $C_{3-8}$ alkenyl, $C_{3-8}$ alkynyl, a (CH$_2$)$_r$—$C_{3-10}$ carbocyclic residue substituted with 0-5 $R^{11e}$, and a (CH$_2$)$_r$-5-10 membered heterocyclic system containing 1-4 heteroatoms selected from N, O, and S, substituted with 0-3 $R^{11e}$;

$R^{11b}$, at each occurrence, is selected from $C_{1-6}$ alkyl, $C_{2-8}$ alkenyl, $C_{2-8}$ alkynyl, a (CH$_2$)$_r$—$C_{3-6}$ carbocyclic residue substituted with 0-2 $R^{11e}$, and a (CH$_2$)$_r$-5-6 membered heterocyclic system containing 1-4 heteroatoms selected from N, O, and S, substituted with 0-3 $R^{11e}$;

$R^{11c}$, at each occurrence, is selected from $C_{1-6}$ alkyl, $C_{2-8}$ alkenyl, $C_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{11f}$R$^{11f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{11b}$, (CH$_2$)$_r$C(O)NR$^{11f}$R$^{11f}$, (CH$_2$)$_r$NR$^{11f}$C(O)R$^{11a}$, (CH$_2$)$_r$C(O)OC$_{1-4}$ alkyl, (CH$_2$)$_r$OC(O)R$^{11b}$, $(CH_2)_rC(=NR^{11f})NR^{11f}R^{11f}$, $(CH_2)_rNHC(=NR^{11f})NR^{11f}R^{11f}$, $(CH_2)_rS(O)_pR^{11b}$, $(CH_2)_rS(O)_2NR^{11f}R^{11f}$, $(CH_2)_rNR^{11f}S(O)_2R^{11b}$, and $(CH_2)_r$phenyl substituted with 0-3 $R^{11e}$;

$R^{11d}$, at each occurrence, is selected from methyl, $CF_3$, $C_{2-6}$ alkyl substituted with 0-3 $R^{11e}$, $C_{3-6}$ alkenyl, $C_{3-6}$ alkynyl, and a $C_{3-10}$ carbocyclic residue substituted with 0-3 $R^{11c}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{11f}R^{11f}$, and $(CH_2)_r$phenyl;

$R^{11f}$, at each occurrence, is selected from H, $C_{1-6}$ alkyl, and $C_{3-6}$ cycloalkyl;

$R^{12}$ is selected from H, $C_{1-6}$ alkyl, $(CH_2)_qOH$, $(CH_2)_rC_{3-6}$ cycloalkyl, and $(CH_2)_r$phenyl substituted with 0-3 $R^{12a}$;

$R^{12a}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{9f}R^{9f}$, and $(CH_2)_r$phenyl;

alternatively, $R^{11}$ and $R^{12}$ join to form $C_{3-7}$ cycloalkyl;

$R^{14}$ is selected from $C_{1-4}$ alkyl, $C_{2-8}$ alkenyl, $C_{2-8}$ alkynyl, $(CH_2)_rC_{3-6}$ cycloalkyl, $C(O)NR^{14a}R^{14a'}$, $C(O)R^{14b}$, $C(O)OC_{1-4}$ alkyl, $(CH_2)_rS(O)_pR^{14b}$, $(CH_2)_r$phenyl substituted with 0-3 $R^{14c}$, $OR^{14a}$, $NR^{14a}R^{14a'}$, =O, and $NR^{14a}C(O)R^{14a'}$;

$R^{14a}$ and $R^{14a'}$, at each occurrence, are selected from H, $C_{1-6}$ alkyl, $(CH_2)_rC_{3-6}$ cycloalkyl, and $(CH_2)_r$phenyl substituted with 0-3 $R^{14c}$, and a $(CH_2)_r$-5-10 membered heterocyclic system containing 1-4 heteroatoms selected from N, O, and S, substituted with 0-2 $R^{14c}$;

$R^{14b}$, at each occurrence, is selected from $C_{1-6}$ alkyl, $(CH_2)_r$ $C_{3-6}$ cycloalkyl, and $(CH_2)_r$phenyl substituted with 0-3 $R^{14c}$, and a $(CH_2)_r$-5-10 membered heterocyclic system containing 1-4 heteroatoms selected from N, O, and S, substituted with 0-2 $R^{14c}$; and $R^{14c}$, at each occurrence, is selected from $C_{1-6}$ alkyl, $(CH_2)_r$ $C_{3-6}$ cycloalkyl, Cl, F, Br, I, CN, $NO_2$, $(CF_2)_rCF_3$, $(CH_2)_r$ $OC_{1-5}$ alkyl, OH, $(CH_2)_w$phenyl;

$R^{15}$, at each occurrence, is selected from $C_{1-8}$ alkyl, $(CH_2)_r$ $C_{3-6}$ cycloalkyl, Cl, Br, I, F, $NO_2$, CN, $(CHR')_rNR^{15a}R^{15a'}$, $(CHR')_rOH$, $(CHR')_rO(CHR')_rR^{15d}$, $(CHR')_rSH$, $(CHR')_r$ $C(O)H$, $(CHR')_rS(CHR')_rR^{15d}$, $(CHR')_rC(O)OH$, $(CHR')_r$ $C(O)(CHR')_rR^{15b}$, $(CHR')_rC(O)NR^{15a}R^{15a'}$, $(CHR')_r$ $NR^{15f}C(O)(CHR')_rR^{15b}$, $(CHR')_rNR^{15f}C(O)NR^{15a}R^{15a'}$, $(CHR')_rC(O)O(CHR')_rR^{15d}$, $(CHR')_rOC(O)(CHR')_rR^{15b}$, $(CHR')_rC(=NR^{15f})NR^{15a}R^{15a'}$, $(CHR')_rNHC(=NR^{15f})NR^{15a}R^{15a'}$, $(CHR')_rS(O)_p(CHR')_rR^{15b}$, $(CHR')_rS(O)_2$ $NR^{15a}R^{15a'}$, $(CHR')_rNR^{15f}S(O)_2(CHR')_rR^{15b}$, $C_{1-6}$ haloalkyl, $C_{2-8}$ alkenyl substituted with 0-3 R', $C_{2-8}$ alkynyl substituted with 0-3 R', $(CHR')_r$phenyl substituted with 0-3 $R^{15e}$, and a $(CH_2)_r$-5-10 membered heterocyclic system containing 1-4 heteroatoms selected from N, O, and S, substituted with 0-2 $R^{15e}$;

R', at each occurrence, is selected from H, $C_{1-6}$ alkyl, $C_{2-8}$ alkenyl, $C_{2-8}$ alkynyl, $(CH_2)_rC_{3-6}$ cycloalkyl, and $(CH_2)_r$ phenyl substituted with $R^{15e}$;

$R^{15a}$ and $R^{15a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{15e}$, and a $(CH_2)_r$-5-10 membered heterocyclic system containing 1-4 heteroatoms selected from N, O, and S, substituted with 0-2 $R^{15e}$;

$R^{15b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0-3 $R^{15e}$, and $(CH_2)_r$-5-6 membered heterocyclic system containing 1-4 heteroatoms selected from N, O, and S, substituted with 0-2 $R^{15e}$;

$R^{15d}$, at each occurrence, is selected from $C_{3-8}$ alkenyl, $C_{3-8}$ alkynyl, methyl, $CF_3$, $C_{2-6}$ alkyl substituted with 0-3 $R^{15e}$, a $(CH_2)_r$—$C_{3-10}$ carbocyclic residue substituted with 0-3 $R^{15e}$, and a $(CH_2)_r$-5-6 membered heterocyclic system containing 1-4 heteroatoms selected from N, O, and S, substituted with 0-3 $R^{15e}$;

$R^{15e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{15f}R^{15f}$, and $(CH_2)_r$phenyl;

$R^{15f}$, at each occurrence, is selected from H, $C_{1-6}$ alkyl, $C_{3-6}$ cycloalkyl, and phenyl;

$R^{16}$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{16a}R^{16a'}$, $(CHR')_rOH$, $(CHR')_rO$ $(CHR')_rR^{16d}$, $(CHR')_rSH$, $(CHR')_rC(O)H$, $(CHR')_rS$ $(CHR')_rR^{16d}$, $(CHR')_rC(O)OH$, $(CHR')_rC(O)(CHR')_r$ $R^{16b}$, $(CHR')_rC(O)NR^{16a}R^{16a'}$, $(CHR')_rNR^{16f}C(O)$ $(CHR')_rR^{16b}$, $(CHR')_rC(O)O(CHR')_rR^{16d}$, $(CHR')_rOC(O)$ $(CHR')_r R^{16b}$, $(CHR')_rC(=NR^{16f})NR^{16a}R^{16a'}$, $(CHR')_r$ $NHC(=NR^{16f})NR^{16a}R^{16a'}$, $(CHR')_rS(O)_p(CHR')_rR^{16b}$, $(CHR')_rS(O)_2NR^{16a}R^{16a'}$, $(CHR')_rNR^{16f}S(O)_2(CHR')_r$ $R^{16b}$, $C_{1-6}$ haloalkyl, $C_{2-8}$ alkenyl substituted with 0-3 R', $C_{2-8}$ alkynyl substituted with 0-3 R', and $(CHR')_r$phenyl substituted with 0-3 $R^{16e}$;

$R^{16a}$ and $R^{16a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{16e}$, and a $(CH_2)_r$-5-10 membered heterocyclic system containing 1-4 heteroatoms selected from N, O, and S, substituted with 0-2 $R^{16e}$;

$R^{16b}$, at each occurrence, is selected from $C_{1-6}$ alkyl, $C_{2-8}$ alkenyl, $C_{2-8}$ alkynyl, a $(CH_2)_rC_{3-6}$ carbocyclic residue substituted with 0-3 $R^{16e}$, and a $(CH_2)_r$-5-6 membered heterocyclic system containing 1-4 heteroatoms selected from N, O, and S, substituted with 0-2 $R^{16e}$;

$R^{16d}$, at each occurrence, is selected from $C_{3-8}$ alkenyl, $C_{3-8}$ alkynyl, methyl, $CF_3$, $C_{2-6}$ alkyl substituted with 0-3 $R^{16e}$, a $(CH_2)_r$—$C_{3-10}$ carbocyclic residue substituted with 0-3 $R^{16e}$, and a $(CH_2)_r$-5-6 membered heterocyclic system containing 1-4 heteroatoms selected from N, O, and S, substituted with 0-3 $R^{16e}$;

$R^{16e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{16f}R^{16f}$, and $(CH_2)_r$phenyl;

$R^{16f}$, at each occurrence, is selected from H, $C_{1-5}$ alkyl, and $C_{3-6}$ cycloalkyl, and phenyl;

$R^{17}$, is selected from H, $C_{1-6}$ alkyl, $C_{2-8}$ alkenyl, $C_{2-8}$ alkynyl, $(CHR')_rOH$, $(CHR')_rSH$, $(CHR')_rOR^{17d}$, $(CHR')_rSR^{17d}$, $(CHR')_rNR^{17a}R^{17a'}$, $(CHR')_rC(O)OH$, $(CHR')_rC(O)R^{17b}$, $(CHR')_rC(O)NR^{17a}R^{17a'}$, $(CHR')_rNR^{17a}C(O)R^{17b}$, $(CHR')_rNR^{17a}C(O)H$, $(CHR')_rC(O)OR^{17d}$, $(CHR')_rOC$ $(O)R^{17b}$, $(CHR')_rS(O)_pR^{17b}$, $(CHR')_rS(O)_2NR^{17a}R^{17a'}$, $(CHR')_rNR^{17a}S(O)_2R^{17b}$, $C_{1-6}$ haloalkyl, a $(CHR')_r$—$C_{3-10}$ carbocyclic residue substituted with 0-3 $R^{17c}$, and a $(CHR')_r$-5-10 membered heterocyclic system containing 1-4 heteroatoms selected from N, O, and S, substituted with 0-2 $R^{17c}$;

$R^{17a}$ and $R^{17a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{17e}$, and a $(CH_2)_r$-5-10 membered heterocyclic system containing 1-4 heteroatoms selected from N, O, and S, substituted with 0-3 $R^{17e}$;

$R^{17b}$, at each occurrence, is selected from $C_{1-6}$ alkyl, $C_{2-8}$ alkenyl, $C_{2-8}$ alkynyl, a $(CH_2)_rC_{3-6}$ carbocyclic residue substituted with 0-2 $R^{17e}$, and a $(CH_2)_r$-5-6 membered heterocyclic system containing 1-4 heteroatoms selected from N, O, and S, substituted with 0-3 $R^{17e}$;

$R^{17c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{17f}R^{17f}$, $(CH_2)_rOH$, $(CH_2)_r$ $OC_{1-4}$ alkyl, $(CH_2)_rSC_{1-4}$ alkyl, $(CH_2)_rC(O)OH$, $(CH_2)_rC(O)R^{17b}$, $(CH_2)_rC(O)NR^{17f}R^{17f}$, $(CH_2)_rNR^{17f}C(O)R^{17a}$, $(CH_2)_rC(O)OC_{1-4}$ alkyl, $(CH_2)_rOC(O)R^{17b}$, $(CH_2)_rC(=NR^{17f})NR^{17f}R^{17f}$, $(CH_2)_rS(O)_pR^{17b}$, $(CH_2)_r$ $NHC(=NR^{17f})NR^{17f}R^{17f}$, $(CH_2)_rS(O)_2NR^{17f}R^{17f}$, $(CH_2)_r$ $NR^{17f}S(O)_2R^{17b}$, and $(CH_2)_r$phenyl substituted with 0-3 $R^{17e}$;

$R^{17d}$, at each occurrence, is selected from methyl, $CF_3$, $C_{1-6}$ alkyl substituted with 0-3 $R^{17e}$, $C_{3-6}$ alkenyl, $C_{3-6}$ alkynyl, and a $C_{3-10}$ carbocyclic residue substituted with 0-3 $R^{17c}$;

$R^{17e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{17f}R^{17f}$, and $(CH_2)_r$phenyl;

$R^{17f}$, at each occurrence, is selected from H, $C_{1-6}$ alkyl, and $C_{3-6}$ cycloalkyl;

$R^{18}$, is selected from H, $C_{1-6}$ alkyl, $C_{2-8}$ alkenyl, $C_{2-8}$ alkynyl, $(CHR')_qOH$, $(CHR')_qSH$, $(CHR')_qOR^{18d}$, $(CHR')_qSR^{18d}$, $(CHR')_qNR^{18a}R^{18a'}$, $(CHR')_rC(O)OH$, $(CHR')_qC(O)R^{18b}$, $(CHR')_rC(O)NR^{18a}R^{18a'}$, $(CHR')_qNR^{18a}C(O)R^{18b}$, $(CHR')_qNR^{18a}C(O)H$, $(CHR')_rC(O)OR^{18a}$, $(CHR')_qOC(O)R^{18b}$, $(CHR')_qS(O)_pR^{18b}$, $(CHR')_qS(O)_2NR^{18a}R^{18a'}$, $(CHR')_qNR^{18a}S(O)_2R^{18b}$, $C_{1-6}$ haloalkyl, a $(CHR')_r$ $—C_{3-10}$ carbocyclic residue substituted with 0-3 $R^{18c}$, and a $(CHR')_r$-5-10 membered heterocyclic system containing 1-4 heteroatoms selected from N, O, and S, substituted with 0-2 $R^{18c}$;

$R^{18a}$ and $R^{18a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{18e}$, and a $(CH_2)_r$-5-10 membered heterocyclic system containing 1-4 heteroatoms selected from N, O, and S, substituted with 0-3 $R^{18e}$;

$R^{18b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0-2 $R^{18e}$, and a $(CH_2)_r$-5-6 membered heterocyclic system containing 1-4 heteroatoms selected from N, O, and S, substituted with 0-3 $R^{18e}$;

$R^{18c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{18f}R^{18f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{18b}$, $(CH_2)_rC(O)NR^{18f}R^{18f}$, $(CH_2)_rNR^{18f}C(O)R^{18b}$, $(CH_2)_rC(O)OC_{1-4}$ alkyl, $(CH_2)_rOC(O)R^{18b}$, $(CH_2)_rC(=NR^{18f})NR^{18f}R^{18f}$, $(CH_2)_rS(O)_pR^{18b}$, $(CH_2)_r$ $NHC(=NR^{18f})NR^{18f}R^{18f}$, $(CH_2)_rS(O)_2NR^{18f}R^{18f}$, $(CH_2)_r$ $NR^{18f}S(O)_2R^{18b}$, and $(CH_2)_r$phenyl substituted with 0-3 $R^{18e}$;

$R^{18d}$, at each occurrence, is selected from methyl, $CF_3$, $C_{1-6}$ alkyl substituted with 0-3 $R^{18e}$, $C_{3-6}$ alkenyl, $C_{3-6}$ alkynyl, and a $C_{3-10}$ carbocyclic residue substituted with 0-3 $R^{18c}$;

$R^{18e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{18f}R^{18f}$, and $(CH_2)_r$phenyl;

$R^{18f}$, at each occurrence, is selected from H, $C_{1-6}$ alkyl, and $C_{3-6}$ cycloalkyl;

a is selected from 0 and 1;

b is selected from 0 and 1, wherein if a=0, then b=1;

c is selected from 0 and 1;

d is selected from 0, 1, and 2, wherein c+d equals 1 or 2;

provided that if b=1, c=1, and d=1 then E cannot be —$(CR^7R^8)$—$(CR^9CR^{10})_v$—$(CR^{11}CR^{12})$—;

e is selected from 0 and 1;

f is selected from 0 and 1, wherein e+f equals 1 or 2;

g is selected from 0, 1, 2 and 3;

h is selected from 0 and 1;

i is selected from 1, 2, 3, 4, and 5;

j is selected from 0, 1, 2, 3, 4, and 5;

k is selected from 0, 1, and 2;

l is selected from 0, 1, 2 and 3, wherein l+h equals 2 or 3;

v, at each occurrence, is independently selected from 0, 1, and 2;

t, at each occurrence, is selected from 1 and 2;

w, at each occurrence, is selected from 0 and 1;

r, at each occurrence, is selected from 0, 1, 2, 3, 4, and 5;

s, at each occurrence, is selected from 0, 1, 2, 3, 4, and 5;

q, at each occurrence, is selected from 1, 2, 3, 4, and 5; and p, at each occurrence, is selected from 1 and 2.

[2] In another embodiment, the present invention provides novel compounds of formula (I), wherein:

$R^4$ is absent or, taken with the nitrogen to which it is attached to form an N-oxide;

$R^7$, is selected from H, $C_{1-6}$ alkyl, $C_{2-8}$ alkenyl, $C_{2-8}$ alkynyl, $(CHR')_qOH$, $(CHR')_qOR^{7d}$, $(CHR')_qNR^{7a}R^{7a'}$, $(CHR')_qC(O)R^{7b}$, $(CHR')_rC(O)NR^{7a}R^{7a'}$, $(CHR')_qNR^{7a}C(O)R^{7b}$, $(CHR')_qNR^{7a}C(O)H$, $(CHR')_qS(O)_2NR^{7a}R^{7a'}$, $(CHR')_q$ $NR^{7a}S(O)_2R^{7b}$, $(CHR')_qNHC(O)NHR^{7a}$, $(CHR')_qNHC(O)OR^{7a}$, $(CHR')_qOC(O)NHR^{7a}$, $C_{1-6}$ haloalkyl, a $(CHR')_r$—$C_{3-10}$ carbocyclic residue substituted with 0-3 $R^{7c}$, and a $(CHR')_r$-5-10 membered heterocyclic system containing 1-4 heteroatoms selected from N, O, and S, substituted with 0-2 $R^{7c}$;

alternatively, $R^7$ and $R^8$ join to form $C_{3-7}$ cycloalkyl, =$NR^{8b}$, or =O;

$R^9$, is selected from H, $C_{1-6}$ alkyl, $C_{2-8}$ alkenyl, $C_{2-8}$ alkynyl, $(CHR')_rOH$, $(CHR')_rOR^{9d}$, $(CHR')_rNR^{9a}R^{9a'}$, $(CHR')_rC(O)R^{9b}$, $(CHR')_rC(O)NR^{9a}R^{9a'}$, $(CHR')_rNR^{9a}C(O)R^{9b}$, $(CHR')_rNR^{9a}C(O)H$, $(CHR')_rNR^{9a}C(O)NHR^{9a}$, $(CHR')_r$ $NR^{9a}S(O)_2R^{9b}$, $C_{1-6}$ haloalkyl, a $(CHR')_r$—$C_{3-10}$ carbocyclic residue substituted with 0-5 $R^{9c}$, and a $(CHR')_r$-5-10 membered heterocyclic system containing 1-4 heteroatoms selected from N, O, and S, substituted with 0-3 $R^{9c}$;

$R^{10}$, is selected from H, $C_{1-6}$ alkyl, $C_{2-8}$ alkenyl, $C_{2-8}$ alkynyl;

$R^{11}$, is selected from H, $C_{1-6}$ alkyl, $C_{2-8}$ alkenyl, $C_{2-8}$ alkynyl, $(CH_2)_qOH$, $(CH_2)_qOR^{11d}$, $(CH_2)_qNR^{11a}R^{11a'}$, $(CH_2)_qC(O)R^{11b}$, $(CH_2)_rC(O)NR^{11a}R^{11a'}$, $(CH_2)_rNR^{11a}C(O)R^{11a}$, $(CH_2)_qNR^{11a}C(O)H$, $(CH_2)_qNHC(O)NHR^{7a}$, $(CH_2)_qNHC(O)OR^{7a}$, $(CH_2)_qOC(O)NHR^{7a}$, $C_{1-6}$ haloalkyl, a $(CH_2)_r$—$C_{3-10}$ carbocyclic residue substituted with 0-5 $R^{11c}$, and a $(CH_2')_r$-5-10 membered heterocyclic system containing 1-4 heteroatoms selected from N, O, and S, substituted with 0-3 $R^{11c}$.

[3] In another embodiment, the present invention provides novel compounds of formula (I), wherein:

E is selected from —$(CR^7R^8)$—$(CR^9R^{10})_v$—$(CR^{11}R^{12})$,

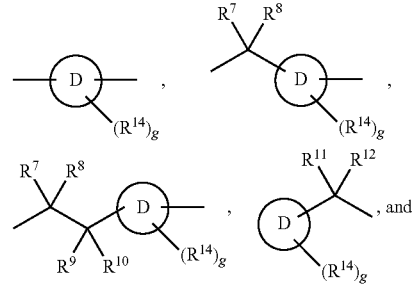

-continued

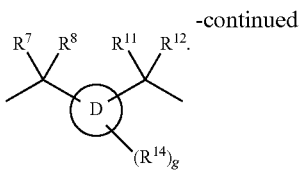

[4] In another embodiment, the present invention provides novel compounds of formula (I), wherein:
G is selected from —C(O)R$^3$, —C(O)NR$^2$R$^3$, —C(O)OR$^3$, —SO$_2$NR$^2$R$^3$, —SO$_2$R$^3$, —C(=S)NR$^2$R$^3$, C(=NR$^{1a}$)NR$^2$R$^3$, C(=CHCN)NR$^2$R$^3$, C(=CHNO$_2$)NR$^2$R$^3$, and C(=C(CN)$_2$)NR$^2$R$^3$.

[5] In another embodiment, the present invention provides novel compounds of formula (I), wherein:
R$^{17}$ is selected from H;
R$^{18}$ is selected from H;
j is selected from 0, 1, and 2;
i is selected from 1 and 2;
s is selected from 0, 1, and 2; and
g is selected from 0, 1, and 2.

[6] In another embodiment, the present invention provides novel compounds of formula (I), wherein:
R$^1$ is selected from H;
R$^2$ is selected from H; and
G is selected from —C(O)NR$^2$R$^3$, C(=CHCN)NR$^2$R$^3$, C(=CHNO$_2$)NR$^2$R$^3$, and C(=C(CN)$_2$)NR$^2$R$^3$.

[7] In another embodiment, the present invention provides novel compounds of formula (I), wherein:
E is selected from —(CR$^7$R$^8$)—(CR$^9$R$^{10}$)$_v$—(CR$^{11}$R$^{12}$).

[8] In a further embodiment, the present invention provides novel compounds of formula (I), wherein:
R$^7$ is selected from H;
R$^8$ is selected from H; and
R$^{12}$ is selected from H.

[9] In a further embodiment, the present invention provides novel compounds of formula (I), wherein:
R$^{16}$, at each occurrence, is selected from methyl, ethyl, propyl, iso-propyl, C$_{2-8}$ alkenyl, C$_{2-8}$ alkynyl, (CH$_2$)$_r$C$_{3-6}$ cycloalkyl, Cl, Br, F, CN, (CHR')$_r$NR$^{16a}$R$^{16a'}$, (CHR')$_r$OH, (CHR')$_r$O(CHR')$_r$R$^{16d}$, (CHR')$_r$C(O)(CHR')$_r$R$^{16b}$, (CHR')$_r$C(O)NR$^{16a}$R$^{16a'}$, (CHR')$_r$NR$^{16f}$C(O)(CHR')$_r$R$^{16b}$, (CHR')$_r$S(O)$_p$(CHR')$_r$R$^{16b}$, (CHR')$_r$S(O)$_2$NR$^{16a}$R$^{16a'}$, (CHR')$_r$NR$^{16f}$S(O)$_2$(CHR')$_r$R$^{16b}$, C$_{1-6}$ haloalkyl, and (CHR')$_r$phenyl substituted with 0-3 R$^{16e}$;
R$^{16a}$ and R$^{16a'}$, at each occurrence, are selected from H, methyl, ethyl, and a (CH$_2$)$_r$—C$_{3-6}$ carbocyclic residue substituted with 0-2 R$^{16e}$;
R$^{16e}$, at each occurrence, is selected from methyl, ethyl, Cl, F, Br, I, CN, CF$_3$, and OCH$_3$;
R$^{16f}$, at each occurrence, is selected from H; and
r is selected from 0, 1, and 2.

[10] In a further embodiment, the present invention provides novel compounds of formula (I), wherein:
R$^3$ is selected from a (CR$^{3'}$R$^{3''}$)$_r$—C$_{3-6}$ carbocyclic residue substituted with 0-2 R$^{15}$ and a (CR$^{3'}$CR$^{3''}$)$_r$-5-10 membered heterocyclic system containing 1-4 heteroatoms selected from N, O, and S, substituted with 0-3 R$^{15}$;
R$^{3'}$ and R$^{3''}$, at each occurrence, are selected from H;
R$^{15}$, at each occurrence, is selected from C$_{1-8}$ alkyl, (CH$_2$)$_r$C$_{3-6}$ cycloalkyl, Cl, Br, F, CN, (CHR')$_r$NR$^{15a}$R$^{15a'}$, (CHR')$_r$OH, (CHR')$_r$O(CHR')$_r$R$^{15d}$, (CHR')$_r$C(O)(CHR')$_r$R$^{15b}$, (CHR')$_r$R$^{15b}$, (CHR')$_r$C(O)NR$^{15a}$R$^{15a'}$, (CHR')$_r$NR$^{15f}$C(O)(CHR')$_r$R$^{15b}$, (CHR')$_r$NR$^{15f}$C(O)NR$^{15a}$R$^{15a'}$, (CHR')$_r$C(O)O(CHR')$_r$R$^{15d}$, (CHR')$_r$OC(O)(CHR')$_r$R$^{15b}$, (CHR')$_r$S(O)$_p$(CHR')$_r$R$^{15b}$, (CHR')$_r$S(O)$_2$NR$^{15a}$R$^{15a'}$, (CHR')$_r$NR$^{15f}$S(O)$_2$(CHR')$_r$R$^{15b}$, C$_{1-6}$ haloalkyl, C$_{2-8}$ alkenyl substituted with 0-3 R', C$_{2-8}$ alkynyl substituted with 0-3 R', (CHR')$_r$phenyl substituted with 0-3 R$^{15e}$, and a (CH$_2$)$_r$-5-10 membered heterocyclic system containing 1-4 heteroatoms selected from N, O, and S, substituted with 0-2 R$^{15e}$;
R', at each occurrence, is selected from H, and C$_{1-6}$ alkyl;
R$^{15a}$ and R$^{15a'}$, at each occurrence, are selected from H, C$_{1-6}$ alkyl, a (CH$_2$)$_r$—C$_{3-6}$ carbocyclic residue substituted with 0-5 R$^{15e}$, and a (CH$_2$)$_r$-5-6 membered heterocyclic system containing 1-2 heteroatoms selected from N, O, and S, substituted with 0-2 R$^{15e}$;
R$^{15b}$, at each occurrence, is selected from C$_{1-6}$ alkyl, a (CH$_2$)$_r$—C$_{3-6}$ carbocyclic residue substituted with 0-3 R$^{15e}$, and (CH$_2$)$_r$-5-6 membered heterocyclic system containing 1-2 heteroatoms selected from N, O, and S, substituted with 0-2 R$^{15e}$; and
R$^{15e}$, at each occurrence, is selected from C$_{1-6}$ alkyl, Cl, F, Br, CN, (CF$_2$)$_r$CF$_3$, and OH.

[11] In another embodiment, the present invention provides novel compounds of formula (I), wherein:
E is

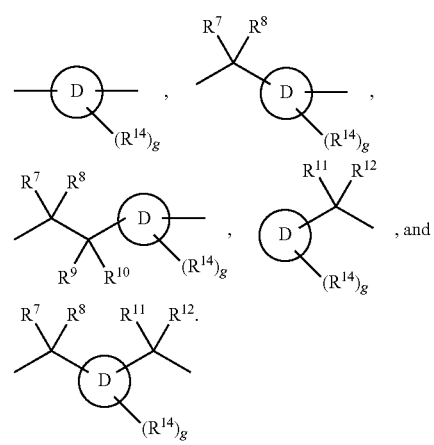

[12] In a further embodiment, the present invention provides novel compounds of formula (I), wherein:
E is

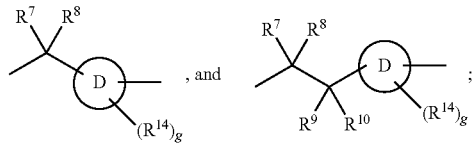

ring D is selected from a C$_{3-6}$ carbocyclic residue;
R$^7$ is selected from H; and
R$^8$ is selected from H.

[13] In a further embodiment, the present invention provides novel compounds of formula (I), wherein:
R$^{16}$, at each occurrence, is selected from methyl, ethyl, propyl, iso-propyl, C$_{2-8}$ alkenyl, C$_{2-8}$ alkynyl, (CH$_2$)$_r$C$_{3-6}$ cycloalkyl, Cl, Br, F, CN, (CHR')$_r$NR$^{16a}$R$^{16a'}$, (CHR')$_r$OH, (CHR')$_r$O(CHR')$_r$R$^{16d}$, (CHR')$_r$C(O)(CHR')$_r$R$^{16b}$, (CHR')$_r$C(O)NR$^{16a}$R$^{16a'}$, (CHR')$_r$NR$^{16f}$C(O)(CHR')$_r$R$^{16b}$, (CHR')$_r$S(O)$_p$(CHR')$_r$R$^{16b}$, (CHR')$_r$S(O)$_2$NR$^{16a}$R$^{16a'}$, (CHR')$_r$NR$^{16f}$S(O)$_2$(CHR')$_r$R$^{16b}$, C$_{1-6}$ haloalkyl, and (CHR')$_r$phenyl substituted with 0-3 R$^{16e}$;

$R^{16a}$ and $R^{16a'}$, at each occurrence, are selected from H, methyl, ethyl, and a $(CH_2)_r$—$C_{3-6}$ carbocyclic residue substituted with 0-2 $R^{16e}$;

$R^{16e}$, at each occurrence, is selected from methyl, ethyl, Cl, F, Br, I, CN, $CF_3$, and $OCH_3$;

$R^{16f}$, at each occurrence, is selected from H; and r is selected from 0, 1, and 2.

[14] In a further embodiment, the present invention provides novel compounds of formula (I), wherein:

$R^3$ is selected from a $(CR^{3'}R^{3''})_r$—$C_{3-6}$ carbocyclic residue substituted with 0-2 $R^{15}$ and a $(CR^{3'}CR^{3''})_r$-5-10 membered heterocyclic system containing 1-4 heteroatoms selected from N, O, and S, substituted with 0-3 $R^{15}$;

$R^{3'}$ and $R^{3''}$, at each occurrence, are selected from H;

$R^{15}$, at each occurrence, is selected from $C_{1-8}$ alkyl, $(CH_2)_r$ $C_{3-6}$ cycloalkyl, Cl, Br, F, CN, $(CHR')_r NR^{15a}R^{15a'}$, $(CHR')_r$ OH, $(CHR')_r O(CHR')_r R^{15d}$, $(CHR')_r C(O)(CHR')_r R^{15b}$, $(CHR')_r C(O)NR^{15a}R^{15a'}$, $(CHR')_r NR^{15f}C(O)(CHR')_r R^{15b}$, $(CHR')_r NR^{15f}C(O)NR^{15a}R^{15a'}$, $(CHR')_r C(O)O(CHR')_r R^{15d}$, $(CHR')_r OC(O)(CHR')_r R^{15b}$, $(CHR')_r S(O)_p (CHR')_r R^{15b}$, $(CHR')_r S(O)_2 NR^{15a}R^{15a'}$, $(CHR')_r NR^{15f}S(O)_2 (CHR')_r R^{15b}$, $C_{1-6}$ haloalkyl, $C_{2-8}$ alkenyl substituted with 0-3 R', $C_{2-8}$ alkynyl substituted with 0-3 R', $(CHR')_r$ phenyl substituted with 0-3 $R^{15e}$, and a $(CH_2)_r$-5-10 membered heterocyclic system containing 1-4 heteroatoms selected from N, O, and S, substituted with 0-2 $R^{15e}$;

R', at each occurrence, is selected from H, and $C_{1-6}$ alkyl;

$R^{15a}$ and $R^{15a'}$, at each occurrence, are selected from H, $C_{1-6}$ alkyl, a $(CH_2)_r$—$C_{3-6}$ carbocyclic residue substituted with 0-5 $R^{15e}$, and a $(CH_2)_r$-5-6 membered heterocyclic system containing 1-2 heteroatoms selected from N, O, and S, substituted with 0-2 $R^{15e}$;

$R^{15b}$, at each occurrence, is selected from $C_{1-6}$ alkyl, a $(CH_2)_r$—$C_{3-6}$ carbocyclic residue substituted with 0-3 $R^{15e}$, and $(CH_2)_r$-5-6 membered heterocyclic system containing 1-2 heteroatoms selected from N, O, and S, substituted with 0-2 $R^{15e}$; and $R^{15e}$, at each occurrence, is selected from $C_{1-6}$ alkyl, Cl, F, Br, I, CN, $(CF_2)_r CF_3$, and OH.

[15] In another embodiment, the present invention provides novel compounds of formula (I), wherein:

G is selected from

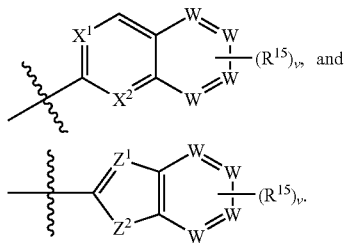

[16] In another embodiment, the present invention provides novel compounds of formula (I), wherein:

$R^1$ is selected from H;

both $X^1$ and $X^2$ cannot be C; and $Z^2$ is selected from $NR^{1'}$, O, and S.

[17] In another embodiment, the present invention provides novel compounds of formula (I), wherein:

$R^{17}$ is selected from H;

$R^{18}$ is selected from H;

j is selected from 0, 1, and 2;

i is selected from 1 and 2;

s is selected from 0, 1, and 2; and g is selected from 0, 1, and 2.

[18] In another embodiment, the present invention provides novel compounds of formula (I), wherein:

E is selected from —$(CR^7R^8)$—$(CR^9R^{10})_v$—$(CR^{11}R^{12})$.

[19] In a further embodiment, the present invention provides novel compounds of formula (I), wherein:

$R^7$ is selected from H;

$R^8$ is selected from H; and $R^{12}$ is selected from H.

[20] In a further embodiment, the present invention provides novel compounds of formula (I), wherein:

$R^{16}$, at each occurrence, is selected from methyl, ethyl, propyl, iso-propyl, $C_{2-8}$ alkenyl, $C_{2-8}$ alkynyl, $(CH_2)_r C_{3-6}$ cycloalkyl, Cl, Br, F, CN, $(CHR')_r NR^{16a}R^{16a'}$, $(CHR')_r OH$, $(CHR')_r O(CHR')_r R^{16d}$, $(CHR')_r C(O)(CHR')_r R^{16b}$, $(CHR')_r C(O)NR^{16a}R^{16a'}$, $(CHR')_r NR^{16f}C(O)(CHR')_r R^{16b}$, $(CHR')_r S(O)_p (CHR')_r R^{16b}$, $(CHR')_r S(O)_2 NR^{16a}R^{16a'}$, $(CHR')_r NR^{16f}S(O)_2 (CHR')_r R^{16b}$, $C_{1-6}$ haloalkyl, and $(CHR')_r$ phenyl substituted with 0-3 $R^{16e}$;

$R^{16a}$ and $R^{16a'}$, at each occurrence, are selected from H, methyl, ethyl, and a $(CH_2)_r$—$C_{3-6}$ carbocyclic residue substituted with 0-2 $R^{16e}$;

$R^{16e}$, at each occurrence, is selected from methyl, ethyl, Cl, F, Br, I, CN, $CF_3$, and $OCH_3$;

$R^{16f}$, at each occurrence, is selected from H; and r is selected from 0, 1, and 2.

[21] In a further embodiment, the present invention provides novel compounds of formula (I), wherein:

$R^{15}$, at each occurrence, is selected from $C_{1-8}$ alkyl, $(CH_2)_r$ $C_{3-6}$ cycloalkyl, Cl, Br, F, CN, $(CHR')_r NR^{15a}R^{15a'}$, $(CHR')_r$ OH, $(CHR')_r O(CHR')_r R^{15d}$, $(CHR')_r C(O)(CHR')_r R^{15b}$, $(CHR')_r C(O)NR^{15a}R^{15a'}$, $(CHR')_r NR^{15f}C(O)(CHR')_r R^{15b}$, $(CHR')_r NR^{15f}C(O)NR^{15a}R^{15a'}$, $(CHR')_r C(O)O(CHR')_r R^{15d}$, $(CHR')_r OC(O)(CHR')_r R^{15b}$, $(CHR')_r S(O)_p (CHR')_r R^{15b}$, $(CHR')_r S(O)_2 NR^{15a}R^{15a'}$, $(CHR')_r NR^{15f}S(O)_2 (CHR')_r R^{15b}$, $C_{1-6}$ haloalkyl, $C_{2-8}$ alkenyl substituted with 0-3 R', $C_{2-8}$ alkynyl substituted with 0-3 R', $(CHR')_r$ phenyl substituted with 0-3 $R^{15e}$, and a $(CH_2)_r$-5-10 membered heterocyclic system containing 1-4 heteroatoms selected from N, O, and S, substituted with 0-2 $R^{15e}$;

R', at each occurrence, is selected from H, and $C_{1-6}$ alkyl;

$R^{15a}$ and $R^{15a'}$, at each occurrence, are selected from H, $C_{1-6}$ alkyl, a $(CH_2)_r$—$C_{3-6}$ carbocyclic residue substituted with 0-5 $R^{15e}$, and a $(CH_2)_r$-5-6 membered heterocyclic system containing 1-2 heteroatoms selected from N, O, and S, substituted with 0-2 $R^{15e}$;

$R^{15b}$, at each occurrence, is selected from $C_{1-6}$ alkyl, a $(CH_2)_r$—$C_{3-6}$ carbocyclic residue substituted with 0-3 $R^{15e}$, and $(CH_2)_r$-5-6 membered heterocyclic system containing 1-2 heteroatoms selected from N, O, and S, substituted with 0-2 $R^{15e}$; and $R^{15e}$, at each occurrence, is selected from $C_{1-6}$ alkyl, Cl, F, Br, I, CN, $(CF_2)_r CF_3$, and OH.

[22] In another embodiment, the present invention provides novel compounds of formula (I), wherein:

E is

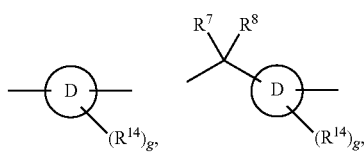

-continued

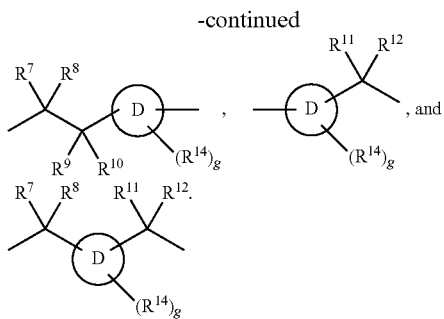

[23] In a further embodiment, the present invention provides novel compounds of formula (I), wherein:
E is

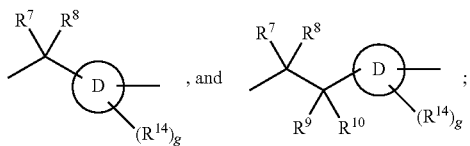

ring D is selected from a $C_{3-6}$ carbocyclic residue;
$R^7$ is selected from H;
$R^8$ is selected from H.

[24] In a further embodiment, the present invention provides novel compounds of formula (I), wherein:
$R^{16}$, at each occurrence, is selected from methyl, ethyl, propyl, iso-propyl, $C_{2-8}$ alkenyl, $C_{2-8}$ alkynyl, $(CH_2)_rC_{3-6}$ cycloalkyl, Cl, Br, F, CN, $(CHR')_rNR^{16a}R^{16a'}$, $(CHR')_rOH$, $(CHR')_rO(CHR')_rR^{16d}$, $(CHR')_rC(O)(CHR')_rR^{16b}$, $(CHR')_rC(O)NR^{16a}R^{16a'}$, $(CHR')_rNR^{16f}C(O)(CHR')_rR^{16b}$, $(CHR')_rS(O)_p(CHR')_rR^{16b}$, $(CHR')_rS(O)_2NR^{16a}R^{16a'}$, $(CHR')_rNR^{16f}S(O)_2(CHR')_rR^{16b}$, $C_{1-6}$ haloalkyl, and $(CHR')_r$phenyl substituted with 0-3 $R^{16e}$;
$R^{16a}$ and $R^{16a'}$, at each occurrence, are selected from H, methyl, ethyl, and a $(CH_2)_r$—$C_{3-6}$ carbocyclic residue substituted with 0-2 $R^{16e}$;
$R^{16e}$, at each occurrence, is selected from methyl, ethyl, Cl, F, Br, CN, $CF_3$, and $OCH_3$;
$R^{16f}$, at each occurrence, is selected from H; and
r is selected from 0, 1, and 2.

[25] In a further embodiment, the present invention provides novel compounds of formula (I), wherein:
$R^{15}$, at each occurrence, is selected from $C_{1-8}$ alkyl, $(CH_2)_r$ $C_{3-6}$ cycloalkyl, Cl, Br, F, CN, $(CHR')_rNR^{15a}R^{15a'}$, $(CHR')_r$ OH, $(CHR')_rO(CHR')_rR^{15d}$, $(CHR')_rC(O)$ $(CHR')_r$ $R^{15b}$, $(CHR')_rC(O)NR^{15a}R^{15a'}$, $(CHR')_rNR^{15f}C(O)(CHR')_r R^{15b}$, $(CHR')_rNR^{15f}C(O)NR^{15a}R^{15a'}$, $(CHR')_r C(O)O(CHR')_rR^{15d}$, $(CHR')_rOC(O)(CHR')_rR^{15b}$, $(CHR')_r S(O)_p(CHR')_rR^{15b}$, $(CHR')_rS(O)_2NR^{15a}R^{15a'}$, $(CHR')_r NR^{15f}S(O)_2(CHR')_rR^{15b}$, $C_{1-6}$ haloalkyl, $C_{2-8}$ alkenyl substituted with 0-3 R', $C_{2-8}$ alkynyl substituted with 0-3 R', $(CHR')_r$ phenyl substituted with 0-3 $R^{15e}$, and a $(CH_2)_r$-5-10 membered heterocyclic system containing 1-4 heteroatoms selected from N, O, and S, substituted with 0-2 $R^{15e}$;
R', at each occurrence, is selected from H, and $C_{1-6}$ alkyl;
$R^{15a}$ and $R^{15a'}$, at each occurrence, are selected from H, $C_{1-6}$ alkyl, a $(CH_2)_r$—$C_{3-6}$ carbocyclic residue substituted with 0-5 $R^{15e}$, and a $(CH_2)_r$-5-6 membered heterocyclic system containing 1-2 heteroatoms selected from N, O, and S, substituted with 0-2 $R^{15e}$;
$R^{15b}$, at each occurrence, is selected from $C_{1-6}$ alkyl, a $(CH_2)_r$—$C_{3-6}$ carbocyclic residue substituted with 0-3 $R^{15e}$, and $(CH_2)_r$-5-6 membered heterocyclic system containing 1-2 heteroatoms selected from N, O, and S, substituted with 0-2 $R^{15e}$; and
$R^{15e}$, at each occurrence, is selected from $C_{1-6}$ alkyl, Cl, F, Br, CN, $(CF_2)_rCF_3$, and OH.

[26] In a further embodiment, the present invention provides novel compounds of formula (I), wherein the compound of formula I is selected from:
N-3-[cis-2,3,3a,4,9,9a-hexahydro-1H-benz[f]isoindol-2-yl]-n-prop-1-yl-N'-3-acetylphenylurea;
N-3-[trans-2,3,3a,4,9,9a-hexahydro-1H-benz[f]isoindol-2-yl]-n-prop-1-yl-N'-3-acetylphenylurea;
(+/−)-N-3-[trans-6-fluoro-2,3,3a,4,9,9a-hexahydro-1H-benz[f]isoindol-2-yl]-n-prop-1-yl-N'-3-acetylphenylurea;
(+/−)-N-3-[trans-6-fluoro-2,3,3a,4,9,9a-hexahydro-1H-benz[f]isoindol-2-yl]-n-prop-1-yl-N'-4-fluorophenylurea;
(+/−)-N-3-[cis-6-fluoro-2,3,3a,4,9,9a-hexahydro-1H-benz[f]isoindol-2-yl]-n-prop-1-yl-N'-3-acetylphenylurea;
(+/−)-N-3-[cis-6-fluoro-2,3,3a,4,9,9a-hexahydro-1H-benz[f]isoindol-2-yl]-n-prop-1-yl-N'-4-fluorophenylurea;
N-(3-acetylphenyl)-N'-[3-[1-[(4-fluorophenyl)methyl]-3-azabicyclo[2.2.2]oct-2-yl]propyl]urea hydrochloride;
N-(4-fluorophenyl)-N'-[3-[1-[(4-fluorophenyl)methyl]-3-azabicyclo[2.2.2]oct-2-yl]propyl]urea hydrochloride;
N-(3-acetylphenyl)-N'-[3-[(1S,4R,6S)-6-[(4-fluorophenyl)methyl]-2-azabicyclo[2.2.2]oct-2-yl]propyl]urea hydrochloride;
N-(3-acetylphenyl)-N'-[3-[(1R,4S,6R)-6-[(4-fluorophenyl)methyl]-2-azabicyclo[2.2.2]oct-2-yl]propyl]urea hydrochloride;
N-(3-acetylphenyl)-N'-[3-[(1S,4R,6R)-6-[(4-fluorophenyl)methyl]-2-azabicyclo[2.2.2]oct-2-yl]propyl]urea hydrochloride;
N-(3-acetylphenyl)-N'-[3-[(1R,4S,6S)-6-[(4-fluorophenyl)methyl]-2-azabicyclo[2.2.2]oct-2-yl]propyl]urea hydrochloride;
N-(4-fluorophenyl)-N'-[3-[(1S,4R,6R)-6-[(4-fluorophenyl)methyl]-2-azabicyclo[2.2.2]oct-2-yl]propyl]urea hydrochloride;
N-(4-fluorophenyl)-N'-[3-[(1R,4S,6S)-6-[(4-fluorophenyl)methyl]-2-azabicyclo[2.2.2]oct-2-yl]propyl]urea hydrochloride;
N-(3-acetylphenyl)-N'-[(2S)-2-[[(3-exo)-3-[(4-fluorophenyl)methyl]-8-azabicyclo[3.2.1]oct-8-yl]methyl]-(2R)-1-cyclohexyl]urea;
N-(4-fluorophenyl)-N'-[(2S)-2-[[(3-exo)-3-[(4-fluorophenyl)methyl]-8-azabicyclo[3.2.1]oct-8-yl]methyl]-(2R)-1-cyclohexyl]urea;
N-(3-acetylphenyl)-N'-[(2S)-2-[[(3-endo)-3-[(4-fluorophenyl)methyl]-8-azabicyclo[3.2.1]oct-8-yl]methyl]-(2R)-1-cyclohexyl]urea;
N-(4-fluorophenyl)-N'-[(2S)-2-[[(3-endo)-3-[(4-fluorophenyl)methyl]-8-azabicyclo[3.2.1]oct-8-yl]methyl]-(2R)-1-cyclohexyl]urea;
N-(4-fluorophenyl)-N'-{3-[(1S,5R,6R)-6-(4-fluorophenyl)-3-azabicyclo[3.2.0]hept-3-yl]propyl}urea;
N-(4-fluorophenyl)-N'-{3-[(1R,5S,6S)-6-(4-fluorophenyl)-3-azabicyclo[3.2.0]hept-3-yl]propyl}urea;
N-(3-acetylphenyl)-N'-{3-[(1S,5R,6R)-6-(4-fluorophenyl)-3-azabicyclo[3.2.0]hept-3-yl]propyl}urea; and
N-(3-acetylphenyl)-N'-{3-[(1R,5S,6S)-6-(4-fluorophenyl)-3-azabicyclo[3.2.0]hept-3-yl]propyl}urea.

[27] In a third embodiment, the present invention provides a pharmaceutical composition, comprising a pharmaceutically acceptable carrier and a therapeutically effective amount of a compound of the present invention.

[28] In a fourth embodiment, the present invention provides a method for modulation of chemokine receptor activity comprising administering to a patient in need thereof a therapeutically effective amount of the compounds of the present invention.

[29] In another embodiment, the present invention provides a method for treating or preventing inflammatory diseases, comprising administering to a patient in need thereof a therapeutically effective amount of the compounds of the present invention.

[29] In another embodiment, the present invention provides a method for treating or preventing asthma, comprising administering to a patient in need thereof a therapeutically effective amount of the compounds of the present invention.

[30] In another embodiment, the present invention provides a method for treating or preventing asthma, comprising administering to a patient in need thereof a therapeutically effective amount of compounds of the present invention.

[31] In another embodiment, the present invention provides a method of modulating chemokine receptor by administering a compound of formula (I):

$$A-E-NR^1-G \quad (I)$$

or stereoisomers or pharmaceutically acceptable salts thereof, wherein:

ring A is selected from

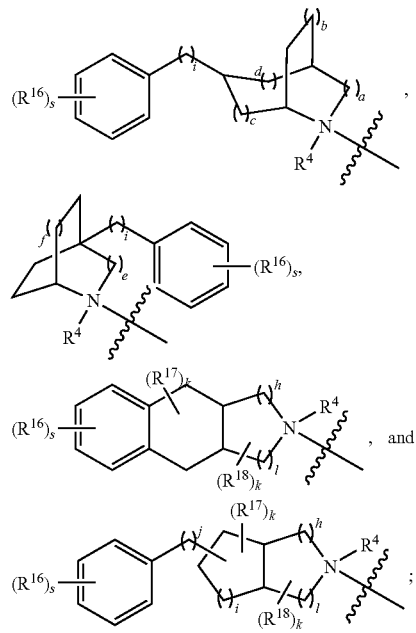

E is selected from $-(CR^7R^8)-(CR^9R^{10})_v-(CR^{11}R^{12})$,

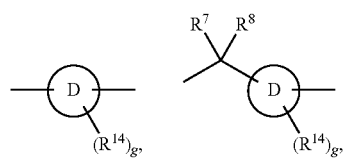

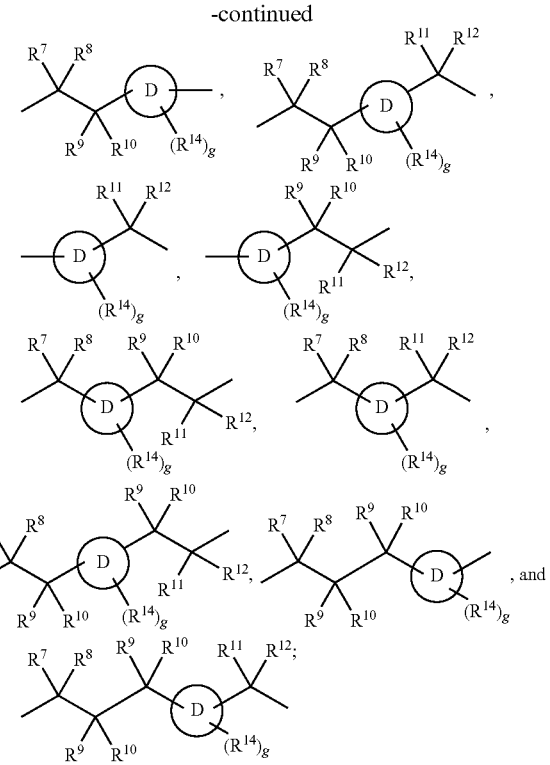

ring D is selected from a $C_{3-6}$ carbocyclic residue and a 5 or 6 membered heterocycle;

G is selected from $-C(O)R^3$, $-C(O)NR^2R^3$, $-C(O)OR^3$, $-SO_2NR^2R^3$, $-SO_2R^3$, $-C(=S)NR^2R^3$, $C(=NR^{1a})NR^2R^3$, $C(=CHCN)NR^2R^3$, $C(=CHNO_2)NR^2R^3$, $C(=C(CN)_2)NR^2R^3$,

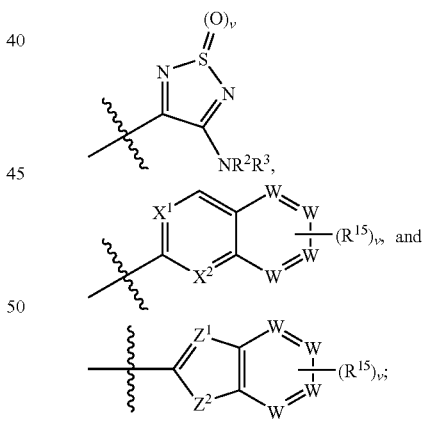

W, at each occurrence, is independently selected from C or N, provided at least two of W are C;

$X^1$ and $X^2$ are independently selected from C and N;

$Z^1$ is selected from C and N;

$Z^2$ is selected from $NR^{1'}$, O, S and C;

$R^1$, $R^{1'}$ and $R^2$ are independently selected from H, $C_{1-8}$ alkyl, $C_{3-8}$ alkenyl, $C_{3-8}$ alkynyl, $(CH_2)_rC_{3-6}$ cycloalkyl, and a $(CH_2)_r-C_{3-10}$ carbocyclic residue substituted with 0-5 $R^a$;

$R^{1a}$ is independently selected from H, $C_{1-6}$ alkyl, —OH, —CN, —NO_2, $(CH_2)_rC_{3-6}$ cycloalkyl, and a $(CH_2)_r-C_{3-10}$ carbocyclic residue substituted with 0-5 $R^a$;

$R^a$, at each occurrence, is selected from $C_{1-4}$ alkyl, $C_{2-8}$ alkenyl, $C_{2-8}$ alkynyl, $(CH_2)_r C_{3-6}$ cycloalkyl, Cl, Br, I, F, $(CF_2)_r CF_3$, $NO_2$, CN, $(CH_2)_r NR^b R^b$, $(CH_2)_r OH$, $(CH_2)_r OR^c$, $(CH_2)_r SH$, $(CH_2)_r SR^c$, $(CH_2)_r C(O)R^b$, $(CH_2)_r C(O)NR^b R^b$, $(CH_2)_r NR^b C(O)R^b$, $(CH_2)_r C(O)OR^b$, $(CH_2)_r OC(O)R^c$, $(CH_2)_r CH(=NR^b)NR^b R^b$, $(CH_2)_r NHC(=NR^b)NR^b R^b$, $(CH_2)_r S(O)_p R^c$, $(CH_2)_r S(O)_2 NR^b R^b$, $(CH_2)_r NR^b S(O)_2 R^c$, and $(CH_2)_r$ phenyl;

$R^b$, at each occurrence, is selected from H, $C_{1-6}$ alkyl, $C_{3-6}$ cycloalkyl, and phenyl;

$R^c$, at each occurrence, is selected from $C_{1-6}$ alkyl, $C_{3-6}$ cycloalkyl, and phenyl;

alternatively, $R^1$ and $R^2$ join to form a 5, 6, or 7-membered ring substituted with 0-3 $R^a$;

$R^3$ is selected from a $(CR^{3'}R^{3''})_r$—$C_{3-10}$ carbocyclic residue substituted with 0-5 $R^{15}$ and a $(CR^{3'}R^{3''})_r$-5-10 membered heterocyclic system containing 1-4 heteroatoms selected from N, O, and S, substituted with 0-3 $R^{15}$;

$R^{3'}$ and $R^{3''}$, at each occurrence, are selected from H, $C_{1-6}$ alkyl, $(CH_2)_r C_{3-6}$ cycloalkyl, and phenyl;

$R^4$ is absent, taken with the nitrogen to which it is attached to form an N-oxide, or selected from $C_{1-8}$ alkyl, $C_{3-8}$ alkenyl, $C_{3-8}$ alkynyl, $(CH_2)_r C_{3-6}$ cycloalkyl, $(CH_2)_q C(O)R^{4b}$, $(CH_2)_q C(O)NR^{4a}R^{4a'}$, $(CH_2)_q C(O)OR^{4a}$, and a $(CH_2)_r$—$C_{3-10}$ carbocyclic residue substituted with 0-3 $R^{4c}$;

$R^{4a}$ and $R^{4a'}$, at each occurrence, are selected from H, $C_{1-6}$ alkyl, $(CH_2)_r C_{3-6}$ cycloalkyl, and phenyl;

$R^{4b}$, at each occurrence, is selected from $C_{1-6}$ alkyl, $C_{2-8}$ alkenyl, $(CH_2)_r C_{3-6}$ cycloalkyl, $C_{2-8}$ alkynyl, and phenyl;

$R^{4c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_r CF_3$, $(CH_2)_r OC_{1-5}$ alkyl, $(CH_2)_r OH$, $(CH_2)_r SC_{1-5}$ alkyl, $(CH_2)_r NR^{4a}R^{4a'}$, and $(CH_2)_r$ phenyl;

$R^7$, is selected from H, $C_{1-6}$ alkyl, $C_{2-8}$ alkenyl, $C_{2-8}$ alkynyl, $(CH_2)_q OH$, $(CH_2)_q SH$, $(CH_2)_q OR^{7d}$, $(CH_2)_q SR^{7d}$, $(CH_2)_q NR^{7a}R^{7a'}$, $(CH_2)_q C(O)OH$, $(CH_2)_q C(O)R^{7b}$, $(CH_2)_q C(O)NR^{7a}R^{7a'}$, $(CH_2)_q NR^{7a}C(O)R^{7b}$, $(CH_2)_q NR^{7a}C(O)H$, $(CH_2)_q C(O)OR^{7a}$, $(CH_2)_q OC(O)R^{7b}$, $(CH_2)_q S(O)_p R^{7b}$, $(CH_2)_q S(O)_2 NR^{7a}R^{7a'}$, $(CH_2)_q NR^{7a}S(O)_2 R^{7b}$, $(CH_2)_q NHC(O)N^{7a}R^{7a}$, $(CH_2)_q NHC(O)OR^{7a}$, $(CH_2)_q OC(O)$ $N^{7a}R^{7a}$, $C_{1-6}$ haloalkyl, a $(CH_2)_r$—$C_{3-10}$ carbocyclic residue substituted with 0-3 $R^{7c}$, and a $(CH_2)_r$-5-10 membered heterocyclic system containing 1-4 heteroatoms selected from N, O, and S, substituted with 0-2 $R^{7c}$;

$R^{7a}$ and $R^{7a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{7e}$, and a $(CH_2)_r$-5-10 membered heterocyclic system containing 1-4 heteroatoms selected from N, O, and S, substituted with 0-3 $R^{7e}$;

$R^{7b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0-2 $R^{7e}$, and a $(CH_2)_r$-5-6 membered heterocyclic system containing 1-4 heteroatoms selected from N, O, and S, substituted with 0-3 $R^{7e}$;

$R^{7c}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, Br, I, F, $(CF_2)_r CF_3$, $NO_2$, CN, $(CH_2)_r NR^{7f}R^{7f}$, $(CH_2)_r OH$, $(CH_2)_r OC_{1-4}$ alkyl, $(CH_2)_r SC_{1-4}$ alkyl, $(CH_2)_r C(O)OH$, $(CH_2)_r C(O)R^{7b}$, $(CH_2)_r C(O)NR^{7f}R^{7f}$, $(CH_2)_r NR^{7f}C(O)R^{7b}$, $(CH_2)_r C(O)OC_{1-4}$ alkyl, $(CH_2)_r OC(O)R^{7b}$, $(CH_2)_r C(=NR^{7f})NR^{7f}R^{7f}$, $(CH_2)_r S(O)_p R^{7b}$, $(CH_2)_r NHC(=NR^{7f})NR^{7f}R^{7f}$, $(CH_2)_r S(O)_2 NR^{7f}R^{7f}$, $(CH_2)_r NR^{7f}S(O)_2 R^{7b}$, and $(CH_2)_r$ phenyl substituted with 0-3 $R^{7e}$;

$R^{7d}$, at each occurrence, is selected from methyl, $CF_3$, $C_{1-6}$ alkyl substituted with 0-3 $R^{7e}$, $C_{3-6}$ alkenyl, $C_{3-6}$ alkynyl, and a $C_{3-10}$ carbocyclic residue substituted with 0-3 $R^{7c}$;

$R^{7e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-5}$ alkyl, $(CH_2)_r NR^{7f}R^{7f}$, and $(CH_2)_r$ phenyl;

$R^{7f}$, at each occurrence, is selected from H, $C_{1-6}$ alkyl, and $C_{3-6}$ cycloalkyl;

$R^8$ is selected from H, $C_{1-6}$ alkyl, $C_{3-6}$ cycloalkyl, and $(CH_2)_r$ phenyl substituted with 0-3 $R^{8a}$;

$R^{8a}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-5}$ alkyl, $(CH_2)_r NR^{7f}R^{7f}$, and $(CH_2)_r$ phenyl;

alternatively, $R^7$ and $R^8$ join to form $C_{3-7}$ cycloalkyl, $=NR^{8b}$, or $=O$;

$R^{8b}$ is selected from H, $C_{1-6}$ alkyl, $C_{3-6}$ cycloalkyl, OH, CN, and $(CH_2)_r$-phenyl;

$R^9$, is selected from H, $C_{1-6}$ alkyl, $C_{2-8}$ alkenyl, $C_{2-8}$ alkynyl, F, Cl, Br, I, $NO_2$, CN, $(CH_2)_r OH$, $(CH_2)_r SH$, $(CH_2)_r OR^{9d}$, $(CH_2)_r SR^{9d}$, $(CH_2)_r NR^{9a}R^{9a'}$, $(CH_2)_r C(O)OH$, $(CH_2)_r C(O)R^{9b}$, $(CH_2)_r C(O)NR^{9a}R^{9a'}$, $(CH_2)_r NR^{9a}C(O)R^{9a}$, $(CH_2)_r NR^{9a}C(O)H$, $(CH_2)_r NR^{9a}C(O)N^{9a}R^{9a}$, $(CH_2)_r C(O)OR^{9a}$, $(CH_2)_r OC(O)R^{9b}$, $(CH_2)_r S(O)_p R^{9b}$, $(CH_2)_r S(O)_2 NR^{9a}R^{9a'}$, $(CH_2)_r NR^{9a}S(O)_2 R^{9b}$, $C_{1-6}$ haloalkyl, a $(CH_2)_r$—$C_{3-10}$ carbocyclic residue substituted with 0-5 $R^{9c}$, and a $(CH_2)_r$-5-10 membered heterocyclic system containing 1-4 heteroatoms selected from N, O, and S, substituted with 0-3 $R^{9c}$;

$R^{9a}$ and $R^{9a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{9e}$, and a $(CH_2)_r$-5-10 membered heterocyclic system containing 1-4 heteroatoms selected from N, O, and S, substituted with 0-3 $R^{9e}$;

$R^{9b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0-2 $R^{9e}$, and a $(CH_2)_r$-5-6 membered heterocyclic system containing 1-4 heteroatoms selected from N, O, and S, substituted with 0-3 $R^{9e}$;

$R^{9c}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, Br, I, F, $(CF_2)_r CF_3$, $NO_2$, CN, $(CH_2)_r NR^{9f}R^{9f}$, $(CH_2)_r OH$, $(CH_2)_r OC_{1-4}$ alkyl, $(CH_2)_r SC_{1-4}$ alkyl, $(CH_2)_r C(O)OH$, $(CH_2)_r C(O)R^{9b}$, $(CH_2)_r C(O)NR^{9f}R^{9f}$, $(CH_2)_r NR^{9f}C(O)R^{9b}$, $(CH_2)_r C(O)OC_{1-4}$ alkyl, $(CH_2)_r OC(O)R^{9b}$, $(CH_2)_r C(=NR^{9f})NR^{9f}R^{9f}$, $(CH_2)_r S(O)_p R^{9b}$, $(CH_2)_r NHC(=NR^{9f})NR^{9f}R^{9f}$, $(CH_2)_r S(O)_2 NR^{9f}R^{9f}$, $(CH_2)_r NR^{9f}S(O)_2 R^{9b}$, and $(CH_2)_r$ phenyl substituted with 0-3 $R^{9e}$;

$R^{9d}$, at each occurrence, is selected from methyl, $CF_3$, $C_{1-6}$ alkyl substituted with 0-3 $R^{9e}$, $C_{3-6}$ alkenyl, $C_{3-6}$ alkynyl, a $C_{3-10}$ carbocyclic residue substituted with 0-3 $R^{9c}$, and a 5-6 membered heterocyclic system containing 1-4 heteroatoms selected from the group consisting of N, O, and S substituted with 0-3 $R^{9c}$;

$R^{9e}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-5}$ alkyl, $(CH_2)_r NR^{9f}R^{9f}$, and $(CH_2)_r$ phenyl;

$R^{9f}$ at each occurrence, is selected from H, $C_{1-6}$ alkyl, and $C_{3-6}$ cycloalkyl;

$R^{10}$, is selected from H, $C_{1-6}$ alkyl, $C_{2-8}$ alkenyl, $C_{2-8}$ alkynyl, F, Cl, Br, I, $NO_2$, CN, $(CH_2)_r OH$, $(CH_2)_r OR^{10d}$, $(CH_2)_r SR^{10d}$, $(CH_2)_r NR^{10a}R^{10a'}$, $(CH_2)_r C(O)OH$, $(CH_2)_r C(O)R^{10b}$, $(CH_2)_r C(O)NR^{10a}R^{10a'}$, $(CH_2)_r NR^{10a}C(O)R^{10a}$, $(CH_2)_r NR^{10a}C(O)H$, $(CH_2)_r C(O)OR^{10a}$, $(CH_2)_r OC(O)R^{10b}$, $(CH_2)_r S(O)_p R^{10b}$, $(CH_2)_r S(O)_2 NR^{10a}R^{10a'}$, $(CH_2)_r NR^{10a}S(O)_2 R^{10b}$, $C_{1-6}$ haloalkyl, a $(CH_2)_r$—$C_{3-10}$ carbocyclic residue substituted with 0-5 $R^{10c}$, and a $(CH_2)_r$-

5-10 membered heterocyclic system containing 1-4 heteroatoms selected from N, O, and S, substituted with 0-3 $R^{10c}$;

$R^{10a}$ and $R^{10a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{10e}$, and a $(CH_2)_r$-5-10 membered heterocyclic system containing 1-4 heteroatoms selected from N, O, and S, substituted with 0-3 $R^{10e}$;

$R^{10b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0-2 $R^{10e}$, and a $(CH_2)_r$-5-6 membered heterocyclic system containing 1-4 heteroatoms selected from N, O, and S, substituted with 0-3 $R^{10e}$;

$R^{10c}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, Br, I, F, $(CF_2)_r CF_3$, $NO_2$, CN, $(CH_2)_r NR^{10f} R^{10f'}$, $(CH_2)_r OH$, $(CH_2)_r$ $OC_{1-4}$ alkyl, $(CH_2)_r SC_{1-4}$ alkyl, $(CH_2)_r C(O)OH$, $(CH_2)_r C(O)R^{10b}$, $(CH_2)_r C(O)NR^{10f} R^{10f'}$, $(CH_2)_r NR^{10f} C(O)R^{10a}$, $(CH_2)_r C(O)OC_{1-4}$ alkyl, $(CH_2)_r OC(O)R^{10b}$, $(CH_2)_r C(=NR^{10f})NR^{10f} R^{10f'}$, $(CH_2)_r S(O)_p R^{10b}$, $(CH_2)_r NHC(=NR^{10f})NR^{10f} R^{10f'}$, $(CH_2)_r S(O)_2 NR^{10f} R^{10f'}$, $(CH_2)_r NR^{10f} S(O)_2 R^{10b}$, and $(CH_2)_r$phenyl substituted with 0-3 $R^{10e}$;

$R^{10d}$, at each occurrence, is selected from methyl, $CF_3$, $C_{1-6}$ alkyl substituted with 0-3 $R^{10e}$, $C_{3-6}$ alkenyl, $C_{3-6}$ alkynyl, a $C_{3-10}$ carbocyclic residue substituted with 0-3 $R^{10c}$, and a 5-6 membered heterocyclic system containing 1-4 heteroatoms selected from the group consisting of N, O, and S substituted with 0-3 $R^{10c}$;

$R^{10e}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-5}$ alkyl, $(CH_2)_r NR^{10f} R^{10f'}$, and $(CH_2)_r$phenyl;

$R^{10f}$, at each occurrence, is selected from H, $C_{1-6}$ alkyl, and $C_{3-6}$ cycloalkyl;

alternatively, $R^9$ and $R^{10}$ join to form $C_{3-7}$ cycloalkyl, 5-6-membered cyclic ketal, or =O;

with the proviso that when $R^{10}$ is —OH, $R^9$ is not halogen, cyano, or bonded to the carbon to which it is attached through a heteroatom;

$R^{11}$, is selected from H, $C_{1-6}$ alkyl, $C_{2-8}$ alkenyl, $C_{2-8}$ alkynyl, $(CH_2)_q OH$, $(CH_2)_q SH$, $(CH_2)_q OR^{11d}$, $(CH_2)_q SR^{11d}$, $(CH_2)_q NR^{11a} R^{11a'}$, $(CH_2)_r C(O)OH$, $(CH_2)_r C(O)R^{11b}$, $(CH_2)_r C(O)NR^{11a} R^{11a'}$, $(CH_2)_r NR^{11a} C(O)R^{11b}$, $(CH_2)_q NR^{11a} C(O)NR^{11a} R^{11a}$, $(CH_2)_r C(O)OR^{11a}$, $(CH_2)_q OC(O) R^{11b}$, $(CH_2)_q S(O)_p R^{11b}$, $(CH_2)_q S(O)_2 NR^{11a} R^{11a'}$, $(CH_2)_q NR^{11a} S(O)_2 R^{11b}$, $C_{1-6}$ haloalkyl, a $(CH_2)_r$—$C_{3-10}$ carbocyclic residue substituted with 0-5 $R^{11c}$, and a $(CH_2)_r$-5-10 membered heterocyclic system containing 1-4 heteroatoms selected from N, O, and S, substituted with 0-3 $R^{11c}$;

$R^{11a}$ and $R^{11a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{11e}$, and a $(CH_2)_r$-5-10 membered heterocyclic system containing 1-4 heteroatoms selected from N, O, and S, substituted with 0-3 $R^{11e}$;

$R^{11b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0-2 $R^{11e}$, and a $(CH_2)_r$-5-6 membered heterocyclic system containing 1-4 heteroatoms selected from N, O, and S, substituted with 0-3 $R^{11e}$;

$R^{11c}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, Br, I, F, $(CF_2)_r CF_3$, $NO_2$, CN, $(CH_2)_r NR^{11f} R^{11f}$, $(CH_2)_r OH$, $(CH_2)_r$ $OC_{1-4}$ alkyl, $(CH_2)_r SC_{1-4}$ alkyl, $(CH_2)_r C(O)OH$, $(CH_2)_r C(O)R^{11b}$, $(CH_2)_r C(O)NR^{11f} R^{11f}$, $(CH_2)_r NR^{11f} C(O)R^{11a}$, $(CH_2)_r C(O)OC_{1-4}$ alkyl, $(CH_2)_r OC(O)R^{11b}$, $(CH_2)_r C(=NR^{11f})NR^{11f} R^{11f}$, $(CH_2)_r NHC(=NR^{11f}) NR^{11f} R^{11f}$, $(CH_2)_r S(O)_p R^{11b}$, $(CH_2)_r S(O)_2 NR^{11f} R^{11f}$, $(CH_2)_r NR^{11f} S(O)_2 R^{11b}$, and $(CH_2)_r$phenyl substituted with 0-3 $R^{11e}$;

$R^{11d}$, at each occurrence, is selected from methyl, $CF_3$, $C_{1-6}$ alkyl substituted with 0-3 $R^{11e}$, $C_{3-6}$ alkenyl, $C_{3-6}$ alkynyl, and a $C_{3-10}$ carbocyclic residue substituted with 0-3 $R^{11c}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-5}$ alkyl, $(CH_2)_r NR^{11f} R^{11f}$, and $(CH_2)_r$phenyl;

$R^{11f}$, at each occurrence, is selected from H, $C_{1-6}$ alkyl, and $C_{3-6}$ cycloalkyl;

$R^{12}$ is selected from H, $C_{1-6}$ alkyl, $(CH_2)_q OH$, $(CH_2)_r C_{3-6}$ cycloalkyl, and $(CH_2)_r$phenyl substituted with 0-3 $R^{12a}$;

$R^{12a}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-5}$ alkyl, $(CH_2)_r NR^{9f} R^{9f}$, and $(CH_2)_r$phenyl;

alternatively, $R^{11}$ and $R^{12}$ join to form $C_{3-7}$ cycloalkyl;

$R^{14}$ is selected from $C_{1-4}$ alkyl, $C_{2-8}$ alkenyl, $C_{2-8}$ alkynyl, $(CH_2)_r C_{3-6}$ cycloalkyl, $C(O)NR^{14a} R^{14a'}$, $C(O)R^{14b}$, $C(O)OC_{1-4}$ alkyl, $(CH_2)_r S(O)_p R^{14b}$, $(CH_2)_r$phenyl substituted with 0-3 $R^{14c}$, $OR^{14a}$, $NR^{14a} R^{14a'}$, =O, and $NR^{14a} C(O) R^{14a'}$;

$R^{14a}$ and $R^{14a'}$, at each occurrence, are selected from H, $C_{1-6}$ alkyl, $(CH_2)_r C_{3-6}$ cycloalkyl, and $(CH_2)_r$phenyl substituted with 0-3 $R^{14c}$, and a $(CH_2)_r$-5-10 membered heterocyclic system containing 1-4 heteroatoms selected from N, O, and S, substituted with 0-2 $R^{14c}$;

$R^{14b}$, at each occurrence, is selected from $C_{1-6}$ alkyl, $(CH_2)_r$ $C_{3-6}$ cycloalkyl, and $(CH_2)_r$phenyl substituted with 0-3 $R^{14c}$, and a $(CH_2)_r$-5-10 membered heterocyclic system containing 1-4 heteroatoms selected from N, O, and S, substituted with 0-2 $R^{14c}$; and $R^{14c}$, at each occurrence, is selected from $C_{1-6}$ alkyl, $(CH_2)_r$ $C_{3-6}$ cycloalkyl, Cl, F, Br, I, CN, $NO_2$, $(CF_2)_r CF_3$, $(CH_2)_r$ $OC_{1-5}$ alkyl, OH, $(CH_2)_w$phenyl;

$R^{15}$, at each occurrence, is selected from $C_{1-8}$ alkyl, $(CH_2)_r$ $C_{3-6}$ cycloalkyl, Cl, Br, I, F, $NO_2$, CN, $(CHR')_r NR^{15a} R^{15a'}$, $(CHR')_r OH$, $(CHR')_r O(CHR')_r R^{15d}$, $(CHR')_r SH$, $(CHR')_r$ $C(O)H$, $(CHR')_r S(CHR')_r R^{15d}$, $(CHR')_r C(O)OH$, $(CHR')_r$ $C(O)(CHR')_r R^{15b}$, $(CHR')_r C(O)NR^{15a} R^{15a'}$, $(CHR')_r$ $NR^{15f} C(O)(CHR')_r R^{15b}$, $(CHR')_r NR^{15f} C(O) NR^{15a} R^{15a'}$, $(CHR')_r C(O)O(CHR')_r R^{15d}$, $(CHR')_r OC(O)(CHR')_r R^{15b}$, $(CHR')_r C(=NR^{15f}) NR^{15a} R^{15a'}$, $(CHR')_r NHC(=NR^{15f})$ $NR^{15a} R^{15a'}$, $(CHR')_r S(O)_p (CHR')_r R^{15b}$, $(CHR')_r S(O)_2$ $NR^{15a} R^{15a'}$, $(CHR')_r NR^{15f} S(O)_2 (CHR')_r R^{15b}$, $C_{1-6}$ haloalkyl, $C_{2-8}$ alkenyl substituted with 0-3 R', $C_{2-8}$ alkynyl substituted with 0-3 R', $(CHR')_r$phenyl substituted with 0-3 $R^{15e}$, and a $(CH_2)_r$-5-10 membered heterocyclic system containing 1-4 heteroatoms selected from N, O, and S, substituted with 0-2 $R^{15e}$;

R', at each occurrence, is selected from H, $C_{1-6}$ alkyl, $C_{2-8}$ alkenyl, $C_{2-8}$ alkynyl, $(CH_2)_r C_{3-6}$ cycloalkyl, and $(CH_2)_r$ phenyl substituted with $R^{15e}$;

$R^{15a}$ and $R^{15a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{15e}$, and a $(CH_2)_r$-5-10 membered heterocyclic system containing 1-4 heteroatoms selected from N, O, and S, substituted with 0-2 $R^{15e}$;

$R^{15b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0-3 $R^{15e}$, and $(CH_2)_r$-5-6 membered heterocyclic system containing 1-4 heteroatoms selected from N, O, and S, substituted with 0-2 $R^{15e}$;

$R^{15d}$, at each occurrence, is selected from $C_{3-8}$ alkenyl, $C_{3-8}$ alkynyl, methyl, $CF_3$, $C_{1-6}$ alkyl substituted with 0-3 $R^{15e}$, a $(CH_2)_r$—$C_{3-10}$ carbocyclic residue substituted with 0-3 $R^{15e}$, and a $(CH_2)_r$ 5-6 membered heterocyclic system containing 1-4 heteroatoms selected from N, O, and S, substituted with 0-3 $R^{15e}$;

$R^{15e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{15f}R^{15f}$, and $(CH_2)_r$phenyl;

$R^{15f}$, at each occurrence, is selected from H, $C_{1-6}$ alkyl, $C_{3-6}$ cycloalkyl, and phenyl;

$R^{16}$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{16a}R^{16a'}$, $(CHR')_rOH$, $(CHR')_rO$ $(CHR')_rR^{16d}$, $(CHR')_rSH$, $(CHR')_rC(O)H$, $(CHR')_rS$ $(CHR')_rR^{16d}$, $(CHR')_rC(O)OH$, $(CHR')_rC(O)(CHR')_r$ $R^{16b}$, $(CHR')_rC(O)NR^{16a}R^{16a'}$, $(CHR')_rNR^{16f}C(O)$ $(CHR')_rR^{16b}$, $(CHR')_rC(O)O(CHR')_rR^{16d}$, $(CHR')_rOC(O)$ $(CHR')_r$ $R^{16b}$, $(CHR')_rC(=NR^{16f})NR^{16a}R^{16a'}$, $(CHR')_r$ $NHC(=NR^{16f})NR^{16a}R^{16a'}$, $(CHR')_rS(O)_p(CHR')_rR^{16b}$, $(CHR')_r$ $S(O)_2NR^{16a}R^{16a'}$, $(CHR')_rNR^{16f}S(O)_2(CHR')_r$ $R^{16b}$, $C_{1-6}$ haloalkyl, $C_{2-8}$ alkenyl substituted with 0-3 R', $C_{2-8}$ alkynyl substituted with 0-3 R', and $(CHR')_r$phenyl substituted with 0-3 $R^{16e}$;

$R^{16a}$ and $R^{16a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{16e}$, and a $(CH_2)_r$-5-10 membered heterocyclic system containing 1-4 heteroatoms selected from N, O, and S, substituted with 0-2 $R^{16e}$;

$R^{16b}$, at each occurrence, is selected from $C_{1-6}$ alkyl, $C_{2-8}$ alkenyl, $C_{2-8}$ alkynyl, a $(CH_2)_rC_{3-6}$ carbocyclic residue substituted with 0-3 $R^{16e}$, and a $(CH_2)_r$-5-6 membered heterocyclic system containing 1-4 heteroatoms selected from N, O, and S, substituted with 0-2 $R^{16e}$;

$R^{16d}$, at each occurrence, is selected from $C_{3-8}$ alkenyl, $C_{3-8}$ alkynyl, methyl, $CF_3$, $C_{1-6}$ alkyl substituted with 0-3 $R^{16e}$, a $(CH_2)_r$—$C_{3-10}$ carbocyclic residue substituted with 0-3 $R^{16e}$, and a $(CH_2)_r$-5-6 membered heterocyclic system containing 1-4 heteroatoms selected from N, O, and S, substituted with 0-3 $R^{16e}$;

$R^{16e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{16f}R^{16f}$, and $(CH_2)_r$phenyl;

$R^{16f}$, at each occurrence, is selected from H, $C_{1-5}$ alkyl, and $C_{3-6}$ cycloalkyl, and phenyl;

$R^{17}$, is selected from H, $C_{1-6}$ alkyl, $C_{2-8}$ alkenyl, $C_{2-8}$ alkynyl, $(CH_2)_qOH$, $(CH_2)_qSH$, $(CH_2)_qOR^{17d}$, $(CH_2)_qSR^{17d}$, $(CH_2)_qNR^{17a}R^{17a'}$, $(CH_2)_rC(O)OH$, $(CH_2)_rC(O)R^{17b}$, $(CH_2)_rC(O)NR^{17a}R^{17a'}$, $(CH_2)_qNR^{17a}C(O)R^{17b}$, $(CH_2)_q$ $NR^{17a}C(O)H$, $(CH_2)_rC(O)OR^{17a}$, $(CH_2)_qOC(O)R^{17b}$, $(CH_2)_qS(O)_pR^{17b}$, $(CH_2)_qS(O)_2NR^{17a}R^{17a'}$, $(CH_2)_q$ $NR^{17a}S(O)_2R^{17b}$, $C_{1-6}$ haloalkyl, a $(CH_2)_r$—$C_{3-10}$ carbocyclic residue substituted with 0-3 $R^{17c}$, and a $(CH_2)_r$-5-10 membered heterocyclic system containing 1-4 heteroatoms selected from N, O, and S, substituted with 0-2 $R^{17c}$;

$R^{17a}$ and $R^{17a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{17e}$, and a $(CH_2)_r$-5-10 membered heterocyclic system containing 1-4 heteroatoms selected from N, O, and S, substituted with 0-3 $R^{17e}$;

$R^{17b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0-2 $R^{17e}$, and a $(CH_2)_r$-5-6 membered heterocyclic system containing 1-4 heteroatoms selected from N, O, and S, substituted with 0-3 $R^{17e}$;

$R^{17c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{17f}R^{17f}$, $(CH_2)_rOH$, $(CH_2)_r$ $OC_{1-4}$ alkyl, $(CH_2)_rSC_{1-4}$ alkyl, $(CH_2)_rC(O)OH$, $(CH_2)_rC(O)R^{17b}$, $(CH_2)_rC(O)NR^{17f}R^{17f}$, $(CH_2)_rNR^{17f}C$ $(O)R^{17a}$, $(CH_2)_rC(O)OC_{1-4}$ alkyl, $(CH_2)_rOC(O)R^{17b}$, $(CH_2)_rC(=NR^{17f})NR^{17f}R^{17f}$, $(CH_2)_rS(O)_pR^{17b}$, $(CH_2)_r$ $NHC(=NR^{17f})NR^{17f}R^{17f}$, $(CH_2)_rS(O)_2NR^{17f}R^{17f}$, $(CH_2)_r$ $NR^{17f}S(O)_2R^{17b}$, and $(CH_2)_r$phenyl substituted with 0-3 $R^{17e}$;

$R^{17d}$, at each occurrence, is selected from $C_{1-6}$ alkyl substituted with 0-3 $R^{17e}$, $C_{3-6}$ alkenyl, $C_{3-6}$ alkynyl, and a $C_{3-10}$ carbocyclic residue substituted with 0-3 $R^{17c}$;

$R^{17e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{17f}R^{17f}$, and $(CH_2)_r$phenyl;

$R^{17f}$, at each occurrence, is selected from H, $C_{1-6}$ alkyl, and $C_{3-6}$ cycloalkyl;

$R^{18}$, is selected from H, $C_{1-6}$ alkyl, $C_{2-8}$ alkenyl, $C_{2-8}$ alkynyl, $(CH_2)_qOH$, $(CH_2)_qSH$, $(CH_2)_qOR^{18d}$, $(CH_2)_qSR^{18d}$, $(CH_2)_qNR^{18a}R^{18a'}$, $(CH_2)_rC(O)OH$, $(CH_2)_rC(O)R^{18b}$, $(CH_2)_rC(O)NR^{18a}R^{18a'}$, $(CH_2)_qNR^{18a}C(O)R^{18b}$, $(CH_2)_q$ $NR^{18a}C(O)H$, $(CH_2)_rC(O)OR^{18a}$, $(CH_2)_qOC(O)R^{18b}$, $(CH_2)_qS(O)_pR^{18b}$, $(CH_2)_qS(O)_2NR^{18a}R^{18a'}$, $(CH_2)_q$ $NR^{18a}S(O)_2R^{18b}$, $C_{1-6}$ haloalkyl, a $(CH_2)_r$—$C_{3-10}$ carbocyclic residue substituted with 0-3 $R^{18c}$, and a $(CH_2)_r$-5-10 membered heterocyclic system containing 1-4 heteroatoms selected from N, O, and S, substituted with 0-2 $R^{18c}$;

$R^{18a}$ and $R^{18a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{18e}$, and a $(CH_2)_r$-5-10 membered heterocyclic system containing 1-4 heteroatoms selected from N, O, and S, substituted with 0-3 $R^{18e}$;

$R^{18b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0-2 $R^{18e}$, and a $(CH_2)_r$-5-6 membered heterocyclic system containing 1-4 heteroatoms selected from N, O, and S, substituted with 0-3 $R^{18e}$;

$R^{18c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{18f}R^{18f}$, $(CH_2)_rOH$, $(CH_2)_r$ $OC_{1-4}$ alkyl, $(CH_2)_rSC_{1-4}$ alkyl, $(CH_2)_rC(O)OH$, $(CH_2)_rC(O)R^{18b}$, $(CH_2)_rC(O)NR^{18f}R^{18f}$, $(CH_2)_rNR^{18f}C$ $(O)R^{18b}$, $(CH_2)_rC(O)OC_{1-4}$ alkyl, $(CH_2)_rOC(O)R^{18b}$, $(CH_2)_rC(=NR^{18f})NR^{18f}R^{18f}$, $(CH_2)_rS(O)_pR^{18b}$, $(CH_2)_r$ $NHC(=NR^{18f})NR^{18f}R^{18f}$, $(CH_2)_rS(O)_2NR^{18f}R^{18f}$, $(CH_2)_r$ $NR^{18f}S(O)_2R^{18b}$, and $(CH_2)_r$phenyl substituted with 0-3 $R^{18e}$;

$R^{18d}$, at each occurrence, is selected from methyl, $CF_3$, $C_{1-6}$ alkyl substituted with 0-3 $R^{18e}$, $C_{3-6}$ alkenyl, $C_{3-6}$ alkynyl, and a $C_{3-10}$ carbocyclic residue substituted with 0-3 $R^{18c}$;

$R^{18e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{18f}R^{18f}$, and $(CH_2)_r$phenyl;

$R^{18f}$, at each occurrence, is selected from H, $C_{1-6}$ alkyl, and $C_{3-6}$ cycloalkyl;

a is selected from 0 and 1;

b is selected from 0 and 1, wherein if a=0, then b=1;

c is selected from 0, 1, and 2;

d is selected from 0, 1, and 2, wherein c+d equals 1 or 2;

e is selected from 0 and 1;

f is selected from 0 and 1, wherein e+f equals 1 or 2;

g is selected from 0, 1, 2 and 3;
h is selected from 0 and 1;
i is selected from 0, 1, 2, 3, 4, and 5;
j is selected from 0, 1, 2, 3, 4, and 5;
k is selected from 0, 1, and 2;
l is selected from 0, 1, 2 and 3, wherein l+h equals 2 or 3;
v, at each occurrence, is independently selected from 0, 1, and 2;
t is selected from 1 and 2;
w is selected from 0 and 1;
r is selected from 0, 1, 2, 3, 4, and 5;
s is selected from 0, 1, 2, 3, 4, and 5;
q is selected from 1, 2, 3, 4, and 5; and
p is selected from 1 and 2.

In another embodiment, the present invention provides method of modulating chemokine receptor by administering a compound of formula (I), wherein:

[32] In another embodiment, method of modulating chemokine receptor by administering a compound of formula (I), wherein:

$R^4$ is absent or, taken with the nitrogen to which it is attached to form an N-oxide;

$R^7$, is selected from H, $C_{1-6}$ alkyl, $C_{2-8}$ alkenyl, $C_{2-8}$ alkynyl, $(CH_2)_qOH$, $(CH_2)_qOR^{7d}$, $(CH_2)_qNR^{7a}R^{7a'}$, $(CH_2)_rC(O)R^{7b}$, $(CH_2)_rC(O)NR^{7a}R^{7a'}$, $(CH_2)_qNR^{7a}C(O)R^{7a}$, $(CH_2)_q NR^{7a}C(O)H$, $(CH_2)_qS(O)_2NR^{7a}R^{7a'}$, $(CH_2)_qNR^{7a}S(O)_2 R^{7b}$, $(CH_2)_qNHC(O)NHR^{7a}$, $(CH_2)_qNHC(O)OR^{7a}$, $(CH_2)_q OC(O)NHR^{7a}$, $C_{1-6}$ haloalkyl, a $(CH_2)_r$—$C_{3-10}$ carbocyclic residue substituted with 0-3 $R^{7c}$, and a $(CH_2)_r$-5-10 membered heterocyclic system containing 1-4 heteroatoms selected from N, O, and S, substituted with 0-2 $R^{7c}$;

alternatively, $R^7$ and $R^8$ join to form $C_{3-7}$ cycloalkyl, $=NR^{8b}$, or $=O$;

$R^9$, is selected from H, $C_{1-6}$ alkyl, $C_{2-8}$ alkenyl, $C_{2-8}$ alkynyl, $(CH_2)_rOH$, $(CH_2)_rOR^{9d}$, $(CH_2)_rNR^{9a}R^{9a'}$, $(CH_2)_rC(O)R^{9b}$, $(CH_2)_rC(O)NR^{9a}R^{9a'}$, $(CH_2)_rNR^{9a}C(O)R^{9b}$, $(CH_2)_r NR^{9a}C(O)H$, $(CH_2)_rNR^{9a}C(O)NHR^{9a}$, $(CH_2)_rNR^{9a}S(O)_2 R^{9b}$, $C_{1-6}$ haloalkyl, a $(CH_2)_r$—$C_{3-10}$ carbocyclic residue substituted with 0-5 $R^{9c}$, and a $(CH_2)_r$-5-10 membered heterocyclic system containing 1-4 heteroatoms selected from N, O, and S, substituted with 0-3 $R^{9c}$;

$R^{10}$, is selected from H, $C_{1-6}$ alkyl, $C_{2-8}$ alkenyl, $C_{2-8}$ alkynyl;

$R^{11}$, is selected from H, $C_{1-6}$ alkyl, $C_{2-8}$ alkenyl, $C_{2-8}$ alkynyl, $(CH_2)_qOH$, $(CH_2)_qOR^{11d}$, $(CH_2)_qNR^{11a}R^{11a'}$, $(CH_2)_rC(O)R^{11b}$, $(CH_2)_rC(O)NR^{11a}R^{11a'}$, $(CH_2)_qNR^{11a}C(O)R^{11a}$, $(CH_2)_qNR^{11a}C(O)NHR^{11a}$, $(CH_2)_qNHC(O)NHR^{7a}$, $(CH_2)_qNHC(O)OR^{7a}$, $(CH_2)_qOC(O)NHR^{7a}$, $C_{1-6}$ haloalkyl, a $(CH_2)_r$—$C_{3-10}$ carbocyclic residue substituted with 0-5 $R^{11c}$, and a $(CH_2)_r$-5-10 membered heterocyclic system containing 1-4 heteroatoms selected from N, O, and S, substituted with 0-3 $R^{11c}$.

[33] In another embodiment, the present invention provides a method of modulating chemokine receptor by administering a compound of formula (I), wherein:

E is selected from —$(CR^7R^8)$—$(CR^9R^{10})_v$—$(CR^{11}R^{12})$,

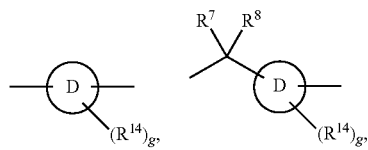

-continued

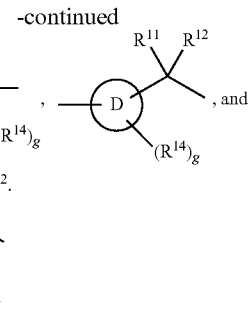

[34] In another embodiment, the present invention provides a method of modulating chemokine receptor by administering a compound of formula (I), wherein:

G is selected from —$C(O)R^3$, —$C(O)NR^2R^3$, —$C(O)OR^3$, —$SO_2NR^2R^3$, —$SO_2R^3$, —$C(=S)NR^2R^3$, $C(=NR^{1a})NR^2R^3$, $C(=CHCN)NR^2R^3$, $C(=CHNO_2)NR^2R^3$, $C(=C(CN)_2)NR^2R^3$, and

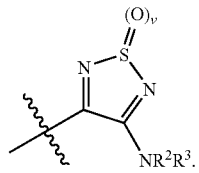

[35] In another embodiment, the present invention provides a method of modulating chemokine receptor by administering a compound of formula (I), wherein:

$R^{17}$ is selected from H;
$R^{18}$ is selected from H;
j is selected from 0, 1, and 2;
i is selected from 1 and 2;
s is selected from 0, 1, and 2; and
g is selected from 0, 1, and 2.

[36] In another embodiment, the present invention provides a method of modulating chemokine receptor by administering a compound of formula (I), wherein:

$R^1$ is selected from H;
$R^2$ is selected from H; and
G is selected from —$C(O)NR^2R^3$, $C(=CHCN)NR^2R^3$, $C(=CHNO_2)NR^2R^3$, and $C(=C(CN)_2)NR^2R^3$.

[37] In a further embodiment, the present invention provides a method of modulating chemokine receptor by administering a compound of formula (I), wherein:

E is selected from —$(CR^7R^8)$—$(CR^9R^{10})_v$—$(CR^{11}R^{12})$.

[38] In a further embodiment, the present invention provides a method of modulating chemokine receptor by administering a compound of formula (I), wherein:

$R^7$ is selected from H;
$R^8$ is selected from H; and
$R^{12}$ is selected from H.

[39] In a further embodiment, the present invention provides a method of modulating chemokine receptor by administering a compound of formula (I), wherein:

$R^{16}$, at each occurrence, is selected from methyl, ethyl, propyl, iso-propyl, $C_{2-8}$ alkenyl, $C_{2-8}$ alkynyl, $(CH_2)_rC_{3-6}$ cycloalkyl, Cl, Br, F, CN, $(CHR')_rNR^{16a}R^{16a'}$, $(CHR')_rOH$, $(CHR')_rO(CHR')_rR^{16d}$, $(CHR')_rC(O)(CHR')_rR^{16b}$, $(CHR')_r C(O)NR^{16a}R^{16a'}$, $(CHR')_rNR^{16f}C(O)(CHR')_r R^{16b}$, $(CHR')_rS(O)_p(CHR')_rR^{16b}$, $(CHR')_rS(O)_2 NR^{16a}R^{16a'}$, $(CHR')_rNR^{16f}S(O)_2(CHR')_rR^{16b}$, $C_{1-6}$ haloalkyl, and $(CHR')_r$phenyl substituted with 0-3 $R^{16e}$;

$R^{16a}$ and $R^{16a'}$, at each occurrence, are selected from H, methyl, ethyl, and a $(CH_2)_r$—$C_{3-6}$ carbocyclic residue substituted with 0-2 $R^{16e}$;

$R^{16e}$, at each occurrence, is selected from methyl, ethyl, Cl, F, Br, I, CN, $CF_3$, and $OCH_3$;

$R^{16f}$, at each occurrence, is selected from H; and r is selected from 0, 1, and 2.

[40] In another embodiment, the present invention provides a method of modulating chemokine receptor by administering a compound of formula (I), wherein:

$R^3$ is selected from a $(CR^{3'}R^{3''})_r$—$C_{3-6}$ carbocyclic residue substituted with 0-2 $R^{15}$;

$R^{3'}$ and $R^{3''}$, at each occurrence, are selected from H;

$R^{15}$, at each occurrence, is selected from $C_{1-8}$ alkyl, $(CH_2)_r$ $C_{3-6}$ cycloalkyl, Cl, Br, F, CN, $(CHR')_r NR^{15a}R^{15a'}$, $(CHR')_r$ OH, $(CHR')_r O(CHR')_r R^{15d}$, $(CHR')_r C(O)(CHR')_r R^{15b}$, $(CHR')_r C(O)NR^{15a}R^{15a'}$, $(CHR')_r NR^{15f}C(O)(CHR')_r R^{15b}$, $(CHR')_r NR^{15f}C(O)NR^{15a}R^{15a'}$, $(CHR')_r C(O)O(CHR')_r R^{15d}$, $(CHR')_r OC(O)(CHR')_r R^{15b}$, $(CHR')_r S(O)_p(CHR')_r R^{15b}$, $(CHR')_r S(O)_2 NR^{15a}R^{15a'}$, $(CHR')_r NR^{15f}S(O)_2(CHR')_r R^{15b}$, $C_{1-6}$ haloalkyl, $C_{2-8}$ alkenyl substituted with 0-3 R', $C_{2-8}$ alkynyl substituted with 0-3 R', $(CHR')_r$ phenyl substituted with 0-3 $R^{15e}$, and a $(CH_2)_r$-5-10 membered heterocyclic system containing 1-4 heteroatoms selected from N, O, and S, substituted with 0-2 $R^{15e}$;

R', at each occurrence, is selected from H, and $C_{1-6}$ alkyl;

$R^{15a}$ and $R^{15a'}$, at each occurrence, are selected from H, $C_{1-6}$ alkyl, a $(CH_2)_r$—$C_{3-6}$ carbocyclic residue substituted with 0-5 $R^{15e}$, and a $(CH_2)_r$-5-6 membered heterocyclic system containing 1-2 heteroatoms selected from N, O, and S, substituted with 0-2 $R^{15e}$;

$R^{15b}$, at each occurrence, is selected from $C_{1-6}$ alkyl, a $(CH_2)_r$—$C_{3-6}$ carbocyclic residue substituted with 0-3 $R^{15e}$, and $(CH_2)_r$-5-6 membered heterocyclic system containing 1-2 heteroatoms selected from N, O, and S, substituted with 0-2 $R^{15e}$; and $R^{15e}$, at each occurrence, is selected from $C_{1-6}$ alkyl, Cl, F, Br, I, CN, $(CF_2)_r CF_3$, and OH.

[41] In a further embodiment, the present invention provides a method of modulating chemokine receptor by administering a compound of formula (I), wherein:

E is

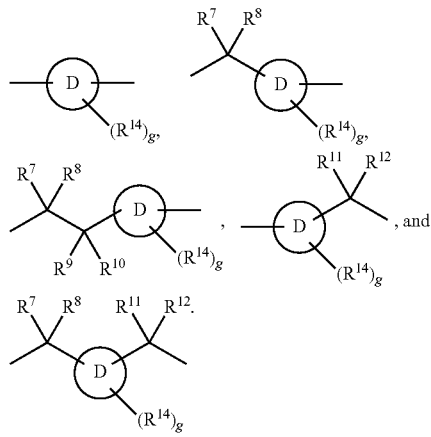

[42] In a further embodiment, the present invention provides a method of modulating chemokine receptor by administering a compound of formula (I), wherein:

E is

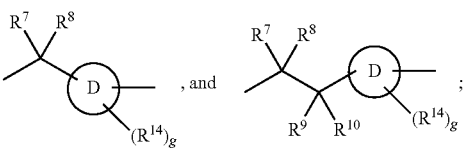

ring D is selected from a $C_{3-6}$ carbocyclic residue;

$R^7$ is selected from H; and $R^8$ is selected from H.

[43] In a further embodiment, the present invention provides a method of modulating chemokine receptor by administering a compound of formula (I), wherein:

$R^{16}$, at each occurrence, is selected from methyl, ethyl, propyl, iso-propyl, $C_{2-8}$ alkenyl, $C_{2-8}$ alkynyl, $(CH_2)_r C_{3-6}$ cycloalkyl, Cl, Br, I, F, CN, $(CHR')_r NR^{16a}R^{16a'}$, $(CHR')_r$ OH, $(CHR')_r O(CHR')_r R^{16d}$, $(CHR')_r C(O)(CHR')_r R^{16b}$, $(CHR')_r C(O)NR^{16a}R^{16a'}$, $(CHR')_r NR^{16f}C(O)(CHR')_r R^{16b}$, $(CHR')_r S(O)_p(CHR')_r R^{16b}$, $(CHR')_r S(O)_2 NR^{16a}R^{16a'}$, $(CHR')_r NR^{16f}S(O)_2(CHR')_r R^{16b}$, $C_{1-6}$ haloalkyl, and $(CHR')_r$ phenyl substituted with 0-3 $R^{16e}$;

$R^{16a}$ and $R^{16a'}$, at each occurrence, are selected from H, methyl, ethyl, and a $(CH_2)_r$—$C_{3-6}$ carbocyclic residue substituted with 0-2 $R^{16e}$;

$R^{16e}$, at each occurrence, is selected from methyl, ethyl, Cl, F, Br, I, CN, $CF_3$, and $OCH_3$;

$R^{16f}$, at each occurrence, is selected from H; and r is selected from 0, 1, and 2.

[44] In another embodiment, the present invention provides a method of modulating chemokine receptor by administering a compound of formula (I), wherein:

$R^3$ is selected from a $(CR^{3'}R^{3''})_r$—$C_{3-6}$ carbocyclic residue substituted with 0-2 $R^{15}$;

$R^{3'}$ and $R^{3''}$, at each occurrence, are selected from H;

$R^{15}$, at each occurrence, is selected from $C_{1-8}$ alkyl, $(CH_2)_r$ $C_{3-6}$ cycloalkyl, Cl, Br, F, CN, $(CHR')_r NR^{15a}R^{15a'}$, $(CHR')_r$ OH, $(CHR')_r O(CHR')_r R^{15d}$, $(CHR')_r C(O)(CHR')_r R^{15b}$, $(CHR')_r C(O)NR^{15a}R^{15a'}$, $(CHR')_r NR^{15f}C(O)(CHR')_r R^{15b}$, $(CHR')_r NR^{15f}C(O)NR^{15a}R^{15a'}$, $(CHR')_r C(O)O(CHR')_r R^{15d}$, $(CHR')_r OC(O)(CHR')_r R^{15b}$, $(CHR')_r S(O)_p(CHR')_r R^{15b}$, $(CHR')_r S(O)_2 NR^{15a}R^{15a'}$, $(CHR')_r NR^{15f}S(O)_2(CHR')_r R^{15b}$, $C_{1-6}$ haloalkyl, $C_{2-8}$ alkenyl substituted with 0-3 R', $C_{2-8}$ alkynyl substituted with 0-3 R', $(CHR')_r$ phenyl substituted with 0-3 $R^{15e}$, and a $(CH_2)_r$-5-10 membered heterocyclic system containing 1-4 heteroatoms selected from N, O, and S, substituted with 0-2 $R^{15e}$;

R', at each occurrence, is selected from H, and $C_{1-6}$ alkyl;

$R^{15a}$ and $R^{15a'}$, at each occurrence, are selected from H, $C_{1-6}$ alkyl, a $(CH_2)_r$—$C_{3-6}$ carbocyclic residue substituted with 0-5 $R^{15e}$, and a $(CH_2)_r$-5-6 membered heterocyclic system containing 1-2 heteroatoms selected from N, O, and S, substituted with 0-2 $R^{15e}$;

$R^{15b}$, at each occurrence, is selected from $C_{1-6}$ alkyl, a $(CH_2)_r$—$C_{3-6}$ carbocyclic residue substituted with 0-3 $R^{15e}$, and $(CH_2)_r$-5-6 membered heterocyclic system containing 1-2 heteroatoms selected from N, O, and S, substituted with 0-2 $R^{15e}$; and $R^{15e}$, at each occurrence, is selected from $C_{1-6}$ alkyl, Cl, F, Br, I, CN, $(CF_2)_r CF_3$, and OH.

[45] In another embodiment, the present invention provides a method of modulating chemokine receptor by administering a compound of formula (I), wherein:

G is selected from

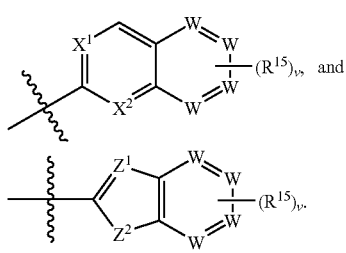

[46] In another embodiment, the present invention provides a method of modulating chemokine receptor by administering a compound of formula (I), wherein:
$R^1$ is selected from H;
both $X^1$ and $X^2$ cannot be C; and
$Z^2$ is selected from NR1', O, and S.

[47] In another embodiment, the present invention provides a method of modulating chemokine receptor by administering a compound of formula (I), wherein:
$R^{17}$ is selected from H;
$R^{18}$ is selected from H;
j is selected from 0, 1, and 2;
i is selected from 1 and 2;
s is selected from 0, 1, and 2; and
g is selected from 0, 1, and 2.

[48] In a further embodiment, the present invention provides a method of modulating chemokine receptor by administering a compound of formula (I), wherein:
E is selected from —$(CR^7R^8)$—$(CR^9R^{10})_v$—$(CR^{11}R^{12})$.

[49] In a further embodiment, the present invention provides a method of modulating chemokine receptor by administering a compound of formula (I), wherein:
$R^7$ is selected from H;
$R^8$ is selected from H; and
$R^{12}$ is selected from H.

[50] In a further embodiment, the present invention provides a method of modulating chemokine receptor by administering a compound of formula (I), wherein:
$R^{16}$, at each occurrence, is selected from methyl, ethyl, propyl, iso-propyl, $C_{2-8}$ alkenyl, $C_{2-8}$ alkynyl, $(CH_2)_rC_{3-6}$ cycloalkyl, Cl, Br, I, F, CN, (CHR')$_r$NR$^{16a}$R$^{16a'}$, (CHR')$_r$OH, (CHR')$_r$O(CHR')$_r$R$^{16d}$, (CHR')$_r$C(O)(CHR')$_r$R$^{16b}$, (CHR')$_r$C(O)NR$^{16a}$R$^{16a'}$, (CHR')$_r$NR$^{16f}$C(O)(CHR')$_r$R$^{16b}$, (CHR')$_r$S(O)$_p$(CHR')$_r$R$^{16b}$, (CHR')$_r$S(O)$_2$NR$^{16a}$R$^{16a'}$, (CHR')$_r$NR$^{16f}$S(O)$_2$(CHR')$_r$R$^{16b}$, $C_{1-6}$ haloalkyl, and (CHR')$_r$phenyl substituted with 0-3 R$^{16e}$;
$R^{16a}$ and $R^{16a'}$, at each occurrence, are selected from H, methyl, ethyl, and a $(CH_2)_r$—$C_{3-6}$ carbocyclic residue substituted with 0-2 $R^{16e}$;
$R^{16e}$, at each occurrence, is selected from methyl, ethyl, Cl, F, Br, I, CN, $CF_3$, and $OCH_3$;
$R^{16f}$, at each occurrence, is selected from H; and
r is selected from 0, 1, and 2.

[51] In another embodiment, the present invention provides a method of modulating chemokine receptor by administering a compound of formula (I), wherein:
$R^3$ is selected from a $(CR^{3'}R^{3''})_r$—$C_{3-6}$ carbocyclic residue substituted with 0-2 $R^{15}$;
$R^{3'}$ and $R^{3''}$, at each occurrence, are selected from H;
$R^{15}$, at each occurrence, is selected from $C_{1-8}$ alkyl, $(CH_2)_r$ $C_{3-6}$ cycloalkyl, Cl, Br, F, CN, (CHR')$_r$NR$^{15a}$R$^{15a'}$, (CHR')$_r$OH, (CHR')$_r$O(CHR')$_r$R$^{15d}$, (CHR')$_r$C(O) (CHR')$_r$ R$^{15b}$, (CHR')$_r$C(O)NR$^{15a}$R$^{15a'}$, (CHR')$_r$NR$^{15f}$C (O)(CHR')$_r$ R$^{15b}$, (CHR')$_r$NR$^{15f}$C(O)NR$^{15a}$R$^{15a'}$, (CHR')$_r$C(O)O(CHR')$_r$R$^{15d}$, (CHR')$_r$OC(O)(CHR')$_r$R$^{15b}$, (CHR')$_r$S(O)$_p$(CHR')$_r$R$^{15b}$, (CHR')$_r$S(O)$_2$NR$^{15a}$R$^{15a'}$, (CHR')$_r$NR$^{15f}$S(O)$_2$(CHR')$_r$R$^{15b}$, $C_{1-6}$ haloalkyl, $C_{2-8}$ alkenyl substituted with 0-3 R', $C_{2-8}$ alkynyl substituted with 0-3 R', (CHR')$_r$phenyl substituted with 0-3 $R^{15e}$, and a $(CH_2)_r$-5-10 membered heterocyclic system containing 1-4 heteroatoms selected from N, O, and S, substituted with 0-2 $R^{15e}$;
R', at each occurrence, is selected from H, and $C_{1-6}$ alkyl;
$R^{15a}$ and $R^{15a'}$, at each occurrence, are selected from H, $C_{1-6}$ alkyl, a $(CH_2)_r$—$C_{3-6}$ carbocyclic residue substituted with 0-5 $R^{15e}$, and a $(CH_2)_r$-5-6 membered heterocyclic system containing 1-2 heteroatoms selected from N, O, and S, substituted with 0-2 $R^{15e}$;
$R^{15b}$, at each occurrence, is selected from $C_{1-6}$ alkyl, a $(CH_2)_r$—$C_{3-6}$ carbocyclic residue substituted with 0-3 $R^{15e}$, and $(CH_2)_r$-5-6 membered heterocyclic system containing 1-2 heteroatoms selected from N, O, and S, substituted with 0-2 $R^{15e}$; and
$R^{15e}$, at each occurrence, is selected from $C_{1-6}$ alkyl, Cl, F, Br, I, CN, $(CF_2)_rCF_3$, and OH.

[52] In a further embodiment, the present invention provides a method of modulating chemokine receptor by administering a compound of formula (I), wherein:
E is

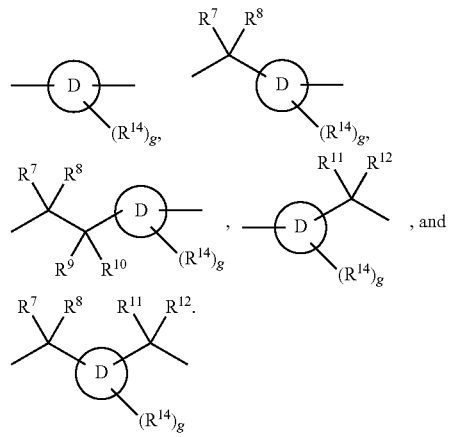

[53] In a further embodiment, the present invention provides a method of modulating chemokine receptor by administering a compound of formula (I), wherein:
E is

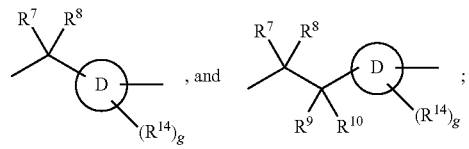

ring D is selected from a $C_{3-6}$ carbocyclic residue;
$R^7$ is selected from H;
$R^8$ is selected from H.

[54] In a further embodiment, the present invention provides a method of modulating chemokine receptor by administering a compound of formula (I), wherein:
$R^{16}$, at each occurrence, is selected from methyl, ethyl, propyl, iso-propyl, $C_{2-8}$ alkenyl, $C_{2-8}$ alkynyl, $(CH_2)_rC_{3-6}$ cycloalkyl, Cl, Br, I, F, CN, (CHR')$_r$NR$^{16a}$R$^{16a'}$, (CHR')$_r$OH, (CHR')$_r$O(CHR')$_r$R$^{16d}$, (CHR')$_r$C(O)(CHR')$_r$R$^{16b}$, (CHR')$_r$C(O)NR$^{16a}$R$^{16a'}$, (CHR')$_r$NR$^{16f}$C(O)(CHR')$_r$ R$^{16b}$, (CHR')$_r$S(O)$_p$(CHR')$_r$R$^{16b}$, (CHR')$_r$S(O)$_2$NR$^{16a}$R$^{16a'}$, (CHR')$_r$NR$^{16f}$S(O)$_2$(CHR')$_r$R$^{16b}$, C$_{1-6}$ haloalkyl, and (CHR')$_r$phenyl substituted with 0-3 R$^{16e}$;

R$^{16a}$ and R$^{16a'}$, at each occurrence, are selected from H, methyl, ethyl, and a (CH$_2$)$_r$—C$_{3-6}$ carbocyclic residue substituted with 0-2 R$^{16e}$;

R$^{16e}$, at each occurrence, is selected from methyl, ethyl, Cl, F, Br, I, CN, CF$_3$, and OCH$_3$;

R$^{16f}$, at each occurrence, is selected from H; and r is selected from 0, 1, and 2.

[55] In a further embodiment, the present invention provides a method of modulating chemokine receptor by administering a compound of formula (I), wherein:

R$^3$ is selected from a (CR$^{3'}$R$^{3''}$)$_r$—C$_{3-6}$ carbocyclic residue substituted with 0-2 R$^{15}$;

R$^{3'}$ and R$^{3''}$, at each occurrence, are selected from H;

R$^{15}$, at each occurrence, is selected from C$_{1-8}$ alkyl, (CH$_2$)$_r$C$_{3-6}$ cycloalkyl, Cl, Br, F, CN, (CHR')$_r$NR$^{15a}$R$^{15a'}$, (CHR')$_r$OH, (CHR')$_r$O(CHR')$_r$R$^{15d}$, (CHR')$_r$C(O)(CHR')$_r$R$^{15b}$, (CHR')$_r$C(O)NR$^{15a}$R$^{15a'}$, (CHR')$_r$NR$^{15f}$C(O)(CHR')$_r$R$^{15b}$, (CHR')$_r$NR$^{15f}$C(O)NR$^{15a}$R$^{15a'}$, (CHR')$_r$C(O)O(CHR')$_r$R$^{15d}$, (CHR')$_r$OC(O)(CHR')$_r$R$^{15b}$, (CHR')$_r$(SO)$_p$(CHR')$_r$R$^{15b}$, (CHR')$_r$S(O)$_2$NR$^{15a}$R$^{15a'}$, (CHR')$_r$NR$^{15f}$S(O)$_2$(CHR')$_r$R$^{15b}$, C$_{1-6}$ haloalkyl, C$_{2-8}$ alkenyl substituted with 0-3 R', C$_{2-8}$ alkynyl substituted with 0-3 R', (CHR')$_r$ phenyl substituted with 0-3 R$^{15e}$, and a (CH$_2$)$_r$-5-10 membered heterocyclic system containing 1-4 heteroatoms selected from N, O, and S, substituted with 0-2 R$^{15e}$;

R', at each occurrence, is selected from H, and C$_{1-6}$ alkyl;

R$^{15a}$ and R$^{15a'}$, at each occurrence, are selected from H, C$_{1-6}$ alkyl, a (CH$_2$)$_r$—C$_{3-6}$ carbocyclic residue substituted with 0-5 R$^{15e}$, and a (CH$_2$)$_r$-5-6 membered heterocyclic system containing 1-2 heteroatoms selected from N, O, and S, substituted with 0-2 R$^{15e}$;

R$^{15b}$, at each occurrence, is selected from C$_{1-6}$ alkyl, a (CH$_2$)$_r$—C$_{3-6}$ carbocyclic residue substituted with 0-3 R$^{15e}$, and (CH$_2$)$_r$-5-6 membered heterocyclic system containing 1-2 heteroatoms selected from N, O, and S, substituted with 0-2 R$^{15e}$; and R$^{15e}$, at each occurrence, is selected from C$_{1-6}$ alkyl, Cl, F, Br, I, CN, (CF$_2$)$_r$CF$_3$, and OH.

[56] In a further embodiment, the present invention provides a method of modulating chemokine receptor by administering a compound of formula (I), wherein the compound is selected from:

N-3-[cis-2,3,3a,4,9,9a-hexahydro-1H-benz[f]isoindol-2-yl]-n-prop-1-yl-N'-3-acetylphenylurea;

N-3-[trans-2,3,3a,4,9,9a-hexahydro-1H-benz[f]isoindol-2-yl]-n-prop-1-yl-N'-3-acetylphenylurea;

(+/−)-N-3-[trans-6-fluoro-2,3,3a,4,9,9a-hexahydro-1H-benz[f]isoindol-2-yl]-n-prop-1-yl-N'-3-acetylphenylurea;

(+/−)-N-3-[trans-6-fluoro-2,3,3a,4,9,9a-hexahydro-1H-benz[f]isoindol-2-yl]-n-prop-1-yl-N'-4-fluorophenylurea;

(+/−)-N-3-[cis-6-fluoro-2,3,3a,4,9,9a-hexahydro-1H-benz[f]isoindol-2-yl]-n-prop-1-yl-N'-3-acetylphenylurea;

(+/−)-N-3-[cis-6-fluoro-2,3,3a,4,9,9a-hexahydro-1H-benz[f]isoindol-2-yl]-n-prop-1-yl-N'-4-fluorophenylurea;

N-(3-acetylphenyl)-N'-[3-[1-[(4-fluorophenyl)methyl]-3-azabicyclo[2.2.2]oct-2-yl]propyl]urea hydrochloride;

N-(4-fluorophenyl)-N'-[3-[1-[(4-fluorophenyl)methyl]-3-azabicyclo[2.2.2]oct-2-yl]propyl]urea hydrochloride;

N-(3-acetylphenyl)-N'-[3-[(1S,4R,6S)-6-[(4-fluorophenyl)methyl]-2-azabicyclo[2.2.2]oct-2-yl]propyl]urea hydrochloride;

N-(3-acetylphenyl)-N'-[3-[(1R,4S,6R)-6-[(4-fluorophenyl)methyl]-2-azabicyclo[2.2.2]oct-2-yl]propyl]urea hydrochloride;

N-(3-acetylphenyl)-N'-[3-[(1S,4R,6R)-6-[(4-fluorophenyl)methyl]-2-azabicyclo[2.2.2]oct-2-yl]propyl]urea hydrochloride;

N-(3-acetylphenyl)-N'-[3-[(1R,4S,6S)-6-[(4-fluorophenyl)methyl]-2-azabicyclo[2.2.2]oct-2-yl]propyl]urea hydrochloride;

N-(4-fluorophenyl)-N'-[3-[(1S,4R,6R)-6-[(4-fluorophenyl)methyl]-2-azabicyclo[2.2.2]oct-2-yl]propyl]urea hydrochloride;

N-(4-fluorophenyl)-N'-[3-[(1R,4S,6S)-6-[(4-fluorophenyl)methyl]-2-azabicyclo[2.2.2]oct-2-yl]propyl]urea hydrochloride;

N-(3-acetylphenyl)-N'-[(2S)-2-[[(3-exo)-3-[(4-fluorophenyl)methyl]-8-azabicyclo[3.2.1]oct-8-yl]methyl]-(2R)-1-cyclohexyl]urea;

N-(4-fluorophenyl)-N'-[(2S)-2-[[(3-exo)-3-[(4-fluorophenyl)methyl]-8-azabicyclo[3.2.1]oct-8-yl]methyl]-(2R)-1-cyclohexyl]urea;

N-(3-acetylphenyl)-N'-[(2S)-2-[[(3-endo)-3-[(4-fluorophenyl)methyl]-8-azabicyclo[3.2.1]oct-8-yl]methyl]-(2R)-1-cyclohexyl]urea;

N-(4-fluorophenyl)-N'-[(2S)-2-[[(3-endo)-3-[(4-fluorophenyl)methyl]-8-azabicyclo[3.2.1]oct-8-yl]methyl]-(2R)-1-cyclohexyl]urea;

N-(4-fluorophenyl)-N'-{3-[(1S,5R,6R)-6-(4-fluorophenyl)-3-azabicyclo[3.2.0]hept-3-yl]propyl}urea;

N-(4-fluorophenyl)-N'-{3-[(1R,5S,6S)-6-(4-fluorophenyl)-3-azabicyclo[3.2.0]hept-3-yl]propyl}urea;

N-(3-acetylphenyl)-N'-{3-[(1S,5R,6R)-6-(4-fluorophenyl)-3-azabicyclo[3.2.0]hept-3-yl]propyl}urea;

N-(3-acetylphenyl)-N'-{3-[(1R,5S,6S)-6-(4-fluorophenyl)-3-azabicyclo[3.2.0]hept-3-yl]propyl}urea;

N-(3-acetylphenyl)-N'-[3-[(3-endo)-3-[(4-fluorophenyl)methyl]-8-azabicyclo[3.2.1]oct-8-yl]propyl]urea;

N-(3-acetylphenyl)-N'-[3-[(3-exo)-3-[(4-fluorophenyl)methyl]-8-azabicyclo[3.2.1]oct-8-yl]propyl]urea;

N-(3-cyanophenyl)-N'-[3-[(3-endo)-3-[(4-fluorophenyl)methyl]-8-azabicyclo[3.2.1]oct-8-yl]propyl]urea; and N-(3-cyanophenyl)-N'-[3-[(3-exo)-3-[(4-fluorophenyl)methyl]-8-azabicyclo[3.2.1]oct-8-yl]propyl]urea.

In another embodiment, E is selected from

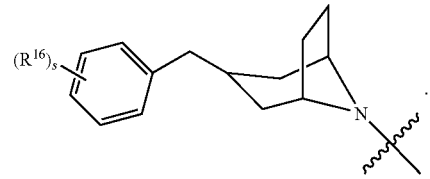

In another embodiment, E is selected from

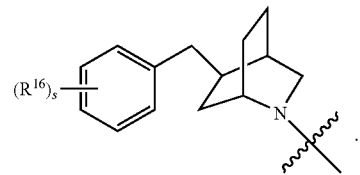

In another embodiment, E is selected from

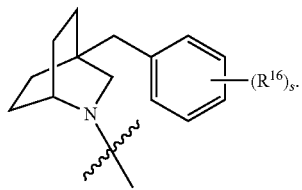

In another embodiment, E is selected from

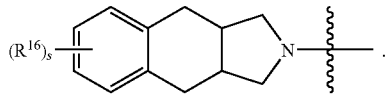

In another embodiment, E is selected from —(CR$^7$R$^8$)—(CR$^9$R$^{10}$)$_v$—(CR$^{11}$R$^{12}$).

In another embodiment, E is selected from

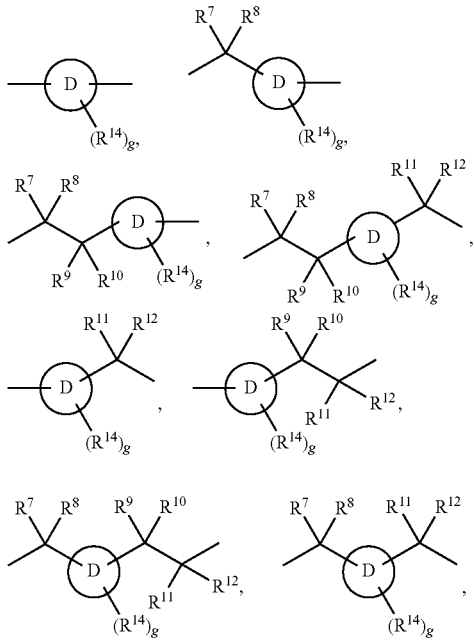

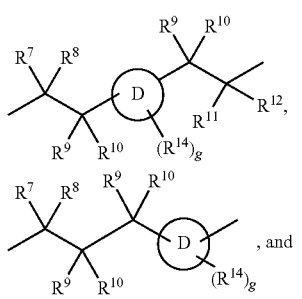

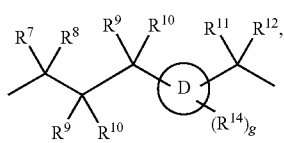

In another embodiment, E is selected from

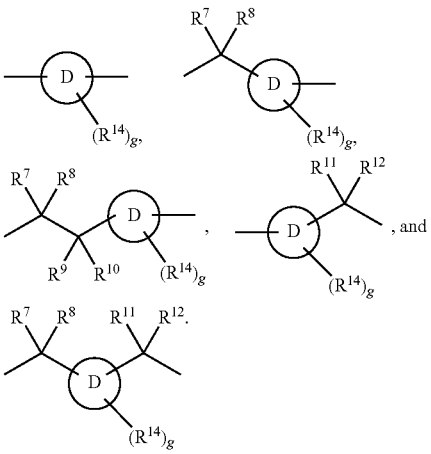

In another embodiment, R$^8$, R$^{10}$, and R$^{12}$ are H.

In another embodiment, R$^7$, R$^8$, R$^9$, R$^{10}$, R$^{11}$, and R$^{12}$, are H.

In another embodiment, ring D is selected from a C$_{3-6}$ carbocyclic residue.

In another embodiment, ring D is selected from cyclopropyl, cyclobutyl, cyclopentyl, cyclohexyl, and phenyl.

In another embodiment, ring D is cyclohexyl.

In another embodiment, G is selected from —C(O)R$^3$, —C(O)NR$^2$R$^3$, —C(O)OR$^3$, —SO$_2$NR$^2$R$^3$, —SO$_2$R$^3$, —C(=S)NR$^2$R$^3$, C(=NR$^{1a}$)NR$^2$R$^3$, C(=CHCN)NR$^2$R$^3$, C(=CHNO$_2$)NR$^2$R$^3$, C(=C(CN)$_2$)NR$^2$R$^3$, and

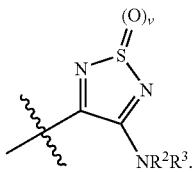

In another embodiment, G is selected from —C(O)NR$^2$R$^3$, C(=CHCN)NR$^2$R$^3$, C(=CHNO$_2$)NR$^2$R$^3$, and C(=C(CN)$_2$)NR$^2$R$^3$.

In another embodiment, G is selected from —C(O)NR$^2$R$^3$.

In another embodiment, G is selected from

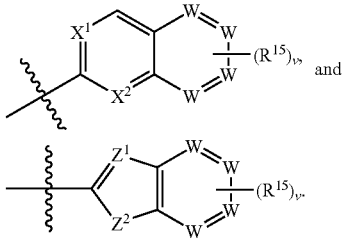

In another embodiment, R$^1$, R$^{1'}$, and R$^2$ are equal to H.

In another embodiment, R$^3$ is selected from a (CR$^{3'}$R$^{3''}$)$_r$—C$_{3-6}$ carbocyclic residue substituted with 0-2 R$^{15}$ and a (CR$^{3'}$CR$^{3''}$)$_r$-5-10 membered heterocyclic system containing 1-4 heteroatoms selected from N, O, and S, substituted with 0-3 R$^{15}$.

In another embodiment, R$^3$ is selected from a (CR$^{3'}$R$^{3''}$)$_r$—C$_{3-6}$ carbocyclic residue substituted with 0-2 R$^{15}$.

In another embodiment, $R^3$ is phenyl substituted with 0-2 $R^{15}$.

In another embodiment, $R^4$ is absent.

In another embodiment, $R^{15}$, at each occurrence, is selected from $C_{1-8}$ alkyl, $(CH_2)_r C_{3-6}$ cycloalkyl, Cl, Br, F, CN, $(CHR')_r NR^{15a}R^{15a'}$, $(CHR')_r OH$, $(CHR')_r O(CHR')_r R^{15d}$, $(CHR')_r C(O)(CHR')_r R^{15b}$, $(CHR')_r C(O)NR^{15a}R^{15a'}$, $(CHR')_r NR^{15f}C(O)(CHR')_r R^{15b}$, $(CHR')_r NR^{15f}C(O)NR^{15a}R^{15a'}$, $(CHR')_r C(O)O(CHR')_r R^{15d}$, $(CHR')_r OC(O)(CHR')_r R^{15b}$, $(CHR')_r S(O)_p(CHR')_r R^{15b}$, $(CHR')_r S(O)_2 NR^{15a}R^{15a'}$, $(CHR')_r NR^{15f}S(O)_2(CHR')_r R^{15b}$, $C_{1-6}$ haloalkyl, $C_{2-8}$ alkenyl substituted with 0-3 R', $C_{2-8}$ alkynyl substituted with 0-3 R', $(CHR')_r$ phenyl substituted with 0-3 $R^{15e}$, and a $(CH_2)_r$-5-10 membered heterocyclic system containing 1-4 heteroatoms selected from N, O, and S, substituted with 0-2 $R^{15e}$.

In another embodiment, the present invention provides a compound of formula (I):

$$A—E—NR^1—G \qquad (I)$$

or stereoisomers or pharmaceutically acceptable salts thereof, wherein:

A is selected from

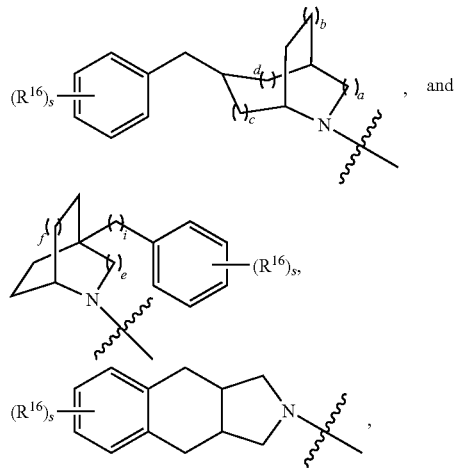

E is selected from $—(CR^7R^8)—(CR^9R^{10})_v—(CR^{11}R^{12})$, and

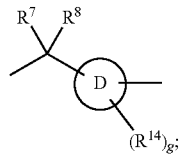

ring D is cyclohexyl;
G is $—C(O)NR^2R^3$;
$R^1$ ad $R^2$ are H;
$R^3$ is phenyl substituted with 0-3 $R^{15}$;
$R^7$, $R^8$, $R^9$, $R^{10}$, $R^{11}$, and $R^{12}$ are H;
$R^{15}$ is selected from F and acetyl;
$R^{16}$ is F;
g is 0;
s is 1;
a is 0 or 1;
b is 1;
d is 0 or 1;
c is 0 or 1;
e is 0; and
f is 0.

The invention may be embodied in other specific forms without departing from the spirit or essential attributes thereof. This invention also encompasses all combinations of preferred aspects of the invention noted herein. It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^a$) occurs more than one time in any constituent or formula for a compound, its definition at each occurrence is independent of its definition at every other occurrence. Thus, for example, if a group is shown to be substituted with 0-2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl. $C_{1-10}$ alkyl, is intended to include $C_1$, $C_2$, $C_3$, $C_4$, $C_5$, $C_6$, $C_7$, $C_8$, $C_9$, and $C_{10}$ alkyl groups. "Alkenyl" is intended to include hydrocarbon chains of either a straight or branched configuration and one or more unsaturated carbon-carbon bonds which may occur in any stable point along the chain, such as ethenyl, propenyl, and the like. $C_{2-10}$ alkenyl, is intended to include $C_2$, $C_3$, $C_4$, $C_5$, $C_6$, $C_7$, $C_8$, $C_9$, and $C_{10}$ alkenyl groups. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Alkynyl" is intended to include hydrocarbon chains of either a straight or branched configuration and one or more unsaturated triple carbon-carbon bonds which may occur in any stable point along the chain, such as ethynyl, propynyl, and the like. $C_{2-10}$ alkynyl, is intended to include $C_2$, $C_3$, $C_4$, $C_5$, $C_6$, $C_7$, $C_8$, $C_9$, and $C_{10}$ alkynyl groups. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl. $C_{3-7}$ cycloalkyl, is intended to include $C_3$, $C_4$, $C_5$, $C_6$, and $C_7$ cycloalkyl groups.

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

The compounds of Formula I can also be quaternized by standard techniques such as alkylation of the cyclic amines with an alkyl halide to yield quaternary piperidinium salt products of Formula I. Such quaternary piperidinium salts would include a counterion. As used herein, "counterion" is used to represent a small, negatively charged species such as chloride, bromide, hydroxide, acetate, sulfate, and the like.

As used herein, the term "5-6-membered cyclic ketal" is intended to mean 2,2-disubstituted 1,3-dioxolane or 2,2-disubstituted 1,3-dioxane and their derivatives.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 4, 5, 6, or 7-membered monocyclic or bicyclic or 7, 8, 9, or 10-membered bicyclic heterocyclic ring which is saturated, partially unsaturated, or unsaturated (aromatic), and which consists of carbon atoms and 1, 2, 3, or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, O and S.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. Preferred heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoindolyl, piperidinyl, pyrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc. . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

The term "therapeutically effective amount" of a compound of this invention means an amount effective to modulate chemokine receptor activity or treat the symptoms of asthma or an allergic disorder in a host.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents that are compatible with the reaction conditions will be readily apparent to one skilled in the art and alternate methods must be used. It will also be recognized that another major consideration in the planning of any synthetic route in this field is the judicious choice of the protecting group used for the protection of the reactive functional groups present in the compounds described in this invention. An authoritative account describing the many alternatives to the trained practitioner is Greene and Wuts (*Protective Groups in Organic Chemistry*, Wiley and Sons, 1991).

SCHEME 1

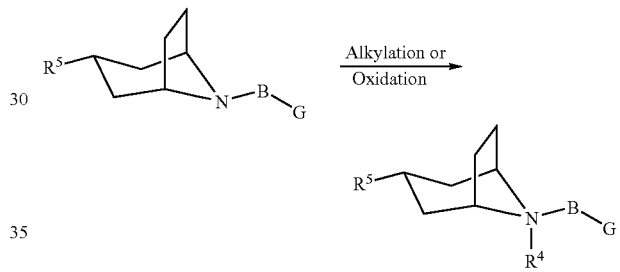

Compounds of Formula I, wherein $R^4$ is present as defined by the scope, may be prepared by procedures depicted in Scheme 1 from compounds of Formula I in which $R^4$ is absent. It is understood that the chemistry is shown for only one A group of Formula I and that similar transformations may be preformed on other A groups. The quaternary salts of Formula I can be synthesized by alkylation with an alkylhalide such as methyl iodide, benzyl bromide, bromoacetate, etc. in a suitable solvent such as THF, DMF, DMSO, etc. at room temperature to reflux temperature of the solvent. The N-oxides of Formula I can be made by the general protocols of Deady, *Syn. Comm.* 1977, 7, 509 and references therein, with minor modification depending on the substitution of Formula I which should be readily recognized by one skilled in the art. The N-oxides are created by oxidation with mCPBA in an inert solvent such as methylene chloride.

The $R^5$ shown in the schemes and in Table 1 are representative of the phenyl ring which is a part of ring A in the claims.

Scheme 2

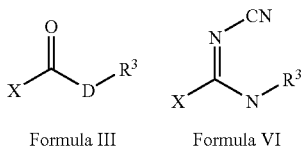

Formula III      Formula VI or               or

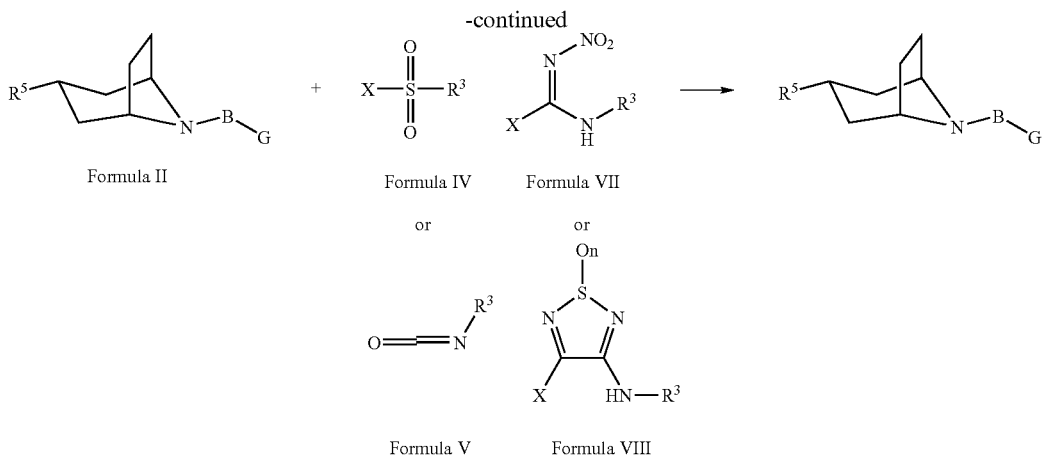

Compounds of Formula I may be prepared as shown in Scheme 2. Compounds in which D is a bond, O or NR$^1$ may be synthesized by reacting Formula II with Formula III, wherein X is a good leaving such as but not limited to Cl, Br, or imidazole, in the presence of a base such as, but not limited to, triethylamine or pyridine. Alternatively, Formula II may be reacted with an isocyanate of Formula V to provide compounds of Formula I where G is CONHR$^3$. Alternatively, Formula II may be reacted with Formula IV, wherein X is a good leaving group such as but not limited to Cl, Br, or imidazole, in the presence of a base such as, but not limited to, triethylamine or pyridine to provide compounds of Formula I where G is SO$_2$R$^3$. Alternatively, Formula II may be reacted with Formulas VI, VII, or VIII wherein X is a good leaving group such as but not limited to ethoxide, phenoxide, or methylsulfide to provide compounds of Formula I according to procedures described in Hoffman, et. al. *J. Med. Chem.* 1983, 26, 140 and references therein.

Scheme 3

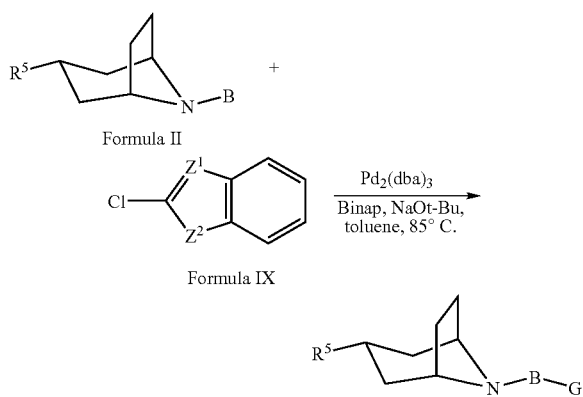

Alternatively, compounds of Formula I can be synthesized by coupling compounds of Formula II with halogenated heterocycles of Formula IX, where Z$^1$ and Z$^2$ are defined in the scope, as described in Scheme 3. It is understood that the chemistry is shown for only one A group of Formula I and heterocycle and that similar transformations may be preformed on other A groups or halogenated heterocycles. This procedure essentially follows the general procedures of Hong, Y. et. al., *Tet. Lett.* 1997, 38, 5607 and references therein, with minor modification depending on the Formula IX which should be readily recognized by one skilled in the art. The reaction can be preformed in an inert solvent such as, but not limited to, toluene at room temperature to the reflux temperature of the solvent with a Pd-catalyst such as Pd$_2$(dba)$_3$ and a base such as sodium t-butoxide. The halogenated heterocycles that are not commercial available can be synthesized by methods known in the art and are exemplified by, but not limited to, Zou. R., *J. Med. Chem.* 1997, 40, 802.

Scheme 4

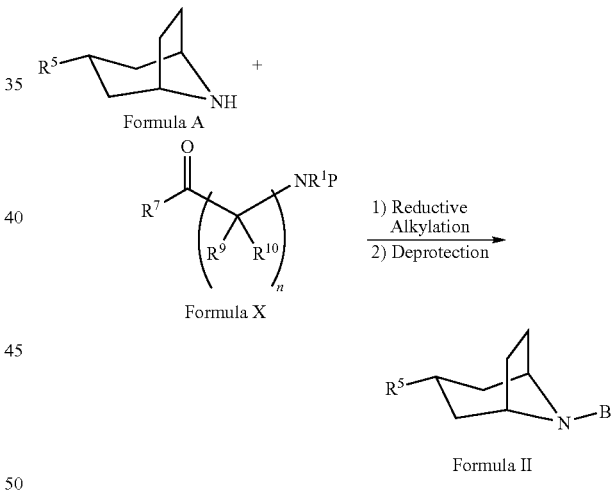

Preparations of intermediates of Formula II are depicted in Scheme 4. Reductive alkylation of the intermediates of Formula A, whose preparations are described later if not commercially available, are reacted with compounds of Formula X, whose preparations are described later if not commercially available, wherein amine on Formula VII is protected with protecting group (P) well familiar to those skilled in the art, and typical examples may be found in Greene, T and Wuts, P. G. M., *Protecting Groups in Organic Synthesis*, John Wiley & Sons, Inc., New York, N.Y., 1991 and references therein, is carried out under conditions known in the art, for example catalytic hydrogenation with hydrogen in the presence of palladium or platinum or with reducing agents such as sodium triacetoxyborohydride. The protecting group P can be removed using the appropriate reagents, well familiar to those skilled in the art, and typical examples may be found in Greene, T and Wuts, P. G. M., which provides the intermediates of Formula II.

Scheme 5

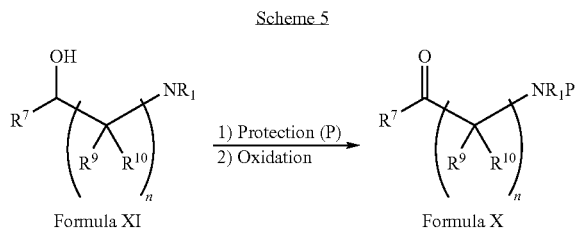

Preparations of intermediates of Formula X are described in Scheme 5. Compounds of Formula X can be made from amino alcohols, Formula XI, by protecting the amine with a suitable protecting (P) under conditions known by those skilled in the art. The alcohol can be oxidized to the aldehyde under conditions known in the art; such as but not limited to tetrapropylammonium perruthenate and N-methyl morpholine N-oxide in acetonitrile. The amino alcohols that are not commercially available can be synthesized by methods known in the art and are exemplified by, but not limited to, Berg et. al., *J. Med. Chem.* 1998, 41, 1934, Larrow et. al., *Chemtracts*, 1997, 10, 1058, Palomo et. al., *Enantiosel. Synth. B-Amino Acids*, 1997, 279, and Yokomatsu et. al., *Heterocycles*, 1992, 33, 1051.

Scheme 6

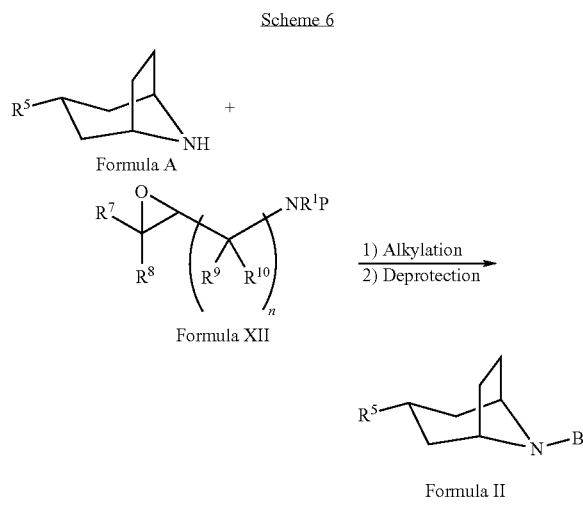

Alternatively, compounds of Formula II can be synthesized by coupling compounds of Formula A with amino epoxides, Formula XII, as described in Scheme 6. It is understood that the chemistry is shown for only one A group of Formula I and that similar transformations may be preformed on other A groups. The reaction can be preformed in an inert solvent such as, but not limited to, DMF, DMSO, or acetonitrile at room temperature to the reflux temperature of the solvent. The amino protecting group (P) can then be removed under conditions known in the art. The amino epoxides that are not commercially available can be synthesized by methods known in the art and are exemplified by, but not limited to, Luly et. al., *J. Org. Chem.* 1985, 50, 4515.

Scheme 7

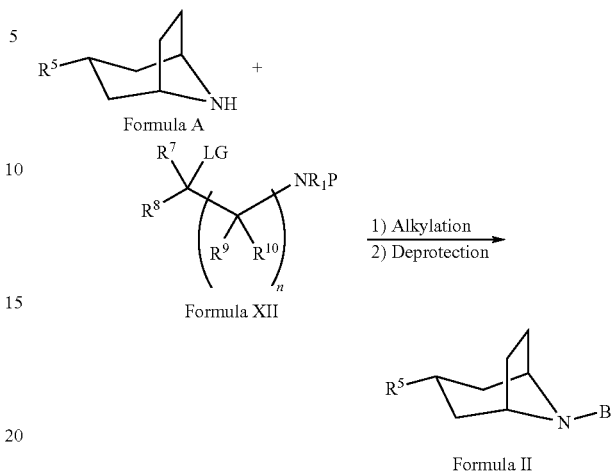

Alternatively, compounds of Formula II can be synthesized by coupling compounds of Formula A with intermediates of Formula XIII, see Scheme 7, that have an amine and a leaving group, such as, but not limited to, halide (halide=Cl, Br, I), mesylate, tosylate, triflate, etc. It is understood that the chemistry is shown for only one A group of Formula I and that similar transformations may be preformed on other A groups. The reaction can be preformed in an inert solvent such as, but not limited to, DMF, 2-butanone, or acetonitrile at room temperature to the reflux temperature of the solvent. The amino protecting group (P) can then be removed under conditions known in the art. Intermediates of Formula XIII that are not commercially available can be synthesized by methods known in the art.

Scheme 8

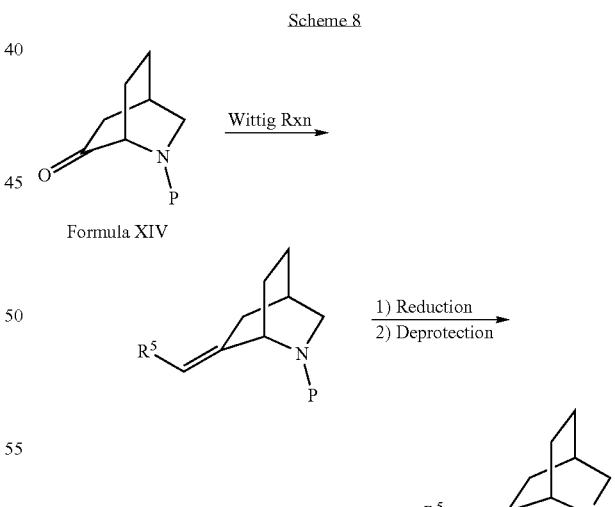

One embodiment of Formula A, monosubstituted 8-azabicyclo[3.2.1]octanes, 2-azabicyclo[2.2.2]octanes, and 7-azabicyclo[2.2.1]heptanes can be synthesized by procedures depicted in Scheme 8. It is understood that the chemistry is shown for only one position on 2-azabicyclo[2.2.2] octane ring system and that similar transformations may be preformed on other ring positions and other azabicycles. Formula XIV can be treated under Wittig reaction conditions followed by reduction and deprotection to yield compounds of Formula A. These synthetic steps employ reactions well familiar to those skilled in the art and procedures are exemplified in Larock, R. C. Comprehensive Organic Transformations, VCH Publishers, New York, 1989 and references therein. Compounds of Formula XIV that are not commercially available can be synthesized by methods known in the art and are exemplified by, but not limited to, Borne et. al. *J. Heterocycl. Chem.* 1974, 11, 311 and Aggarwal et. al. *Tetrahedron,* 1999, 55, 293.

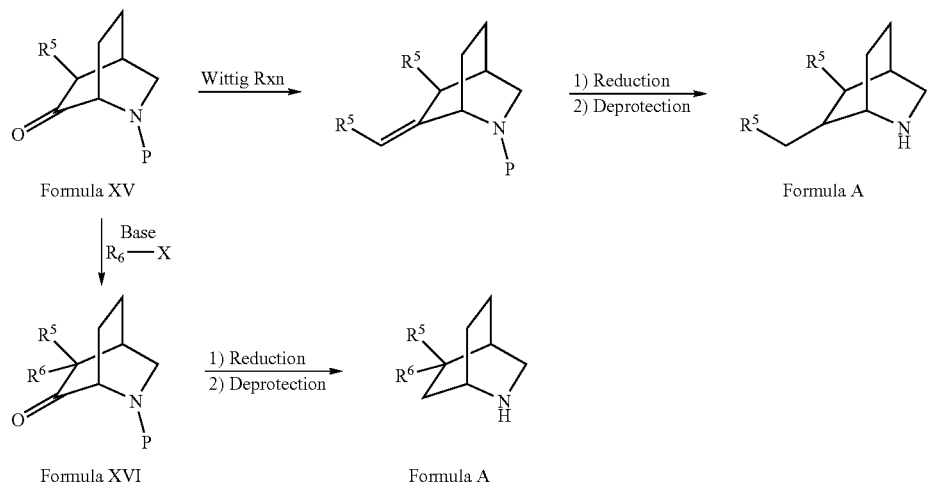

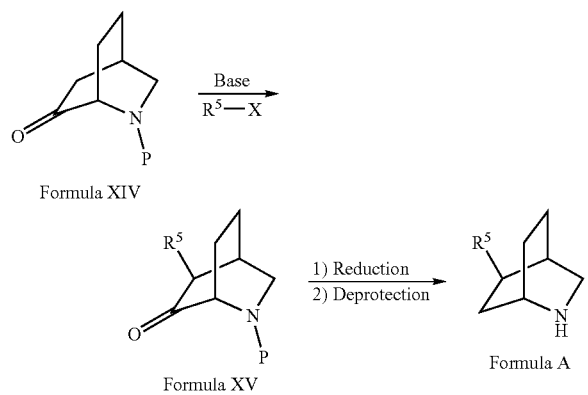

Alternatively, monosubstituted 8-azabicyclo[3.2.1]octanes, 2-azabicyclo[2.2.2]octanes, and 7-azabicyclo[2.2.1]heptanes can be synthesized by procedures depicted in Scheme 9. It is understood that the chemistry is shown for only one position on 2-azabicyclo[2.2.2]octane ring system and that similar transformations may be preformed on other ring positions and other azabicycles. Compounds of Formula XIV can be treated with a base such as LDA, KHMDS, LHMDS, etc. in THF, ether, dioxane, etc., at −78° C. to room temperature and an alkylating agent $R^5X$ where X can be a halide, mesylate, triflate, etc. to yield compounds of Formula XV. The ketone of Formula XV can be reduced to the methylene by methods described by Larock and references therein, which are well known to one skilled in the art, to produce compounds of Formula A.

Disubstituted 8-azabicyclo[3.2.1]octanes, 2-azabicyclo[2.2.2]octanes, and 7-azabicyclo[2.2.1]heptanes can be synthesized by procedures depicted in Scheme 10 for intermediates of Formula XV. It is understood that the chemistry is shown for only one position on the 2-azabicyclo[2.2.2]octane ring system and that similar transformations may be preformed on other ring positions and other azabicycles. Intermediates of Formula XV can be treated under Wittig reaction conditions followed by reduction and then deprotection of the protecting group (P) to produce compounds of Formula A. These synthetic steps employ reactions well familiar to those skilled in the art and procedures are exemplified in Larock, R. C. Comprehensive Organic Transformations. Alternatively, compounds of Formula XV can be treated with a base such as LDA, KHMDS, LHMDS, etc. in THF, ether, dioxane, etc., at −78° C. to room temperature and an alkylating agent $R^6X$ where X is a halide, mesylate, triflate, etc. to yield compounds of Formula XVI. The ketone of Formula XVI can be reduced to the methylene by methods described by Larock and references therein, which are well known to one skilled in the art, to produce compounds of Formula A.

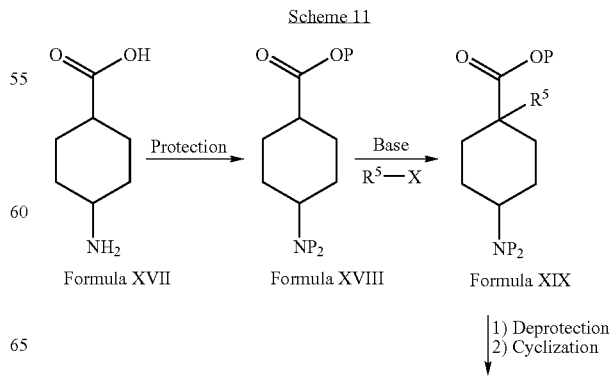

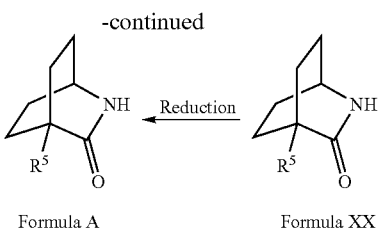

Formula A     Formula XX

Another embodiment of Formula A, monosubstituted 2-azabicyclo[2.2.2]octanes, and 2-azabicyclo[2.2.1]heptanes can be synthesized by procedures depicted in Scheme 11. It is understood that the chemistry is shown for the 2-azabicyclo[2.2.2]octane ring system and that similar transformations may be preformed to form other azabicycles. Compounds of Formula XVII, which are commercially available, can be protected on the acid and amino groups under conditions well known to one skilled in the art. Formula XVIII can be treated with a base such as LDA, KHMDS, LHMDS, etc. in THF, ether, dioxane, etc., at −78° C. to room temperature and an alkylating agent $R^5X$ where X is a halide, mesylate, triflate, etc. to yield compounds of Formula XIX. Formula XIX can be deprotected under conditions well known to one skilled in the art. Cyclization can achieved under dehydrating condition well known in the literature and exemplified by, but not limited to, Pearlman, W. M. Org. Syn. 1969, 49, 75. The bicyclic lactam, Formula XX, can then be reduced to the bicyclic amine of Formula A under conditions well known in the art such as, but not limited to, borane in THF at reflux.

Another embodiment of Formula A, the cis- and/or trans-3a,4,9,9a-tetrahydro-1H-Benz[f]isoindoline and 1,2,3,4,4a,5,10,10a-octahydro-Benz[g]isoquinoline ring systems may be synthesized by the intramolecular and intermolecular Diels-Alder routes depicted in Scheme 12 (see for example, W. Oppolzer et al. Helv. Chim. Acta, 1976, 59, 1186-1202; Neth. Appl. 75 03,392, Sep. 30, 1975 by Sandoz, Ltd.). The symbol P can be hydrogen or a protecting group such as benzyl, trifluoroacetyl, etc., or E or E-Y in precursor or final form. It to be understood that appropriate functionality may be present in Formula A, XXI-XXV in precursor or final form and that only the parent unsubstituted molecules are shown in Scheme 12 for sake of clarity.

Scheme 12

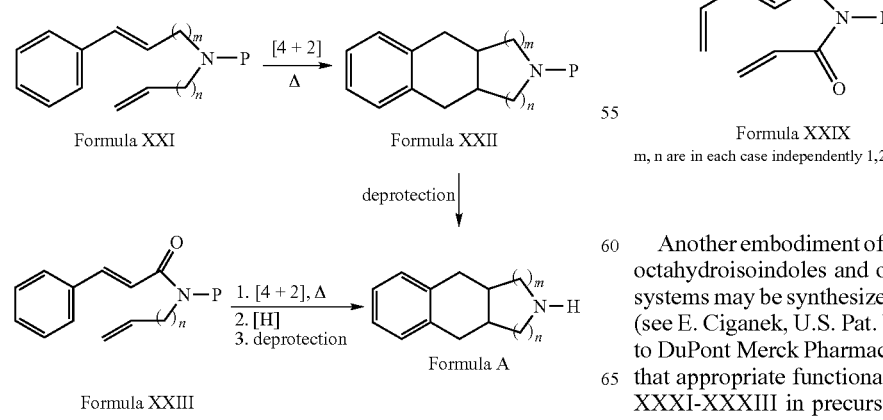

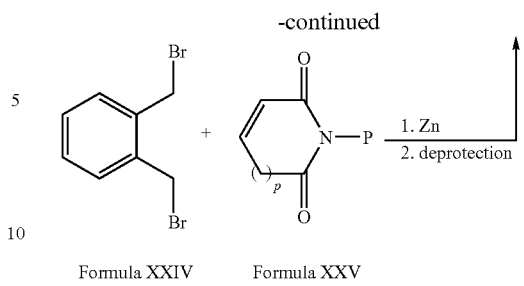

Formula XXIV     Formula XXV m, n are in each case independently 1,2
p is 0 or 1

Another embodiment of Formula A, the octahydroisoindoles, decahydroisoquinolines and related bicyclic systems, may be synthesized by an intramolecular Diels-Alder reaction (see for example S. F. Martin, et al., J. Org. Chem. 1983, 48, 5170-5180; Carmosin, et al., U.S. Pat. No. 5,508,424, issued Apr. 16, 1996 to Ortho Pharmaceutical Corp.) as shown in Scheme 13. It to be understood that appropriate functionality may be present (such as a substituted or unsubstituted phenyl group, for example) in Formula A, XXVI-XXX in precursor or final form and that only the parent unsubstituted molecules are shown in Scheme 13 for sake of clarity. The symbol P can be hydrogen or a protecting group such as benzyl, trifluoroacetyl, etc., or E or E-Y in precursor or final form.

Scheme 13

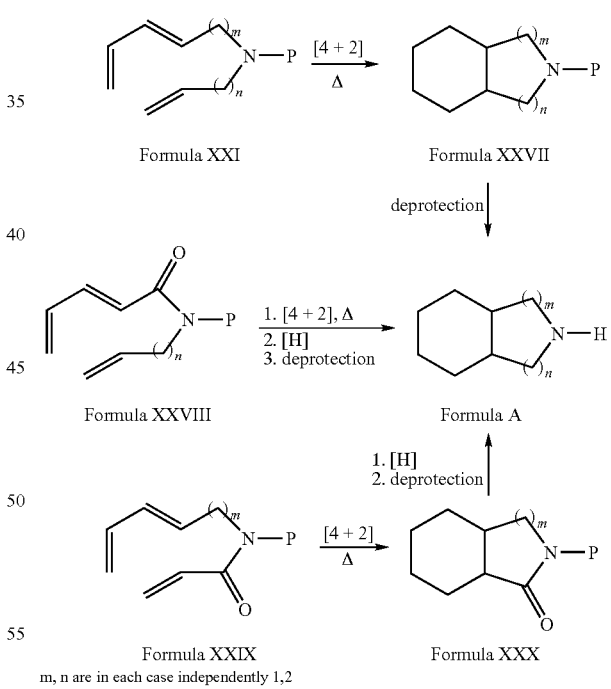

m, n are in each case independently 1,2

Another embodiment of Formula A, the 3a-(phenylmethyl) octahydroisoindoles and other similar bicyclic and tricyclic systems may be synthesized by methods shown in Scheme 14 (see E. Ciganek, U.S. Pat. No. 5,216,018, issued Jun. 1, 1993 to DuPont Merck Pharmaceutical Co.). It is to be understood that appropriate functionality may be present in Formula A, XXXI-XXXIII in precursor or final form and that only the parent unsubstituted molecules are shown in Scheme 14 for sake of clarity. Thus a cyclic anhydride of Formula XXXI which is commercially available or can be easily synthesized by methods familiar to one skilled in the art is reacted with benzylamine to yield imide XXXII. Deprotonation with a strong non-nucleophilic base such as LDA or KHMDS in an inert solvent such as ether or THF followed by quenching with a benzyl bromide, chloride, iodide, tosylate, mesylate, or triflate, yields a benzylated imide which can be reduced to cyclic amine XXXIII. Deprotection yields a cyclic amine of Formula A.

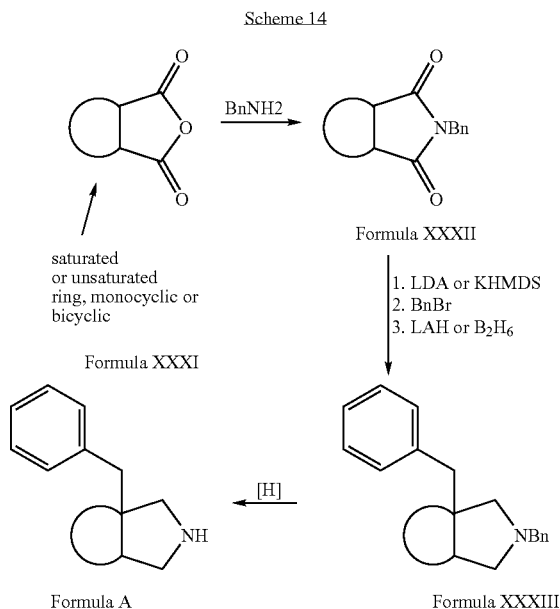

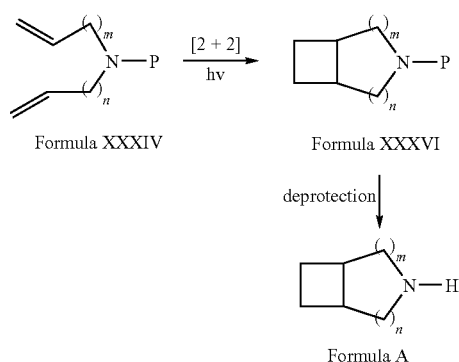

m, n are in each case independently 1,2

Another embodiment of Formula A, namely compounds containing a fused cyclobutyl ring can be synthesized as depicted in Scheme 15 (see W. Oppolzer, et ala *Helv. Chim. Acta*, 1976, 59, 1186-1202; G. Steiner, et al., *Heterocycles*, 1995, 40, 319-330; Steiner, G. et al., U.S. Pat. No. 5,475,105, issued Dec. 12, 1995 to BASF Akt.). It is to be understood that appropriate functionality may be present (such as a substituted or unsubstituted phenyl group, for example) in Formula A, XXXIV-XXXVI in precursor or final form and that only the parent unsubstituted molecules are shown in Scheme 15 for sake of clarity. The symbol P can be hydrogen or a protecting group such as benzyl, trifluoroacetyl, or E or E-Y in precursor or final form.

The compounds of this invention and their preparation can be understood further by the following working examples, which do not constitute a limitation of the invention.

EXAMPLES

Example 1

Preparation of N-3-[cis-2,3,3a,4,9,9a-hexahydro-1H-benz[f]isoindol-2-yl]-n-prop-1-yl-N'-3-acetylphenylurea Part A. Preparation of cis-N-Benzyl-1,2,3,4-tetrahydro-2,3-naphthalenedicarboximide To a stirred mixture of N-benzylmaleimide (10 g, 53.41 mmol) and zinc dust (2 g, 30.59 mmol) in 250 mL DMF was added in a 6 hour period a mixture of α,α'-dibromo-o-xylene (23 g, 87.13 mmol) and n-benzylmaleimide (5 g, 26.71 mmol) in 50 mL DMF, as well as six portions of zinc dust (1 g, 15.30 mmol). The mixture was stirred at room temperature for 20 hours, over which time a homogeneous solution was observed. The mixture was poured into 1 L water, and 10 mL of concentrated hydrochloric acid was added. The solids were removed by filtration, and the filtrate was extracted with three 500 mL portions of ethyl acetate. The combined extracts were dried over sodium sulfate, and concentrated to an amber oil which was subjected to flash chromatography, eluting with 50% ethyl acetate/hexanes, followed by 20% methanol/chloroform. The methanol/chloroform fractions were combined and stripped to yield 2.6 g of a yellow oil. This was purified by flash chromatography, eluting with 20% ethyl acetate/toluene to yield 1.0 g of a white solid as product. Yield=4.2%. NMR (300 MHz, Acetone) δ 7.84-7.79 (m, 2H), 7.71-7.66 (m, 2H), 7.14-7.06 (m, 4H), 3.74 (t, 2H, J=7 Hz), 2.95-2.90 (m, 2H), 2.74-2.68 (m, 2H), 2.55-2.35 (m, 6H), 1.91-1.80 (m, 4H).

Part B. Preparation of cis-2-benzyl-2,3,3a,4,9,9a-hexahydro-1H-benz[f]isoindole Hydrochloride A solution of aluminum chloride (0.55 g, 4.2 mmol) in 5 ml of diethyl ether was added to a 1 M lithium aluminum hydride solution (10 mL, 10 mmol) in diethyl ether at 0° C., causing a white solid to precipitate. The mixture was stirred at 0° C. for 20 minutes, then cis-N-benzyl-1,2,3,4-tetrahydro-2,3-naphthalenedicarboximide was added neat (0.58 g, 2.2 mmol). The mixture was allowed to come to room temperature and stirred for 30 minutes, then brought to reflux for 90 minutes. The mixture was cooled to 0° C., and the excess aluminum hydrides were destroyed using the Steinhardt procedure (see Fieser and Fieser, Reagents for Organic Synthesis; John Wiley & Sons, Inc.: New York, N.Y., 1967; p. 584.). The resulting filtrate was diluted with 200 mL water, acidified with 1 N hydrochloric acid, and extracted with methylene chloride. The methylene chloride was stripped, the residue was taken up in 1 N sodium hydroxide, and the mixture was extracted with chloroform. The combined extracts were dried over sodium sulfate, and stripped to an amber oil. This was diluted with 20 mL of ethyl acetate, and 20 mL of 1 N hydrochloric acid solution in diethyl ether was added. The mixture was extracted with 1 N hydrochloric acid, and the combined aqueous extracts were washed with a 2:1 mixture of diethyl ether and ethyl acetate. The aqueous was then extracted with chloroform, and the combined extracts were dried over sodium sulfate, and stripped to yield 220 mg of a yellow oil as product. Yield=42%. NMR (300 MHz, CDCl$_3$) δ 7.52 (m, 2H), 7.39 (m, 3H), 7.25-7.20 (m, 2H), 7.16-7.12

(m, 2H), 3.92 (d, 2H, J=6 Hz), 3.59-3.56 (m, 2H), 3.32 (m, 2H), 2.77 (dd, 2H, J=6 Hz, 15 Hz), 2.49 (d, 2H, J=13 Hz), 2.10-2.05 (m, 2H).

Part C. Preparation of cis-2,3,3a,4,9,9a-hexahydro-1H-benz[f]isoindole

To a solution of cis-2-benzyl-2,3,3a,4,9,9a-hexahydro-1H-benz[f]isoindole hydrochloride (210 mg, 0.80 mmol) in 10 mL of ethanol was added palladium hydroxide (210 mg, 20 wt % on carbon) and 4 N hydrochloric acid solution in dioxane (1 mL, 4 mmol). The mixture was placed on a Parr apparatus, the vessel was pressurized to 50 psi with hydrogen, and the mixture was shaken for 2 days. TLC of the mixture showed very little reaction, so the same amounts of palladium hydroxide and hydrochloric acid were added again. The vessel was pressurized to 50 psi with hydrogen, and the mixture was shaken for an additional 3 days. TLC of the mixture showed that the reaction was still incomplete, and so the same amounts of palladium hydroxide and hydrochloric acid were added, the vessel was pressurized to 50 psi with hydrogen, and the mixture was shaken for an additional 6 days. The mixture was filtered through celite, and the cake was rinsed with methanol. The filtrate was stripped, the residue was taken up in 20 mL of 1 N sodium hydroxide, and the aqueous was extracted with ethyl acetate. The combined extracts were dried over sodium sulfate and stripped to yield 90 mg of an amber oil, which was purified by flash chromatography, eluting with ethyl acetate followed by 20% methanol/chloroform. Obtained 35 mg of a colorless oil. Yield=25%. NMR (300 MHz, $CDCl_3$) δ 7.17-7.09 (m, 4H), 3.17-3.16 (m, 2H), 2.79 (bd, 2H, J=9 Hz), 2.58-2.43 (m, 6H), 2.36 (s, 1H).

Part D. Preparation of 2-(3-Phthalimido-n-prop-1-yl)-cis-2,3,3a,4,9,9a-hexahydro-1H-benz[f]isoindole A mixture of cis-2,3,3a,4,9,9a-hexahydro-1H-benz[f]isoindole (32 mg, 0.018 mmol), N-(3-bromopropyl)phthalimide (49 mg, 0.18 mmol), potassium iodide (31 mg, 0.18 mmol), and potassium carbonate (51 mg, 0.37 mmol) in 3 mL of methylethyl ketone was heated at reflux for 8 hours. The mixture was cooled to room temperature, the solids were filtered, and the filtrate was concentrated in-vacuo. The residue was dry-loaded onto a 1×5 cm silica column, and eluted with ethyl acetate followed by 20% methanol/chloroform. Obtained 50 mg of white solids. Yield=78%. NMR (300 MHz, $CDCl_3$) δ 7.84-7.79 (m, 2H), 7.71-7.66 (m, 2H), 7.14-7.06 (m, 4H), 3.74 (t, 2H, J=7 Hz), 2.95-2.90 (m, 2H), 2.74-2.68 (m, 2H), 2.55-2.35 (m, 6H), 1.91-1.80 (m, 4H).

Part E. Preparation of 2-(3-amino-n-prop-1-yl)-cis-2,3,3a,4,9,9a-hexahydro-1H-benz[f]isoindole Hydrazine (9 mg, 0.28 mmol) was added to a solution of 2-(3-Phthalimido-n-prop-1-yl)-cis-2,3,3a,4,9,9a-hexahydro-1H-benz[f]isoindole (50 mg, 0.14 mmol) in 1 mL of ethanol, and the mixture was refluxed for 6 hours. The mixture was cooled to room temperature, and 5 mL of diethyl ether was added with stirring. After 30 minutes, a white solid had precipitated. The solid was collected by filtration, rinsed with diethyl ether, then stirred in 10 mL of chloroform. The solids were filtered and washed with chloroform. The filtrate was concentrated to yield 20 mg of a colorless oil as product. Yield=63%. NMR (300 MHz, $CD_3OD$) δ 7.09-7.05 (m, 4H), 3.03-2.97 (m, 2H), 2.77-2.70 (dd, 2H, J=6 Hz, 14 Hz), 2.68-2.58 (m, 4H), 2.50-2.44 (dd, 2H, J=5 Hz, 14 Hz), 2.30 (t, 2H, J=7 Hz), 1.82 (t, 2H, J=7 Hz), 1.61 (tt, 2H, J=7 Hz, 8 Hz, 7 Hz).

Part F. Preparation of N-3-[cis-2,3,3a,4,9,9a-hexahydro-1H-benz[f]isoindol-2-yl]-n-prop-1-yl-N'-3-acetylphenylurea To a solution of N-(3-amino-n-prop-1-yl)-cis-2,3,3a,4,9,9a-hexahydro-1H-benz[f]isoindole (20 mg, 0.09 mmol) in 1 mL of chloroform was added 3-acetylphenyl isocyanate (16 mg, 0.10 mmol). The mixture was stirred overnight, then applied directly to a 1×5 cm silica column and eluted with ethyl acetate followed by 20% methanol/chloroform. Obtained 27 mg of a yellow, viscous oil as product. Yield=77%. NMR (300 MHz, $CD_3OD$) δ 7.98 (s, 1H), 7.59-7.54 (m, 2H), 7.35 (dd, 1H, J=8 Hz, 8 Hz), 7.12-7.06 (m, 4H), 3.19 (t, 2H, J=6 Hz), 3.14 (t, 2H, J=7 Hz, 8 Hz), 2.76 (dd, 2H, J=5 Hz, 15 Hz), 2.66 (m, 2H), 2.56 (s, 3H), 2.50 (dd, 2H, J=5, 14), 2.44 (t, 2H, J=8), 1.93 (it, 2H, J=9), 1.75-1.70 (m, 2H).

Example 2

Preparation of N-3-[trans-2,3,3a,4,9,9a-hexahydro-1H-benz[f]isoindol-2-yl]-n-prop-1-yl-N'-3-acetylphenylurea Part A: Preparation of N-(3-phenylallyl)-allylamine A solution of cinnamyl bromide (10 g, 50.7 mmol) in 250 mL tetrahydrofuran was added dropwise to a solution of allyl amine (38 ml, 507 mmol) in 50 mL tetrahydrofuran at 0° C. the mixture was allowed to slowly come to room temperature then stirred 20 hours. The tetrahydrofuran was removed in-vacuo, and the residue was partitioned between 500 mL of ethyl acetate and 200 ml of water. The layers were separated, the organic phase was washed with water followed by brine, then dried over sodium sulfate and concentrated to an amber oil. The oil was purified by flash chromatography on an 8×15 cm silica column, eluting with 5% methanol/chloroform followed by 10% methanol/chloroform. Obtained 7.2 g of an amber oil as product. Yield=81%. NMR (300 MHz, $CDCl_3$) δ 7.39-7.20 (m, 5H), 6.54 (d, 1H, J=16 Hz), 6.35-6.26 (m, 1H), 6.01-5.87 (m, 1H), 5.24-5.14 (m, 2H), 3.43 (d, 2H, J=7 Hz), 3.31 (d, 2H, J=6 Hz).

Part B. Preparation of N-(3-phenylallyl)-N-allyltrifluoroacetamide

A solution of trifluoroacetic anhydride (1.33 g, 6.35 mmol) in 10 mL of methylene chloride was added dropwise to a mixture of N-(3-phenylallyl)-allylamine (1.0 g, 5.77 mmol) and triethylamine (8.1 mL, 57.7 mmol) in 20 ml methylene chloride at 0° C. The mixture was allowed to come to room temperature and stirred for 16 hours. The mixture was washed with water followed by brine, then dried over sodium sulfate, and concentrated in-vacuo to an amber oil. The oil was purified by flash chromatography, eluting with 10% ethyl acetate/hexanes. Obtained 1.3 g of a colorless oil as product. Yield=84%. NMR (300 MHz, $CDCl_3$) δ (7.40-7.24 (m, 5H), 6.53 (d, 1H, J=16 Hz), 6.17-6.03 (m, 1H), 5.85-5.72 (m, 1H), 5.34-5.18 (M, 2H), 4.19-4.03 (m, 4H).

Part C. Preparation of cis- and trans-2-trifluoro-acetyl-2,3,3a,4,9,9a-hexahydro-1H-benz[f]isoindole A solution of N-(3-phenylallyl)-N-allyl-trifluoroacetamide (1.2 g, 4.46 mmol) in 13 mL toluene was heated to 235° C. in a sealed tube for 20 hours. The mixture was cooled to room temperature and concentrated. The residue was purified by flash chromatography on a 3.5×20 cm silica column, eluting with toluene. Obtained 400 mg of white solids which contained a 3:2 mixture of trans and cis isomers of the product. Yield=33%. NMR (300 MHz, CDCl$_3$) δ 7.19-7.12 (m, 4H), 4.15-4.04 (m, 1.2H), 3.93-3.84 (m, 0.8H), 3.41-2.92 (m, 4H), 2.77-2.58 (m, 2.7H), 2.23-1.99 (m, 1.3H).

Part D. Preparation 2,3,3a,4,9,9a-hexahydro-1H-benz[f]isoindole

To a stirred solution of potassium hydroxide (8.67 g, 154.6 mmol) in 100 mL of methanol was trans-2-trifluoroacetyl-2, 3,3a,4,9,9a-hexahydro-1H-benz[f]isoindole (8.32 g, 30.91 mmol), and the mixture was stirred at room temperature for four hours. The mixture was concentrated in-vacuo, and the residue was partitioned between diethyl ether and water. The layers were separated, and the aqueous phase was extracted with three 200 mL portions of diethyl ether. The combined organic phases were dried over sodium sulfate, and concentrated in-vacuo to a yellow oil. The oil was purified by flash chromatography on an 8×15 cm silica column, eluting with a 40:10:1 mixture of methylene chloride, methanol, and 25% aqueous ammonium hydroxide. Obtained 2.5 g of the trans isomer as a white solid, and 2.0 g of the cis isomer as a pale yellow solid. Yield=46% (trans), 37% (cis). NMR (trans) (300 MHz, CDCl$_3$) δ 7.12 (m, 4H), 3.36-3.31 (m, 2H), 3.08-3.03 (m, 2H), 2.71-2.58 (m, 4H), 2.46 (bs, 1H), 1.90 (m, 2H).

Part E. Preparation of 2-(3-Phthalimido-n-prop-1-yl)-2,3,3a,4,9,9a-hexahydro-1H-benz[f]isoindole A mixture of trans-2,3,3a,4,9,9a-hexahydro-1H-benz[f]isoindole (200 mg, 1.15 mmol), N-(3-bromopropyl)-phthalimide (309 mg, 1.15 mmol), potassium iodide (192 mg, 1.15 mmol), and potassium carbonate (320 mg, 2.31 mmol) in 10 mL of methylethyl ketone was heated at reflux for 8 hours. The mixture was cooled to room temperature, the solids were filtered, and the filtrate was concentrated in-vacuo. The residue was dry-loaded onto a 1×5 cm silica column, and eluted with ethyl acetate followed by 20% methanol/chloroform. Obtained 200 mg of an amber oil. Yield=48%. NMR (300 MHz, CDCl$_3$) δ 7.87-7.83 (m, 2H), 7.76-7.70 (m, 2H), 7.15-7.07 (m, 4H), 3.80 (t, 2H, J=7 Hz), 3.22 (m, 2H), 3.01-2.87 (m, 4H), 2.76-2.56 (m, 4H), 2.11-1.96 (m, 4H).

Part F. Preparation of 2-(3-Amino-n-prop-1-yl)-2,3,3a,4,9,9a-hexahydro-1H-benz[f]isoindole Hydrazine (42 mg, 1.31 mmol) was added to a solution of 2-(3-Phthalimido-n-prop-1-yl)-2,3,3a,4,9,9a-hexahydro-1H-benz[f]isoindole (200 mg, 0.65 mmol) in 5 mL of ethanol, and the mixture was refluxed for 20 hours, over which time a white solid had precipitated. The mixture was cooled to room temperature, the solid was removed by filtration, and the filtrate was concentrated in-vacuo. The residue was suspended in chloroform, and the solids were removed by filtration. The filtrate was concentrated in-vacuo to 90 mg of a yellow oil as product. NMR (300 MHz, CDCl$_3$) δ 7.16-7.08 (m, 4H), 3.39-3.32 (m, 2H), 3.04-2.98 (m, 6H), 2.80-2.61 (m, 4H), 2.08-2.05 (m, 2H), 1.90-1.79 (m, 2H).

Part G. Preparation of N-3-[trans-2,3,3a,4,9,9a-hexahydro-1H-benz[f]isoindol-2-yl]-n-prop-1-yl-N'-3-acetylphenylurea To a solution of N-(3-aminopropyl)-trans-3a,4,9,9a-tetrahydro-benz[f]indoline (90 mg, 0.39 mmol) in 2 mL of chloroform was added 3-acetylphenyl isocyanate (70 mg, 0.43 mmol), and the mixture was stirred for two days. The crude mixture was purified by flash chromatography on a 1×8 cm silica column, eluting with ethyl acetate followed by 20% methanol/chloroform. Obtained 50 mg of white solids as product. NMR (300 MHz, CDCl$_3$) δ 8.01 (s, 1H), 7.65 (d, 1H, J=8 Hz), 7.55 (d, 1H, J=8 Hz), 7.33 (dd, 1H, J=8 Hz, 8 Hz), 7.18-7.07 (m, 4H), 3.49-3.41 (m, 2H), 3.34-3.22 (m, 2H), 2.78-2.59 (m, 4H), 2.53 (s, 3H), 2.18-1.93 (m, 4H), 1.85-1.79 (m, 2H).

Example 3

Preparation of (+/−)-N-3-[trans-6-fluoro-2,3,3a,4,9,9a-hexahydro-1H-benz[f]isoindol-2-yl]-n-prop-1-yl-N'-3-acetylphenylurea Step A. Preparation of 3-(4-fluorophenyl)-3-hydroxy-1-propene A solution of 4-fluorobenzaldehyde (8.5 g, 68.2 mmol, Aldrich) in 50 mL of tetrahydrofuran was added dropwise to a solution of vinylmagnesium bromide (9.84 g, 75 mmol, Aldrich) in 150 mL of tetrahydrofuran at 0° C. The mixture was stirred for min and then allowed to warm to room temperature. The reaction was stirred overnight and quenched by the addition of water (100 mL). The resulting precipitate was removed by filtration. The filtrate was concentrated in vacuo and then dissolved in 200 mL of ethyl acetate. This solution was washed with water, brine, dried over sodium sulfate, and concentrated in vacuo to 10.3 g of an amber oil as product. NMR (300 MHz, CDCl$_3$) δ 7.37-7.29 (m, 2H), 7.04 (dd, 2H, J=9 Hz, 9 Hz), 6.08-5.97 (m, 1H), 5.35 (d, 1H, J=17 Hz), 5.21 (d, 2H, J=10 Hz), 1.90 (d, 1H, J=4 Hz).

Step B. Preparation of 1-(4-fluorophenyl)-3-chloro-1-propene

A gas dispersion tube was immersed in a solution of 3-(4-fluorophenyl)-3-hydroxy-1-propene (1.0 g, 6.57 mmol) in 50 mL of toluene. Hydrochloric acid gas was bubbled through this solution for 10 min, causing a slight exotherm and a brown color. The tube was removed and the solution was diluted with 100 mL of ethyl acetate. This solution was washed with water, brine, dried over sodium sulfate and concentrated to 0.9 g of a brown oil as product. NMR (300 MHz, CDCl$_3$) δ 7.407-7.29 (m, 2H), 7.02 (dd, 2H, J=8 Hz, 9 Hz), 6.63 (d, H, J=16 Hz), 6.29-6.19 (m, 1H), 4.23 (d, 2H, J=8 Hz).

Part C: Preparation of (+/−)-N-3-[trans-6-fluoro-2,3,3a,4,9,9a-hexahydro-1H-benz[f]isoindol-2-yl]-n-prop-1-yl-N'-3-acetylphenylurea Prepared according to procedures described in Example 2 with modification at Step A. MS (ESI) 409 (M+H).

Example 4

Preparation of (+/−)-N-3-[trans-6-fluoro-2,3,3a,4,9,9a-hexahydro-1H-benz[f]isoindol-2-yl]-n-prop-1-yl-N'-4-fluorophenylurea Prepared according to procedures described in Example 3 with modification at last step. MS (ESI) 385 (M+H).

Example 5

Preparation of (+/−)-N-3-[cis-6-fluoro-2,3,3a,4,9,9a-hexahydro-1H-benz[f]isoindol-2-yl]-n-prop-1-yl-N'-3-acetylphenylurea Prepared according to procedures described in Example 3 with modification using cis isomer instead of trans. MS (ESI) 409 (M+H).

Example 6

Preparation of (+/−)-N-3-[cis-6-fluoro-2,3,3a,4,9,9a-hexahydro-1H-benz[f]isoindol-2-yl]-n-prop-1-yl-N'-4-fluorophenylurea Prepared according to procedures described in Example 5 with modification at last step. MS (ESI) 385 (M+H).

Example 7

Preparation of N-(3-acetylphenyl)-N'-[3-[1-[(4-fluorophenyl)methyl]-3-azabicyclo[2.2.2]oct-2-yl]propyl]urea Hydrochloride

Step A. Preparation of Ethyl 4-oxocyclohexanecarboxylate

To a vigorously stirring suspension of ethyl 4-hydroxycyclohexanecarboxylate (2.0 g, 12 mmol, Aldrich) and activated 4 Å MS (1.0 g) in acetonitrile (70 mL) at 23° C. was sequentially added 4-methylmorpholine-N-oxide (2.0 g, 17 mmol) and tetrapropylammonium perruthenate (410 mg, 1.2 mmol). After stirring the resulting black suspension for 30 min, the mixture was concentrated in vacuo, and the resulting residue was filtered through a plug of silica gel (30% ethyl acetate in hexanes) to provide ethyl 4-oxocyclohexanecarboxylate as a clear oil (1.93 g, 98%). MS (APCI) 171 (M+H).

Step B. Preparation of Ethyl 4-(N,N-di(phenylmethyl)amino)cyclohexanecarboxylate To a solution of ethyl 4-oxocyclohexanecarboxylate (1.9 g, 11 mmol) in 1,2-dichloroethane (113 mL) at 23° C. was added dibenzylamine (3.4 g, 3.3 mL, 17 mmol) in one portion. After 10 min, sodium triacetoxyborohydride (4.81 g, 22.7 mmol) was added, and the resulting cloudy suspension was stirred for 48 hrs. The suspension was poured into 1N aqueous hydrogen chloride (100 mL), the resulting mixture was basified to pH 9.0-10.0 with 12.5 M aqueous sodium hydroxide. The basic layer was extracted with ethyl acetate (3×50 mL), and the combined organic layers were washed with saturated aqueous sodium chloride (70 mL), dried over sodium sulfate, and concentrated in vacuo. The resulting residue was purified by flash chromatography (5-10% ethyl acetate in hexanes) to yield ethyl 4-(N,N-dibenzylamino)cyclohexanecarboxylate (3.4 g, 84%) as a clear oil. MS (ESI) 352 (M+H).

Step C. Preparation of Ethyl 4-(N,N-diphenylmethylamino)-1-(4-(fluorophenyl)methyl)cyclohexane-1-carboxylate To a stirring solution of diisopropylamine (1.2 g, 1.7 mL, 12 mmol) in dry tetrahydrofuran (45 mL) at −78° C. was added 2.5 M n-butyllithium (4.6 mL, 11 mmol) in hexanes. After 3 hr, ethyl 4-(N,N-di(phenylmethyl)amino)cyclohexanecarboxylate (3.4 g, 9.5 mmol) was added as a solution in tetrahydrofuran (45 mL) via cannula. The resulting solution became first pink, then red, and finally orange. After stirring at −78° C. for 3 hr, the reaction was poured into saturated aqueous sodium chloride (100 mL). The resulting aqueous layer was extracted with ethyl acetate (3×80 mL), and the combined organic layers were washed with saturated aqueous sodium chloride (30 mL), dried over sodium sulfate, and concentrated in vacuo. The resulting residue was purified by flash chromatography to yield exclusively ethyl 4-(N,N-di(phenylmethyl)amino)-1-(4-(fluorophenyl)methyl)cyclohexane-1-carboxylate (3.7 g, 85%) with ester and amine functionalities in a cis conformation. The product was a white solid. MS (ESI) 460 (M+H).

Step D. Preparation of Ethyl 4-amino-1-(4-(fluorophenyl)methyl)cyclohexane-1-carboxylate To a solution of ethyl 4-(N,N-di(phenylmethyl)amino)-1-(4-(fluorophenyl)methyl)cyclohexane-1-carboxylate (1.0 g, 2.2 mmol) in methanol (50 mL) and glacial acetic acid (100 mL) was added 10% palladium on carbon (200 mg, Degussa type) under a stream of nitrogen. The resulting black suspension was shaken vigorously under a hydrogen atmosphere (52 psi) for 48 hrs. The suspension was then filtered and the resulting filtrate was concentrated in vacuo. The residue was dissolved in a minimal amount of water and poured into saturated aqueous sodium bicarbonate (30 mL). The resulting aqueous layer was extracted with ethyl acetate (4×50 mL), and the combined organic layers were dried over sodium sulfate and concentrated in vacuo to yield ethyl 4-amino-1-(4-(fluorophenyl)methyl)cyclohexane-1-carboxylate as a pale yellow oil. The oil was used directly in step E without further purification. MS (ESI) 280 (M+H).

Step E. Preparation of 1-(4-(fluorophenyl)methyl)-3-azabicyclo[2.2.2]octan-2-one Neat ethyl 4-amino-1-(4-fluorophenyl)methyl)cyclohexane-1-carboxylate from step D in a round bottom flask was heated to 200° C. for 40 min under an open atmosphere. The resulting brown solid was dissolved in a minimal amount of dichloromethane, and the resulting solution was purified by flash chromatography (50-100% ethyl acetate in hexanes, then 5% methanol in ethyl acetate) to yield ring 1-(4-(fluorophenyl)methyl)-3-azabicyclo[2.2.2]octan-2-one (200 mg, 39% two steps) as a clear oil. MS (ESI) 234 (M+H).

Step F. Preparation of N-(t-butoxycarbonyl)-1-(4-fluorophenyl)methyl)-3-azabicyclo[2.2.2]octane To a solution of 1-(4-(fluorophenyl)methyl)-3-azabicyclo[2.2.2]octan-2-one (200 mg, 0.86 mmol) in dry tetrahydrofuran (8 mL) at 23° C. was added borane-tetrahydrofuran (3.4 mL, 3.4 mmol; 1.0 M in tetrahydrofuran). After 10 min, the resulting clear solution was maintained under reflux conditions for 3 hr. The reaction was quenched with 1N aqueous hydrogen chloride (10 mL); this was followed by the addition of a 1-mL portion of concentrated hydrogen chloride, and the resulting solution was maintained under reflux conditions for 10 min. Upon cooling to 23° C., the reaction solution was basified to pH 9.0-10.0 with 12.5 M aqueous sodium hydroxide. The aqueous layer was then extracted with ethyl acetate (4×60 mL), and the combined organic layers were concentrated in vacuo to a colorless oil. The oil was dissolved in tetrahydrofuran (100 mL) at 23° C. and to the solution was added di-t-butyl dicarbonate (210 mg, 0.94 mmol). After 12 hr, the reaction was concentrated and the resulting residue was purified by flash chromatography (10-20% ethyl acetate in hexanes) to yield N-(t-butoxycarbonyl)-1-(4-fluorophenyl)methyl)-3-azabicyclo[2.2.2]octane (270 mg, 99% two steps). MS (ESI) 320 (M+H).

Step G. Preparation of 1-(4-(fluorophenyl)methyl)-3-azabicyclo[2.2.2]octane Hydrochloride To neat N-(t-butoxycarbonyl)-1-(4-fluorophenyl)methyl)-3-azabicyclo[2.2.2]octane (270 mg, 0.85 mmol) was added 4 M hydrogen chloride in dioxane (50 mL). After stirring the resulting pale yellow solution for 30 min, the reaction was concentrated to give 1-(4-(fluorophenyl)methyl)-3-azabicyclo[2.2.2]octane hydrochloride (220 mg, 100%) as a viscous yellow oil. MS (ESI) 220 (M+H).

Step H. Preparation of N-3-[N'-(t-butoxycarbonyl)-3-aminopropyl]-1-(4-(fluorophenyl)methyl)-3-azabicyclo[2.2.2]octane To a stirring solution of 1-(4-(fluorophenyl)methyl)-3-azabicyclo[2.2.2]octane hydrochloride (220 mg, 0.85 mmol) in 1,2-dichloroethane (20 mL) was added N-(t-butoxycarbonyl)-3-aminopropional (230 mg, 1.3 mmol). After 10 min, sodium triacetoxyborohydride (380 mg, 1.80 mmol) was added in one portion and the resulting cloudy white mixture was stirred for 72 hr. The reaction was poured into 1N aqueous hydrogen chloride (100 mL), and the resulting mixture was basified to pH 9.0-10.0 with 12.5 M aqueous sodium hydroxide. The basic layer was extracted with ethyl acetate (3×70 mL), and the combined organic layers were washed with saturated aqueous sodium chloride (70 mL), dried over sodium sulfate, and concentrated in vacuo. The resulting residue was purified by flash chromatography (100% ethyl acetate-5% methanol, 5% triethylamine in ethyl acetate) to yield N-3-[N'-(t-butoxycarbonyl)-3-aminopropyl]-1-(4-(fluorophenyl)methyl)-3-azabicyclo[2.2.2]octane (320 mg, 100%) as a clear viscous oil. MS (ESI) 377 (M+H).

Step I. Preparation of N-3-(3-aminopropyl)-1-(4-(fluorophenyl)methyl)-3-azabicyclo[2.2.2]octane Dihydrochloride To neat N-3-[N'-(t-butoxycarbonyl)-3-aminopropyl]-1-(4-(fluorophenyl)methyl)-3-azabicyclo[2.2.2]octane (320 mg, 0.85 mmol) was added 4N hydrogen chloride in dioxane (85 mL). The resulting solution was stirred for 15 min and then concentrated. The resulting pale yellow oil was redissolved in toluene, and the resulting solution was again concentrated to give N-3-(3-aminopropyl)-1-(4-(fluorophenyl)methyl)-3-azabicyclo[2.2.2]octane dihydrochloride (290 mg, 98%) as a white solid. MS (ESI) 277 (M+H).

Step J. Preparation of N-(3-acetylphenyl)-N'-[3-[1-[(4-fluorophenyl)methyl]-3-azabicyclo[2.2.2]oct-2-yl]propyl]urea Hydrochloride To a solution of N-3-(3-aminopropyl)-1-(4-(fluorophenyl)methyl)-3-azabicyclo[2.2.2]octane dihydrochloride (30 mg, 0.086 mmol) in dichloromethane (1 mL) was added triethylamine (0.1 mL) and 3-acetylphenylisocyanate (19 mg, 0.12 mmol). After vigorous shaking for 20 s, the yellow solution was concentrated in vacuo. The resulting residue was purified by flash chromatography to a pale yellow oil. The oil was dissolved in dichloromethane (5 mL) and to this solution was added 1N hydrogen chloride in diethyl ether (0.14 mL, 0.14 mmol). After 5 min, the resulting solution was concentrated in vacuo. The resulting residue was redissolved in acetonitrile (1 mL) and water (7 mL) and lyopholized to give N'-(3-acetylphenyl)-N'-[3-[1-[(4-fluorophenyl)methyl]-3-azabicyclo[2.2.2]oct-2-yl]propyl]urea hydrochloride (41 mg, 100%) as a white solid. MS (ESI) 438 (M-Cl).

Example 8

Preparation of N-(4-fluorophenyl)-N'-[3-[1-[(4-fluorophenyl)methyl]-3-azabicyclo[2.2.2]oct-2-yl]propyl]urea Hydrochloride Prepared according to procedures described in Example 7 with modification at Step J. MS (ESI) 414 (M-Cl).

Example 9

N-(3-acetylphenyl)-N'-[3-[(1S,4R,6S)-6-[(4-fluorophenyl)methyl]-2-azabicyclo[2.2.2]oct-2-yl]propyl]urea Hydrochloride and N-(3-acetylphenyl)-N'-[3-[(1R,4S,6R)-6-[(4-fluorophenyl)methyl]-2-azabicyclo[2.2.2]oct-2-yl]propyl]urea hydrochloride

Step A. Preparation of N-benzyl-2-azabicyclo[2.2.2]octan-6-one

To a vigorously stirring suspension of (6S)—N-benzyl-2-azabicyclo[2.2.2]octan-6-ol (1.5 g, 6.9 mmol, Maybridge) and activated 4 Å MS (1.0 g) in acetonitrile (70 mL) at 23° C. was sequentially added 4-methylmorpholine-N-oxide (1.2 g, 10 mmol) and tetrapropylammonium perruthenate (240 mg, 0.69 mmol). After stirring the resulting black suspension for 30 min, the mixture was concentrated in vacuo, and the resulting residue was purified by flash chromatography (20-50% ethyl acetate in hexanes) to provide N-benzyl-2-azabicyclo[2.2.2]octan-6-one as an orange oil (1.2 g, 81%). MS (APCI) 216 (M+H).

Step B. Preparation of 6-[4-fluorophenyl)methylene]-2-(phenylmethyl)-2-azabicyclo[2.2.2]octane To a vigorously stirring suspension of p-fluorobenzyltriphenylphosphonium chloride (5.7 g, 14 mmol, Aldrich) in dry tetrahydrofuran (30 mL) at −78° C. was added 2.5 M n-butyllithium (4.7 mL, 12 mmol) in hexanes via syringe. After 30 min, the orange-yellow mixture was warmed to 0° C., and the suspension became deep red. After 5 min, 2-benzyl-2-azabicyclo[2.2.2]octan-6-one (1.2 g, 5.6 mmol) was added as a solution in dry tetrahydrofuran (25 mL) via cannula. Upon stirring vigorously for 2.5 hrs, the reaction was poured into saturated aqueous sodium chloride (70 mL), and the aqueous layer was extracted with ethyl acetate (3×70 mL). The combined organic layers were washed with saturated aqueous sodium chloride (50 mL), dried over sodium sulfate, and concentrated in vacuo. The resulting yellow solid was purified by flash chromatography (20%-70% ethyl acetate in hexanes) to yield 6-[4-fluorophenyl)methylene]-2-(phenylmethyl)-2-azabicyclo[2.2.2]octane (1.7 g, 99%) as a pale yellow oil. MS (ESI) 308 (M+H).

Step C. Preparation of 6-(4-(fluorophenyl)methyl)-2-azabicyclo[2.2.2]octane Acetate To a solution of 6-[4-fluorophenyl)methylene]-2-(phenylmethyl)-2-azabicyclo[2.2.2]octane (800 mg, 2.6 mmol) in methanol (50 mL) and acetic acid (100 mL) was added 10% palladium on carbon (160 mg, Degussa type) under a stream of nitrogen. The resulting black suspension was shaken vigorously for 24 hrs before being filtered. The filtrate was concentrated to provide 6-(4-(fluorophenyl)methyl)-2-azabicyclo[2.2.2]octane acetate (745 mg, 100%) as a pale yellow oil. The oil was used in step D without further purification. MS (ESI) 220 (M+H).

Step D. Preparation of Enantiomeric Mixture of (1S, 4R,6S)—N-(t-butoxycarbonyl)-6-(4-(fluorophenyl) methyl)-2-azabicyclo[2.2.2]octane and (1R,4S,6R)—N-(t-butoxycarbonyl)-6-(4-(fluorophenyl)methyl)-2-azabicyclo[2.2.2]octane and enantiomeric mixture of (1S,4R,6R)—N-(t-butoxycarbonyl)-6-(4-(fluorophenyl)methyl)-2-azabicyclo[2.2.2]octane and (1R,4S, 6S)—N-(t-butoxycarbonyl)-6-(4-(fluorophenyl)methyl)-2-azabicyclo[2.2.2]octane To a suspension of 6-(4-(fluorophenyl)methyl)-2-azabicyclo[2.2.2]octane hydroacetate (750 mg, 2.6 mmol) and di-t-butyl dicarbonate (1.3 g, 5.7 mmol) in tetrahydrofuran at 23° C. was added saturated aqueous sodium bicarbonate (30 mL). The resulting cloudy suspension was stirred vigorously for 2 hr and was then poured into saturated aqueous sodium chloride (100 mL). The aqueous layer was extracted with ethyl acetate (3×70 mL), and the combined organic layers were washed with saturated aqueous sodium chloride (50 mL), dried over sodium sulfate, and concentrated in vacuo. The resulting mixture of diasteromeric compounds were purified and separated by flash chromatography (5-20% ethyl acetate in hexanes) to yield faster-running enantiomeric mixture of (1S,4R,6S)—N-(t-butoxycarbonyl)-6-(4-(fluorophenyl)methyl)-2-azabicyclo[2.2.2]octane and (1R,4S,6R)—N-(t-butoxycarbonyl)-6-(4-(fluorophenyl)methyl)-2-azabicyclo[2.2.2]octane (180 mg, 24%) and slower-enantiomeric mixture of (1S,4R,6R)—N-(t-butoxycarbonyl)-6-(4-(fluorophenyl)methyl)-2-azabicyclo[2.2.2]octane and (1R,4S,6S)—N-(t-butoxycarbonyl)-6-(4-(fluorophenyl)methyl)-2-azabicyclo[2.2.2]octane (300 mg, 40%) as clear oils. MS (ESI) 320 (6S, M+H), 320 (6R, M+H).

Step E. Preparation of (1S,4R,6S)-6-(4-(fluorophenyl)methyl)-2-azabicyclo[2.2.2]octane hydrochloride and (1R,4S,6R)-6-(4-(fluorophenyl)methyl)-2-azabicyclo[2.2.2]octane Hydrochloride To neat (1S,4R,6S)—N-(t-butoxycarbonyl)-6-(4-(fluorophenyl)methyl)-2-azabicyclo[2.2.2]octane and (1R,4S,6R)—N-(t-butoxycarbonyl)-6-(4-(fluorophenyl)methyl)-2-azabicyclo[2.2.2]octane (180 mg, 0.57 mmol) was added 4N hydrogen chloride in dioxane (40 mL). The resulting yellow solution was stirred for min and was then concentrated. The residue was further concentrated under high-vacuum for 20 min to yield (1S,4R,6S)-6-(4-(fluorophenyl)methyl)-2-azabicyclo[2.2.2]octane hydrochloride and (1R,4S,6R)-6-(4-(fluorophenyl)methyl)-2-azabicyclo[2.2.2]octane hydrochloride (150 mg, 100%) as a highly viscous yellow oil that was used in step F without further purification. MS (ESI) 220 (M+H).

Step F. Preparation of (1S,4R,6S)-6-(4-(fluorophenyl)methyl)-2-(N-(t-butoxycarbonyl)-3-aminopropyl)-2-azabicyclo[2.2.2]octane and (1R,4S,6R)-6-(4-(fluorophenyl)methyl)-2-(N-(t-butoxycarbonyl)-3-aminopropyl)-2-azabicyclo[2.2.2]octane To a stirring solution of (1S,4R,6S)-6-(4-(fluorophenyl)methyl)-2-azabicyclo[2.2.2]octane hydrochloride and (1R, 4S,6R)-6-(4-(fluorophenyl)methyl)-2-azabicyclo[2.2.2]octane hydrochloride (150 mg, 0.57 mmol) in 1,2-dichloroethane (8 mL) at 23° C. was added N-(t-butoxycarbonyl)-3-aminopropional (220 mg, 1.3 mmol). After 10 min, sodium triacetoxyborohydride (350 mg, 1.7 mmol) was added in one portion, and the resulting suspension was stirred for 6 hr. The reaction was then poured into 1N aqueous hydrogen chloride (50 mL), and the resulting mixture was basified to pH 9.0-10.0 with 12.5 M aqueous sodium hydroxide. The basic layer was extracted with ethyl acetate (3×50 mL), and the combined organic layers were washed with saturated aqueous sodium chloride (70 mL), dried over sodium sulfate, and concentrated in vacuo. The resulting residue was purified by flash chromatography (10% methanol in dichloromethane then 5% triethylamine, 10% methanol in dichloromethane) to yield (1S,4R,6S)-6-(4-(fluorophenyl)methyl)-2-(N-(t-butoxycarbonyl)-3-aminopropyl)-2-azabicyclo[2.2.2]octane and (1R,4S,6R)-6-(4-(fluorophenyl)methyl)-2-(N-(t-butoxycarbonyl)-3-aminopropyl)-2-azabicyclo[2.2.2]octane (68 mg, 0.18 mmol) as a pale yellow oil. MS (ESI) 377 (M+H).

Step G. Preparation of (1S,4R,6S)-2-(3-aminopropyl)-6-(4-(fluorophenyl)methyl)-2-azabicyclo[2.2.2]octane Dihydrochloride and (1R,4S,6R)-2-(3-aminopropyl)-6-(4-(fluorophenyl)methyl)-2-azabicyclo[2.2.2]octane Dihydrochloride To neat (1S,4R,6S)-6-(4-(fluorophenyl)methyl)-2-(N-(t-butoxycarbonyl)-3-aminopropyl)-2-azabicyclo[2.2.2]octane and (1R,4S,6R)-6-(4-(fluorophenyl)methyl)-2-(N-(t-butoxycarbonyl)-3-aminopropyl)-2-azabicyclo[2.2.2]octane (68 mg, 0.18 mmol) was added 4N hydrogen chloride (20 mL). The yellow solution was stirred for 1 hr and was then concentrated. The resulting residue (63 mg, 100%) was used directly in the next step without further purification. MS (ESI) 277 (M+H).

Step H. Preparation of N-(3-acetylphenyl)-N'-[3-[(1S,4R,6S)-6-[(4-fluorophenyl)methyl]-2-azabicyclo[2.2.2]oct-2-yl]propyl]urea and N-(3-acetylphenyl)-N'-[3-[(1R,4S,6R)-6-[(4-fluorophenyl)methyl]-2-azabicyclo[2.2.2]oct-2-yl]propyl]urea To a solution of (1S,4R,6S)-2-(3-aminopropyl)-6-(4-(fluorophenyl)methyl)-2-azabicyclo[2.2.2]octane dihydrochloride and (1R,4S,6R)-2-(3-aminopropyl)-6-(4-(fluorophenyl)methyl)-2-azabicyclo[2.2.2]octane dihydrochloride (63 mg, 0.09 mmol) and triethylamine (100 µL) in dichloromethane (1 mL) was added 3-acetylphenylisocyanate (16 mg, 0.10 mmol). The yellow solution was shaken vigorously for 20 s and was then concentrated in vacuo. The resulting residue was purified by flash chromatography (100% ethyl acetate then 5% methanol, 10% triethylamine in ethyl acetate) to yield N-(3-acetylphenyl)-N'-[3-[(1S,4R,6S)-6-[(4-fluorophenyl)methyl]-2-azabicyclo[2.2.2]oct-2-yl]propyl]urea and N-(3-acetylphenyl)-N'-[3-[(1R,4S,6R)-6-[(4-fluorophenyl)methyl]-2-azabicyclo[2.2.2]oct-2-yl]propyl]urea (8.5 mg, 23%) as a pale yellow oil. MS (ESI) 438 (M+H).

Step I. Preparation of N-(3-acetylphenyl)-N'-[3-[(1S,4R,6S)-6-[(4-fluorophenyl)methyl]-2-azabicyclo[2.2.2]oct-2-yl]propyl]urea Hydrochloride and N-(3-acetylphenyl)-N'-[3-[(1R,4S,6R)-6-[(4-fluorophenyl)methyl]-2-azabicyclo[2.2.2]oct-2-yl]propyl]urea Hydrochloride To a solution of N-(3-acetylphenyl)-N'-[3-[(1S,4R,6S)-6-[(4-fluorophenyl)methyl]-2-azabicyclo[2.2.2]oct-2-yl]propyl]urea and N-(3-acetylphenyl)-N'-[3-[(1R,4S,6R)-6-[(4-fluorophenyl)methyl]-2-azabicyclo[2.2.2]oct-2-yl]propyl]urea (8.5 mg, 0.019 mmol) in dichloromethane (10 mL) was added 1N hydrogen chloride in diethyl ether (21 µL, 0.021 mmol). The resulting suspension was stirred for 10 min and was then concentrated. The residue was dissolved in acetonitrile (1 mL) and water (7 mL) and lyophilized to afford N-(3-acetylphenyl)-N'-[3-[(1S,4R,6S)-6-[(4-fluorophenyl)methyl]-2-azabicyclo[2.2.2]oct-2-yl]propyl]urea hydrochloride and N-(3-acetylphenyl)-N'-[3-[(1R,4S,6R)-6-[(4-fluorophenyl)methyl]-2-azabicyclo[2.2.2]oct-2-yl]propyl]urea hydrochloride (9.0 mg, 100%) as an amorphous solid. MS (ESI) 438 (M-Cl).

Example 10

N-(4-fluorophenyl)-N'-[3-[(1S,4R,6S)-6-[(4-fluorophenyl)methyl]-2-azabicyclo[2.2.2]oct-2-yl]propyl]urea Hydrochloride and N-(4-fluorophenyl)-N'-[3-[(1R,4S,6R)-6-[(4-fluorophenyl)methyl]-2-azabicyclo[2.2.2]oct-2-yl]propyl]urea Hydrochloride Prepared according to procedures described in Example 9 with modification at Step H. MS (ESI) 414 (M-Cl).

Example 11

N-(3-acetylphenyl)-N'-[3-[(1S,4R,6R)-6-[(4-fluorophenyl)methyl]-2-azabicyclo[2.2.2]oct-2-yl]propyl]urea Hydrochloride and N-(3-acetylphenyl)-N'-[3-[(1R,4S,6S)-6-[(4-fluorophenyl)methyl]-2-azabicyclo[2.2.2]oct-2-yl]propyl]urea Hydrochloride Prepared according to procedures described in Example 9 with modification at Step D. MS (ESI) 438 (M-Cl).

Example 12

N-(4-fluorophenyl)-N'-[3-[(1S,4R,6R)-6-[(4-fluorophenyl)methyl]-2-azabicyclo[2.2.2]oct-2-yl]propyl]urea Hydrochloride and N-(4-fluorophenyl)-N'-[3-[(1R,4S,6S)-6-[(4-fluorophenyl)methyl]-2-azabicyclo[2.2.2]oct-2-yl]propyl]urea Hydrochloride Prepared according to procedures described in Example 9 with modification at Step D. MS (ESI) 414 (M-Cl).

Example 13

N-(3-acetylphenyl)-N'-[(2S)-2-[[(3-exo)-3-[(4-fluorophenyl)methyl]-8-azabicyclo[3.2.1]oct-8-yl]methyl]-(2R)-1-cyclohexyl]urea Step A. Preparation of N-(t-butoxycarbonyl)-3-[(4-fluorophenyl)methylene]-8-azabicyclo[3.2.1]octane To a vigorously stirring suspension of 4-fluorobenzyltriphenylphosphonium chloride (4.96 g, 12.2 mmol) in tetrahydrofuran 25 mL) at −78° C. was added 2.5 M n-butyllithium (4.12 mL, 10.3 mmol) in hexanes. The resulting yellow suspension was maintained at −78° C. for 25 min and was then warmed to 0° C. After 30 min, N-(t-butoxycarbonyl)-nortropinone (1.1 g, 4.9 mmol) was added to the now red suspension as a solution in tetrahydrofuran (25 mL). The suspension changed color from red to orange, and the reaction was heated to 80° C. The reaction was maintained at reflux conditions for 60 hrs prior to being quenched with saturated aqueous ammonium chloride (30 mL). The layers were separated, and the aqueous layer was washed with ethyl acetate (3×30 mL). The combined organic layers were dried over sodium sulfate, concentrated in vacuo, and the resulting residue was purified by flash column chromatography (10-30% ethyl acetate in hexanes) to N-(t-butoxycarbonyl)-3-[(4-fluorophenyl)methylene]-8-azabicyclo[3.2.1]octane (1.37 g, 88%) as a white solid. MS (ESI) 218 (M+H).

Step B. Preparation of N-(t-butoxycarbonyl)-(3-exo)-3-[(4-fluorophenylmethyl]-8-azabicyclo[3.2.1]octane and N-(t-butoxycarbonyl)-(3-endo)-3-[(4-fluorophenylmethyl]-8-azabicyclo[3.2.1]octane To a solution of N-(t-butoxycarbonyl)-3-[(4-fluorophenyl)methylene]-8-azabicyclo[3.2.1]octane (300 mg, 0.95 mmol) in methanol was added 10% palladium on carbon (60 mg, Degussa type) under a nitrogen atmosphere. The resulting black suspension was subjected to a hydrogen atmosphere (51 psi) for 14 hrs, and the reaction was then filtered, and the filtrate was concentrated in vacuo to yield a 2.6:1.0 mixture of endo:exo isomers as determined by $^1$H-NMR. Separation of exo and endo isomers by high-performance liquid chromatography using a Chiralpak AD column (10% acetonitrile and 90% $CO_2$) yielding N-(t-butoxycarbonyl)-(3-exo)-3-[(4-fluorophenylmethyl]-8-azabicyclo[3.2.1]octane (84 mg) as a colorless oil and N-(t-butoxycarbonyl)-(3-exo)-3-[(4-fluorophenylmethyl]-8-azabicyclo[3.2.1]octane (166 mg) as a colorless oil. MS (AP CI) 320 (M+H).

Step C. Preparation of (3-exo)-3-[(4-fluorophenyl)methyl]-8-azabicyclo[3.2.1]octane Hydrochloride To neat N-(t-butoxycarbonyl)-(3-exo)-3-[(4-fluorophenylmethyl]-8-azabicyclo[3.2.1]octane (120 mg, 0.38 mmol) was added 4 M hydrogen chloride in dioxane (30 mL, 120 mmol). After stirring for 30 min, the resulting pale yellow solution was concentrated in vacuo to provide (3-exo)-3-[(4-fluorophenyl)methyl]-8-azabicyclo[3.2.1]octane hydrochloride (96 mg, 100%) as a pale yellow oil. MS (AP CI) 220 (M+H).

Step D. Preparation of N-(benzyloxycarbonyl)-[(2S)-2-[[(3-exo)-3-[(4-fluorophenyl)methyl]-8-azabicyclo[3.2.1]oct-8-yl]methyl]-(1R)-1-amino-cyclohexane Dichloroethane (4 mL) was added to (3-exo)-3-[(4-fluorophenyl)methyl]-8-azabicyclo[3.2.1]octane hydrochloride (96 mg, 0.38 mmol) followed by the sequential addition of (1R,2R)—N-(benzyloxycarbonyl)-2-formylcyclohexylamine (128 mg, 0.49 mmol). The resulting solution was maintained at 23° C. for 5 min. Following the addition of sodium triacetoxyborohydride (159 mg, 0.75 mmol) in one portion, the resulting white suspension was stirred for 12 hr and then added to aqueous 1N hydrogen chloride (30 mL). The aqueous layer was basified with aqueous 12.5N sodium hydroxide (3 mL), and the layers were separated. The aqueous layer was extracted with ethyl acetate (3×40 mL), and the combined organic layers were washed with saturated aqueous sodium chloride (10 mL) and dried over sodium sulfate. Upon concentration in vacuo, the resulting residue was purified by flash column chromatography (10% methanol in dichloromethane) to give N-(benzyloxycarbonyl)-[(2S)-2-[[(3-exo)-3-[(4-fluorophenyl)methyl]-8-azabicyclo[3.2.1]oct-8-yl]methyl]-(1R)-1-amino-cyclohexane. (145 mg, 83%) as a pale yellow oil. MS (ESI) 465 (M+H).

Step E. Preparation of (2S)-2-[[(3-exo)-3-[(4-fluorophenyl)methyl]-8-azabicyclo[3.2.1]oct-8-yl]methyl]-(1R)-1-amino-cyclohexane Diacetate To N-(benzyloxycarbonyl)-[(2S)-2-[[(3-exo)-3-[(4-fluorophenyl)methyl]-8-azabicyclo[3.2.1]oct-8-yl]methyl]-(1R)-1-amino-cyclohexane was added methanol (100 mL) and glacial acetic acid (10 mL) prior to the addition of 10% palladium on carbon (50 mg, Degussa type) under a nitrogen atmosphere. The resulting black suspension was subjected to a hydrogen atmosphere (50 psi) with vigorous shaking for 4 hrs. The suspension was then filtered, and the filtrate was concentrated in vacuo to provide (2S)-2-[[(3-exo)-3-[(4-fluorophenyl)methyl]-8-azabicyclo[3.2.1]oct-8-yl]methyl]-(1R)-1-amino-cyclohexane diacetate as a pale brown oil (140 mg, 100%). MS (ESI) 331 (M+H).

Step F. Preparation of N-(3-acetylphenyl)-N'-[(2S)-2-[[(3-exo)-3-[(4-fluorophenyl)methyl]-8-azabicyclo[3.2.1]oct-8-yl]methyl]-(2R)-1-cyclohexyl]urea To a solution of (2S)-2-[[(3-exo)-3-[(4-fluorophenyl)methyl]-8-azabicyclo[3.2.1]oct-8-yl]methyl]-(1R)-1-cyclohexyl]amine diacetate (30 mg, 0.091 mmol) and triethylamine (100 µL, 0.72 mmol) in dichloromethane (2 mL) was added 3-acetylphenylisocyanate (16 mg, 0.10 mmol). The resulting pale yellow solution was shaken for 20 s and then concentrated. The resulting residue was purified by flash column chromatography (0 to 5% triethylamine in ethyl acetate) to give N-(3-acetylphenyl)-N'-[(2S)-2-[[(3-exo)-3-[(4-fluorophenyl)methyl]-8-azabicyclo[3.2.1]oct-8-yl]methyl]-(2R)-1-cyclohexyl]urea as a pale yellow oil (18 mg, 40%). MS (ESI) 492 (M-Cl).

Example 14

N-(4-fluorophenyl)-N'-[(2S)-2-[[(3-exo)-3-[(4-fluorophenyl)methyl]-8-azabicyclo[3.2.1]oct-8-yl]methyl]-(2R)-1-cyclohexyl]urea Prepared according to procedures described in Example 13 with modification at Step F. MS (ESI) 468 (M-Cl).

Example 15

N-(3-acetylphenyl)-N'-[(2S)-2-[[(3-endo)-3-[(4-fluorophenyl)methyl]-8-azabicyclo[3.2.1]oct-8-yl]methyl]-(2R)-1-cyclohexyl]urea Prepared according to procedures described in Example 13 using endo instead of exo isomer. MS (ESI) 492 (M-Cl).

Example 16

N-(4-fluorophenyl)-N'-[(2S)-2-[[(3-endo)-3-[(4-fluorophenyl)methyl]-8-azabicyclo[3.2.1]oct-8-yl]methyl]-(2R)-1-cyclohexyl]urea Prepared according to procedures described in Example 15 with modification at Step F. MS (ESI) 468 (M-Cl).

Example 17

N-(3-acetylphenyl)-N'-{3-[(1S,5R,6R)-6-(4-fluorophenyl)-3-azabicyclo[3.2.0]hept-3-yl]propyl}urea and N-(3-acetylphenyl)-N'-{3-[(1R,5S,6S)-6-(4-fluorophenyl)-3-azabicyclo[3.2.0]hept-3-yl]propyl}urea A racemic mixture of (1S,5R,6R)-6-(4-fluorophenyl)-3-azabicyclo[3.2.0]heptane and (1R,5S,6S)-6-(4-fluorophenyl)-3-azabicyclo[3.2.0]heptane (Steiner, G., Nunschauer, R., Klebe, G., Siggel, L. Heterocycles, 1995, 40, 319-330) was converted to the titled compounds using the procedures described in Example 1, parts D, E, and F. MS (ESI) 410 (M+H).

Example 18

N-(4-fluorophenyl)-N'-{3-[(1S,5R,6R)-6-(4-fluorophenyl)-3-azabicyclo[3.2.0]hept-3-yl]propyl}urea and N-(4-fluorophenyl)-N'-{3-[(1R,5S,6S)-6-(4-fluorophenyl)-3-azabicyclo[3.2.0]hept-3-yl]propyl}urea A racemic mixture of (1S,5R,6R)-6-(4-fluorophenyl)-3-azabicyclo[3.2.0]heptane and (1R,5S,6S)-6-(4-fluorophenyl)-3-azabicyclo[3.2.0]heptane (Steiner, G., Nunschauer, R., Klebe, G., Siggel, L. Heterocycles, 1995, 40, 319-330) was converted to the titled compounds using the procedures described in Example 1, parts D, E, and F, where instead of 3-acetylisocyanate in part F, 4-fluorophenylisocyanate was used instead. MS (ESI) 386 (M+H).

The following table contains representative examples of the present invention. Each entry in the table is intended to be paired with each formulae at the start of the table. For example, entry 1 in Table 1 is intended to be paired with a-h.

TABLE 1

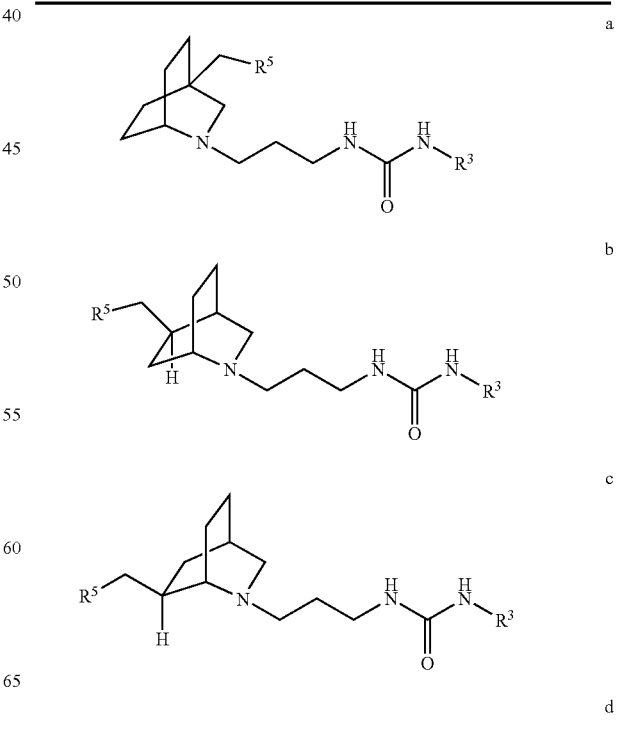

a b c d

TABLE 1-continued

| ENTRY | R5 | R3 |
|---|---|---|
| 1 | 4-F—Ph | Ph |
| 2 | 4-F—Ph | 3-CN—Ph |
| 3 | 4-F—Ph | 3-COCH3—Ph |
| 4 | 4-F—Ph | 3-CO2Me—Ph |
| 5 | 4-F—Ph | 3-CO2Et—Ph |
| 6 | 4-F—Ph | 3-CO2H—Ph |
| 7 | 4-F—Ph | 3-CONH2—Ph |
| 8 | 4-F—Ph | 3-CONHMe—Ph |
| 9 | 4-F—Ph | 3-F—Ph |
| 10 | 4-F—Ph | 3-Cl—Ph |
| 11 | 4-F—Ph | 3-Br—Ph |
| 12 | 4-F—Ph | 3-NO2—Ph |
| 13 | 4-F—Ph | 3-NH2—Ph |
| 14 | 4-F—Ph | 3-NHMe—Ph |
| 15 | 4-F—Ph | 3-NMe2—Ph |
| 16 | 4-F—Ph | 3-NHCOCH3—Ph |
| 17 | 4-F—Ph | 3-SO2NH2—Ph |
| 18 | 4-F—Ph | 3-SO2NHMe—Ph |
| 19 | 4-F—Ph | 3-CF3—Ph |
| 20 | 4-F—Ph | 3-OCH3—Ph |
| 21 | 4-F—Ph | 3-OPh—Ph |
| 22 | 4-F—Ph | 3-OCF3—Ph |
| 23 | 4-F—Ph | 3-SCH3—Ph |
| 24 | 4-F—Ph | 3-SOCH3—Ph |
| 25 | 4-F—Ph | 3-SO2CH3—Ph |
| 26 | 4-F—Ph | 3-OH—Ph |
| 27 | 4-F—Ph | 3-CH2OH—Ph |
| 28 | 4-F—Ph | 3-CHOHCH3—Ph |
| 29 | 4-F—Ph | 3-COH(CH3)2—Ph |
| 30 | 4-F—Ph | 3-CHOHPh—Ph |
| 31 | 4-F—Ph | 3-CH3—Ph |
| 32 | 4-F—Ph | 3-C2H5—Ph |
| 33 | 4-F—Ph | 3-iPr—Ph |
| 34 | 4-F—Ph | 3-tBu—Ph |
| 35 | 4-F—Ph | 3-Ph—Ph |
| 36 | 4-F—Ph | 3-CH2Ph—Ph |
| 37 | 4-F—Ph | 3-CH2CO2Me—Ph |
| 38 | 4-F—Ph | 3-(1-piperidinyl)-Ph |
| 39 | 4-F—Ph | 3-(1-pyrrolidinyl)-Ph |
| 40 | 4-F—Ph | 3-(2-imidazolyl)-Ph |
| 41 | 4-F—Ph | 3-(1-imidazolyl)-Ph |
| 42 | 4-F—Ph | 3-(2-thiazolyl)-Ph |
| 43 | 4-F—Ph | 3-(3-pyrazolyl)-Ph |
| 44 | 4-F—Ph | 3-(1-pyrazolyl)-Ph |
| 45 | 4-F—Ph | 3-(1-tetrazolyl)-Ph |
| 46 | 4-F—Ph | 3-(5-tetrazolyl)-Ph |
| 47 | 4-F—Ph | 3-(2-pyridyl)-Ph |
| 48 | 4-F—Ph | 3-(2-thienyl)-Ph |
| 49 | 4-F—Ph | 3-(2-furanyl)-Ph |
| 50 | 4-F—Ph | 4-CN—Ph |
| 51 | 4-F—Ph | 4-COCH3—Ph |
| 52 | 4-F—Ph | 4-CO2Me—Ph |
| 53 | 4-F—Ph | 4-CO2Et—Ph |
| 54 | 4-F—Ph | 4-CO2H—Ph |
| 55 | 4-F—Ph | 4-CONH2—Ph |
| 56 | 4-F—Ph | 4-CONHMe—Ph |
| 57 | 4-F—Ph | 4-CONHPh—Ph |
| 58 | 4-F—Ph | 4-NHCONH2—Ph |
| 59 | 4-F—Ph | 4-F—Ph |
| 60 | 4-F—Ph | 4-Cl—Ph |
| 61 | 4-F—Ph | 4-Br—Ph |
| 62 | 4-F—Ph | 4-NO2—Ph |
| 63 | 4-F—Ph | 4-NH2—Ph |
| 64 | 4-F—Ph | 4-NHMe—Ph |
| 65 | 4-F—Ph | 4-NMe2—Ph |
| 66 | 4-F—Ph | 4-NHCOCH3—Ph |
| 67 | 4-F—Ph | 4-SO2NH2—Ph |
| 68 | 4-F—Ph | 4-SO2NHMe—Ph |
| 69 | 4-F—Ph | 4-CF3—Ph |
| 70 | 4-F—Ph | 4-OCH3—Ph |
| 71 | 4-F—Ph | 4-OPh—Ph |
| 72 | 4-F—Ph | 4-OCF3—Ph |
| 73 | 4-F—Ph | 4-SCH3—Ph |
| 74 | 4-F—Ph | 4-SOCH3—Ph |
| 75 | 4-F—Ph | 4-SO2CH3—Ph |
| 76 | 4-F—Ph | 4-OH—Ph |
| 77 | 4-F—Ph | 4-CH2OH—Ph |
| 78 | 4-F—Ph | 4-CHOHCH3—Ph |
| 79 | 4-F—Ph | 4-COH(CH3)2—Ph |
| 80 | 4-F—Ph | 4-CH3—Ph |
| 81 | 4-F—Ph | 4-C2H5—Ph |
| 82 | 4-F—Ph | 4-iPr—Ph |
| 83 | 4-F—Ph | 4-tBu—Ph |
| 84 | 4-F—Ph | 4-Ph—Ph |
| 85 | 4-F—Ph | 4-CH2Ph—Ph |
| 86 | 4-F—Ph | 4-CH2CO2Me—Ph |
| 87 | 4-F—Ph | 4-(1-piperidinyl)-Ph |
| 88 | 4-F—Ph | 4-(1-pyrrolidinyl)-Ph |
| 89 | 4-F—Ph | 4-(2-imidazolyl)-Ph |
| 90 | 4-F—Ph | 4-(1-imidazolyl)-Ph |
| 91 | 4-F—Ph | 4-(2-thiazolyl)-Ph |
| 92 | 4-F—Ph | 4-(3-pyrazolyl)-Ph |

TABLE 1-continued

| | | |
|---|---|---|
| 93 | 4-F—Ph | 4-(1-pyrazolyl)-Ph |
| 94 | 4-F—Ph | 4-(1-tetrazolyl)-Ph |
| 95 | 4-F—Ph | 4-(5-tetrazolyl)-Ph |
| 96 | 4-F—Ph | 4-(2-pyridyl)-Ph |
| 97 | 4-F—Ph | 4-(2-thienyl)-Ph |
| 98 | 4-F—Ph | 4-(2-furanyl)-Ph |
| 99 | 4-F—Ph | 2-CN—Ph |
| 100 | 4-F—Ph | 2-COCH3—Ph |
| 101 | 4-F—Ph | 2-CO2Me—Ph |
| 102 | 4-F—Ph | 2-CO2Et—Ph |
| 103 | 4-F—Ph | 2-CO2H—Ph |
| 104 | 4-F—Ph | 2-CONH2—Ph |
| 105 | 4-F—Ph | 2-CONHMe—Ph |
| 106 | 4-F—Ph | 2-F—Ph |
| 107 | 4-F—Ph | 2-Cl—Ph |
| 108 | 4-F—Ph | 2-Br—Ph |
| 109 | 4-F—Ph | 2-NO2—Ph |
| 110 | 4-F—Ph | 2-NH2—Ph |
| 111 | 4-F—Ph | 2-NHMe—Ph |
| 112 | 4-F—Ph | 2-NMe2—Ph |
| 113 | 4-F—Ph | 2-NHCOCH3—Ph |
| 114 | 4-F—Ph | 2-SO2NH2—Ph |
| 115 | 4-F—Ph | 2-SO2NHMe—Ph |
| 116 | 4-F—Ph | 2-CF3—Ph |
| 117 | 4-F—Ph | 2-OCH3—Ph |
| 118 | 4-F—Ph | 2-OPh—Ph |
| 119 | 4-F—Ph | 2-OCF3—Ph |
| 120 | 4-F—Ph | 2-SCH3—Ph |
| 121 | 4-F—Ph | 2-SOCH3—Ph |
| 122 | 4-F—Ph | 2-SO2CH3—Ph |
| 123 | 4-F—Ph | 2-OH—Ph |
| 124 | 4-F—Ph | 2-CH2OH—Ph |
| 125 | 4-F—Ph | 2-CHOHCH3—Ph |
| 126 | 4-F—Ph | 2-COH(CH3)2—Ph |
| 127 | 4-F—Ph | 2-CHOHPh—Ph |
| 128 | 4-F—Ph | 2-CH3—Ph |
| 129 | 4-F—Ph | 2-C2H5—Ph |
| 130 | 4-F—Ph | 2-iPr—Ph |
| 131 | 4-F—Ph | 2-tBu—Ph |
| 132 | 4-F—Ph | 2-Ph—Ph |
| 133 | 4-F—Ph | 2-CH2Ph—Ph |
| 134 | 4-F—Ph | 2-CH2CO2Me—Ph |
| 135 | 4-F—Ph | 2-(1-piperidinyl)-Ph |
| 136 | 4-F—Ph | 2-(1-pyrrolidinyl)-Ph |
| 137 | 4-F—Ph | 2-(2-imidazolyl)-Ph |
| 138 | 4-F—Ph | 2-(1-imidazolyl)-Ph |
| 139 | 4-F—Ph | 2-(2-thiazolyl)-Ph |
| 140 | 4-F—Ph | 2-(3-pyrazolyl)-Ph |
| 141 | 4-F—Ph | 2-(1-pyrazolyl)-Ph |
| 142 | 4-F—Ph | 2-(1-tetrazolyl)-Ph |
| 143 | 4-F—Ph | 2-(5-tetrazolyl)-Ph |
| 144 | 4-F—Ph | 2-(2-pyridyl)-Ph |
| 145 | 4-F—Ph | 2-(2-thienyl)-Ph |
| 146 | 4-F—Ph | 2-(2-furanyl)-Ph |
| 147 | 4-F—Ph | 2,4-diF—Ph |
| 148 | 4-F—Ph | 2,5-diF—Ph |
| 149 | 4-F—Ph | 2,6-diF—Ph |
| 150 | 4-F—Ph | 3,4-diF—Ph |
| 151 | 4-F—Ph | 3,5-diF—Ph |
| 152 | 4-F—Ph | 2,4-diCl—Ph |
| 153 | 4-F—Ph | 2,5-diCi—Ph |
| 154 | 4-F—Ph | 2,6-diCi—Ph |
| 155 | 4-F—Ph | 3,4-diCl—Ph |
| 156 | 4-F—Ph | 3,5-diCl—Ph |
| 157 | 4-F—Ph | 3,4-diCF3—Ph |
| 158 | 4-F—Ph | 3,5-diCF3—Ph |
| 159 | 4-F—Ph | 5-Cl-2-MeO—Ph |
| 160 | 4-F—Ph | 5-Cl-2-Me—Ph |
| 161 | 4-F—Ph | 2-F-5-Me—Ph |
| 162 | 4-F—Ph | 2-F-5-NO2—Ph |
| 163 | 4-F—Ph | 3,4-OCH2O—Ph |
| 164 | 4-F—Ph | 3,4-OCH2CH2O—Ph |
| 165 | 4-F—Ph | 2-MeO-4-Me—Ph |
| 166 | 4-F—Ph | 2-MeO-5-Me—Ph |
| 167 | 4-F—Ph | 1-naphthyl |
| 168 | 4-F—Ph | 2-naphthyl |
| 169 | 4-F—Ph | 2-thienyl |
| 170 | 4-F—Ph | 3-thienyl |
| 171 | 4-F—Ph | 2-furanyl |
| 172 | 4-F—Ph | 3-furanyl |
| 173 | 4-F—Ph | 2-pyridyl |
| 174 | 4-F—Ph | 3-pyridyl |
| 175 | 4-F—Ph | 4-pyridyl |
| 176 | 4-F—Ph | 2-indolyl |
| 177 | 4-F—Ph | 3-indolyl |
| 178 | 4-F—Ph | 5-indolyl |
| 179 | 4-F—Ph | 6-indolyl |
| 180 | 4-F—Ph | 3-indazolyl |
| 181 | 4-F—Ph | 5-indazolyl |
| 182 | 4-F—Ph | 6-indazolyl |
| 183 | 4-F—Ph | 2-imidazolyl |
| 184 | 4-F—Ph | 3-pyrazolyl |
| 185 | 4-F—Ph | 2-thiazolyl |
| 186 | 4-F—Ph | 5-tetrazolyl |
| 187 | 4-F—Ph | 2-benzimidazolyl |
| 188 | 4-F—Ph | 5-benzimidazolyl |
| 189 | 4-F—Ph | 2-benzothiazolyl |
| 190 | 4-F—Ph | 5-benzothiazolyl |
| 191 | 4-F—Ph | 2-benzoxazolyl |
| 192 | 4-F—Ph | 5-benzoxazolyl |
| 193 | 2-F—Ph | 3-CN—Ph |
| 194 | 2-F—Ph | 3-COCH3—Ph |
| 195 | 2-F—Ph | 3-CO2Me—Ph |
| 196 | 2-F—Ph | 3-CO2Et—Ph |
| 197 | 2-F—Ph | 3-CO2H—Ph |
| 198 | 2-F—Ph | 3-CONH2—Ph |
| 199 | 2-F—Ph | 3-F—Ph |
| 200 | 2-F—Ph | 3-Cl—Ph |
| 201 | 2-F—Ph | 3-NH2—Ph |
| 202 | 2-F—Ph | 3-SO2NH2—Ph |
| 203 | 2-F—Ph | 3-CF3—Ph |
| 204 | 2-F—Ph | 3-OCH3—Ph |
| 205 | 2-F—Ph | 3-OEt—Ph |
| 206 | 2-F—Ph | 3-OCF3—Ph |
| 207 | 2-F—Ph | 3-SO2CH3—Ph |
| 208 | 2-F—Ph | 3-OH—Ph |
| 209 | 2-F—Ph | 3-CH3—Ph |
| 210 | 2-F—Ph | 3-C2H5—Ph |
| 211 | 2-F—Ph | 4-CN—Ph |
| 212 | 2-F—Ph | 4-COCH3—Ph |
| 213 | 2-F—Ph | 4-CO2Me—Ph |
| 214 | 2-F—Ph | 4-CO2Et—Ph |
| 215 | 2-F—Ph | 4-CO2H—Ph |
| 216 | 2-F—Ph | 4-CONH2—Ph |
| 217 | 2-F—Ph | 4-F—Ph |
| 218 | 2-F—Ph | 4-Cl—Ph |
| 219 | 2-F—Ph | 4-NH2—Ph |
| 220 | 2-F—Ph | 4-SO2NH2—Ph |
| 221 | 2-F—Ph | 4-CF3—Ph |
| 222 | 2-F—Ph | 4-OCH3—Ph |
| 223 | 2-F—Ph | 4-OEt—Ph |
| 224 | 2-F—Ph | 4-OCF3—Ph |
| 225 | 2-F—Ph | 4-SO2CH3—Ph |
| 226 | 2-F—Ph | 4-OH—Ph |
| 227 | 2-F—Ph | 4-CH3—Ph |
| 228 | 2-F—Ph | 4-C2H5—Ph |
| 229 | 2-F—Ph | 2,4-diF—Ph |
| 230 | 2-F—Ph | 2,5-diF—Ph |
| 231 | 2-F—Ph | 3,4-diF—Ph |
| 232 | 2-F—Ph | 3,5-diF—Ph |
| 233 | 2-F—Ph | 2,4-diCl—Ph |
| 234 | 2-F—Ph | 2,5-diCl—Ph |
| 235 | 2-F—Ph | 3,4-diCl—Ph |
| 236 | 2-F—Ph | 3,5-diCl—Ph |
| 237 | 2-F—Ph | 3,4-OCH2O—Ph |
| 238 | 2-F—Ph | 3,4-OCH2CH2O—Ph |
| 239 | 2-F—Ph | 2-thienyl |
| 240 | 2-F—Ph | 2-furanyl |
| 241 | 2-F—Ph | 2-pyridyl |
| 242 | 2-F—Ph | 4-pyridyl |
| 243 | 2-F—Ph | 2-imidazolyl |
| 244 | 2-F—Ph | 3-pyrazolyl |
| 245 | 2-F—Ph | 2-thiazolyl |
| 246 | 2-F—Ph | 5-tetrazolyl |
| 247 | 2-F—Ph | 1-adamantyl |
| 248 | 2,4-diF—Ph | 3-CN—Ph |
| 249 | 2,4-diF—Ph | 3-COCH3—Ph |
| 250 | 2,4-diF—Ph | 3-CO2Me—Ph |

TABLE 1-continued

| | | |
|---|---|---|
| 251 | 2,4-diF—Ph | 3-CO2Et—Ph |
| 252 | 2,4-diF—Ph | 3-CO2H—Ph |
| 253 | 2,4-diF—Ph | 3-CONH2—Ph |
| 254 | 2,4-diF—Ph | 3-F—Ph |
| 255 | 2,4-diF—Ph | 3-Cl—Ph |
| 256 | 2,4-diF—Ph | 3-NH2—Ph |
| 257 | 2,4-diF—Ph | 3-SO2NH2—Ph |
| 258 | 2,4-diF—Ph | 3-CF3—Ph |
| 259 | 2,4-diF—Ph | 3-OCH3—Ph |
| 260 | 2,4-diF—Ph | 3-OEt—Ph |
| 261 | 2,4-diF—Ph | 3-OCF3—Ph |
| 262 | 2,4-diF—Ph | 3-SO2CH3—Ph |
| 263 | 2,4-diF—Ph | 3-OH—Ph |
| 264 | 2,4-diF—Ph | 3-CH3—Ph |
| 265 | 2,4-diF—Ph | 3-C2H5—Ph |
| 266 | 2,4-diF—Ph | 4-CN—Ph |
| 267 | 2,4-diF—Ph | 4-COCH3—Ph |
| 268 | 2,4-diF—Ph | 4-CO2Me—Ph |
| 269 | 2,4-diF—Ph | 4-CO2Et—Ph |
| 270 | 2,4-diF—Ph | 4-CO2H—Ph |
| 271 | 2,4-diF—Ph | 4-CONH2—Ph |
| 272 | 2,4-diF—Ph | 4-F—Ph |
| 273 | 2,4-diF—Ph | 4-Cl—Ph |
| 274 | 2,4-diF—Ph | 4-NH2—Ph |
| 275 | 2,4-diF—Ph | 4-SO2NH2—Ph |
| 276 | 2,4-diF—Ph | 4-CF3—Ph |
| 277 | 2,4-diF—Ph | 4-OCH3—Ph |
| 278 | 2,4-diF—Ph | 4-OEt—Ph |
| 279 | 2,4-diF—Ph | 4-OCF3—Ph |
| 280 | 2,4-diF—Ph | 4-SO2CH3—Ph |
| 281 | 2,4-diF—Ph | 4-OH—Ph |
| 282 | 2,4-diF—Ph | 4-CH3—Ph |
| 283 | 2,4-diF—Ph | 4-C2H5—Ph |
| 284 | 2,4-diF—Ph | 2,4-diF—Ph |
| 285 | 2,4-diF—Ph | 2,5-diF—Ph |
| 286 | 2,4-diF—Ph | 3,4-diF—Ph |
| 287 | 2,4-diF—Ph | 3,5-diF—Ph |
| 288 | 2,4-diF—Ph | 2,4-diCl—Ph |
| 289 | 2,4-diF—Ph | 2,5-diCl—Ph |
| 290 | 2,4-diF—Ph | 3,4-diCl—Ph |
| 291 | 2,4-diF—Ph | 3,5-diCl—Ph |
| 292 | 2,4-diF—Ph | 3,4-OCH2O—Ph |
| 293 | 2,4-diF—Ph | 3,4-OCH2CH2O—Ph |
| 294 | 2,4-diF—Ph | 2-thienyl |
| 295 | 2,4-diP—Ph | 2-furanyl |
| 296 | 2,4-diP—Ph | 2-pyridyl |
| 297 | 2,4-diF—Ph | 4-pyridyl |
| 298 | 2,4-diF—Ph | 2-imidazolyl |
| 299 | 2,4-diF—Ph | 3-pyrazolyl |
| 300 | 2,4-diF—Ph | 2-thiazolyl |
| 301 | 2,4-diF—Ph | 5-tetrazolyl |
| 302 | 4-Cl—Ph | Ph |
| 303 | 4-Cl—Ph | 3-CN—Ph |
| 304 | 4-Cl—Ph | 3-COCH3—Ph |
| 305 | 4-Cl—Ph | 3-CO2Me—Ph |
| 306 | 4-Cl—Ph | 3-CO2Et—Ph |
| 307 | 4-Cl—Ph | 3-CO2H—Ph |
| 308 | 4-Cl—Ph | 3-CONH2—Ph |
| 309 | 4-Cl—Ph | 3-CONHMe—Ph |
| 310 | 4-Cl—Ph | 3-F—Ph |
| 311 | 4-Cl—Ph | 3-Cl—Ph |
| 312 | 4-Cl—Ph | 3-Br—Ph |
| 313 | 4-Cl—Ph | 3-NO2—Ph |
| 314 | 4-Cl—Ph | 3-NH2—Ph |
| 315 | 4-Cl—Ph | 3-NHMe—Ph |
| 316 | 4-Cl—Ph | 3-NMe2—Ph |
| 317 | 4-Cl—Ph | 3-NHCOCH3—Ph |
| 318 | 4-Cl—Ph | 3-SO2NH2—Ph |
| 319 | 4-Cl—Ph | 3-SO2NHMe—Ph |
| 320 | 4-Cl—Ph | 3-CF3—Ph |
| 321 | 4-Cl—Ph | 3-OCH3—Ph |
| 322 | 4-Cl—Ph | 3-OPh—Ph |
| 323 | 4-Cl—Ph | 3-OCF3—Ph |
| 324 | 4-Cl—Ph | 3-SCH3—Ph |
| 325 | 4-Cl—Ph | 3-SOCH3—Ph |
| 326 | 4-Cl—Ph | 3-SO2CH3—Ph |
| 327 | 4-Cl—Ph | 3-OH—Ph |
| 328 | 4-Cl—Ph | 3-CH2OH—Ph |
| 329 | 4-Cl—Ph | 3-CHOHCH3—Ph |
| 330 | 4-Cl—Ph | 3-COH(CH3)2—Ph |
| 331 | 4-Cl—Ph | 3-CHOHPh—Ph |
| 332 | 4-Cl—Ph | 3-CH3—Ph |
| 333 | 4-Cl—Ph | 3-C2H5—Ph |
| 334 | 4-Cl—Ph | 3-iPr—Ph |
| 335 | 4-Cl—Ph | 3-tBu—Ph |
| 336 | 4-Cl—Ph | 3-Ph—Ph |
| 337 | 4-Cl—Ph | 3-CH2Ph—Ph |
| 338 | 4-Cl—Ph | 3-CH2CO2Me—Ph |
| 339 | 4-Cl—Ph | 3-(1-piperidinyl)-Ph |
| 340 | 4-Cl—Ph | 3-(1-pyrrolidinyl)-Ph |
| 341 | 4-Cl—Ph | 3-(2-imidazolyl)-Ph |
| 342 | 4-Cl—Ph | 3-(1-imidazolyl)-Ph |
| 343 | 4-Cl—Ph | 3-(2-thiazolyl)-Ph |
| 344 | 4-Cl—Ph | 3-(3-pyrazolyl)-Ph |
| 345 | 4-Cl—Ph | 3-(1-pyrazolyl)-Ph |
| 346 | 4-Cl—Ph | 3-(1-tetrazolyl)-Ph |
| 347 | 4-Cl—Ph | 3-(5-tetrazolyl)-Ph |
| 348 | 4-Cl—Ph | 3-(2-pyridyl)-Ph |
| 349 | 4-Cl—Ph | 3-(2-thienyl)-Ph |
| 350 | 4-Cl—Ph | 3-(2-furanyl)-Ph |
| 351 | 4-Cl—Ph | 4-CN—Ph |
| 352 | 4-Cl—Ph | 4-COCH3—Ph |
| 353 | 4-Cl—Ph | 4-CO2Me—Ph |
| 354 | 4-Cl—Ph | 4-CO2Et—Ph |
| 355 | 4-Cl—Ph | 4-CO2H—Ph |
| 356 | 4-Cl—Ph | 4-CONH2—Ph |
| 357 | 4-Cl—Ph | 4-CONHMe—Ph |
| 358 | 4-Cl—Ph | 4-CONHPh—Ph |
| 359 | 4-Cl—Ph | 4-NHCONH2—Ph |
| 360 | 4-Cl—Ph | 4-F—Ph |
| 361 | 4-Cl—Ph | 4-Cl—Ph |
| 362 | 4-Cl—Ph | 4-Br—Ph |
| 363 | 4-Cl—Ph | 4-NO2—Ph |
| 364 | 4-Cl—Ph | 4-NH2—Ph |
| 365 | 4-Cl—Ph | 4-NHMe—Ph |
| 366 | 4-Cl—Ph | 4-NMe2—Ph |
| 367 | 4-Cl—Ph | 4-NHCOCH3—Ph |
| 368 | 4-Cl—Ph | 4-SO2NH2—Ph |
| 369 | 4-Cl—Ph | 4-SO2NHMe—Ph |
| 370 | 4-Cl—Ph | 4-CF3—Ph |
| 371 | 4-Cl—Ph | 4-OCH3—Ph |
| 372 | 4-Cl—Ph | 4-OPh—Ph |
| 373 | 4-Cl—Ph | 4-OCF3—Ph |
| 374 | 4-Cl—Ph | 4-SCH3—Ph |
| 375 | 4-Cl—Ph | 4-SOCH3—Ph |
| 376 | 4-Cl—Ph | 4-SO2CH3—Ph |
| 377 | 4-Cl—Ph | 4-OH—Ph |
| 378 | 4-Cl—Ph | 4-CH2OH—Ph |
| 379 | 4-Cl—Ph | 4-CHOHCH3—Ph |
| 380 | 4-Cl—Ph | 4-COH(CH3)2—Ph |
| 381 | 4-Cl—Ph | 4-CH3—Ph |
| 382 | 4-Cl—Ph | 4-C2H5—Ph |
| 383 | 4-Cl—Ph | 4-iPr—Ph |
| 384 | 4-Cl—Ph | 4-tBu—Ph |
| 385 | 4-Cl—Ph | 4-Ph—Ph |
| 386 | 4-Cl—Ph | 4-CH2Ph—Ph |
| 387 | 4-Cl—Ph | 4-CH2CO2Me—Ph |
| 388 | 4-Cl—Ph | 4-(1-piperidinyl)-Ph |
| 389 | 4-Cl—Ph | 4-(1-pyrrolidinyl)-Ph |
| 390 | 4-Cl—Ph | 4-(2-imidazolyl)-Ph |
| 391 | 4-Cl—Ph | 4-(1-imidazolyl)-Ph |
| 392 | 4-Cl—Ph | 4-(2-thiazolyl)-Ph |
| 393 | 4-Cl—Ph | 4-(3-pyrazolyl)-Ph |
| 394 | 4-Cl—Ph | 4-(1-pyrazolyl)-Ph |
| 395 | 4-Cl—Ph | 4-(1-tetrazolyl)-Ph |
| 396 | 4-Cl—Ph | 4-(5-tetrazolyl)-Ph |
| 397 | 4-Cl—Ph | 4-(2-pyridyl)-Ph |
| 398 | 4-Cl—Ph | 4-(2-thienyl)-Ph |
| 399 | 4-Cl—Ph | 4-(2-furanyl)-Ph |
| 400 | 4-Cl—Ph | 2-CN—Ph |
| 401 | 4-Cl—Ph | 2-COCH3—Ph |
| 402 | 4-Cl—Ph | 2-CO2Me—Ph |
| 403 | 4-Cl—Ph | 2-CO2Et—Ph |
| 404 | 4-Cl—Ph | 2-CO2H—Ph |
| 405 | 4-Cl—Ph | 2-CONH2—Ph |
| 406 | 4-Cl—Ph | 2-CONHMe—Ph |
| 407 | 4-Cl—Ph | 2-F—Ph |
| 408 | 4-Cl—Ph | 2-Cl—Ph |

TABLE 1-continued

| | | |
|---|---|---|
| 409 | 4-Cl—Ph | 2-Br—Ph |
| 410 | 4-Cl—Ph | 2-NO2—Ph |
| 411 | 4-Cl—Ph | 2-NH2—Ph |
| 412 | 4-Cl—Ph | 2-NHMe—Ph |
| 413 | 4-Cl—Ph | 2-NMe2—Ph |
| 414 | 4-Cl—Ph | 2-NHCOCH3—Ph |
| 415 | 4-Cl—Ph | 2-SO2NH2—Ph |
| 416 | 4-Cl—Ph | 2-SO2NHMe—Ph |
| 417 | 4-Cl—Ph | 2-CF3—Ph |
| 418 | 4-Cl—Ph | 2-OCH3—Ph |
| 419 | 4-Cl—Ph | 2-OPh—Ph |
| 420 | 4-Cl—Ph | 2-OCF3—Ph |
| 421 | 4-Cl—Ph | 2-SCH3—Ph |
| 422 | 4-Cl—Ph | 2-SOCH3—Ph |
| 423 | 4-Cl—Ph | 2-SO2CH3—Ph |
| 424 | 4-Cl—Ph | 2-OH—Ph |
| 425 | 4-Cl—Ph | 2-CH2OH—Ph |
| 426 | 4-Cl—Ph | 2-CHOHCH3—Ph |
| 427 | 4-Cl—Ph | 2-COH(CH3)2—Ph |
| 428 | 4-Cl—Ph | 2-CHOHPh—Ph |
| 429 | 4-Cl—Ph | 2-CH3—Ph |
| 430 | 4-Cl—Ph | 2-C2H5—Ph |
| 431 | 4-Cl—Ph | 2-iPr—Ph |
| 432 | 4-Cl—Ph | 2-tBu—Ph |
| 433 | 4-Cl—Ph | 2-Ph—Ph |
| 434 | 4-Cl—Ph | 2-CH2Ph—Ph |
| 435 | 4-Cl—Ph | 2-CH2CO2Me—Ph |
| 436 | 4-Cl—Ph | 2-(1-piperidinyl)-Ph |
| 437 | 4-Cl—Ph | 2-(1-pyrrolidinyl)-Ph |
| 438 | 4-Cl—Ph | 2-(2-imidazolyl)-Ph |
| 439 | 4-Cl—Ph | 2-(1-imidazolyl)-Ph |
| 440 | 4-Cl—Ph | 2-(2-thiazolyl)-Ph |
| 441 | 4-Cl—Ph | 2-(3-pyrazolyl)-Ph |
| 442 | 4-Cl—Ph | 2-(1-pyrazolyl)-Ph |
| 443 | 4-Cl—Ph | 2-(1-tetrazolyl)-Ph |
| 444 | 4-Cl—Ph | 2-(5-tetrazolyl)-Ph |
| 445 | 4-Cl—Ph | 2-(2-pyridyl)-Ph |
| 446 | 4-Cl—Ph | 2-(2-thienyl)-Ph |
| 447 | 4-Cl—Ph | 2-(2-furanyl)-Ph |
| 448 | 4-Cl—Ph | 2,4-diF—Ph |
| 449 | 4-Cl—Ph | 2,5-diF—Ph |
| 450 | 4-Cl—Ph | 2,6-diF—Ph |
| 451 | 4-Cl—Ph | 3,4-diF—Ph |
| 452 | 4-Cl—Ph | 3,5-diF—Ph |
| 453 | 4-Cl—Ph | 2,4-diCl—Ph |
| 454 | 4-Cl—Ph | 2,5-diCl—Ph |
| 455 | 4-Cl—Ph | 2,6-diCl—Ph |
| 456 | 4-Cl—Ph | 3,4-diCl—Ph |
| 457 | 4-Cl—Ph | 3,5-diCl—Ph |
| 458 | 4-Cl—Ph | 3,4-diCF3—Ph |
| 459 | 4-Cl—Ph | 3,5-diCF3—Ph |
| 460 | 4-Cl—Ph | 5-Cl-2-MeO—Ph |
| 461 | 4-Cl—Ph | 5-Cl-2-Me—Ph |
| 462 | 4-Cl—Ph | 2-F-5-Me—Ph |
| 463 | 4-Cl—Ph | 2-F-5-NO2—Ph |
| 464 | 4-Cl—Ph | 3,4-OCH2O—Ph |
| 465 | 4-Cl—Ph | 3,4-OCH2CH2O—Ph |
| 466 | 4-Cl—Ph | 2-MeO-4-Me—Ph |
| 467 | 4-Cl—Ph | 2-MeO-5-Me—Ph |
| 468 | 4-Cl—Ph | 1-naphthyl |
| 469 | 4-Cl—Ph | 2-naphthyl |
| 470 | 4-Cl—Ph | 2-thienyl |
| 471 | 4-Cl—Ph | 3-thienyl |
| 472 | 4-Cl—Ph | 2-furanyl |
| 473 | 4-Cl—Ph | 3-furanyl |
| 474 | 4-Cl—Ph | 2-pyridyl |
| 475 | 4-Cl—Ph | 3-pyridyl |
| 476 | 4-Cl—Ph | 4-pyridyl |
| 477 | 4-Cl—Ph | 2-indolyl |
| 478 | 4-Cl—Ph | 3-indolyl |
| 479 | 4-Cl—Ph | 5-indolyl |
| 480 | 4-Cl—Ph | 6-indolyl |
| 481 | 4-Cl—Ph | 3-indazolyl |
| 482 | 4-Cl—Ph | 5-indazolyl |
| 483 | 4-Cl—Ph | 6-indazolyl |
| 484 | 4-Cl—Ph | 2-imidazolyl |
| 485 | 4-Cl—Ph | 3-pyrazolyl |
| 486 | 4-Cl—Ph | 2-thiazolyl |
| 487 | 4-Cl—Ph | 5-tetrazolyl |
| 488 | 4-Cl—Ph | 2-benzimidazolyl |
| 489 | 4-Cl—Ph | 5-benzimidazolyl |
| 490 | 4-Cl—Ph | 2-benzothiazolyl |
| 491 | 4-Cl—Ph | 5-benzothiazolyl |
| 492 | 4-Cl—Ph | 2-benzoxazolyl |
| 493 | 4-Cl—Ph | 5-benzoxazolyl |
| 494 | 2-Cl—Ph | 3-CN—Ph |
| 495 | 2-Cl—Ph | 3-COCH3—Ph |
| 496 | 2-Cl—Ph | 3-CO2Me—Ph |
| 497 | 2-Cl—Ph | 3-CO2Et—Ph |
| 498 | 2-Cl—Ph | 3-CO2H—Ph |
| 499 | 2-Cl—Ph | 3-CONH2—Ph |
| 500 | 2-Cl—Ph | 3-F—Ph |
| 501 | 2-Cl—Ph | 3-Cl—Ph |
| 502 | 2-Cl—Ph | 3-NH2—Ph |
| 503 | 2-Cl—Ph | 3-SO2NH2—Ph |
| 504 | 2-Cl—Ph | 3-CF3—Ph |
| 505 | 2-Cl—Ph | 3-OCH3—Ph |
| 506 | 2-Cl—Ph | 3-OEt—Ph |
| 507 | 2-Cl—Ph | 3-OCF3—Ph |
| 508 | 2-Cl—Ph | 3-SO2CH3—Ph |
| 509 | 2-Cl—Ph | 3-OH—Ph |
| 510 | 2-Cl—Ph | 3-CH3—Ph |
| 511 | 2-Cl—Ph | 3-C2H5—Ph |
| 512 | 2-Cl—Ph | 4-CN—Ph |
| 513 | 2-Cl—Ph | 4-COCH3—Ph |
| 514 | 2-Cl—Ph | 4-CO2Me—Ph |
| 515 | 2-Cl—Ph | 4CO2Et—Ph |
| 516 | 2-Cl—Ph | 4-CO2H—Ph |
| 517 | 2-Cl—Ph | 4-CONH2—Ph |
| 518 | 2-Cl—Ph | 4-F—Ph |
| 519 | 2-Cl—Ph | 4-Cl—Ph |
| 520 | 2-Cl—Ph | 4-NH2—Ph |
| 521 | 2-Cl—Ph | 4-SO2NH2—Ph |
| 522 | 2-Cl—Ph | 4-CF3—Ph |
| 523 | 2-Cl—Ph | 4-OCH3—Ph |
| 524 | 2-Cl—Ph | 4-OEt—Ph |
| 525 | 2-Cl—Ph | 4-OCF3—Ph |
| 526 | 2-Cl—Ph | 4-SO2CH3—Ph |
| 527 | 2-Cl—Ph | 4-OH—Ph |
| 528 | 2-Cl—Ph | 4-CH3—Ph |
| 529 | 2-Cl—Ph | 4-C2H5—Ph |
| 530 | 2-Cl—Ph | 2,4-diF—Ph |
| 531 | 2-Cl—Ph | 2,5-diF—Ph |
| 532 | 2-Cl—Ph | 3,4-diF—Ph |
| 533 | 2-Cl—Ph | 3,5-diF—Ph |
| 534 | 2-Cl—Ph | 2,4-diCl—Ph |
| 535 | 2-Cl—Ph | 2,5-diCl—Ph |
| 536 | 2-Cl—Ph | 3,4-diCl—Ph |
| 537 | 2-Cl—Ph | 3,5-diCl—Ph |
| 538 | 2-Cl—Ph | 3,4-OCH2O—Ph |
| 539 | 2-Cl—Ph | 3,4-OCH2CH2O—Ph |
| 540 | 2-Cl—Ph | 2-thienyl |
| 541 | 2-Cl—Ph | 2-furanyl |
| 542 | 2-Cl—Ph | 2-pyridyl |
| 543 | 2-Cl—Ph | 4-pyridyl |
| 544 | 2-Cl—Ph | 2-imidazolyl |
| 545 | 2-Cl—Ph | 3-pyrazolyl |
| 546 | 2-Cl—Ph | 2-thiazolyl |
| 547 | 2-Cl—Ph | 5-tetrazolyl |
| 548 | 2,4-diCl—Ph | 3-CN—Ph |
| 549 | 2,4-diCl—Ph | 3-COCH3—Ph |
| 550 | 2,4-diCl—Ph | 3-CO2Me—Ph |
| 551 | 2,4-diCl—Ph | 3-CO2Et—Ph |
| 552 | 2,4-diCl—Ph | 3-CO2H—Ph |
| 553 | 2,4-diCl—Ph | 3-CONH2—Ph |
| 554 | 2,4-diCl—Ph | 3-F—Ph |
| 555 | 2,4-diCl—Ph | 3-Cl—Ph |
| 556 | 2,4-diCl—Ph | 3-NH2—Ph |
| 557 | 2,4-diCl—Ph | 3-SO2NH2—Ph |
| 558 | 2,4-diCl—Ph | 3-CF3—Ph |
| 559 | 2,4-diCl—Ph | 3-OCH3—Ph |
| 560 | 2,4-diCl—Ph | 3-OEt—Ph |
| 561 | 2,4-diCl—Ph | 3-OCF3—Ph |
| 562 | 2,4-diCl—Ph | 3-SO2CH3—Ph |
| 563 | 2,4-diCl—Ph | 3-OH—Ph |
| 564 | 2,4-diCl—Ph | 3-CH3—Ph |
| 565 | 2,4-diCl—Ph | 3-C2H5—Ph |
| 566 | 2,4-diCl—Ph | 4-CN—Ph |

TABLE 1-continued

| | | |
|---|---|---|
| 567 | 2,4-diCl—Ph | 4-COCH3—Ph |
| 568 | 2,4-diCl—Ph | 4-CO2Me—Ph |
| 569 | 2,4-diCl—Ph | 4-CO2Et—Ph |
| 570 | 2,4-diCl—Ph | 4-CO2H—Ph |
| 571 | 2,4-diCl—Ph | 4-CONH2—Ph |
| 572 | 2,4-diCl—Ph | 4-F—Ph |
| 573 | 2,4-diCl—Ph | 4-Cl—Ph |
| 574 | 2,4-diCl—Ph | 4-NH2—Ph |
| 575 | 2,4-diCl—Ph | 4-SO2NH2—Ph |
| 576 | 2,4-diCl—Ph | 4-CF3—Ph |
| 577 | 2,4-diCl—Ph | 4-OCH3—Ph |
| 578 | 2,4-diCl—Ph | 4-OEt—Ph |
| 579 | 2,4-diCl—Ph | 4-OCF3—Ph |
| 580 | 2,4-diCl—Ph | 4-SO2CH3—Ph |
| 581 | 2,4-diCl—Ph | 4-OH—Ph |
| 582 | 2,4-diCl—Ph | 4-CH3—Ph |
| 583 | 2,4-diCl—Ph | 4-C2H5—Ph |
| 584 | 2,4-diCl—Ph | 2,4-diF—Ph |
| 585 | 2,4-diCl—Ph | 2,5-diF—Ph |
| 586 | 2,4-diCl—Ph | 3,4-diF—Ph |
| 587 | 2,4-diCl—Ph | 3,5-diF—Ph |
| 588 | 2,4-diCl—Ph | 2,4-diCl—Ph |
| 589 | 2,4-diCl—Ph | 2,5-diCl—Ph |
| 590 | 2,4-diCl—Ph | 3,4-diCl—Ph |
| 591 | 2,4-diCl—Ph | 3,5-diCl—Ph |
| 592 | 2,4-diCl—Ph | 3,4-OCH2O—Ph |
| 593 | 2,4-diCl—Ph | 3,4-OCH2CH2O—Ph |
| 594 | 2,4-diCl—Ph | 2-thienyl |
| 595 | 2,4-diCl—Ph | 2-furanyl |
| 596 | 2,4-diCl—Ph | 2-pyridyl |
| 597 | 2,4-diCl—Ph | 4-pyridyl |
| 598 | 2,4-diCl—Ph | 2-imidazolyl |
| 599 | 2,4-diCl—Ph | 3-pyrazolyl |
| 600 | 2,4-diCl—Ph | 2-thiazolyl |
| 601 | 2,4-diCl—Ph | 5-tetrazolyl |
| 602 | 3-OCH3—Ph | 3-CN—Ph |
| 603 | 3-OCH3—Ph | 3-COCH3—Ph |
| 604 | 3-OCH3—Ph | 3-CO2Me—Ph |
| 605 | 3-OCH3—Ph | 3-CO2Et—Ph |
| 606 | 3-OCH3—Ph | 3-CO2H—Ph |
| 607 | 3-OCH3—Ph | 3-CONH2—Ph |
| 608 | 3-OCH3—Ph | 3-F—Ph |
| 609 | 3-OCH3—Ph | 3-Cl—Ph |
| 610 | 3-OCH3—Ph | 3-NH2—Ph |
| 611 | 3-OCH3—Ph | 3-SO2NH2—Ph |
| 612 | 3-OCH3—Ph | 3-CF3—Ph |
| 613 | 3-OCH3—Ph | 3-OCH3—Ph |
| 614 | 3-OCH3—Ph | 3-OEt—Ph |
| 615 | 3-OCH3—Ph | 3-OCF3—Ph |
| 616 | 3-OCH3—Ph | 3-SO2CH3—Ph |
| 617 | 3-OCH3—Ph | 3-OH—Ph |
| 618 | 3-OCH3—Ph | 3-CH3—Ph |
| 619 | 3-OCH3—Ph | 3-C2H5—Ph |
| 620 | 3-OCH3—Ph | 4-CN—Ph |
| 621 | 3-OCH3—Ph | 4-COCH3—Ph |
| 622 | 3-OCH3—Ph | 4-CO2Me—Ph |
| 623 | 3-OCH3—Ph | 4-CO2Et—Ph |
| 624 | 3-OCH3—Ph | 4-CO2H—Ph |
| 625 | 3-OCH3—Ph | 4-CONH2—Ph |
| 626 | 3-OCH3—Ph | 4-F—Ph |
| 627 | 3-OCH3—Ph | 4-Cl—Ph |
| 628 | 3-OCH3—Ph | 4-NH2—Ph |
| 629 | 3-OCH3—Ph | 4-SO2NH2—Ph |
| 630 | 3-OCH3—Ph | 4-CF3—Ph |
| 631 | 3-OCH3—Ph | 4-OCH3—Ph |
| 632 | 3-OCH3—Ph | 4-OEt—Ph |
| 633 | 3-OCH3—Ph | 4-OCF3—Ph |
| 634 | 3-OCH3—Ph | 4-SO2CH3—Ph |
| 635 | 3-OCH3—Ph | 4-OH—Ph |
| 636 | 3-OCH3—Ph | 4-CH3—Ph |
| 637 | 3-OCH3—Ph | 4-C2H5—Ph |
| 638 | 3-OCH3—Ph | 2,4-diF—Ph |
| 639 | 3-OCH3—Ph | 2,5-diF—Ph |
| 640 | 3-OCH3—Ph | 3,4-diF—Ph |
| 641 | 3-OCH3—Ph | 3,5-diF—Ph |
| 642 | 3-OCH3—Ph | 2,4-diCl—Ph |
| 643 | 3-OCH3—Ph | 2,5-diCl—Ph |
| 644 | 3-OCH3—Ph | 3,4-diCl—Ph |
| 645 | 3-OCH3—Ph | 3,5-diCl—Ph |

TABLE 1-continued

| | | |
|---|---|---|
| 646 | 3-OCH3—Ph | 3,4-OCH2O—Ph |
| 647 | 3-OCH3—Ph | 3,4-OCH2CH2O—Ph |
| 648 | 3-OCH3—Ph | 2-thienyl |
| 649 | 3-OCH3—Ph | 2-furanyl |
| 650 | 3-OCH3—Ph | 2-pyridyl |
| 651 | 3-OCH3—Ph | 4-pyridyl |
| 652 | 3-OCH3—Ph | 2-imidazolyl |
| 653 | 3-OCH3—Ph | 3-pyrazolyl |
| 654 | 3-OCH3—Ph | 2-thiazolyl |
| 655 | 3-OCH3—Ph | 5-tetrazolyl |

TABLE 2

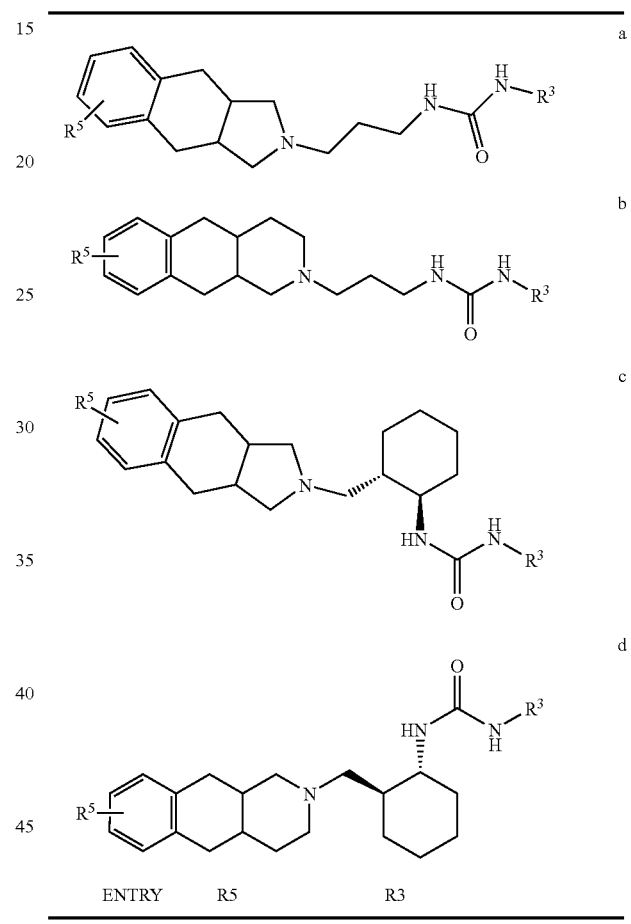

| ENTRY | R5 | R3 |
|---|---|---|
| 1 | 6-F | Ph |
| 2 | 6-F | 3-CN—Ph |
| 3 | 6-F | 3-COCH3—Ph |
| 4 | 6-F | 3-CO2Me—Ph |
| 5 | 6-F | 3-CO2Et—Ph |
| 6 | 6-F | 3-CO2H—Ph |
| 7 | 6-F | 3-CONH2—Ph |
| 8 | 6-F | 3-CONHMe—Ph |
| 9 | 6-F | 3-F—Ph |
| 10 | 6-F | 3-Cl—Ph |
| 11 | 6-F | 3-Br—Ph |
| 12 | 6-F | 3-NO2—Ph |
| 13 | 6-F | 3-NH2—Ph |
| 14 | 6-F | 3-NHMe—Ph |
| 15 | 6-F | 3-NMe2—Ph |
| 16 | 6-F | 3-NHCOCH3—Ph |
| 17 | 6-F | 3-SO2NH2—Ph |
| 18 | 6-F | 3-SO2NHMe—Ph |
| 19 | 6-F | 3-CF3—Ph |
| 20 | 6-F | 3-OCH3—Ph |
| 21 | 6-F | 3-OPh—Ph |
| 22 | 6-F | 3-OCF3—Ph |

TABLE 2-continued

| | | |
|---|---|---|
| 23 | 6-F | 3-SCH3—Ph |
| 24 | 6-F | 3-SOCH3—Ph |
| 25 | 6-F | 3-SO2CH3—Ph |
| 26 | 6-F | 3-OH—Ph |
| 27 | 6-F | 3-CH2OH—Ph |
| 28 | 6-F | 3-CHOHCH3—Ph |
| 29 | 6-F | 3-COH(CH3)2—Ph |
| 30 | 6-F | 3-CHOHPh—Ph |
| 31 | 6-F | 3-CH3—Ph |
| 32 | 6-F | 3-C2H5—Ph |
| 33 | 6-F | 3-iPr—Ph |
| 34 | 6-F | 3-tBu—Ph |
| 35 | 6-F | 3-Ph—Ph |
| 36 | 6-F | 3-CH2Ph—Ph |
| 37 | 6-F | 3-CH2CO2Me—Ph |
| 38 | 6-F | 3-(1-piperidinyl)-Ph |
| 39 | 6-F | 3-(1-pyrrolidinyl)-Ph |
| 40 | 6-F | 3-(2-imidazolyl)-Ph |
| 41 | 6-F | 3-(1-imidazolyl)-Ph |
| 42 | 6-F | 3-(2-thiazolyl)-Ph |
| 43 | 6-F | 3-(3-pyrazolyl)-Ph |
| 44 | 6-F | 3-(1-pyrazolyl)-Ph |
| 45 | 6-F | 3-(1-tetrazolyl)-Ph |
| 46 | 6-F | 3-(5-tetrazolyl)-Ph |
| 47 | 6-F | 3-(2-pyridyl)-Ph |
| 48 | 6-F | 3-(2-thienyl)-Ph |
| 49 | 6-F | 3-(2-furanyl)-Ph |
| 50 | 6-F | 4-CN—Ph |
| 51 | 6-F | 4-COCH3—Ph |
| 52 | 6-F | 4-CO2Me—Ph |
| 53 | 6-F | 4-CO2Et—Ph |
| 54 | 6-F | 4-CO2H—Ph |
| 55 | 6-F | 4-CONH2—Ph |
| 56 | 6-F | 4-CONHMe—Ph |
| 57 | 6-F | 4-CONHPh—Ph |
| 58 | 6-F | 4-NHCONH2—Ph |
| 59 | 6-F | 6-F |
| 60 | 6-F | 4-Cl—Ph |
| 61 | 6-F | 4-Br—Ph |
| 62 | 6-F | 4-NO2—Ph |
| 63 | 6-F | 4-NH2—Ph |
| 64 | 6-F | 4-NHMe—Ph |
| 65 | 6-F | 4-NMe2—Ph |
| 66 | 6-F | 4-NHCOCH3—Ph |
| 67 | 6-F | 4-SO2NH2—Ph |
| 68 | 6-F | 4-SO2NHMe—Ph |
| 69 | 6-F | 4-CF3—Ph |
| 70 | 6-F | 4-OCH3—Ph |
| 71 | 6-F | 4-OPh—Ph |
| 72 | 6-F | 4-OCF3—Ph |
| 73 | 6-F | 4-SCH3—Ph |
| 74 | 6-F | 4-SOCH3—Ph |
| 75 | 6-F | 4-SO2CH3—Ph |
| 76 | 6-F | 4-OH—Ph |
| 77 | 6-F | 4-CH2OH—Ph |
| 78 | 6-F | 4-CHOHCH3—Ph |
| 79 | 6-F | 4-COH(CH3)2—Ph |
| 80 | 6-F | 4-CH3—Ph |
| 81 | 6-F | 4-C2H5—Ph |
| 82 | 6-F | 4-iPr—Ph |
| 83 | 6-F | 4-tBu—Ph |
| 84 | 6-F | 4-Ph—Ph |
| 85 | 6-F | 4-CH2Ph—Ph |
| 86 | 6-F | 4-CH2CO2Me—Ph |
| 87 | 6-F | 4-(1-piperidinyl)-Ph |
| 88 | 6-F | 4-(1-pyrrolidinyl)-Ph |
| 89 | 6-F | 4-(2-imidazolyl)-Ph |
| 90 | 6-F | 4-(1-imidazolyl)-Ph |
| 91 | 6-F | 4-(2-thiazolyl)-Ph |
| 92 | 6-F | 4-(3-pyrazolyl)-Ph |
| 93 | 6-F | 4-(1-pyrazolyl)-Ph |
| 94 | 6-F | 4-(1-tetrazolyl)-Ph |
| 95 | 6-F | 4-(5-tetrazolyl)-Ph |
| 96 | 6-F | 4-(2-pyridyl)-Ph |
| 97 | 6-F | 4-(2-thienyl)-Ph |
| 98 | 6-F | 4-(2-furanyl)-Ph |
| 99 | 6-F | 2-CN—Ph |
| 100 | 6-F | 2-COCH3—Ph |
| 101 | 6-F | 2-CO2Me—Ph |
| 102 | 6-F | 2-CO2Et—Ph |
| 103 | 6-F | 2-CO2H—Ph |
| 104 | 6-F | 2-CONH2—Ph |
| 105 | 6-F | 2-CONHMe—Ph |
| 106 | 6-F | 2-F—Ph |
| 107 | 6-F | 2-Cl—Ph |
| 108 | 6-F | 2-Br—Ph |
| 109 | 6-F | 2-NO2—Ph |
| 110 | 6-F | 2-NH2—Ph |
| 111 | 6-F | 2-NHMe—Ph |
| 112 | 6-F | 2-NMe2—Ph |
| 113 | 6-F | 2-NHCOCH3—Ph |
| 114 | 6-F | 2-SO2NH2—Ph |
| 115 | 6-F | 2-SO2NHMe—Ph |
| 116 | 6-F | 2-CF3—Ph |
| 117 | 6-F | 2-OCH3—Ph |
| 118 | 6-F | 2-OPh—Ph |
| 119 | 6-F | 2-OCF3—Ph |
| 120 | 6-F | 2-SCH3—Ph |
| 121 | 6-F | 2-SOCH3—Ph |
| 122 | 6-F | 2-SO2CH3—Ph |
| 123 | 6-F | 2-OH—Ph |
| 124 | 6-F | 2-CH2OH—Ph |
| 125 | 6-F | 2-CHOHCH3—Ph |
| 126 | 6-F | 2-COH(CH3)2—Ph |
| 127 | 6-F | 2-CHOHPh—Ph |
| 128 | 6-F | 2-CH3—Ph |
| 129 | 6-F | 2-C2H5—Ph |
| 130 | 6-F | 2-iPr—Ph |
| 131 | 6-F | 2-tBu—Ph |
| 132 | 6-F | 2-Ph—Ph |
| 133 | 6-F | 2-CH2Ph—Ph |
| 134 | 6-F | 2-CH2CO2Me—Ph |
| 135 | 6-F | 2-(1-piperidinyl)-Ph |
| 136 | 6-F | 2-(1-pyrrolidinyl)-Ph |
| 137 | 6-F | 2-(2-imidazolyl)-Ph |
| 138 | 6-F | 2-(1-imidazolyl)-Ph |
| 139 | 6-F | 2-(2-thiazolyl)-Ph |
| 140 | 6-F | 2-(3-pyrazolyl)-Ph |
| 141 | 6-F | 2-(1-pyrazolyl)-Ph |
| 142 | 6-F | 2-(1-tetrazolyl)-Ph |
| 143 | 6-F | 2-(5-tetrazolyl)-Ph |
| 144 | 6-F | 2-(2-pyridyl)-Ph |
| 145 | 6-F | 2-(2-thienyl)-Ph |
| 146 | 6-F | 2-(2-faranyl)-Ph |
| 147 | 6-F | 2,4-diF—Ph |
| 148 | 6-F | 2,5-diF—Ph |
| 149 | 6-F | 2,6-diF—Ph |
| 150 | 6-F | 3,4-diF—Ph |
| 151 | 6-F | 3,5-diF—Ph |
| 152 | 6-F | 2,4-diCl—Ph |
| 153 | 6-F | 2,5-diCl—Ph |
| 154 | 6-F | 2,6-diCl—Ph |
| 155 | 6-F | 3,4-diCl—Ph |
| 156 | 6-F | 3,5-diCl—Ph |
| 157 | 6-F | 3,4-diCF3—Ph |
| 158 | 6-F | 3,5-diCF3—Ph |
| 159 | 6-F | 5-Cl-2-MeO—Ph |
| 160 | 6-F | 5-Cl-2-Me—Ph |
| 161 | 6-F | 2-F-5-Me—Ph |
| 162 | 6-F | 2-F-5-NO2—Ph |
| 163 | 6-F | 3,4-OCH2O—Ph |
| 164 | 6-F | 3,4-OCH2CH2O—Ph |
| 165 | 6-F | 2-MeO-4-Me—Ph |
| 166 | 6-F | 2-MeO-5-Me—Ph |
| 167 | 6-F | 1-naphthyl |
| 168 | 6-F | 2-naphthyl |
| 169 | 6-F | 2-thienyl |
| 170 | 6-F | 3-thienyl |
| 171 | 6-F | 2-furanyl |
| 172 | 6-F | 3-furanyl |
| 173 | 6-F | 2-pyridyl |
| 174 | 6-F | 3-pyridyl |
| 175 | 6-F | 4-pyridyl |
| 176 | 6-F | 2-indolyl |
| 177 | 6-F | 3-indolyl |
| 178 | 6-F | 5-indolyl |
| 179 | 6-F | 6-indolyl |
| 180 | 6-F | 3-indazolyl |

TABLE 2-continued

| | | |
|---|---|---|
| 181 | 6-F | 5-indazolyl |
| 182 | 6-F | 6-indazolyl |
| 183 | 6-F | 2-imidazolyl |
| 184 | 6-F | 3-pyrazolyl |
| 185 | 6-F | 2-thiazolyl |
| 186 | 6-F | 5-tetrazolyl |
| 187 | 6-F | 2-benzimidazolyl |
| 188 | 6-F | 5-benzimidazolyl |
| 189 | 6-F | 2-benzothiazolyl |
| 190 | 6-F | 5-benzothiazolyl |
| 191 | 6-F | 2-benzoxazolyl |
| 192 | 6-F | 5-benzoxazolyl |
| 193 | 7-F | 3-CN—Ph |
| 194 | 7-F | 3-COCH3—Ph |
| 195 | 7-F | 3-CO2Me—Ph |
| 196 | 7-F | 3-CO2Et—Ph |
| 197 | 7-F | 3-CO2H—Ph |
| 198 | 7-F | 3-CONH2—Ph |
| 199 | 7-F | 3-F—Ph |
| 200 | 7-F | 3-Cl—Ph |
| 201 | 7-F | 3-NH2—Ph |
| 202 | 7-F | 3-SO2NH2—Ph |
| 203 | 7-F | 3-CF3—Ph |
| 204 | 7-F | 3-OCH3—Ph |
| 205 | 7-F | 3-OEt—Ph |
| 206 | 7-F | 3-OCF3—Ph |
| 207 | 7-F | 3-SO2CH3—Ph |
| 208 | 7-F | 3-OH—Ph |
| 209 | 7-F | 3-CH3—Ph |
| 210 | 7-F | 3-C2H5—Ph |
| 211 | 7-F | 4-CN—Ph |
| 212 | 7-F | 4-COCH3—Ph |
| 213 | 7-F | 4-CO2Me—Ph |
| 214 | 7-F | 4-CO2Et—Ph |
| 215 | 7-F | 4-CO2H—Ph |
| 216 | 7-F | 4-CONH2—Ph |
| 217 | 7-F | 4-F—Ph |
| 218 | 7-F | 4-Cl—Ph |
| 219 | 7-F | 4-NH2—Ph |
| 220 | 7-F | 4-SO2NH2—Ph |
| 221 | 7-F | 4-CF3—Ph |
| 222 | 7-F | 4-OCH3—Ph |
| 223 | 7-F | 4-OEt—Ph |
| 224 | 7-F | 4-OCF3—Ph |
| 225 | 7-F | 4-SO2CH3—Ph |
| 226 | 7-F | 4-OH—Ph |
| 227 | 7-F | 4-CH3—Ph |
| 228 | 7-F | 4-C2H5—Ph |
| 229 | 7-F | 2,4-diF—Ph |
| 230 | 7-F | 2,5-diF—Ph |
| 231 | 7-F | 3,4-diF—Ph |
| 232 | 7-F | 3,5-diF—Ph |
| 233 | 7-F | 2,4-diCl—Ph |
| 234 | 7-F | 2,5-diCl—Ph |
| 235 | 7-F | 3,4-diCl—Ph |
| 236 | 7-F | 3,5-diCl—Ph |
| 237 | 7-F | 3,4-OCH2O—Ph |
| 238 | 7-F | 3,4-OCH2CH2O—Ph |
| 239 | 7-F | 2-thienyl |
| 240 | 7-F | 2-furanyl |
| 241 | 7-F | 2-pyridyl |
| 242 | 7-F | 4-pyridyl |
| 243 | 7-F | 2-imidazolyl |
| 244 | 7-F | 3-pyrazolyl |
| 245 | 7-F | 2-thiazolyl |
| 246 | 7-F | 5-tetrazolyl |
| 247 | 7-F | 1-adamantyl |
| 248 | 6,7-diF | 3-CN—Ph |
| 249 | 6,7-diF | 3-COCH3—Ph |
| 250 | 6,7-diF | 3-CO2Me—Ph |
| 251 | 6,7-diF | 3-CO2Et—Ph |
| 252 | 6,7-diF | 3-CO2H—Ph |
| 253 | 6,7-diF | 3-CONH2—Ph |
| 254 | 6,7-diF | 3-F—Ph |
| 255 | 6,7-diF | 3-Cl—Ph |
| 256 | 6,7-diF | 3-NH2—Ph |
| 257 | 6,7-diF | 3-SO2NH2—Ph |
| 258 | 6,7-diF | 3-CF3—Ph |
| 259 | 6,7-diF | 3-OCH3—Ph |
| 260 | 6,7-diF | 3-OEt—Ph |
| 261 | 6,7-diF | 3-OCF3—Ph |
| 262 | 6,7-diF | 3-SO2CH3—Ph |
| 263 | 6,7-diF | 3-OH—Ph |
| 264 | 6,7-diF | 3-CH3—Ph |
| 265 | 6,7-diF | 3-C2H5—Ph |
| 266 | 6,7-diF | 4-CN—Ph |
| 267 | 6,7-diF | 4-COCH3—Ph |
| 268 | 6,7-diF | 4-CO2Me—Ph |
| 269 | 6,7-diF | 4-CO2Et—Ph |
| 270 | 6,7-diF | 4-CO2H—Ph |
| 271 | 6,7-diF | 4-CONH2—Ph |
| 272 | 6,7-diF | 4-F—Ph |
| 273 | 6,7-diF | 4-Cl—Ph |
| 274 | 6,7-diF | 4-NH2—Ph |
| 275 | 6,7-diF | 4-SO2NH2—Ph |
| 276 | 6,7-diF | 4-CF3—Ph |
| 277 | 6,7-diF | 4-OCH3—Ph |
| 278 | 6,7-diF | 4-OEt—Ph |
| 279 | 6,7-diF | 4-OCF3—Ph |
| 280 | 6,7-diF | 4-SO2CH3—Ph |
| 281 | 6,7-diF | 4-OH—Ph |
| 282 | 6,7-diF | 4-CH3—Ph |
| 283 | 6,7-diF | 4-C2H5—Ph |
| 284 | 6,7-diF | 6,7-diF |
| 285 | 6,7-diF | 2,5-diF—Ph |
| 286 | 6,7-diF | 3,4-diF—Ph |
| 287 | 6,7-diF | 3,5-diF—Ph |
| 288 | 6,7-diF | 2,4-diCl—Ph |
| 289 | 6,7-diF | 2,5-diCl—Ph |
| 290 | 6,7-diF | 3,4-diCl—Ph |
| 291 | 6,7-diF | 3,5-diCl—Ph |
| 292 | 6,7-diF | 3,4-OCH2O—Ph |
| 293 | 6,7-diF | 3,4-OCH2CH2O—Ph |
| 294 | 6,7-diF | 2-thienyl |
| 295 | 6,7-diF | 2-furanyl |
| 296 | 6,7-diF | 2-pyridyl |
| 297 | 6,7-diF | 4-pyridyl |
| 298 | 6,7-diF | 2-imidazolyl |
| 299 | 6,7-diF | 3-pyrazolyl |
| 300 | 6,7-diF | 2-thiazolyl |
| 301 | 6,7-diF | 5-tetrazolyl |
| 302 | 6-Cl | Ph |
| 303 | 6-Cl | 3-CN—Ph |
| 304 | 6-Cl | 3-COCH3—Ph |
| 305 | 6-Cl | 3-CO2Me—Ph |
| 306 | 6-Cl | 3-CO2Et—Ph |
| 307 | 6-Cl | 3-CO2H—Ph |
| 308 | 6-Cl | 3-CONH2—Ph |
| 309 | 6-Cl | 3-CONHMe—Ph |
| 310 | 6-Cl | 3-F—Ph |
| 311 | 6-Cl | 3-Cl—Ph |
| 312 | 6-Cl | 3-Br—Ph |
| 313 | 6-Cl | 3-NO2—Ph |
| 314 | 6-Cl | 3-NH2—Ph |
| 315 | 6-Cl | 3-NHMe—Ph |
| 316 | 6-Cl | 3-NMe2—Ph |
| 317 | 6-Cl | 3-NHCOCH3—Ph |
| 318 | 6-Cl | 3-SO2NH2—Ph |
| 319 | 6-Cl | 3-SO2NHMe—Ph |
| 320 | 6-Cl | 3-CF3—Ph |
| 321 | 6-Cl | 3-OCH3—Ph |
| 322 | 6-Cl | 3-OPh—Ph |
| 323 | 6-Cl | 3-OCF3—Ph |
| 324 | 6-Cl | 3-SCH3—Ph |
| 325 | 6-Cl | 3-SOCH3—Ph |
| 326 | 6-Cl | 3-SO2CH3—Ph |
| 327 | 6-Cl | 3-OH—Ph |
| 328 | 6-Cl | 3-CH2OH—Ph |
| 329 | 6-Cl | 3-CHOHCH3—Ph |
| 330 | 6-Cl | 3-COH(CH3)2—Ph |
| 331 | 6-Cl | 3-CHOHPh—Ph |
| 332 | 6-Cl | 3-CH3—Ph |
| 333 | 6-Cl | 3-C2H5—Ph |
| 334 | 6-Cl | 3-iPr—Ph |
| 335 | 6-Cl | 3-tBu—Ph |
| 336 | 6-Cl | 3-Ph—Ph |
| 337 | 6-Cl | 3-CH2Ph—Ph |
| 338 | 6-Cl | 3-CH2CO2Me—Ph |

TABLE 2-continued

| | | |
|---|---|---|
| 339 | 6-Cl | 3-(1-piperidinyl)-Ph |
| 340 | 6-Cl | 3-(1-pyrrolidinyl)-Ph |
| 341 | 6-Cl | 3-(2-imidazolyl)-Ph |
| 342 | 6-Cl | 3-(1-imidazolyl)-Ph |
| 343 | 6-Cl | 3-(2-thiazolyl)-Ph |
| 344 | 6-Cl | 3-(3-pyrazolyl)-Ph |
| 345 | 6-Cl | 3-(1-pyrazolyl)-Ph |
| 346 | 6-Cl | 3-(1-tetrazolyl)-Ph |
| 347 | 6-Cl | 3-(5-tetrazolyl)-Ph |
| 348 | 6-Cl | 3-(2-pyridyl)-Ph |
| 349 | 6-Cl | 3-(2-thienyl)-Ph |
| 350 | 6-Cl | 3-(2-furanyl)-Ph |
| 351 | 6-Cl | 4-CN—Ph |
| 352 | 6-Cl | 4-COCH3—Ph |
| 353 | 6-Cl | 4-CO2Me—Ph |
| 354 | 6-Cl | 4-CO2Et—Ph |
| 355 | 6-Cl | 4-CO2H—Ph |
| 356 | 6-Cl | 4-CONH2—Ph |
| 357 | 6-Cl | 4-CONHMe—Ph |
| 358 | 6-Cl | 4-CONHPh—Ph |
| 359 | 6-Cl | 4-NHCONH2—Ph |
| 360 | 6-Cl | 4-F—Ph |
| 361 | 6-Cl | 4-Cl—Ph |
| 362 | 6-Cl | 4-Br—Ph |
| 363 | 6-Cl | 4-NO2—Ph |
| 364 | 6-Cl | 4-NH2—Ph |
| 365 | 6-Cl | 4-NHMe—Ph |
| 366 | 6-Cl | 4-NMe2—Ph |
| 367 | 6-Cl | 4-NHCOCH3—Ph |
| 368 | 6-Cl | 4-SO2NH2—Ph |
| 369 | 6-Cl | 4-SO2NHMe—Ph |
| 370 | 6-Cl | 4-CF3—Ph |
| 371 | 6-Cl | 4-OCH3—Ph |
| 372 | 6-Cl | 4-OPh—Ph |
| 373 | 6-Cl | 4-OCF3—Ph |
| 374 | 6-Cl | 4-SCH3—Ph |
| 375 | 6-Cl | 4-SOCH3—Ph |
| 376 | 6-Cl | 4-SO2CH3—Ph |
| 377 | 6-Cl | 4-OH—Ph |
| 378 | 6-Cl | 4-CH2OH—Ph |
| 379 | 6-Cl | 4-CHOHCH3—Ph |
| 380 | 6-Cl | 4-COH(CH3)2—Ph |
| 381 | 6-Cl | 4-CH3—Ph |
| 382 | 6-Cl | 4-C2H5—Ph |
| 383 | 6-Cl | 4-iPr—Ph |
| 384 | 6-Cl | 4-tBu—Ph |
| 385 | 6-Cl | 4-Ph—Ph |
| 386 | 6-Cl | 4-CH2Ph—Ph |
| 387 | 6-Cl | 4-CH2CO2Me—Ph |
| 388 | 6-Cl | 4-(1-piperidinyl)-Ph |
| 389 | 6-Cl | 4-(1-pyrrolidinyl)-Ph |
| 390 | 6-Cl | 4-(2-imidazolyl)-Ph |
| 391 | 6-Cl | 4-(1-imidazolyl)-Ph |
| 392 | 6-Cl | 4-(2-thiazolyl)-Ph |
| 393 | 6-Cl | 4-(3-pyrazolyl)-Ph |
| 394 | 6-Cl | 4-(1-pyrazolyl)-Ph |
| 395 | 6-Cl | 4-(1-tetrazolyl)-Ph |
| 396 | 6-Cl | 4-(5-tetrazolyl)-Ph |
| 397 | 6-Cl | 4-(2-pyridyl)-Ph |
| 398 | 6-Cl | 4-(2-thienyl)-Ph |
| 399 | 6-Cl | 4-(2-furanyl)-Ph |
| 400 | 6-Cl | 2-CN—Ph |
| 401 | 6-Cl | 2-COCH3—Ph |
| 402 | 6-Cl | 2-CO2Me—Ph |
| 403 | 6-Cl | 2-CO2Et—Ph |
| 404 | 6-Cl | 2-CO2H—Ph |
| 405 | 6-Cl | 2-CONH2—Ph |
| 406 | 6-Cl | 2-CONHMe—Ph |
| 407 | 6-Cl | 2-F—Ph |
| 408 | 6-Cl | 2-Cl—Ph |
| 409 | 6-Cl | 2-Br—Ph |
| 410 | 6-Cl | 2-NO2—Ph |
| 411 | 6-Cl | 2-NH2—Ph |
| 412 | 6-Cl | 2-NHMe—Ph |
| 413 | 6-Cl | 2-NMe2—Ph |
| 414 | 6-Cl | 2-NHCOCH3—Ph |
| 415 | 6-Cl | 2-SO2NH2—Ph |
| 416 | 6-Cl | 2-SO2NHMe—Ph |
| 417 | 6-Cl | 2-CF3—Ph |
| 418 | 6-Cl | 2-OCH3—Ph |
| 419 | 6-Cl | 2-OPh—Ph |
| 420 | 6-Cl | 2-OCF3—Ph |
| 421 | 6-Cl | 2-SCH3—Ph |
| 422 | 6-Cl | 2-SOCH3—Ph |
| 423 | 6-Cl | 2-SO2CH3—Ph |
| 424 | 6-Cl | 2-OH—Ph |
| 425 | 6-Cl | 2-CH2OH—Ph |
| 426 | 6-Cl | 2-CHOHCH3—Ph |
| 427 | 6-Cl | 2-COH(CH3)2—Ph |
| 428 | 6-Cl | 2-CHOHPh—Ph |
| 429 | 6-Cl | 2-CH3—Ph |
| 430 | 6-Cl | 2-C2H5—Ph |
| 431 | 6-Cl | 2-iPr—Ph |
| 432 | 6-Cl | 2-tBu—Ph |
| 433 | 6-Cl | 2-Ph—Ph |
| 434 | 6-Cl | 2-CH2Ph—Ph |
| 435 | 6-Cl | 2-CH2CO2Me—Ph |
| 436 | 6-Cl | 2-(1-piperidinyl)-Ph |
| 437 | 6-Cl | 2-(1-pyrrolidinyl)-Ph |
| 438 | 6-Cl | 2-(2-imidazolyl)-Ph |
| 439 | 6-Cl | 2-(1-imidazolyl)-Ph |
| 440 | 6-Cl | 2-(2-thiazolyl)-Ph |
| 441 | 6-Cl | 2-(3-pyrazolyl)-Ph |
| 442 | 6-Cl | 2-(1-pyrazolyl)-Ph |
| 443 | 6-Cl | 2-(1-tetrazolyl)-Ph |
| 444 | 6-Cl | 2-(5-tetrazolyl)-Ph |
| 445 | 6-Cl | 2-(2-pyridyl)-Ph |
| 446 | 6-Cl | 2-(2-thienyl)-Ph |
| 447 | 6-Cl | 2-(2-furanyl)-Ph |
| 448 | 6-Cl | 6,7-diF |
| 449 | 6-Cl | 2,5-diF—Ph |
| 450 | 6-Cl | 2,6-diF—Ph |
| 451 | 6-Cl | 3,4-diF—Ph |
| 452 | 6-Cl | 3,5-diF—Ph |
| 453 | 6-Cl | 2,4-diCl—Ph |
| 454 | 6-Cl | 2,5-diCl—Ph |
| 455 | 6-Cl | 2,6-diCl—Ph |
| 456 | 6-Cl | 3,4-diCl—Ph |
| 457 | 6-Cl | 3,5-diCl—Ph |
| 458 | 6-Cl | 3,4-diCF3—Ph |
| 459 | 6-Cl | 3,5-diCF3—Ph |
| 460 | 6-Cl | 5-Cl-2-MeO—Ph |
| 461 | 6-Cl | 5-Cl-2-Me—Ph |
| 462 | 6-Cl | 2-F-5-Me—Ph |
| 463 | 6-Cl | 2-F-5-NO2—Ph |
| 464 | 6-Cl | 3,4-OCH2O—Ph |
| 465 | 6-Cl | 3,4-OCH2CH2O—Ph |
| 466 | 6-Cl | 2-MeO-4-Me—Ph |
| 467 | 6-Cl | 2-MeO-5-Me—Ph |
| 468 | 6-Cl | 1-naphthyl |
| 469 | 6-Cl | 2-naphthyl |
| 470 | 6-Cl | 2-thienyl |
| 471 | 6-Cl | 3-thienyl |
| 472 | 6-Cl | 2-furanyl |
| 473 | 6-Cl | 3-furanyl |
| 474 | 6-Cl | 2-pyridyl |
| 475 | 6-Cl | 3-pyridyl |
| 476 | 6-Cl | 4-pyridyl |
| 477 | 6-Cl | 2-indolyl |
| 478 | 6-Cl | 3-indolyl |
| 479 | 6-Cl | 5-indolyl |
| 480 | 6-Cl | 6-indolyl |
| 481 | 6-Cl | 3-indazolyl |
| 482 | 6-Cl | 5-indazolyl |
| 483 | 6-Cl | 6-indazolyl |
| 484 | 6-Cl | 2-imidazolyl |
| 485 | 6-Cl | 3-pyrazolyl |
| 486 | 6-Cl | 2-thiazolyl |
| 487 | 6-Cl | 5-tetrazolyl |
| 488 | 6-Cl | 2-benzimidazolyl |
| 489 | 6-Cl | 5-benzimidazolyl |
| 490 | 6-Cl | 2-benzothiazolyl |
| 491 | 6-Cl | 5-benzothiazolyl |
| 492 | 6-Cl | 2-benzoxazolyl |
| 493 | 6-Cl | 5-benzoxazolyl |
| 494 | 7-Cl | 3-CN—Ph |
| 495 | 7-Cl | 3-COCH3—Ph |
| 496 | 7-Cl | 3-CO2Me—Ph |

TABLE 2-continued

| | | |
|---|---|---|
| 497 | 7-Cl | 3-CO2Et—Ph |
| 498 | 7-Cl | 3-CO2H—Ph |
| 499 | 7-Cl | 3-CONH2—Ph |
| 500 | 7-Cl | 3-F—Ph |
| 501 | 7-Cl | 3-Cl—Ph |
| 502 | 7-Cl | 3-NH2—Ph |
| 503 | 7-Cl | 3-SO2NH2—Ph |
| 504 | 7-Cl | 3-CF3—Ph |
| 505 | 7-Cl | 3-OCH3—Ph |
| 506 | 7-Cl | 3-OEt—Ph |
| 507 | 7-Cl | 3-OCF3—Ph |
| 508 | 7-Cl | 3-SO2CH3—Ph |
| 509 | 7-Cl | 3-OH—Ph |
| 510 | 7-Cl | 3-CH3—Ph |
| 511 | 7-Cl | 3-C2H5—Ph |
| 512 | 7-Cl | 4-CN—Ph |
| 513 | 7-Cl | 4-COCH3—Ph |
| 514 | 7-Cl | 4-CO2Me—Ph |
| 515 | 7-Cl | 4-CO2Et—Ph |
| 516 | 7-Cl | 4-CO2H—Ph |
| 517 | 7-Cl | 4-CONH2—Ph |
| 518 | 7-Cl | 4-F—Ph |
| 519 | 7-Cl | 4-Cl—Ph |
| 520 | 7-Cl | 4-NH2—Ph |
| 521 | 7-Cl | 4-SO2NH2—Ph |
| 522 | 7-Cl | 4-CF3—Ph |
| 523 | 7-Cl | 4-OCH3—Ph |
| 524 | 7-Cl | 4-OEt—Ph |
| 525 | 7-Cl | 4-OCF3—Ph |
| 526 | 7-Cl | 4-SO2CH3—Ph |
| 527 | 7-Cl | 4-OH—Ph |
| 528 | 7-Cl | 4-CH3—Ph |
| 529 | 7-Cl | 4-C2H5—Ph |
| 530 | 7-Cl | 6,7-diF |
| 531 | 7-Cl | 2,5-diF—Ph |
| 532 | 7-Cl | 3,4-diF—Ph |
| 533 | 7-Cl | 3,5-diF—Ph |
| 534 | 7-Cl | 2,4-diCl—Ph |
| 535 | 7-Cl | 2,5-diCl—Ph |
| 536 | 7-Cl | 3,4-diCl—Ph |
| 537 | 7-Cl | 3,5-diCl—Ph |
| 538 | 7-Cl | 3,4-OCH2O—Ph |
| 539 | 7-Cl | 3,4-OCH2CH2O—Ph |
| 540 | 7-Cl | 2-thienyl |
| 541 | 7-Cl | 2-furanyl |
| 542 | 7-Cl | 2-pyridyl |
| 543 | 7-Cl | 4-pyridyl |
| 544 | 7-Cl | 2-imidazolyl |
| 545 | 7-Cl | 3-pyrazolyl |
| 546 | 7-Cl | 2-thiazolyl |
| 547 | 7-Cl | 5-tetrazolyl |
| 548 | 6,7-diCl | 3-CN—Ph |
| 549 | 6,7-diCl | 3-COCH3—Ph |
| 550 | 6,7-diCl | 3-CO2Me—Ph |
| 551 | 6,7-diCl | 3-CO2Et—Ph |
| 552 | 6,7-diCl | 3-CO2H—Ph |
| 553 | 6,7-diCl | 3-CONH2—Ph |
| 554 | 6,7-diCl | 3-F—Ph |
| 555 | 6,7-diCl | 3-Cl—Ph |
| 556 | 6,7-diCl | 3-NH2—Ph |
| 557 | 6,7-diCl | 3-SO2NH2—Ph |
| 558 | 6,7-diCl | 3-CF3—Ph |
| 559 | 6,7-diCl | 3-OCH3—Ph |
| 560 | 6,7-diCl | 3-OEt—Ph |
| 561 | 6,7-diCl | 3-OCF3—Ph |
| 562 | 6,7-diCl | 3-SO2CH3—Ph |
| 563 | 6,7-diCl | 3-OH—Ph |
| 564 | 6,7-diCl | 3-CH3—Ph |
| 565 | 6,7-diCl | 3-C2H5—Ph |
| 566 | 6,7-diCl | 4-CN—Ph |
| 567 | 6,7-diCl | 4-COCH3—Ph |
| 568 | 6,7-diCl | 4-CO2Me—Ph |
| 569 | 6,7-diCl | 4-CO2Et—Ph |
| 570 | 6,7-diCl | 4-CO2H—Ph |
| 571 | 6,7-diCl | 4-CONH2—Ph |
| 572 | 6,7-diCl | 4-F—Ph |
| 573 | 6,7-diCl | 4-Cl—Ph |
| 574 | 6,7-diCl | 4-NH2—Ph |
| 575 | 6,7-diCl | 4-SO2NH2—Ph |
| 576 | 6,7-diCl | 4-CF3—Ph |
| 577 | 6,7-diCl | 4-OCH3—Ph |
| 578 | 6,7-diCl | 4-OEt—Ph |
| 579 | 6,7-diCl | 4-OCF3—Ph |
| 580 | 6,7-diCl | 4-SO2CH3—Ph |
| 581 | 6,7-diCl | 4-OH—Ph |
| 582 | 6,7-diCl | 4-CH3—Ph |
| 583 | 6,7-diCl | 4-C2H5—Ph |
| 584 | 6,7-diCl | 6,7-diF |
| 585 | 6,7-diCl | 2,5-diF—Ph |
| 586 | 6,7-diCl | 3,4-diF—Ph |
| 587 | 6,7-diCl | 3,5-diF—Ph |
| 588 | 6,7-diCl | 2,4-diCl—Ph |
| 589 | 6,7-diCl | 2,5-diCl—Ph |
| 590 | 6,7-diCl | 3,4-diCl—Ph |
| 591 | 6,7-diCl | 3,5-diCl—Ph |
| 592 | 6,7-diCl | 3,4-OCH2O—Ph |
| 593 | 6,7-diCl | 3,4-OCH2CH2O—Ph |
| 594 | 6,7-diCl | 2-thienyl |
| 595 | 6,7-diCl | 2-furanyl |
| 596 | 6,7-diCl | 2-pyridyl |
| 597 | 6,7-diCl | 4-pyridyl |
| 598 | 6,7-diCl | 2-imidazolyl |
| 599 | 6,7-diCl | 3-pyrazolyl |
| 600 | 6,7-diCl | 2-thiazolyl |
| 601 | 6,7-diCl | 5-tetrazolyl |

Utility

The utility of the compounds in accordance with the present invention as modulators of chemokine receptor activity may be demonstrated by methodology known in the art, such as the assays for CCR-2 and CCR-3 ligand binding, as disclosed by Ponath et al., J. Exp. Med., 183, 2437-2448 (1996) and Uguccioni et al., J. Clin. Invest., 100, 1137-1143 (1997). Cell lines for expressing the receptor of interest include those naturally expressing the chemokine receptor, such as EOL-3 or THP-1, those induced to express the chemokine receptor by the addition of chemical or protein agents, such as HL-60 or AML14.3D10 cells treated with, for example, butyric acid with interleukin-5 present, or a cell engineered to express a recombinant chemokine receptor, such as CHO or HEK-293. Finally, blood or tissue cells, for example human peripheral blood eosinophils, isolated using methods as described by Hansel et al., J. Immunol. Methods, 145, 105-110 (1991), can be utilized in such assays. In particular, the compound of the present invention have activity in binding to the CCR-3 receptor in the aforementioned assays. As used herein, "activity" is intended to mean a compound demonstrating an IC50 of 10 μM or lower in concentration when measured in the aforementioned assays. Such a result is indicative of the intrinsic activity of the compounds as modulators of chemokine receptor activity. A general binding protocol is described below.

CCR3-Receptor Binding Protocol

Millipore filter plates (#MABVN1250) are treated with 5 μg/ml protamine in phosphate buffered saline, pH 7.2, for ten minutes at room temperature. Plates are washed three times with phosphate buffered saline and incubated with phosphate buffered saline for thirty minutes at room temperature. For binding, 50 μl of binding buffer (0.5% bovine serum albumen, 20 mM HEPES buffer and 5 mM magnesium chloride in RPMI 1640 media) with or without a test concentration of a compound present at a known concentration is combined with 50 μl of 125-I labeled human eotaxin (to give a final concentration of 150 pM radioligand) and 50 μl of cell suspension in binding buffer containing 5×10$^5$ total cells. Cells used for such binding assays can include cell lines transfected with a gene expressing CCR3 such as that described by Daugherty et al. (1996), isolated human eosinophils such as described by Hansel et al. (1991) or the AML14.3D10 cell line after differentiation with butyric acid as described by Tiffany et al. (1998). The mixture of compound, cells and radioligand are incubated at room temperature for thirty minutes. Plates are placed onto a vacuum manifold, vacuum applied, and plates washed three times with binding buffer with 0.5M NaCl added. The plastic skirt is removed from the plate, the plate allowed to air dry, the wells punch out and CPM counted. The percent inhibition of binding is calculated using the total count obtained in the absence of any competing compound or chemokine ligand and the background binding determined by addition of 100 nM eotaxin in place of the test compound.

The utility of the compounds in accordance with the present invention as inhibitors of the migration of eosinophils or cell lines expressing the chemokine receptors may be demonstrated by methodology known in the art, such as the chemotaxis assay disclosed by Bacon et al., Brit. J. Pharmacol., 95, 966-974 (1988). In particular, the compound of the present invention have activity in inhibition of the migration of eosinophils in the aforementioned assays. As used herein, "activity" is intended to mean a compound demonstrating an IC50 of 10 μM or lower in concentration when measured in the aforementioned assays. Such a result is indicative of the intrinsic activity of the compounds as modulators of chemokine receptor activity. A human eosinophil chemotaxis assay protocol is described below.

Human Eosinophil Chemotaxis Assay

Neuroprobe MBA96 96-well chemotaxis chambers with Neuroprobe polyvinylpyrrolidone-free polycarbonate PFD5 5-micron filters in place are warmed in a 37° C. incubator prior to assay. Freshly isolated human eosinophils, isolated according to a method such as that described by Hansel et al. (1991), are suspended in RPMI 1640 with 0.1% bovine serum albumin at 1×10$^6$ cells/ml and warmed in a 37° C. incubator prior to assay. A 20 nM solution of human eotaxin in RPMI 1640 with 0.1% bovine serum albumin is warmed in a 37° C. incubator prior to assay. The eosinophil suspension and the 20 nM eotaxin solution are each mixed 1:1 with prewarmed RPMI 1640 with 0.1% bovine serum albumin with or without a dilution of a test compound that is at two fold the desired final concentration. These mixtures are warmed in a 37° C. incubator prior to assay. The filter is separated from the prewarmed Neuroprobe chemotaxis chamber and the eotaxin/compound mixture is placed into a Polyfiltronics MPC 96 well plate that has been placed in the bottom part of the Neuro Probe chemotaxis chamber. The approximate volume is 370 microliters and there should be a positive meniscus after dispensing. The filter is replaced above the 96 well plate, the rubber gasket is attached to the bottom of the upper chamber, and the chamber assembled. A 200 μl volume of the cell suspension/compound mixture is added to the appropriate wells of the upper chamber. The upper chamber is covered with a plate sealer, and the assembled unit placed in a 37° C. incubator for 45 minutes. After incubation, the plate sealer is removed and all remaining cell suspension is aspirated off. The chamber is disassembled and, while holding the filter by the sides at a 90-degree angle, unmigrated cells are washed away using a gentle stream of phosphate buffered saline dispensed from a squirt bottle and then the filter wiped with a rubber tipped squeegee. The filter is allowed to completely dry and immersed completely in Wright Giemsa stain for 30-45 seconds. The filter is rinsed with distilled water for 7 minutes, rinsed once with water briefly, and allowed to dry. Migrated cells are enumerated by microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited. For example, eosinophilic infiltration to inflammatory sites (e.g., in asthma or allergic rhinitis) can be inhibited according to the present method. In particular, the compound of the following examples has activity in blocking the migration of cells expressing the CCR-3 receptor using the appropriate chemokines in the aforementioned assays. As used herein, "activity" is intended to mean a compound demonstrating an IC50 of 10 μM or lower in concentration when measured in the aforementioned assays. Such a result is also indicative of the intrinsic activity of the compounds as modulators of chemokine receptor activity.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., *Toxocara*), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102,203), leukotriene biosynthesis inhibitors (zileuton, BAY-1005); (f) non-steroidal antiinflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-W); (I) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise than as specifically described herein.

What is claimed is:

1. A compound of formula (I):

$$A\text{—}E\text{—}NR^1\text{—}G \quad (I)$$

or stereoisomers or pharmaceutically acceptable salts thereof, wherein:

A is

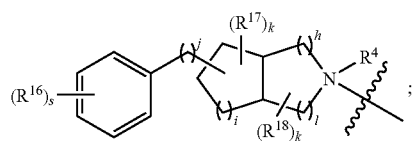

E is selected from $-(CR^7R^8)-(CR^9R^{10})_y-(CR^{11}R^{12})$,

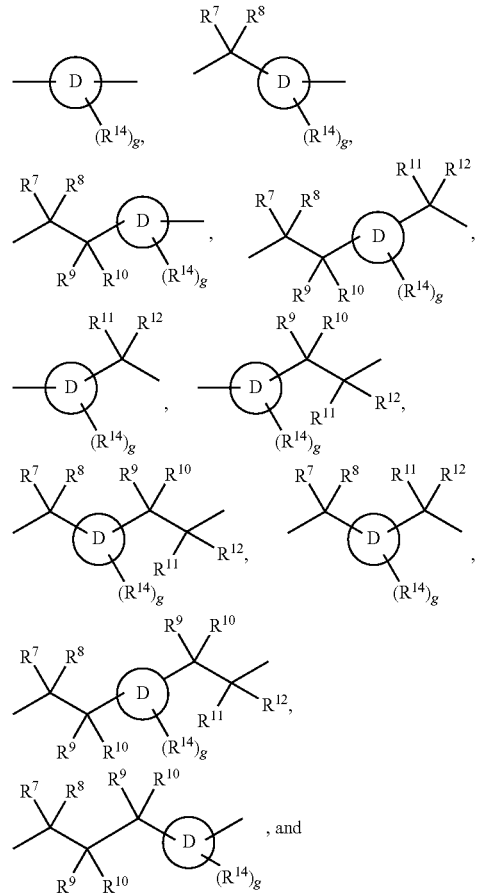

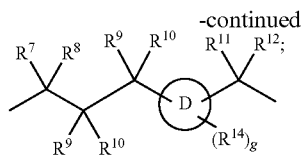

ring D is selected from a $C_{3-6}$ carbocyclic residue and a 5 or 6 membered heterocycle;

G is selected from $-C(O)R^3$, $-C(O)NR^2R^3$, $-C(O)OR^3$, $-SO_2NR^2R^3$, $-SO_2R^3$, $-C(=S)NR^2R^3$, $C(=NR^{1a})NR^2R^3$, $C(=CHCN)NR^2R^3$, $C(=CHNO_2)NR^2R^3$, $C(=C(CN)_2)NR^2R^3$,

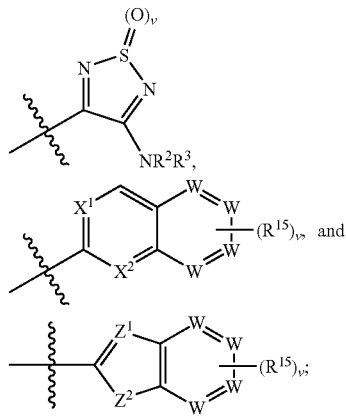

W, at each occurrence, is independently selected from C or N, provided at least two of W are C;

$X^1$ and $X^2$ are independently selected from C and N;

$Z^1$ is selected from C and N;

$Z^2$ is selected from $NR^{1'}$, O, S and C;

$R^1$, $R^{1'}$ and $R^2$ are independently selected from H, $C_{1-8}$ alkyl, $C_{3-8}$ alkenyl, $C_{3-8}$ alkynyl, $(CH_2)_r C_{3-6}$ cycloalkyl, and a $(CH_2)_r-C_{3-10}$ carbocyclic residue substituted with 0-5 $R^a$;

$R^{1a}$ is independently selected from H, $C_{1-6}$ alkyl, $-OH$, $-CN$, $-NO_2$, $(CH_2)_r C_{3-6}$ cycloalkyl, and a $(CH_2)_r-C_{3-10}$ carbocyclic residue substituted with 0-5 $R^a$;

$R^a$, at each occurrence, is selected from $C_{1-4}$ alkyl, $C_{2-3}$ alkenyl, $C_{2-8}$ alkynyl, $(CHR')_r C_{3-6}$ cycloalkyl, Cl, Br, I, F, $(CF_2)_r CF_3$, $NO_2$, CN, $(CHR')_r NR^bR^b$, $(CHR')_r OH$, $(CHR')_r OR^c$, $(CHR')_r SH$, $(CHR')_r SR^c$, $(CHR')_r C(O)R^b$, $(CHR')_r C(O)NR^bR^b$, $(CHR')_r NR^bC(O)R^b$, $(CHR')_r C(O)OR^b$, $(CHR')_r OC(O)R^c$, $(CHR')_r CH(=NR^b)NR^bR^b$, $(CHR')_r NHC(=NR^bC(O)NR^bR^b$, $(CHR')_r S(O)_p R^c$, $(CHR')_r S(O)_2 NR^bR^b$, $(CHR')_r NR^bS(O)_2R^c$, and $(CHR')_r phenyl$;

$R^b$, at each occurrence, is selected from H, $C_{1-6}$ alkyl, $C_{3-6}$ cycloalkyl, and phenyl;

$R^c$, at each occurrence, is selected from $C_{1-6}$ alkyl, $C_{3-6}$ cycloalkyl, and phenyl;

alternatively, $R^1$ and $R^2$ join to form a 5, 6, or 7-membered ring substituted with 0-3 $R^a$;

$R^3$ is selected from a $(CR^{3'}R^{3''})_r-C_{3-10}$ carbocyclic residue substituted with 0-5 $R^{15}$ and a $(CR^{3'}R^{3''})_r$-5-10 membered heterocyclic system containing 1-4 heteroatoms selected from N, O, and S, substituted with 0-3 $R^{15}$;

$R^{3'}$ and $R^{3''}$, at each occurrence, are selected from H, $C_{1-6}$ alkyl, $(CH_2)_r C_{3-6}$ cycloalkyl, and phenyl;

R⁴ is absent, taken with the nitrogen to which it is attached to form an N-oxide, or selected from $C_{1-8}$ alkyl, $C_{3-8}$ alkenyl, $C_{3-8}$ alkynyl, $(CH_2)_rC_{3-6}$ cycloalkyl, $(CH_2)_qC(O)R^{4b}$, $(CH_2)_qC(O)NR^{4a}R^{4a'}$, $(CH_2)_qC(O)OR^{4a}$, and a $(CH_2)_r$—$C_{3-10}$ carbocyclic residue substituted with 0-3 $R^{4c}$;

$R^{4a}$ and $R^{4a'}$, at each occurrence, are selected from H, $C_{1-6}$ alkyl, $(CH_2)_rC_{3-6}$ cycloalkyl, and phenyl;

$R^{4b}$, at each occurrence, is selected from $C_{1-6}$ alkyl, $C_{2-8}$ alkenyl, $(CH_2)_rC_{3-6}$ cycloalkyl, $C_{2-8}$ alkynyl, and phenyl;

$R^{4c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, $(CH_2)_rNR^{4a}R^{4a'}$, and $(CH_2)_r$phenyl;

$R^7$, is selected from H, $C_{1-6}$ alkyl, $C_{2-8}$ alkenyl, $C_{2-8}$ alkynyl, $(CHR')_qOH$, $(CHR')_qSH$, $(CHR')_qOR^{7d}$, $(CHR')_qSR^{7d}$, $(CH_2CHR')_qNR^{7a}R^{7a'}$, $(CHR')_rC(O)OH$, $(CHR')_rC(O)R^{7b}$, $(CHR')_rC(O)NR^{7a}R^{7a'}$, $(CHR')_q NR^{7a}C(O)R^{7b}$, $(CHR')_qNR^{7a}C(O)H$, $(CHR')_rC(O)OR^{7a}$, $(CHR')_qOC(O)R^{7b}$, $(CHR')_qS(O)_pR^{7b}$, $(CHR')_qS(O)_2NR^{7a}R^{7a'}$, $(CHR')_qNR^{7a}S(O)_2R^{7b}$, $(CHR')_qNHC(O)NR^{7a}R^{7a'}$, $(CHR')_qNHC(O)OR^{7a}$, $(CHR')_qOC(O)NR^{7a}R^{7a'}$, $C_{1-6}$ haloalkyl, a $(CHR')_r$—$C_{3-10}$ carbocyclic residue substituted with 0-3 $R^{7c}$, and a $(CHR')_r$-5-10 membered heterocyclic system containing 1-4 heteroatoms selected from N, O, and S, substituted with 0-2 $R^{7c}$;

$R^{7a}$ and $R^{7a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{7e}$, and a $(CH_2)_r$-5-10 membered heterocyclic system containing 1-4 heteroatoms selected from N, O, and S, substituted with 0-3 $R^{7e}$;

$R^{7b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0-2 $R^{7e}$, and a $(CH_2)_r$-5-6 membered heterocyclic system containing 1-4 heteroatoms selected from N, O, and S, substituted with 0-3 $R^{7e}$;

$R^{7c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{7f}R^{7f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{7b}$, $(CH_2)_rC(O)NR^{7f}R^{7f}$, $(CH_2)_rNR^{7f}C(O)R^{7b}$, $(CH_2)_rC(O)OC_{1-4}$ alkyl, $(CH_2)_rOC(O)R_{7b}$, $(CH_2)_rC(=NR^{7f})NR^{7f}R^{7f}$, $(CH_2)_rS(O)_pR^{7b}$, $(CH_2)_rNHC(=NR^{7f})NR^{7f}R^{7f}$, $(CH_2)_rS(O)_2NR^{7f}R^{7f}$, $(CH_2)_rNR^{7f}S(O)_2R^{7b}$, and $(CH_2)_r$phenyl substituted with 0-3 $R^{7e}$;

$R^{7d}$, at each occurrence, is selected from methyl, $CF_3$, $C_{2-6}$ alkyl substituted with 0-3 $R^{7e}$, $C_{3-6}$ alkenyl, $C_{3-6}$ alkynyl, and a $C_{3-10}$ carbocyclic residue substituted with 0-3 $R^{7c}$;

$R^{7e}$, at each occurrence, is selected from $C_{1-6}$ alkyl, $C_{2-8}$ alkenyl, $C_{2-8}$ alkynyl, $C_{3-6}$ cycloalkyl, Cl, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, and $(CH_2)_r$phenyl;

$R^{7f}$, at each occurrence, is selected from H, $C_{1-6}$ alkyl, and $C_{3-6}$ cycloalkyl;

$R^8$ is selected from H, $C_{1-6}$ alkyl, $C_{3-6}$ cycloalkyl, and $(CH_2)_r$phenyl substituted with 0-3 $R^{8a}$;

$R^{8a}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, and $(CH_2)_r$phenyl;

alternatively, $R^7$ and $R^8$ join to form $C_{3-7}$ cycloalkyl, =$NR^{8b}$, or =O;

$R^{8b}$ is selected from H, $C_{1-6}$ alkyl, $C_{3-6}$ cycloalkyl, OH, CN, and $(CH_2)_r$-phenyl;

$R^9$, is selected from H, $C_{1-6}$ alkyl, $C_{2-8}$ alkenyl, $C_{2-8}$ alkynyl, F, Cl, Br, I, $NO_2$, CN, $(CHR')_rOH$, $(CHR')_rSH$, $(CHR')_rOR^{9d}$, $(CHR')_rSR^{9d}$, $(CHR')_rNR^{9a}R^{9a'}$, $(CHR')_rC(O)OH$, $(CHR')_rC(O)R^{9b}$, $(CHR')_rC(O)NR^{9a}R^{9a'}$, $(CHR')_rNR^{9a}C(O)R^{9b}$, $(CHR')_rNR^{9a}C(O)H$, $(CHR')_rNR^{9a}C(O)NR^{9a}R^{9a'}$, $(CHR')_rC(O)OR^{9a}$, $(CHR')_rOC(O)R^{9b}$, $(CHR')_rS(O)_pR^{9b}$, $(CHR')_rS(O)_2NR^{9a}R^{9a'}$, $(CHR')_rNR^{9a}S(O)_2R^{9b}$, $C_{1-6}$ haloalkyl, a $(CHR')_r$—$C_{3-10}$ carbocyclic residue substituted with 0-5 $R^{9c}$, and a $(CHR')_r$-5-10 membered heterocyclic system containing 1-4 heteroatoms selected from N, O, and S, substituted with 0-3 $R^{9c}$;

$R^{9a}$ and $R^{9a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{9e}$, and a $(CH_2)_r$-5-10 membered heterocyclic system containing 1-4 heteroatoms selected from N, O, and S, substituted with 0-3 $R^{9e}$;

$R^{9b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0-2 $R^{9e}$, and a $(CH_2)_r$-5-6 membered heterocyclic system containing 1-4 heteroatoms selected from N, O, and S, substituted with 0-3 $R^{9e}$;

$R^{9c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{9f}R^{9f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{9b}$, $(CH_2)_rC(O)NR^{9f}R^{9f}$, $(CH_2)_rNR^{9f}C(O)R^{9b}$, $(CH_2)_rC(O)OC_{1-4}$ alkyl, $(CH_2)_rOC(O)R^{9b}$, $(CH_2)_rC(=NR^{9f})NR^{9f}R^{9f}$, $(CH_2)_rS(O)_pR^{9b}$, $(CH_2)_rNHC(=NR^{9f})NR^{9f}R^{9f}$, $(CH_2)_rS(O)_2NR^{9f}R^{9f}$, $(CH_2)_rNR^{9f}S(O)_2R^{9b}$, and $(CH_2)_r$phenyl substituted with 0-3 $R^{9e}$;

$R^{9d}$, at each occurrence, is selected from methyl, $CF_3$, $C_{2-6}$ alkyl substituted with 0-3 $R^{9e}$, $C_{3-6}$ alkenyl, $C_{3-6}$ alkynyl, a $C_{3-10}$ carbocyclic residue substituted with 0-3 $R^{9c}$, and a 5-6 membered heterocyclic system containing 1-4 heteroatoms selected from the group consisting of N, O, and S substituted with 0-3 $R^{9c}$;

$R^{9e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{9f}R^{9f}$, and $(CH_2)_r$phenyl;

$R^{9f}$, at each occurrence, is selected from H, $C_{1-6}$ alkyl, and $C_{3-6}$ cycloalkyl;

$R^{10}$, is selected from H, $C_{1-6}$ alkyl, $C_{2-8}$ alkenyl, $C_{2-8}$ alkynyl, F, Cl, Br, I, $NO_2$, CN, $(CH_2)_rOH$, $(CH_2)_rOR^{10d}$, $(CH_2)_rSR^{10d}$, $(CH_2)_rNR^{10a}R^{10a'}$, $(CH_2)_rC(O)OH$, $(CH_2)_rC(O)R^{10b}$, $(CH_2)_rC(O)NR^{10a}R^{10a'}$, $(CH_2)_rNR^{10a}C(O)R^{10a}$, $(CH_2)_rNR^{10a}C(O)H$, $(CH_2)_rC(O)OR^{10a}$, $(CH_2)_rOC(O)R^{10b}$, $(CH_2)_rS(O)_pR^{10b}$, $(CH_2)_rS(O)_2NR^{10a}R^{10a'}$, $(CH_2)_rNR^{10a}S(O)_2R^{10b}$, $C_{1-6}$ haloalkyl, a $(CH_2)_r$—$C_{3-10}$ carbocyclic residue substituted with 0-5 $R^{10c}$, and a $(CH_2)_r$-5-10 membered heterocyclic system containing 1-4 heteroatoms selected from N, O, and S, substituted with 0-3 $R^{10c}$;

$R^{10a}$ and $R^{10a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{10e}$, and a $(CH_2)_r$-5-10 membered heterocyclic system containing 1-4 heteroatoms selected from N, O, and S, substituted with 0-3 $R^{10e}$;

$R^{10b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0-2 $R^{10e}$, and a $(CH_2)_r$-5-6 membered heterocyclic system containing 1-4 heteroatoms selected from N, O, and S, substituted with 0-3 $R^{10e}$;

$R^{10c}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, Br, I, F, $(CF_2)_r CF_3$, $NO_2$, CN, $(CH_2)_r NR^{10f}R^{10f'}$, $(CH_2)_r OH$, $(CH_2)_r OC_{1-4}$ alkyl, $(CH_2)_r SC_{1-4}$ alkyl, $(CH_2)_r C(O)OH$, $(CH_2)_r C(O)R^{10b}$, $(CH_2)_r C(O)NR^{10f}R^{10f'}$, $(CH_2)_r NR^{10f}C(O)R^{10a}$, $(CH_2)_r C(O)OC_{1-4}$ alkyl, $(CH_2)_r OC(O)R_{10b}$, $(CH_2)_r C(=NR^{10f})NR^{10f}R^{10f'}$, $(CH_2)_r S(O)_p R^{10b}$, $(CH_2)_r NHC(=NR^{10f})NR^{10f}R^{10f'}$, $(CH_2)_r S(O)_2 NR^{10f}R^{10f'}$, $(CH_2)_r NR^{10f}S(O)_2 R^{10b}$, and $(CH_2)_r$phenyl substituted with 0-3 $R^{10e}$;

$R^{10d}$, at each occurrence, is selected from methyl, $CF_3$, $C_{2-6}$ alkyl substituted with 0-3 $R^{10e}$, $C_{3-6}$ alkenyl, $C_{3-6}$ alkynyl, a $C_{3-10}$ carbocyclic residue substituted with 0-3 $R^{10c}$, and a 5-6 membered heterocyclic system containing 1-4 heteroatoms selected from the group consisting of N, O, and S substituted with 0-3 $R^{10c}$;

$R^{10e}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-5}$ alkyl, $(CH_2)_r NR^{10f}R^{10f'}$, and $(CH_2)_r$phenyl;

$R^{10f}$, at each occurrence, is selected from H, $C_{1-6}$ alkyl, and $C_{3-6}$ cycloalkyl;

alternatively, $R^9$ and $R^{10}$ join to form $C_{3-4}$ cycloalkyl, 5-6-membered cyclic ketal, or $=O$;

with the proviso that when $R^{10}$ is —OH, $R^9$ is not halogen, cyano, or bonded to the carbon to which it is attached through a heteroatom;

$R^{11}$, is selected from H, $C_{1-6}$ alkyl, $C_{2-8}$ alkenyl, $C_{2-8}$ alkynyl, $(CH_2)_q OH$, $(CH_2)_q SH$, $(CH_2)_q OR^{11d}$, $(CH_2)_q SR^{11d}$, $(CH_2)_q NR^{11a}R^{11a'}$, $(CH_2)_r C(O)OH$, $(CH_2)_r C(O)R^{11b}$, $(CH_2)_r C(O)NR^{11a}R^{11a'}$, $(CH_2)_q NR^{11a}C(O)R^{11b}$, $(CH_2)_q NR^{11a}C(O)NR^{11a}R^{11a'}$, $(CH_2)_r C(O)OR^{11a}$, $(CH_2)_q OC(O)R^{11b}$, $(CH_2)_r S(O)_p R^{11b}$, $(CH_2)_q S(O)_2 NR^{11a}R^{11a'}$, $(CH_2)_q NR^{11a}S(O)_2 R^{11b}$, $C_{1-6}$ haloalkyl, a $(CH_2)_r - C_{3-10}$ carbocyclic residue substituted with 0-5 $R^{11c}$, and a $(CH_2)_r$-5-10 membered heterocyclic system containing 1-4 heteroatoms selected from N, O, and S, substituted with 0-3 $R^{11c}$;

$R^{11a}$ and $R^{11a'}$, at each occurrence, are selected from H, $C_{1-6}$ alkyl, $C_{3-8}$ alkenyl, $C_{3-8}$ alkynyl, a $(CH_2)_r - C_{3-10}$ carbocyclic residue substituted with 0-5 $R^{11e}$, and a $(CH_2)_r$-5-10 membered heterocyclic system containing 1-4 heteroatoms selected from N, O, and S, substituted with 0-3 $R^{11e}$;

$R^{11b}$, at each occurrence, is selected from $C_{1-6}$ alkyl, $C_{2-8}$ alkenyl, $C_{2-8}$ alkynyl, a $(CH_2)_r - C_{3-6}$ carbocyclic residue substituted with 0-2 $R^{11e}$, and a $(CH_2)_r$-5-6 membered heterocyclic system containing 1-4 heteroatoms selected from N, O, and S, substituted with 0-3 $R^{11e}$;

$R^{11c}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, Br, I, F, $(CF_2)_r CF_3$, $NO_2$, CN, $(CH_2)_r NR^{11f}R^{11f'}$, $(CH_2)_r OH$, $(CH_2)_r OC_{1-4}$ alkyl, $(CH_2)_r SC_{1-4}$ alkyl, $(CH_2)_r C(O)OH$, $(CH_2)_r C(O)R_{11b}$, $(CH_2)_r C(O)NR^{11f}R^{11f'}$, $(CH_2)_r NR^{11f}C(O)R^{11a}$, $(CH_2)_r C(O)OC_{1-4}$ alkyl, $(CH_2)_r OC(O)R^{11b}$, $(CH_2)_r C(=NR^{11f})NR^{11f}R^{11f'}$, $(CH_2)_r NHC(=NR^{11f})NR^{11f}CR^{11f}$, $(CH_2)_r S(O)_p R^{11b}$, $(CH_2)_r S(O)_2 NR^{11f}R^{11f'}$, $(CH_2)_r N^{11f}S(O)_2 R^{11b}$, and $(CH_2)_r$phenyl substituted with 0-3 $R^{11e}$;

$R^{11d}$, at each occurrence, is selected from methyl, $CF_3$, $C_{2-6}$ alkyl substituted with 0-3 $R^{11e}$, $C_{3-6}$ alkenyl, $C_{3-6}$ alkynyl, and a $C_{3-10}$ carbocyclic residue substituted with 0-3 $R^{11c}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-5}$ alkyl, $(CH_2)_r NR^{11f}R^{11f'}$, and $(CH_2)_r$phenyl;

$R^{11f}$, at each occurrence, is selected from H, $C_{1-6}$ alkyl, and $C_{3-6}$ cycloalkyl;

$R^{12}$ is selected from H, $C_{1-6}$ alkyl, $(CH_2)_q OH$, $(CH_2)_r C_{3-6}$ cycloalkyl, and $(CH_2)_r$phenyl substituted with 0-3 $R^{12a}$;

$R^{12a}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-5}$ alkyl, $(CH_2)_r NR^{9f}R^{9f'}$, and $(CH_2)_r$phenyl;

alternatively, $R^{11}$ and $R^{12}$ join to form $C_{3-7}$ cycloalkyl;

$R^{14}$ is selected from $C_{1-4}$ alkyl, $C_{2-8}$ alkenyl, $C_{2-8}$ alkynyl, $(CH_2)_r C_{3-6}$ cycloalkyl, $C(O)NR^{14a}R^{14a'}$, $C(O)R^{14b}$, $C(O)OC_{1-4}$ alkyl, $(CH_2)_r S(O)_p R^{14b}$, $(CH_2)_r$phenyl substituted with 0-3 $R^{14c}$, $OR^{14a}$, $NR^{14a}R^{14a'}$, $=O$, and $NR^{14a}C(O)R^{14a'}$;

$R^{14a}$ and $R^{14a'}$, at each occurrence, are selected from H, $C_{1-6}$ alkyl, $(CH_2)_r C_{3-6}$ cycloalkyl, and $(CH_2)_r$phenyl substituted with 0-3 $R^{14c}$, and a $(CH_2)_r$-5-10 membered heterocyclic system containing 1-4 heteroatoms selected from N, O, and S, substituted with 0-2 $R^{14c}$;

$R^{14b}$, at each occurrence, is selected from $C_{1-6}$ alkyl, $(CH_2)_r C_{3-6}$ cycloalkyl, and $(CH_2)_r$phenyl substituted with 0-3 $R^{14c}$, and a $(CH_2)_r$-5-10 membered heterocyclic system containing 1-4 heteroatoms selected from N, O, and S, substituted with 0-2 $R^{14c}$; and $R^{14c}$, at each occurrence, is selected from $C_{1-6}$ alkyl, $(CH_2)_r C_{3-6}$ cycloalkyl, Cl, F, Br, I, CN, $NO_2$, $(CF_2)_r CF_3$, $(CH_2)_r OC_{1-5}$ alkyl, OH, $(CH_2)_w$phenyl;

$R^{15}$, at each occurrence, is selected from $C_{1-8}$ alkyl, $(CH_2)_r C_{3-6}$ cycloalkyl, Cl, Br, I, F, $NO_2$, CN, $(CHR')_r NR^{15a}R^{15a'}$, $(CHR')_r OH$, $(CHR')_r O(CHR')_r R^{15d}$, $(CHR')_r SH$, $(CHR')_r C(O)H$, $(CHR')_r S(CHR')_r R^{15d}$, $(CHR')_r C(O)OH$, $(CHR')_r C(O)(CHR')_r R^{15b}$, $(CHR')_r C(O)NR^{15a}R^{15a'}$, $(CHR')_r NR^{15f}C(O)(CHR')_r R^{15b}$, $(CHR')_r NR^{15f}C(O)NR^{15a}R^{15a'}$, $(CHR')_r C(O)O(CHR')_r R^{15d}$, $(CHR')_r OC(O)(CHR')_r R^{15b}$, $(CHR')_r C(=NR^{15f})NR^{15a}R^{15a'}$, $(CHR')_r NHC(=NR^{15f})NR^{15a}R^{15a'}$, $(CHR')_r S(O)_p (CHR')_r R^{15b}$, $(CHR')_r S(O)_2 NR^{15a}R^{15a'}$, $(CHR')_r NR^{15f}S(O)_2 (CHR')_r R^{15b}$, $C_{1-6}$ haloalkyl, $C_{2-8}$ alkenyl substituted with 0-3 R', $C_{2-8}$ alkynyl substituted with 0-3 R', $(CHR')_r$phenyl substituted with 0-3 $R^{15e}$, and a $(CH_2)_r$-5-10 membered heterocyclic system containing 1-4 heteroatoms selected from N, O, and S, substituted with 0-2 $R^{15e}$;

R', at each occurrence, is selected from H, $C_{1-6}$ alkyl, $C_{2-8}$ alkenyl, $C_{2-8}$ alkynyl, $(CH_2)_r C_{3-6}$ cycloalkyl, and $(CH_2)_r$phenyl substituted with $R^{15e}$;

$R^{15a}$ and $R^{15a'}$, at each occurrence, are selected from H, $C_{1-6}$ alkyl, $C_{3-8}$ alkenyl, $C_{3-8}$ alkynyl, a $(CH_2)_r - C_{3-10}$ carbocyclic residue substituted with 0-5 $R^{15e}$, and a $(CH_2)_r$-5-10 membered heterocyclic system containing 1-4 heteroatoms selected from N, O, and S, substituted with 0-2 $R^{15e}$;

$R^{15b}$, at each occurrence, is selected from $C_{1-6}$ alkyl, $C_{2-8}$ alkenyl, $C_{2-8}$ alkynyl, a $(CH_2)_r - C_{3-6}$ carbocyclic residue substituted with 0-3 $R^{15e}$, and $(CH_2)_r$-5-6 membered heterocyclic system containing 1-4 heteroatoms selected from N, O, and S, substituted with 0-2 $R^{15e}$;

$R^{15d}$, at each occurrence, is selected from $C_{3-8}$ alkenyl, $C_{3-8}$ alkynyl, methyl, $CF_3$, $C_{2-6}$ alkyl substituted with 0-3 $R^{15e}$, a $(CH_2)_r - C_{3-10}$ carbocyclic residue substituted with 0-3 $R^{15e}$, and a $(CH_2)_r$-5-6 membered heterocyclic system containing 1-4 heteroatoms selected from N, O, and S, substituted with 0-3 $R^{15e}$;

$R^{15e}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{15f}$R$^{15f}$, and (CH$_2$)$_r$phenyl;

R$^{15f}$, at each occurrence, is selected from H, C$_{1-6}$ alkyl, C$_{3-6}$ cycloalkyl, and phenyl;

R$^{16}$, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CHR')$_r$NR$^{16a}$R$^{16a'}$, (CHR')$_r$OH, (CHR')$_r$O (CHR')$_r$R$^{16d}$, (CHR')$_r$SH, (CHR')$_r$C(O)H, (CHR')$_r$S (CHR')$_r$R$^{16d}$, (CHR')$_r$C(O)OH, (CHR')$_r$C(O)(CHR')$_r$ R$^{16b}$, (CHR')$_r$C(O)NR$^{16a}$R$^{16a'}$, (CHR')$_r$NR$^{16f}$C(O) (CHR')$_r$R$^{16b}$, (CHR')$_r$C(O)O(CHR')$_r$R$^{16d}$, (CHR')$_r$OC (O)(CHR')$_r$R$^{16b}$, (CHR')$_r$C(=NR$^{16f}$)NR$^{16a}$R$^{16a'}$, (CHR')$_r$NHC(=NR$^{16f}$)NR$^{16a}$R$^{16a'}$, (CHR')$_r$S(O)$_p$ (CHR')$_r$R$^{16b}$, (CHR')$_r$S(O)$_2$NR$^{16a}$R$^{16a'}$, (CHR')$_r$ NR$^{16f}$S(O)$_2$(CHR')$_r$R$^{16b}$, C$_{1-6}$ haloalkyl, C$_{2-8}$ alkenyl substituted with 0-3 R', C$_{2-8}$ alkynyl substituted with 0-3 R', and (CHR')$_r$phenyl substituted with 0-3 R$^{16e}$;

R$^{16a}$ and R$^{16a'}$, at each occurrence, are selected from H, C$_{1-6}$ alkyl, C$_{3-6}$ alkenyl, C$_{3-8}$ alkynyl, a (CH$_2$)$_r$—C$_{3-10}$ carbocyclic residue substituted with 0-5 R$^{16e}$, and a (CH$_2$)$_r$-5-10 membered heterocyclic system containing 1-4 heteroatoms selected from N, O, and S, substituted with 0-2 R$^{16e}$;

R$^{16b}$, at each occurrence, is selected from C$_{1-6}$ alkyl, C$_{2-8}$ alkenyl, C$_{2-8}$ alkynyl, a (CH$_2$)$_r$C$_{3-6}$ carbocyclic residue substituted with 0-3 R$^{16e}$, and a (CH$_2$)$_r$-5-6 membered heterocyclic system containing 1-4 heteroatoms selected from N, O, and S, substituted with 0-2 R$^{16e}$;

R$^{16d}$, at each occurrence, is selected from C$_{3-8}$ alkenyl, C$_{3-8}$ alkynyl, methyl, CF$_3$, C$_{2-6}$ alkyl substituted with 0-3 R$^{16e}$, a (CH$_2$)$_r$—C$_{3-10}$ carbocyclic residue substituted with 0-3 R$^{16e}$, and a (CH$_2$)$_r$-5-6 membered heterocyclic system containing 1-4 heteroatoms selected from N, O, and S, substituted with 0-3 R$^{16e}$;

R$^{16e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{16f}$R$^{16f}$, and (CH$_2$)$_r$phenyl;

R$^{16f}$, at each occurrence, is selected from H, C$_{1-5}$ alkyl, and C$_{3-6}$ cycloalkyl, and phenyl;

R$^{17}$, is selected from H, C$_{1-6}$ alkyl, C$_{2-8}$ alkenyl, C$_{2-8}$ alkynyl, (CHR')$_q$OH, (CHR')$_q$SH, (CHR')$_q$OR$^{17d}$, (CHR')$_r$ SR$^{17d}$, (CHR')$_q$NR$^{17a}$R$^{17a'}$, (CHR')$_r$C(O)OH, (CHR')$_r$ C(O)R$^{17b}$, (CHR')$_r$C(O)NR$^{17a}$R$^{17a'}$, (CHR')$_r$NR$^{17a}$C (O)R$^{17b}$, (CHR')$_r$NR$^{17a}$C(O)H, (CHR')$_r$C(O)OR$^{17a}$, (CHR')$_r$OC(O)R$^{17b}$, (CHR')$_r$S(O)$_p$R$^{17b}$, (CHR')$_r$S(O)$_2$ NR$^{17a}$R$^{17a'}$, (CHR')$_r$NR$^{17a}$S(O)$_2$R$^{17b}$, C$_{1-6}$ haloalkyl, a (CHR')$_r$—C$_{3-10}$ carbocyclic residue substituted with 0-3 R$^{17c}$, and a (CHR')$_r$-5-10 membered heterocyclic system containing 1-4 heteroatoms selected from N, O, and S, substituted with 0-2 R$^{17c}$;

R$^{17a}$ and R$^{17a'}$, at each occurrence, are selected from H, C$_{1-6}$ alkyl, C$_{3-8}$ alkenyl, C$_{3-8}$ alkynyl, a (CH$_2$)$_r$—C$_{3-10}$ carbocyclic residue substituted with 0-5 R$^{17e}$, and a (CH$_2$)$_r$-5-10 membered heterocyclic system containing 1-4 heteroatoms selected from N, O, and S, substituted with 0-3 R$^{17e}$;

R$^{17b}$, at each occurrence, is selected from C$_{1-6}$ alkyl, C$_{2-8}$ alkenyl, C$_{2-8}$ alkynyl, a (CH$_2$)$_r$—C$_{3-6}$ carbocyclic residue substituted with 0-2 R$^{17e}$, and a (CH$_2$)$_r$-5-6 membered heterocyclic system containing 1-4 heteroatoms selected from N, O, and S, substituted with 0-3 R$^{17e}$;

R$^{17c}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{17f}$R$^{17f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{17b}$, (CH$_2$)$_r$C(O)NR$^{17f}$R$^{17f}$, (CH$_2$)$_r$ NR$^{17f}$C(O)R$^{17a}$, (CH$_2$)$_r$C(O)OC$_{1-4}$ alkyl, (CH$_2$)$_r$OC(O) R$^{17b}$, (CH$_2$)$_r$C(=NR$^{17f}$)NR$^{17f}$R$^{17f}$, (CH$_2$)$_r$S(O)$_p$R$^{17b}$, (CH$_2$)$_r$NHC(=NR$^{17f}$)NR$^{17f}$R$^{17f}$, (CH$_2$)$_r$S(O)$_2$ NR$^{17f}$R$^{17f}$, (CH$_2$)$_r$NR$^{17f}$S(O)$_2$R$^{17b}$, and (CH$_2$)$_r$phenyl substituted with 0-3 R$^{17e}$;

R$^{17d}$, at each occurrence, is selected from methyl, CF$_3$, C$_{1-6}$ alkyl substituted with 0-3 R$^{17e}$, C$_{3-6}$ alkenyl, C$_{3-6}$ alkynyl, and a C$_{3-10}$ carbocyclic residue substituted with 0-3 R$^{17c}$;

R$^{17e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$ SC$_{1-5}$ alkyl, (CH$_2$)$_r$NR$^{17f}$R$^{17f}$, and (CH$_2$)$_r$phenyl;

R$^{17f}$, at each occurrence, is selected from H, C$_{1-6}$ alkyl, and C$_{3-6}$ cycloalkyl;

R$^{18}$, is selected from H, C$_{1-6}$ alkyl, C$_{2-8}$ alkenyl, C$_{2-8}$ alkynyl, (CHR')$_q$OH, (CHR')$_q$SH, (CHR')$_q$OR$^{18d}$, (CHR')$_q$ SR$^{18d}$, (CHR')$_q$NR$^{18a}$R$^{18a'}$, (CHR')$_r$C(O)OH, (CHR')$_r$ C(O)R$^{18b}$, (CHR')$_r$C(O)NR$^{18a}$R$^{18a'}$, (CHR')$_r$NR$^{18a}$C (O)R$^{18b}$, (CHR')$_r$NR$^{18a}$C(O)H, (CHR')$_r$C(O)OR$^{18a}$, (CHR')$_q$OC(O)R$^{18b}$, (CHR')$_q$S(O)$_p$R$^{18b}$, (CHR')$_q$S(O)$_2$ NR$^{18a}$R$^{18a'}$, (CHR')$_q$NR$^{18a}$S(O)$_2$R$^{18b}$, C$_{1-6}$ haloalkyl, a (CHR')$_r$—C$_{3-10}$ carbocyclic residue substituted with 0-3 R$^{18c}$, and a (CHR')$_r$-5-10 membered heterocyclic system containing 1-4 heteroatoms selected from N, O, and S, substituted with 0-2 R$^{18c}$;

R$^{18a}$ and R$^{18a'}$, at each occurrence, are selected from H, C$_{1-6}$ alkyl, C$_{3-8}$ alkenyl, C$_{3-8}$ alkynyl, a (CH$_2$)$_r$—C$_{3-10}$ carbocyclic residue substituted with 0-5 R$^{18e}$, and a (CH$_2$)$_r$-5-10 membered heterocyclic system containing 1-4 heteroatoms selected from N, O, and S, substituted with 0-3 R$^{18e}$;

R$^{18b}$, at each occurrence, is selected from C$_{1-6}$ alkyl, C$_{2-8}$ alkenyl, C$_{2-8}$ alkynyl, a (CH$_2$)$_r$—C$_{3-6}$ carbocyclic residue substituted with 0-2 R$^{18e}$, and a (CH$_2$)$_r$-5-6 membered heterocyclic system containing 1-4 heteroatoms selected from N, O, and S, substituted with 0-3 R$^{18e}$;

R$^{18c}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{18f}$R$^{18f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{18b}$, (CH$_2$)$_r$C(O)NR$^{18f}$R$^{18f}$, (CH$_2$)$_r$ NR$^{18f}$C(O)R$^{18b}$, (CH$_2$)$_r$C(O)OC$_{1-4}$ alkyl, (CH$_2$)$_r$OC(O) R$^{18b}$, (CH$_2$)$_r$C(=NR$^{18f}$)NR$^{18f}$R$^{18f}$, (CH$_2$)$_r$S(O)$_p$R$^{18b}$, (CH$_2$)$_r$NHC(=NR$^{18f}$)NR$^{18f}$R$^{18f}$, (CH$_2$)$_r$S(O)$_2$ NR$^{18f}$R$^{18f}$, (CH$_2$)$_r$NR$^{18f}$S(O)$_2$R$^{18b}$, and (CH$_2$)$_r$phenyl substituted with 0-3 R$^{18e}$;

R$^{18d}$, at each occurrence, is selected from methyl, CF$_3$, C$_{1-6}$ alkyl substituted with 0-3 R$^{18e}$, C$_{3-6}$ alkenyl, C$_{3-6}$ alkynyl, and a C$_{3-10}$ carbocyclic residue substituted with 0-3 R$^{18c}$;

R$^{18e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$ SC$_{1-5}$ alkyl, (CH$_2$)$_r$NR$^{18f}$R$^{18f}$, and (CH$_2$)$_r$phenyl;

R$^{18f}$, at each occurrence, is selected from H, C$_{1-6}$ alkyl, and C$_{3-6}$ cycloalkyl;

g is selected from 0, 1, 2 and 3;

h is selected from 0 and 1;

i is selected from 1, 2, 3, 4, and 5;

j is selected from 0, 1, 2, 3, 4, and 5;

k is selected from 0, 1, and 2;

l is selected from 0, 1, 2 and 3, wherein l+h equals 2 or 3;

v, at each occurrence, is independently selected from 0, 1, and 2;

t, at each occurrence, is selected from 1 and 2;
w, at each occurrence, is selected from 0 and 1;
r, at each occurrence, is selected from 0, 1, 2, 3, 4, and 5;
s, at each occurrence, is selected from 0, 1, 2, 3, 4, and 5;
q, at each occurrence, is selected from 1, 2, 3, 4, and 5; and
p, at each occurrence, is selected from 1 and 2.

2. The compound according to claim 1, wherein:
$R^4$ is absent or, taken with the nitrogen to which it is attached to form an N-oxide;
$R^7$, is selected from H, $C_{1-6}$ alkyl, $C_{2-8}$ alkenyl, $C_{2-8}$ alkynyl, $(CHR')_q OH$, $(CHR')_q OR^{7d}$, $(CHR')_q NR^{7a}R^{7a'}$, $(CHR')_r C(O)R^{7b}$, $(CHR')_r C(O)NR^{7a}R^{7a'}$, $(CHR')_q NR^{7a}C(O)R^{7b}$, $(CHR')_q NR^{7a}C(O)H$, $(CHR')_q S(O)_2 NR^{7a}R^{17a'}$, $(CHR')_q NR^{7a}S(O)_2 R^{7b}$, $(CHR')_q NHC(O)NHR^{7a}$, $(CHR')_q NHC(O)OR^{7a}$, $(CHR')_q OC(O)NHR^{7a}$, $C_{1-6}$ haloalkyl, a $(CHR')_r$—$C_{3-10}$ carbocyclic residue substituted with 0-3 $R^{7c}$, and a $(CHR')_r$-5-10 membered heterocyclic system containing 1-4 heteroatoms selected from N, O, and S, substituted with 0-2 $R^{7c}$;
alternatively, $R^7$ and $R^8$ join to form $C_{3-7}$ cycloalkyl, $=NR^{8b}$, or $=O$;
$R^9$, is selected from H, $C_{1-6}$ alkyl, $C_{2-8}$ alkenyl, $C_{2-8}$ alkynyl, $(CHR')_r OH$, $(CHR')_r OR^{9d}$, $(CHR')_r NR^{9a}R^{9a'}$, $(CHR')_r C(O)R^{9b}$, $(CHR')_r C(O)NR^{9a}R^{9a'}$, $(CHR')_r NR^{9a}C(O)R^{9b}$, $(CHR')_r NR^{9a}C(O)H$, $(CHR')_r NR^{9a}C(O)NHR^{9a}$, $(CHR')_r NR^{9a}S(O)_2 R^{9b}$, $C_{1-6}$ haloalkyl, a $(CHR')_r$—$C_{3-10}$ carbocyclic residue substituted with 0-5 $R^{9c}$, and a $(CHR')_r$-5-10 membered heterocyclic system containing 1-4 heteroatoms selected from N, O, and S, substituted with 0-3 $R^{9c}$;
$R^{10}$, is selected from H, $C_{1-6}$ alkyl, $C_{2-8}$ alkenyl, $C_{2-8}$ alkynyl;
$R^{11}$, is selected from H, $C_{1-6}$ alkyl, $C_{2-8}$ alkenyl, $C_{2-8}$ alkynyl, $(CH_2)_q OH$, $(CH_2)_q OR^{11d}$, $(CH_2)_q NR^{11a}R^{11a'}$, $(CH_2)_r C(O)R^{11b}$, $(CH_2)_r C(O)NR^{11a}R^{11a'}$, $(CH_2)_q NR^{11a}C(O)R^{11a}$, $(CH_2)_q NR^{11a}C(O)NHR^{11a}$, $(CH_2)_q NHC(O)NHR^{7a}$, $(CH_2)_q NHC(O)OR^{7a}$, $(CH_2)_q OC(O)NHR^{7a}$, $C_{1-6}$ haloalkyl, a $(CH_2)_r$—$C_{3-10}$ carbocyclic residue substituted with 0-5 $R^{11c}$, and a $(CH_2')_r$-5-10 membered heterocyclic system containing 1-4 heteroatoms selected from N, O, and S, substituted with 0-3 $R^{11c}$.

3. The compound of claim 2, wherein:
E is selected from $-(CR^7R^8)-(CR^9R^{10})_v-(CR^{11}R^{12})$,

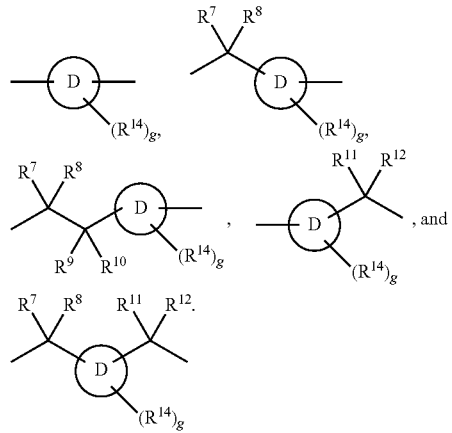

4. The compound according to claim 3, wherein:
G is selected from $-C(O)R^3$, $-C(O)NR^2R^3$, $-C(O)OR^3$, $-SO_2NR^2R^3$, $-SO_2R^3$, $-C(=S)NR^2R^3$, $C(=NR^{1a})NR^2R^3$, $C(=CHCN)NR^2R^3$, $C(=CHNO_2)NR^2R^3$, and $C(=C(CN)_2)NR^2R^3$.

5. The compound according to claim 4, wherein:
$R^{17}$ is selected from H;
$R^{18}$ is selected from H;
j is selected from 0, 1, and 2;
i is selected from 1 and 2;
s is selected from 0, 1, and 2; and
g is selected from 0, 1, and 2.

6. The compound of claim 5, wherein:
$R^1$ is selected from H;
$R^2$ is selected from H; and
G is selected from $-C(O)NR^2R^3$, $C(=CHCN)NR^2R^3$, $C(=CHNO_2)NR^2R^3$, and $C(=C(CN)_2)NR^2R^3$.

7. The compound according to claim 6, wherein:
E is selected from $-(CR^7R^8)-(CR^9R^{10})_v-(CR^{11}R^{12})$.

8. The compound according to claim 7, wherein:
$R^7$ is selected from H;
$R^8$ is selected from H; and
$R^{12}$ is selected from H.

9. The compound of claim 8, wherein:
$R^{16}$, at each occurrence, is selected from methyl, ethyl, propyl, iso-propyl, $C_{2-8}$ alkenyl, $C_{2-8}$ alkynyl, $(CH_2)_r$-$C_{3-6}$ cycloalkyl, Cl, Br, F, CN, $(CHR')_r NR^{16a}R^{16a'}$, $(CHR')_r OH$, $(CHR')_r O(CHR')_r R^{16d}$, $(CHR')_r C(O)(CHR')_r R^{16b}$, $(CHR')_r C(O)NR^{16a}R^{16a'}$, $(CHR')_r NR^{16f}C(O)(CHR')_r R^{16b}$, $(CHR')_r S(O)_p(CHR')_r R^{16b}$, $(CHR')_r S(O)_2 NR^{16a}R^{16a'}$, $(CHR')_r NR^{16f}S(O)_2(CHR')_r R^{16b}$, $C_{1-6}$ haloalkyl, and $(CHR')_r$phenyl substituted with 0-3 $R^{16e}$;
$R^{16a}$ and $R^{16a'}$, at each occurrence, are selected from H, methyl, ethyl, and a $(CH_2)_r$—$C_{3-6}$ carbocyclic residue substituted with 0-2 $R^{16e}$;
$R^{16e}$, at each occurrence, is selected from methyl, ethyl, Cl, F, Br, I, CN, $CF_3$, and $OCH_3$;
$R^{16f}$, at each occurrence, is selected from H; and
r is selected from 0, 1, and 2.

10. The compound of claim 9, wherein:
$R^3$ is selected from a $(CR^{3'}R^{3''})_r$—$C_{3-6}$ carbocyclic residue substituted with 0-2 $R^{15}$ and a $(CR^{3'}CR^{3''})_r$-5-10 membered heterocyclic system containing 1-4 heteroatoms selected from N, O, and S, substituted with 0-3 $R^{15}$;
$R^{3'}$ and $R^{3''}$, at each occurrence, are selected from H;
$R^{15}$, at each occurrence, is selected from $C_{1-8}$ alkyl, $(CH_2)_r$-$C_{3-6}$ cycloalkyl, Cl, Br, F, CN, $(CHR')_r NR^{15a}R^{15a'}$, $(CHR')_r OH$, $(CHR')_r O(CHR')_r R^{15d}$, $(CHR')_r C(O)(CHR')_r R^{15b}$, $(CHR')_r C(O)NR^{15a}R^{15a'}$, $(CHR')_r NR^{15f}C(O)(CHR')_r R^{15b}$, $(CHR')_r NR^{15f}C(O)NR^{15a}R^{15a'}$, $(CHR')_r C(O)O(CHR')_r R^{15d}$, $(CHR')_r OC(O)(CHR')_r R^{15b}$, $(CHR')_r S(O)_p(CHR')_r R^{15b}$, $(CHR')_r S(O)_2 NR^{15a}R^{15a'}$, $(CHR')_r NR^{15f}S(O)_2(CHR')_r R^{15b}$, $C_{1-6}$ haloalkyl, $C_{2-8}$ alkenyl substituted with 0-3 R', $C_{2-8}$ alkynyl substituted with 0-3 R', $(CHR')_r$phenyl substituted with 0-3 $R^{15e}$, and a $(CH_2)_r$-5-10 membered heterocyclic system containing 1-4 heteroatoms selected from N, O, and S, substituted with 0-2 $R^{15e}$;
R', at each occurrence, is selected from H, and $C_{1-6}$ alkyl;
$R^{15a}$ and $R^{15a'}$, at each occurrence, are selected from H, $C_{1-6}$ alkyl, a $(CH_2)_r$—$C_{3-6}$ carbocyclic residue substituted with 0-5 $R^{15e}$, and a $(CH_2)_r$-5-6 membered heterocyclic system containing 1-2 heteroatoms selected from N, O, and S, substituted with 0-2 $R^{15e}$;
$R^{15b}$, at each occurrence, is selected from $C_{1-6}$ alkyl, a $(CH_2)_r$-5-6 carbocyclic residue substituted with 0-3 $R^{15e}$, and $(CH_2)_r$-5-6 membered heterocyclic system containing 1-2 heteroatoms selected from N, O, and S, substituted with 0-2 $R^{15e}$; and $R^{15e}$, at each occurrence, is selected from $C_{1-6}$ alkyl, Cl, F, Br, CN, $(CF_2)_rCF_3$, and OH.

11. The compound of claim 6, wherein:
E is

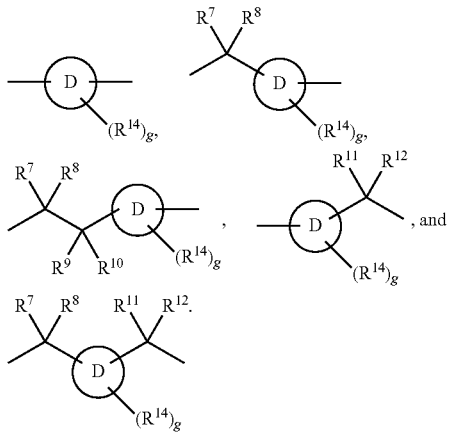

12. The compound of claim 11, wherein:
E is

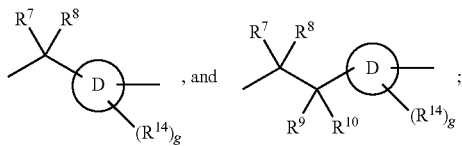

ring D is selected from a $C_{3-6}$ carbocyclic residue;
$R^7$ is selected from H; and
$R^8$ is selected from H.

13. The compound of claim 12, wherein:
$R^{16}$, at each occurrence, is selected from methyl, ethyl, propyl, iso-propyl, $C_{2-8}$ alkenyl, $C_{2-8}$ alkynyl, $(CH_2)_r$-$C_{3-6}$ cycloalkyl, Cl, Br, F, CN, $(CHR')_rNR^{16a}R^{16a'}$, $(CHR')_rOH$, $(CHR')_rO(CHR')_rR^{16d}$, $(CHR')_rC(O)(CHR')_rR^{16b}$, $(CHR')_rC(O)NR^{16a}R^{16a'}$, $(CHR')_rNR^{16f}C(O)(CHR')_rR^{16b}$, $(CHR')_rS(O)_p(CHR')_rR^{16b}$, $(CHR')_rS(O)_2NR^{16a}R^{16a'}$, $(CHR')_rNR^{16f}S(O)_2(CHR')_rR^{16b}$, $C_{1-6}$ haloalkyl, and $(CHR')_r$phenyl substituted with 0-3 $R^{16e}$;
$R^{16a}$ and $R^{16a'}$, at each occurrence, are selected from H, methyl, ethyl, and a $(CH_2)_r$-$C_{3-6}$ carbocyclic residue substituted with 0-2 $R^{16e}$;
$R^{16e}$, at each occurrence, is selected from methyl, ethyl, Cl, F, Br, I, CN, $CF_3$, and $OCH_3$;
$R^{16f}$, at each occurrence, is selected from H; and
r is selected from 0, 1, and 2.

14. The compound of claim 13, wherein:
$R^3$ is selected from a $(CR^{3'}R^{3''})_r$-$C_{3-6}$ carbocyclic residue substituted with 0-2 $R^{15}$ and a $(CR^{3'}CR^{3''})_r$-5-10 membered heterocyclic system containing 1-4 heteroatoms selected from N, O, and S, substituted with 0-3 $R^{15}$;
$R^{3'}$ and $R^{3''}$, at each occurrence, are selected from H;
$R^{15}$, at each occurrence, is selected from $C_{1-8}$ alkyl, $(CH_2)_r$-$C_{3-6}$ cycloalkyl, Cl, Br, F, CN, $(CHR')_rNR^{15a}R^{15a'}$, $(CHR')_rOH$, $(CHR')_rO(CHR')_rR^{15d}$, $(CHR')_rC(O)(CHR')_rR^{15b}$, $(CHR')_rC(O)NR^{15a}R^{15a'}$, $(CHR')_rNR^{15f}C(O)(CHR')_rR^{15b}$, $(CHR')_rNR^{15f}C(O)NR^{15a}R^{15a'}$, $(CHR')_rC(O)O(CHR')_rR^{15d}$, $(CHR')_rOC(O)(CHR')_rR^{15b}$, $(CHR')_rS(O)_p(CHR')_rR^{15b}$, $(CHR')_rS(O)_2NR^{15a}R^{15a'}$, $(CHR')_rNR^{15f}S(O)_2(CHR')_rR^{15b}$, $C_{1-6}$ haloalkyl, $C_{2-8}$ alkenyl substituted with 0-3 R', $C_{2-8}$ alkynyl substituted with 0-3 R', $(CHR')_r$phenyl substituted with 0-3 $R^{15e}$, and a $(CH_2)_r$-5-10 membered heterocyclic system containing 1-4 heteroatoms selected from N, O, and S, substituted with 0-2 $R^{15e}$;
R', at each occurrence, is selected from H, and $C_{1-6}$ alkyl;
$R^{15a}$ and $R^{15a'}$, at each occurrence, are selected from H, $C_{1-6}$ alkyl, a $(CH_2)_r$-$C_{3-6}$ carbocyclic residue substituted with 0-5 $R^{15e}$, and a $(CH_2)_r$-5-6 membered heterocyclic system containing 1-2 heteroatoms selected from N, O, and S, substituted with 0-2 $R^{15e}$;
$R^{15b}$, at each occurrence, is selected from $C_{1-6}$ alkyl, a $(CH_2)_r$-$C_{3-6}$ carbocyclic residue substituted with 0-3 $R^{15e}$, and $(CH_2)_r$-5-6 membered heterocyclic system containing 1-2 heteroatoms selected from N, O, and S, substituted with 0-2 $R^{15e}$; and
$R^{15e}$, at each occurrence, is selected from $C_{1-6}$ alkyl, Cl, F, Br, I, CN, $(CF_2)_rCF_3$, and OH.

15. The compound of claim 3, wherein:
G is selected from

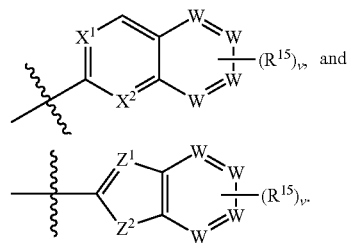

16. The compound of claim 15, wherein:
$R^1$ is selected from H;
both $X^1$ and $X^2$ cannot be C; and
$Z^2$ is selected from $NR^{1'}$, O, and S.

17. The compound of claim 16, wherein:
$R^{17}$ is selected from H;
$R^{18}$ is selected from H;
j is selected from 0, 1, and 2;
i is selected from 1 and 2;
s is selected from 0, 1, and 2; and
g is selected from 0, 1, and 2.

18. The compound of claim 17, wherein:
E is selected from —$(CR^7R^8)$—$(CR^9R^{10})_v$—$(CR^{11}R^{12})$.

19. The compound of claim 18, wherein:
$R^7$ is selected from H;
$R^8$ is selected from H; and
$R^{12}$ is selected from H.

20. The compound of claim 19, wherein:
$R^{16}$, at each occurrence, is selected from methyl, ethyl, propyl, iso-propyl, $C_{2-8}$ alkenyl, $C_{2-8}$ alkynyl, $(CH_2)_r$-$C_{3-6}$ cycloalkyl, Cl, Br, F, CN, $(CHR')_rNR^{16a}R^{16a'}$, $(CHR')_rOH$, $(CHR')_rO(CHR')_rR^{16d}$, $(CHR')_rC(O)(CHR')_rR^{16b}$, $(CHR')_rC(O)NR^{16a}R^{16a'}$, $(CHR')_rNR^{16f}C(O)(CHR')_rR^{16b}$, $(CHR')_rS(O)_p(CHR')_rR^{16b}$, $(CHR')_rS(O)_2NR^{16a}R^{16a'}$, $(CHR')_rNR^{16f}S(O)_2(CHR')_rR^{16b}$, $C_{1-6}$ haloalkyl, and $(CHR')_r$phenyl substituted with 0-3 $R^{16e}$;
$R^{16a}$ and $R^{16a'}$, at each occurrence, are selected from H, methyl, ethyl, and a $(CH_2)_r$-$C_{3-6}$ carbocyclic residue substituted with 0-2 $R^{16e}$;
$R^{16e}$, at each occurrence, is selected from methyl, ethyl, Cl, F, Br, I, CN, $CF_3$, and $OCH_3$;
$R^{16f}$, at each occurrence, is selected from H; and
r is selected from 0, 1, and 2.

21. The compound of claim 20, wherein:
$R^{15}$, at each occurrence, is selected from $C_{1-8}$ alkyl, $(CH_2)_r$-$C_{3-6}$ cycloalkyl, Cl, Br, F, CN, $(CHR')_rNR^{15a}R^{15a'}$, (CHR')$_r$OH, (CHR')$_r$O(CHR')$_r$R$^{15d}$, (CHR')$_r$C(O) (CHR')$_r$R$^{15b}$, (CHR')$_r$C(O)NR$^{15a}$R$^{15a'}$, (CHR')$_r$NR$^{15f}$C (O)(CHR')$_r$R$^{15b}$, (CHR')$_r$NR$^{15f}$C(O)NR$^{15a}$R$^{15a'}$, (CHR')$_r$C(O)O(CHR')$_r$R$^{15d}$, (CHR')$_r$OC(O)(CHR')$_r$R$^{15b}$, (CHR')$_r$S(O)$_p$(CHR')$_r$R$^{15b}$, (CHR')$_r$S(O)$_2$ NR$^{15a}$R$^{15a'}$, (CHR')$_r$NR$^{15f}$S(O)$_2$(CHR')$_r$R$^{15b}$, C$_{1-6}$ haloalkyl, C$_{2-8}$ alkenyl substituted with 0-3 R', C$_{2-8}$ alkynyl substituted with 0-3 R', (CHR')$_r$phenyl substituted with 0-3 R$^{15e}$, and a (CH$_2$)$_r$-5-10 membered heterocyclic system containing 1-4 heteroatoms selected from N, O, and S, substituted with 0-2 R$^{15e}$;

R', at each occurrence, is selected from H, and C$_{1-6}$ alkyl;

R$^{15a}$ and R$^{15a'}$, at each occurrence, are selected from H, C$_{1-6}$ alkyl, a (CH$_2$)$_r$—C$_{3-6}$ carbocyclic residue substituted with 0-5 R$^{15e}$, and a (CH$_2$)$_r$-5-6 membered heterocyclic system containing 1-2 heteroatoms selected from N, O, and S, substituted with 0-2 R$^{15e}$;

R$^{15b}$, at each occurrence, is selected from C$_{1-6}$ alkyl, a (CH$_2$)$_r$—C$_{3-6}$ carbocyclic residue substituted with 0-3 R$^{15e}$, and (CH$_2$)$_r$-5-6 membered heterocyclic system containing 1-2 heteroatoms selected from N, O, and S, substituted with 0-2 R$^{15e}$; and R$^{15e}$, at each occurrence, is selected from C$_{1-6}$ alkyl, Cl, F, Br, I, CN, (CF$_2$)$_r$CF$_3$, and OH.

22. The compound of claim 17, wherein:
E is

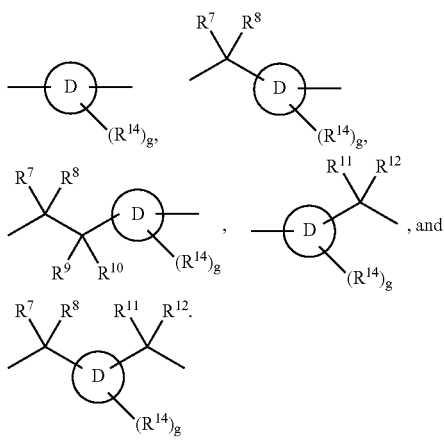

23. The compound of claim 22, wherein:
E is

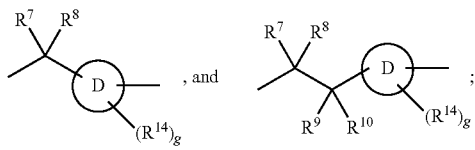

ring D is selected from a C$_{3-6}$ carbocyclic residue;
R$^7$ is selected from H;
R$^8$ is selected from H.

24. The compound of claim 23, wherein:
R$^{16}$, at each occurrence, is selected from methyl, ethyl, propyl, iso-propyl, C$_{2-8}$ alkenyl, C$_{2-8}$ alkynyl, (CH$_2$)$_r$ C$_{3-6}$ cycloalkyl, Cl, Br, F, CN, (CHR')$_r$NR$^{16a}$R$^{16a'}$, (CHR')$_r$OH, (CHR')$_r$O(CHR')$_r$R$^{16d}$, (CHR')$_r$C(O) (CHR')$_r$R$^{16b}$, (CHR')$_r$C(O)NR$^{16a}$R$^{16a'}$, (CHR')$_r$NR$^{16f}$C (O)(CHR')$_r$R$^{16b}$, (CHR')$_r$S(O)$_p$(CHR')$_r$R$^{16b}$, (CHR')$_r$S (O)$_2$NR$^{16a}$R$^{16a'}$, (CHR')$_r$NR$^{16f}$S(O)$_2$(CHR')$_r$R$^{16b}$, C$_{1-6}$ haloalkyl, and (CHR')$_r$phenyl substituted with 0-3 R$^{16e}$;

R$^{16a}$ and R$^{16a'}$, at each occurrence, are selected from H, methyl, ethyl, and a (CH$_2$)$_r$—C$_{3-6}$ carbocyclic residue substituted with 0-2 R$^{16e}$;

R$^{16e}$, at each occurrence, is selected from methyl, ethyl, Cl, F, Br, CN, CF$_3$, and OCH$_3$;

R$^{16f}$, at each occurrence, is selected from H; and
r is selected from 0, 1, and 2.

25. The compound of claim 24, wherein:
R$^{15}$, at each occurrence, is selected from C$_{1-8}$ alkyl, (CH$_2$)$_r$ C$_{3-6}$ cycloalkyl, Cl, Br, F, CN, (CHR')$_r$NR$^{15a}$R$^{15a'}$, (CHR')$_r$OH, (CHR')$_r$O(CHR')$_r$R$^{15d}$, (CHR')$_r$C(O) (CHR')$_r$R$^{15b}$, (CHR')$_r$C(O)NR$^{15a}$R$^{15a'}$, (CHR')$_r$NR$^{15f}$C (O)(CHR')$_r$R$^{15b}$, (CHR')$_r$NR$^{15f}$C(O)NR$^{15a}$R$^{15a'}$, (CHR')$_r$C(O)O(CHR')$_r$R$^{15d}$, (CHR')$_r$OC(O)(CHR')$_r$ R$^{15b}$, (CHR')$_r$S(O)$_p$(CHR')$_r$R$^{15b}$, (CHR')$_r$S(O)$_2$ NR$^{15a}$R$^{15a'}$, (CHR')$_r$NR$^{15f}$S(O)$_2$(CHR')$_r$R$^{15b}$, C$_{1-6}$ haloalkyl, C$_{2-8}$ alkenyl substituted with 0-3 R', C$_{2-8}$ alkynyl substituted with 0-3 R', (CHR')$_r$phenyl substituted with 0-3 R$^{15e}$, and a (CH$_2$)$_r$-5-10 membered heterocyclic system containing 1-4 heteroatoms selected from N, O, and S, substituted with 0-2 R$^{15e}$;

R', at each occurrence, is selected from H, and C$_{1-6}$ alkyl;

R$^{15a}$ and R$^{15a'}$, at each occurrence, are selected from H, C$_{1-6}$ alkyl, a (CH$_2$)$_r$—C$_{3-6}$ carbocyclic residue substituted with 0-5 R$^{15e}$, and a (CH$_2$)$_r$-5-6 membered heterocyclic system containing 1-2 heteroatoms selected from N, O, and S substituted with 0-2 R$^{15e}$;

R$^{15b}$, at each occurrence, is selected from C$_{1-6}$ alkyl, a (CH$_2$)$_r$—C$_{3-6}$ carbocyclic residue substituted with 0-3 R$^{15e}$, and (CH$_2$)$_r$-5-6 membered heterocyclic system containing 1-2 heteroatoms selected from N, O, and S, substituted with 0-2 R$^{15e}$; and R$^{15e}$, at each occurrence, is selected from C$_{1-6}$ alkyl, Cl, F, Br, CN, (CF$_2$)$_r$CF$_3$, and OH.

26. A method for treating asthma, comprising administering to a patient in need thereof a therapeutically effective amount of a compound of claim 1.

27. A pharmaceutical composition, comprising a pharmaceutically acceptable carrier and a therapeutically effective amount of a compound of claim 1.

* * * * *

UNITED STATES PATENT AND TRADEMARK OFFICE
CERTIFICATE OF CORRECTION

PATENT NO. : 7,550,500 B2  
APPLICATION NO. : 11/225227  
DATED : June 23, 2009  
INVENTOR(S) : John Duncia et al.

Page 1 of 1

It is certified that error appears in the above-identified patent and that said Letters Patent is hereby corrected as shown below:

Column 94,  
Line 46, Claim 1, delete "$C_{2-3}$" and insert -- $C_{2-8}$ --.  
Line 52, Claim 1, delete "$(CHR')_rNHC(=NR^bC(O)NR^bR^b$," and  
  insert -- $(CHR')_rNHC(=NR^b)NR^bR^b$, --.

Column 95, line 44, Claim 1, delete "$(CH_2)_rOC(O)R_{7b}$," and insert  
  -- $(CH_2)_rOC(O)R^{7b}$, --.

Column 96, lines 29 to 30, Claim 1, delete "$(CH_2)_rC(=NR^{9f})NR^{9f}R^{9f}(CH_2)_rS(O)_pR^{9b}$,"  
  and insert -- $(CH_2)_rC(=NR^{9f})NR^{9f}R^{9f}, (CH_2)_rS(O)_pR^{9b}$, --.

Column 97,  
Lines 6 to 7, Claim 1, delete "$(CH_2)_rOC(O)R_{10b}$," and insert -- $(CH_2)_rOC(O)R^{10b}$, --.  
Line 24, Claim 1, delete "$C_{3-4}$" and insert -- $C_{3-7}$ --.  
Line 56, Claim 1, delete "$(CH_2)_rC(O)R_{11b}$," and insert -- $(CH_2)_rC(O)R^{11b}$, --.  
Lines 58 to 59, Claim 1, delete "$(CH_2)_rNHC(=NR^{11f})NR^{11f}CR^{11f}$," and  
  insert -- $(CH_2)_rNHC(=NR^{11f})NR^{11f}R^{11f}$, --.

Column 99, line 20, Claim 1, delete "$C_{3-6}$" and insert -- $C_{3-8}$ --.

Column 101, lines 14 to 15, Claim 2, delete "$(CHR')_qS(O)_2NR^{7a}R^{17a'}$," and  
  insert -- $(CHR')_qS(O)_2NR^{7a}R^{7a'}$, --.

Column 102, line 64, Claim 10, delete "$(CH_2)_r$-5-6" and insert -- $(CH_2)_r$-$C_{3-6}$ --.

Column 106, line 39, Claim 25, delete "S" and insert -- S, --.

Signed and Sealed this

Fifteenth Day of June, 2010

David J. Kappos  
*Director of the United States Patent and Trademark Office*